(12) United States Patent
Kim et al.

(10) Patent No.: US 12,384,822 B2
(45) Date of Patent: Aug. 12, 2025

(54) TAM RECEPTOR-BINDING FUSION MOLECULE HAVING NON-INFLAMMATORY PHAGOCYTOSIS INDUCING ACTIVITY

(71) Applicant: ILLIMIS THERAPEUTICS, INC., Seoul (KR)

(72) Inventors: Chan Hyuk Kim, Daejeon (KR); Won Suk Chung, Daejeon (KR); Hyun Cheol Jung, Daejeon (KR); Se Young Lee, Daejeon (KR)

(73) Assignee: ILLIMIS THERAPEUTICS, INC., Seoul (KR)

( * ) Notice: Subject to any disclaimer, the term of this patent is extended or adjusted under 35 U.S.C. 154(b) by 0 days.

(21) Appl. No.: 18/360,984

(22) Filed: Jul. 28, 2023

(65) Prior Publication Data
US 2024/0018204 A1  Jan. 18, 2024

Related U.S. Application Data

(63) Continuation-in-part of application No. PCT/KR2022/001671, filed on Jan. 28, 2022.

(30) Foreign Application Priority Data

Jan. 29, 2021  (KR) .................. 10-2021-0013045

(51) Int. Cl.
*C07K 19/00* (2006.01)
*A61P 25/28* (2006.01)
(Continued)

(52) U.S. Cl.
CPC .......... *C07K 14/4703* (2013.01); *A61P 25/28* (2018.01); *C07K 16/18* (2013.01);
(Continued)

(58) Field of Classification Search
None
See application file for complete search history.

(56) References Cited

U.S. PATENT DOCUMENTS 8,268,973 B2  9/2012 Schenk et al.
8,753,628 B2  6/2014 Lazar et al.
(Continued)

FOREIGN PATENT DOCUMENTS

WO  2010/130751 A1  11/2010
WO  2010/131733 A1  11/2010
(Continued)

OTHER PUBLICATIONS

Caberoy et al., Tubby and tubby-like protein 1 are new MerTK ligands for phagocytosis, The EMBO J. 29: 3898-3910, 2010.*
(Continued)

*Primary Examiner* — Claire Kaufman
(74) *Attorney, Agent, or Firm* — Sughrue Mion, PLLC

(57) ABSTRACT

A fusion molecule having phagocytosis-inducing activity is disclosed. The fusion molecule contains a first region capable of binding a TAM receptor and a second region capable of binding to a target substance of which aberrant accumulation is associated with or characteristic of diseases. The fusion molecule effectively clears and/or reduces and/or suppresses accumulated abnormal proteins, such as beta-amyloid, tau, alpha-synuclein, huntingtin, or prion, or the like. Uses of the fusion molecule are disclosed. The fusion molecule can be used for prevention or treatment of proteinosis caused by the abnormal accumulation of substances.

13 Claims, 35 Drawing Sheets

Specification includes a Sequence Listing.

(51) Int. Cl.
  *C07K 14/47* (2006.01)
  *C07K 16/18* (2006.01)
  *C07K 16/46* (2006.01)
  *A61K 38/00* (2006.01)

(52) U.S. Cl.
  CPC .......... *A61K 38/00* (2013.01); *C07K 2317/73* (2013.01); *C07K 2319/74* (2013.01)

(56) References Cited

U.S. PATENT DOCUMENTS

| | | |
|---|---|---|
| 9,283,271 B2 | 3/2016 | Montrasio et al. |
| 9,587,014 B2 | 3/2017 | Nitsch et al. |
| 10,882,902 B2 | 1/2021 | Grimm et al. |
| 10,961,306 B2 | 3/2021 | Keane et al. |
| 11,040,086 B2 * | 6/2021 | Zhang ................ A61K 38/1709 |
| 11,267,877 B2 | 3/2022 | Salmans et al. |
| 11,873,337 B2 * | 1/2024 | Takahashi ................ A61P 25/00 |
| 2018/0327465 A1 | 11/2018 | Caberoy |
| 2020/0181221 A1 | 6/2020 | Kotenko et al. |
| 2020/0390853 A1 | 12/2020 | Zhang et al. |
| 2021/0070870 A1 | 3/2021 | Gardener et al. |
| 2021/0079075 A1 | 3/2021 | Heneka et al. |
| 2022/0332808 A1 | 10/2022 | Maier et al. |
| 2022/0411485 A1 | 12/2022 | Holtzman et al. |

FOREIGN PATENT DOCUMENTS

| | | | | |
|---|---|---|---|---|
| WO | WO-2011107591 A1 * | 9/2011 | ............ | A61K 38/16 |
| WO | 2011/159980 A1 | 12/2011 | | |
| WO | 2012/088461 A2 | 6/2012 | | |
| WO | 2012/130831 A1 | 10/2012 | | |
| WO | 2012/175691 A1 | 12/2012 | | |
| WO | 2015/193428 A1 | 12/2015 | | |
| WO | 2015/193430 A1 | 12/2015 | | |
| WO | 2016/005593 A1 | 1/2016 | | |
| WO | 2016/097370 A2 | 6/2016 | | |
| WO | 2016/106221 A1 | 6/2016 | | |
| WO | 2016/166302 A1 | 10/2016 | | |
| WO | 2016/166348 A1 | 10/2016 | | |
| WO | 2017/009258 A1 | 1/2017 | | |
| WO | WO-2017083700 A1 * | 5/2017 | ............ | A61K 38/00 |
| WO | 2017/200493 A1 | 11/2017 | | |
| WO | 2017/220695 A1 | 12/2017 | | |
| WO | 2019/201970 A1 | 10/2019 | | |
| WO | 2020/076799 A1 | 4/2020 | | |
| WO | 2020/176497 A1 | 9/2020 | | |

OTHER PUBLICATIONS

Burstyn-Cohen et al., TAM receptors in phagocytosis: Beyond the mere internalization of particles, Immunological Rev., 139:7-26, 2023.*
Nomura et al., Activated Microglia Desialylate and Phagocytose Cells via Neuraminidase, Galectin-3, and Mer Tyrosine Kinase, J. Immunol. 198 (12): 4792-4801, 2017.*
Sasaki et al., Crystal structure of a C-terminal fragment of growth arrest-specific protein Gas6, J. Biol. Chem. 277(46): 44164-44170, 2002.*
Van der Meer et al., TAM receptors, Gas6, and protein S: roles in inflammation and hemostasis, Blood. 123(16):2460-2469, 2014.*
International Search Report dated May 16, 2023 in International Application No. PCT/KR2022/001671.
Written Opinion dated May 16, 2023 in International Application No. PCT/KR2022/001671.
Kedage et al., "Harnessing MerTK agonism for targeted therapeutics", MABS, 2020, vol. 12, No. 1, pp. 1-8 (8 pages total).
Tondo et al., "TAM Receptor Pathways at the Crossroads of Neuroinflammation and Neurodegeneration", Hindawi Disease Markers, 2019, vol. 2019, pp. 1-13 (13 pages total).
Lew et al., "Differential TAM receptor-ligand-phospholipid interactions delimit differential TAM bioactivities", eLIFE, 2014, pp. 1-23 (23 pages total).

Hutchison et al., "A complete library of point substitution mutations in the glucocorticoid response element of mouse mammary tumor virus", Proc. Natl. Acad. Sci. USA, 1986, vol. 83, pp. 710-714, (5 pages total).
Higuchi, "Using PCR to Engineer DNA", PCR Technology: Principles and Applications for DNA Amplification, 1989, H. Erlich, ed., Stockton Press, 1989, Chapter 6, pp. 61-70, (10 pages total).
Zheng et al., "Advances in aptamers against AB and applications in AB detection and regulation for Alzheimer's disease", Theranostics, 2022, vol. 12, No. 5, pp. 2095-2114, (20 pages total).
Donahue et al., "Rage, LRP-1, and amyloid-beta protein in Alzheimer's disease", Acta Neuropathol, 2006, vol. 112, pp. 405-415, (11 pages total).
Schwarzman et al., "Selection of peptides binding to the amyloid b-protein reveals potential inhibitors of amyloid formation", Amyloid, 2005, vol. 12, No. 4, pp. 199-209, (12 pages total).
Sambrook et al., "Molecular Cloning: A laboratory Manual", Cold Spring Harbor Laboratory Press, 1989, vol. 1, No. 4, (34 pages total).
Deuscher et al., "Guide to Protein Purification", Methods Enzymology, 1990, vol. 463, No. 2, (854 pages total).
Rowe et al., "Handbook of Pharmaceutical Excipients", American Pharmaceuticals Association, 2003, 4th Edition, (917 pages total).
Gennaro et al., "Remington: the Science and Practice of Pharmacy", Lippincott Williams & Wilkins, 2000, vol. 1, 20th Edition, (1053 pages total).
"Tyrosine-protein kinase receptor UFO isoform 1 precursor [*Homo sapiens*]", NCBI Reference Sequence: NP_068713.2, cbi.nlm.nih.gov/protein/NP_068713, last visited Aug. 15, 2023, pp. 1-5 (5 pages total).
"*Homo sapiens* AXL receptor tyrosine kinase (AXL), transcript variant 1, mRNA", NCBI Reference Sequence: NM_021913.5, https://www.ncbi.nlm.nih.gov/nuccore/NM_021913, last visited Aug. 15, 2023, pp. 1-6 (6 pages total).
"AXL receptor tyrosine kinase [Mus musculus]", GenBank: AAH46618.1, https://www.ncbi.nlm.nih.gov/protein/AAH46618, last visited Aug. 15, 2023, pp. 1-4 (4 pages total).
"Mus musculus AXL receptor tyrosine kinase, mRNA (cDNA clone MGC:54698 Image:6494383), complete cds", GenBank: BC046618.1, https://www.ncbi.nlm.nih.gov/nuccore/BC046618, last visited Aug. 15, 2023, pp. 1-3 (3 pages total).
"Tyrosine-protein kinase receptor UFO isoform 3 [*Homo sapiens*]", NCBI Reference Sequence: NP_001265528.1, https://www.ncbi.nlm.nih.gov/protein/NP_001265528.1 last visited Aug. 15, 2023, pp. 1-4 (4 pages total).
"Tyrosine-protein kinase receptor UFO isoform 2 precursor [*Homo sapiens*]", NCBI Reference Sequence: NP_001690.2, https://www.ncbi.nlm.nih.gov/protein/NP_001690.2 last visited Aug. 15, 2023, pp. 1-5 (5 pages total).
"AXL receptor tyrosine kinase, isoform CRA_a [*Homo Sapiens*]", GenBank: EAW57022.1, https://www.ncbi.nlm.nih.gov/protein/EAW57022, last visited Aug. 15, 2023, pp. 1-2 (2 pages total).
"AXL receptor Tyrosine kinase, isoform CRA_b [*Homo sapiens*]", GenBank: EAW57023.1, https://www.ncbi.nlm.nih.gov/protein/EAW57023.1, last visited Aug. 15, 2023, pp. 1-2 (2 pages total).
"AXL receptor tyrosine kinase [*Homo sapiens*]", GenBank: AAH32229.1 https://www.ncbi.nlm.nih.gov/protein/AAH32229.1 last visited Aug. 15, 2023, pp. 1-4 (4 pages total).
"RecName: Full=Tubby protein homolog", UniProtKB/Swiss-Prot: P50607.1, https://www.ncbi.nlm.nih.gov/protein/P50607 last visited Aug. 15, 2023, pp. 1-5 (5 pages total).
"Human tub homolog mRNA, complete cds" GenBank: U54644.1, https://www.ncbi.nlm.nih.gov/nuccore/U54644.1 last visited Aug. 15, 2023, pp. 1-2 (2 pages total).
"Tub homolog [*Homo sapiens*]", GenBank: AAB53494.1, https://www.ncbi.nlm.nih.gov/protein/AAB53494.1, last visited Aug. 15, 2023, pp. 1-2 (2 pages total).
"Human tub homolog (Tub) mRNA, complete cds", GenBank: U82467.1, https://www.ncbi.nlm.nih.gov/nuccore/U82467.1, last visited Aug. 15, 2023, pp. 1-2 (2 pages total).
"Tub homolog [*Homo sapiens*]", GenBank: AAB53699.1, https://www.ncbi.nlm.nih.gov/protein/AAB53699.1, last visited Aug. 15, 2023, pp. 1-2 (2 pages total).

(56) References Cited

OTHER PUBLICATIONS

"*Homo sapiens* 211000035833915 genomic scaffold, whole genome shotgun sequence" GenBank: CH471064.2, https://www.ncbi.nlm.nih.gov/nuccore/CH471064.2, last visited Aug. 15, 2023, pp. 1-8 (8 pages total).
"Tubby homolog (mouse), isoform CRA_b [*Homo sapiens*]", GenBank: EAW68634.1, https://www.ncbi.nlm.nih.gov/protein/EAW68634.1, last visited Aug. 15, 2023, pp. 1-3 (3 pages total).
"*Homo sapiens* tubby homolog (mouse), mRNA (cDNA clone MGC: 104164 Image:30915625), complete cds", GenBank: BC075031.2, https://www.ncbi.nlm.nih.gov/nuccore/BC075031.2, last visited Aug. 15, 2023, pp. 1-3 (3 pages total).
"Tubby homolog (mouse) [*Homo sapiens*]", GenBank: AAH75031.1. https://www.ncbi.nlm.nih.gov/protein/AAH75031.1, last visited Aug. 15, 2023, pp. 1-2 (2 pages total).
"*Homo sapiens* tubby homolog (mouse), mRNA (cDNA clone MGC: 104008 Image:30915418), complete cds", GenBank: BC075032.2, https://www.ncbi.nlm.nih.gov/nuccore/BC075032.2, last visited Aug. 15, 2023, pp. 1-3 (3 pages total).
"Tubby homolog (mouse) [*Homo sapiens*]", GenBank: AAH75032.1, https://www.ncbi.nlm.nih.gov/protein/AAH75032.1, last visited Aug. 15, 2023, pp. 1-2 (2 pages total).
"Tubby protein homolog isoform a [*Homo sapiens*]", NCBI Reference Sequence: NP_003311.2, https://www.ncbi.nlm.nih.gov/protein/NP_003311.2, last visited Aug. 15, 2023, pp. 1-3 (3 pages total).
"Tubby protein homolog isoform b [*Homo sapiens*]", NCBI Reference Sequence: NP_813977.1, https://www.ncbi.nlm.nih.gov/protein/NP_813977.1, last visited Aug. 15, 2023, pp. 1-3 (3 pages total).
"Chain A, tubby isoform a", PDB: 1S31_A, https://www.ncbi.nlm.nih.gov/protein/1S31_A, last visited Aug. 15, 2023, pp. 1-2 (2 pages total).
"Tubby related protein 1 TULP1 [*Homo sapiens*]", GenBank: AAB53700.1, https://www.ncbi.nlm.nih.gov/protein/AAB53700.1, last visited Aug. 15, 2023, pp. 1-2 (2 pages total).
"TULP1 protein [*Homo sapiens*]", GenBank: AAH32714.1, https://www.ncbi.nlm.nih.gov/protein/AAH32714.1, last visited Aug. 15, 2023, pp. 1-2 (2 pages total).
"TULP1 protein [*Homo sapiens*]" GenBank: AAH65261.1, https://www.ncbi.nlm.nih.gov/protein/AAH65261.1, last visited Aug. 15, 2023, pp. 1-2 (2 pages total).
"Tubby-related protein 1 isoform 2 [*Homo sapiens*]", NCBI Reference Sequence: NP_001276324.1, https://www.ncbi.nlm.nih.gov/protein/NP_001276324.1, last visited Aug. 15, 2023, pp. 1-3 (3 pages total).
"Tubby like protein 1 [*Homo sapiens*]", GenBank: AAB97966.1, https://www.ncbi.nlm.nih.gov/protein/AAB97966.1, last visited Aug. 15, 2023, pp. 1-2 (2 pages total).
"Tubby like protein 1, isoform CRA_b [*Homo sapiens*]", GenBank: EAX03840.1, https://www.ncbi.nlm.nih.gov/protein/EAX03840.1, last visited Aug. 15, 2023, pp. 1-2 (2 pages total).
"Tubby like protein 1, isoform CRA_a [*Homo sapiens*]", GeneBank: EAX03839.1, https://www.ncbi.nlm.nih.gov/protein/EAX03839.1, last visited Aug. 15, 2023, pp. 1-2 (2 pages total).
"Tubby-related protein 1 [*Homo sapiens*]", GenBank: BAJ84064.1, https://www.ncbi.nlm.nih.gov/protein/BAJ84064.1, last visited Aug. 15, 2023, pp. 1-2 (2 pages total).
"Tubby-related protein 1 [*Homo sapiens*]", GenBank: BAJ84063.1, https://www.ncbi.nlm.nih.gov/protein/BAJ84063.1, last visited Aug. 15, 2023, pp. 1-2 (2 pages total).
"Tubby-like protein 1 [*Homo sapiens*]", GenBank: AKU84911.1, https://www.ncbi.nlm.nih.gov/protein/AKU84911.1, last visited Aug. 15, 2023, pp. 1-2 (2 pages total).
"Galectin-3 isoform 1 [*Homo sapiens*]", NCBI Reference Sequence: NP_002297.2, https://www.ncbi.nlm.nih.gov/protein/NP_002297, last visited Aug. 15, 2023, pp. 1-4 (4 pages total).
"Beta-amyloid, A beta=neuritic plaque amyloid {N-terminal} [human, familial Alzheimer's disease patient, Peptide Partial, 30 aa]", GenBank: AAB29908.1, https://www.ncbi.nlm.nih.gov/protein/AAB29908.1, last visited Aug. 15, 2023, p. 1 (1 page total).

"Chain A, Amyloid Beta-Peptide", PDB: 1BJC_A, https://www.ncbi.nlm.nih.gov/protein/1BJC_A, last visited Aug. 15, 2023, p. 1 (1 page total).
"Major prion protein preproprotein Prp precursor [*Homo sapiens*]", NCBI Reference Sequence: NP_001073592.1, https://www.ncbi.nlm.nih.gov/protein/NP_001073592.1, last visited Aug. 15, 2023, pp. 1-4 (4 pages total).
"Huntingtin isoform 1 [*Homo sapiens*]", NCBI Reference Sequence: NP_001375421.1, https://www.ncbi.nlm.nih.gov/protein/NP_001375421.1, last visited Aug. 15, 2023, pp. 1-6 (6 pages total).
"SOD1 [*Homo sapiens*]", GenBank: CAG46542.1, https://www.ncbi.nlm.nih.gov/protein/CAG46542.1, last visited Aug. 15, 2023, pp. 1-3 (3 pages total).
"Serum amyloid A [*Homo sapiens*]", GenBank: AAB24060.1, https://www.ncbi.nlm.nih.gov/protein/AAB24060.1, last visited Aug. 15, 2023, p. 1 (1 page total).
"Serum amyloid A [*Homo sapiens*]", GenBank: AAA85338.1, https://www.ncbi.nlm.nih.gov/protein/AAA85338.1, last visited Aug. 15, 2023, p. 1 (1 page total).
"Serum amyloid A-2 protein isoform a preproprotein [*Homo sapiens*]", NCBI Reference Sequence: NP_001372595.1, https://www.ncbi.nlm.nih.gov/protein/NP_001372595.1, last visited Aug. 15, 2023, pp. 1-3 (3 pages total).
"Serum amyloid A-2 protein isoform a preproprotein [*Homo sapiens*]", NCBI Reference Sequence: NP_110381.2, https://www.ncbi.nlm.nih.gov/protein/NP_110381.2, last visited Aug. 15, 2023, pp. 1-4 (4 pages total).
"RecName: Full=Tyrosine-protein kinase receptor UFO; AltName: Full=AXL oncogene; Flags: Precursor", UniProtKB/Swiss-Prot: P30530.4, https://www.ncbi.nlm.nih.gov/protein/P30530.4, last visited Aug. 15, 2023, pp. 1-14 (14 pages total).
"RecName: Full=Alpha-synuclein; Altname: Full=Non-A beta component of AD amyloid; Altname: Full=Non-A4 component of amyloid precursor; Short=NACP", UniProtKB/Swiss-Prot: P37840.1, https://www.ncbi.nlm.nih.gov/protein/P37840.1, last visited Aug. 15, 2023, pp. 1-17 (17 pages total).
"RecName: Full=Mircotubule-associated protein tau; AltName: Full=Neurofibrillary tangle protein; AltName: Full=Paired helical filament-tau; Short=PHF-tau", UniProtKB/Swiss-Prot P10636.5, https://www.ncbi.nlm.nih.gov/protein/P10636.5, last visited Aug. 15, 2023, pp. 1-33 (33 pages total).
"RecName: Full=TAR DNA-binding protein 43; Short=TDP-43", UniProtKB/Swiss-Prot: Q13148.1, https://www.ncbi.nlm.nih.gov/protein/Q13148.1, last visited Aug. 15, 2023, pp. 1-21 (21 pages total).
"RecName: Full=Transthyretin; AltName: Full=ATTR; AltName: Full=Prealbumin; AltName: Full=TBPA; Flags: Precursor", UniProtKB/Swiss-Prot: P02766.1, https://www.ncbi.nlm.nih.gov/protein/P02766.1, last visited Aug. 15, 2023, pp. 1-29 (29 pages total).
"RecName: Full=Islet amyloid polypeptide; AltName: Full=Amylin; AltName: Full=Diabetes-associated peptide; Short=DAP; AltName: Full=Insulinoma amyloid peptide; Flags: Precursor", UniProtKB/Swiss-Prot: P10997, https://www.ncbi.nlm.nih.gov/protein/P10997, last visited Aug. 15, 2023, pp. 1-6 (6 pages total).
"RecName: Full=Apolipoprotein E; Short=Apo-E; Flags: Precursor", UniProtKB/Swiss-Prot: P02649.1, https://www.ncbi.nlm.nih.gov/protein/P02649.1, last visited Aug. 15, 2023, pp. 1-23 (23 pages total).
"RecName: Full=Apoptosis-associated speck-like protein containing a Card; Short=hASC; AltName: Full=Caspase recruitment domain-containing protein 5; AltName: Full=PYD and Card domain-containing protein; AltName: Full=Target of methylation-induced silencing 1", UniProtKB/Swiss-Prot: Q9ULZ3.2, https://www.ncbi.nlm.nih.gov/protein/Q9ULZ3.2, last visited Aug. 15, 2023, pp. 1-16 (16 pages total).
Picken, "The Pathology of Amyloidosis in Classification: A Review", Acta Haematologica, 2020, pp. 1-13 (13 pages total).
Kabat et al., "Sequences of Proteins of Immunological Interest", National Institute of Health, 1991, vol. 1, No. 5, (1,243 pages total).
Altschul et al., "Basic Local Alignment Search Tool", J. Mol. Biol., 1990, vol. 215, pp. 403-410, (8 pages total).
Shpaer, "GeneAssist", Methods in Molecular Biology, 1997, vol. 70, pp. 173-187 (15 pages total).

(56) References Cited

OTHER PUBLICATIONS

Needleman et al., "A General Method Applicable to the Search for Similarities in the Amino Acid Sequence of Two Proteins", J. Mol. Biol, 1970, vol. 48, pp. 443-453, (11 pages total).

Hutchison et al., "Mutagenesis at a Specific Position in a DNA Sequence", The Journal of Biological Chemistry, 1978, vol. 253, No. 18, pp. 6551-6560, (10 pages total).

Zoller et al., "Oligonucleotide-Directed Mutagenesis: A Simple Method Using Two Oligonucleotide Primers and a Single-Stranded DNA Template", DNA, 1984, vol. 3, No. 6, pp. 479-488, (10 pages total).

Oliphant et al., "Cloning of random-sequence oligodeoxynucleotides", Gene, 1986, vol. 44, 177-183, (7 pages total).

Geng et al., "Requirement of Gamma-Carboxyglutamic Acid Modification and Phosphatidylserine Binding for the Activation of Tyro3, Axl, and Mertk Receptors by Growth Arrest-Specific 6", Frontiers in Immunology, vol. 8, Article 1521, Nov. 2017.

Lew et al., "Differential TAM receptor-ligand-phospholipid interactions delimit differential TAM bioactivities", eLife 2014;3:e03385. DOI: 10.7554/eLife.03385.

Hasanbasic et al., The role of γ-carboxylation in the anti-apoptotic function of gas6, Journal of Thrombosis and Haemostasis, 2005, pp. 2790-2797.

Hall et al., "Gas6 Binding to Photoreceptor Outer Segments Requires γ-Carboxyglutamic Acid (Gla) and Ca2+ and is Required for OS Phagocytosis by RPE Cells in vitro", Exp. Eye Res., 2002, 75, pp. 391-400.

Nakano et al., "Requirement of γ-carboxyglutamic acid residues for the biological activity of Gas6: contribution of endogenous Gas6 to the proliferation of vascular smooth muscle cells", Biochem. J., 1997, 323, pp. 387-392.

Rajotte et al., "Gas6-mediated signaling is dependent on the engagement of its gamma-carboxyglutamic acid domain with phosphatidylserine", Biochemical and Biophysical Research Communications, 376, 2008, pp. 70-73.

Dransfield et al., "Mer receptor tyrosine kinase mediates both tethering and phagocytosis of apoptotic cells", Cell Death and Disease, 2015, 6, e1646; doi:10.1038/cddis.2015.18.

Lemke, "Phosphatidylserine Is the Signal for TAM Receptors and Their Ligands", Trends in Biochemical Sciences, Sep. 2017, vol. 42, No. 9, pp. 738-748.

Moon, "Curcumin in Cancer and Inflammation: An In-Depth Exploration of Molecular Interactions, Therapeutic Potentials, and the Role in Disease Management", Int. J. Mol. Sci. 2024, 25, 2911.

Asadian et al., "The therapeutic effect of GAS6 in remyelination is dependent upon Tyro3", Glia. 2024; 1-10, DOI: 10.1002/glia.24534.

Grondal et al., "Dynamic changes in immune cell populations by AXL kinase targeting diminish liver inflammation and fibrosis in experimental MASH", Frontiers in Immunology, 15:1400553. doi: 10.3389/fimmu.2024.1400553, May 16, 2024.

Burstyn-Cohen et al., "TAM receptors in phagocytosis: Beyond the mere internalization of particles", Immunological Reviews, 2023:319, pp. 7-26.

Tutusaus et al., "GAS6/TAM Axis as Therapeutic Target in Liver Diseases", Seminars in Liver Disease, vol. 44, No. Jan. 2024, 2024, pp. 99-114.

Miao et al., "Therapeutic targeting of the functionally elusive TAM receptor family", Nature Reviews Drug Discovery, vol. 23, Mar. 2024, pp. 201-217.

Zhuang et al., "Phosphatidylserine in the Nervous System: Cytoplasmic Regulator of the AKT and PKC Signaling Pathways and Extracellular "Eat-Me" Signal in Microglial Phagocytosis", Molecular Neurobiology, 2023, 60, pp. 1050-1066.

Zhou et al., "An insight into the TAM system in Alzheimer's disease", International Immunopharmacology, 116, 2023, 109791.

Prasad et al., "TAM receptor function in the retinal pigment epithelium", Mol. Cell. Neurosci., 33, 2006, pp. 96-10.

Burstyn-Cohen et al., "TAM receptors, Phosphatidylserine, inflammation, and Cancer", Cell Communication and Signaling, 2019, 17:156.

McCloskey et al., "GAS6 Mediates Adhesion of Cells Expressing the Receptor Tyrosine Kinase Axl", The Journal of Biological Chemistry, vol. 272, No. 37, Sep. 12, 1997, pp. 23285-23291.

Sasaki et al., "Structural basis for Gas6-Axl signaling", The EMBO Journal, vol. 25, No. 1, 2006, pp. 80-87.

Owlett, Laura, "Modulation of acute inflammation and Alzheimer's disease pathology by Gas6-Axl interaction", Submitted in Partial Fulfillment of the Requirements for the Degree Neurobiology and Anatomy, University of Rochester, Rochester, New York, 2020.

\* cited by examiner

FIG. 1G
FIG. 1H
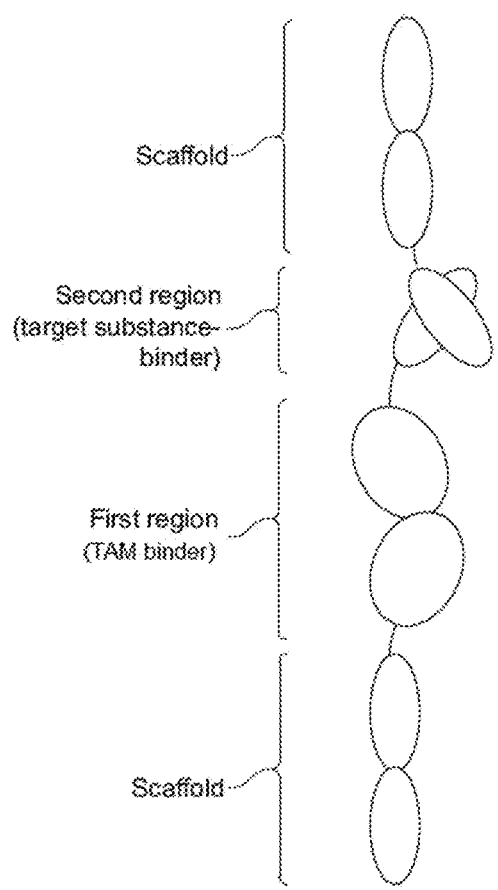
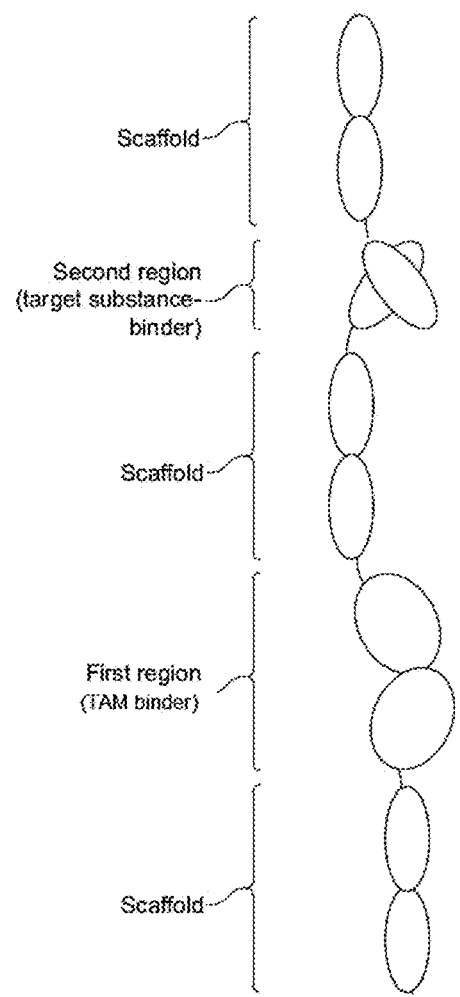

FIG. 13
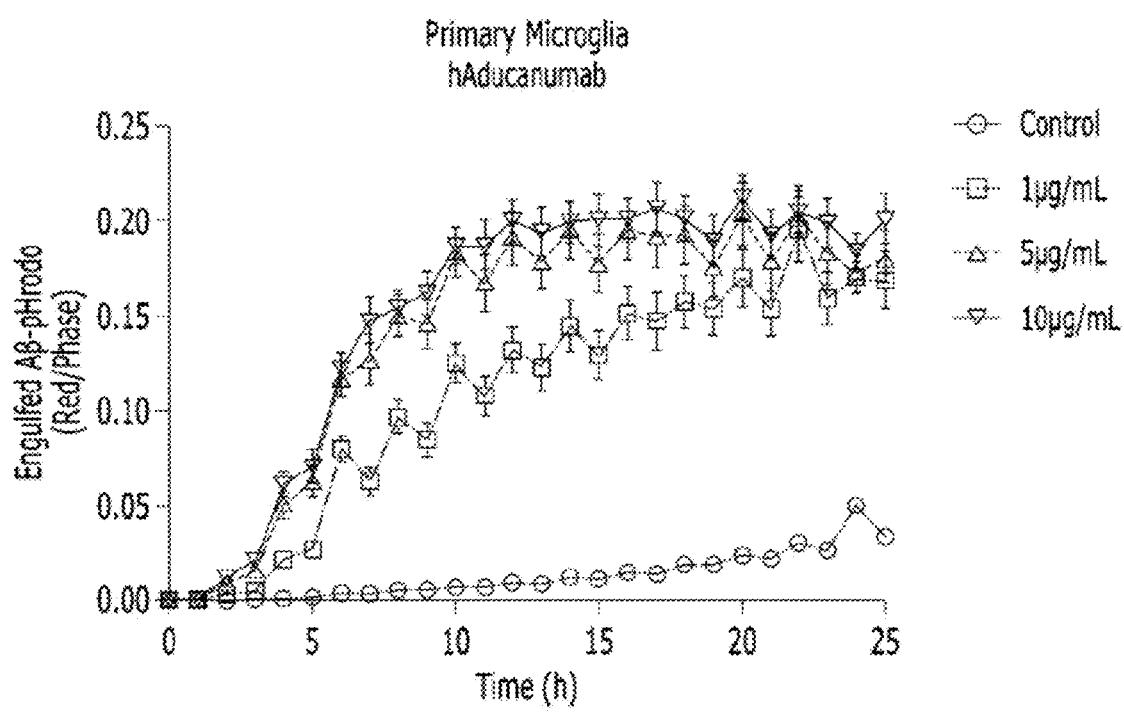
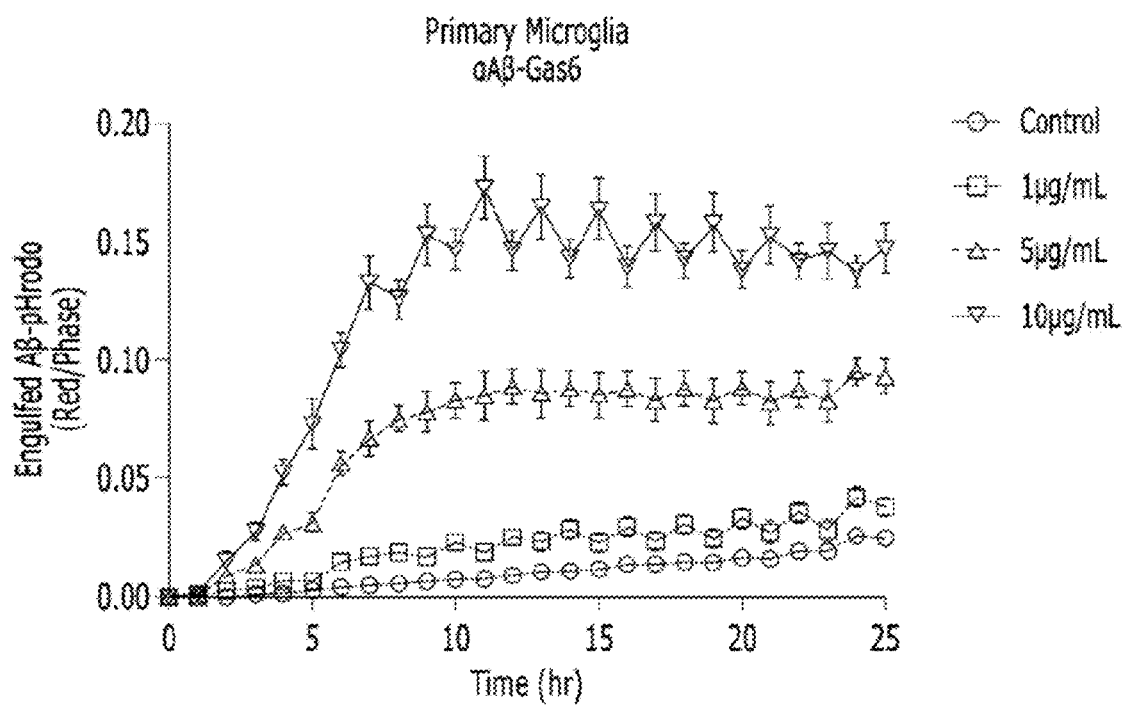

FIG. 14
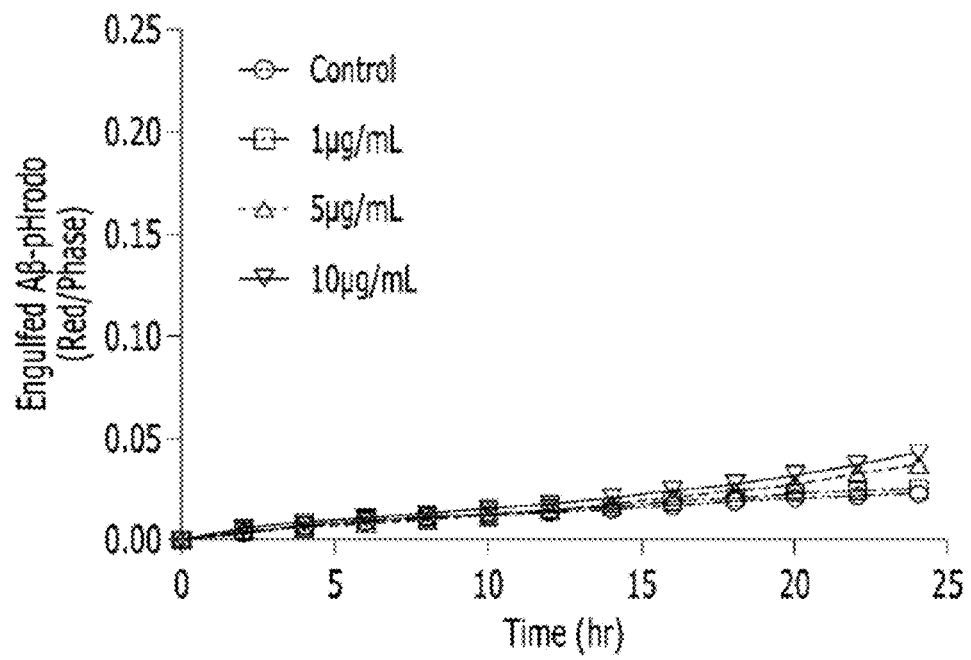
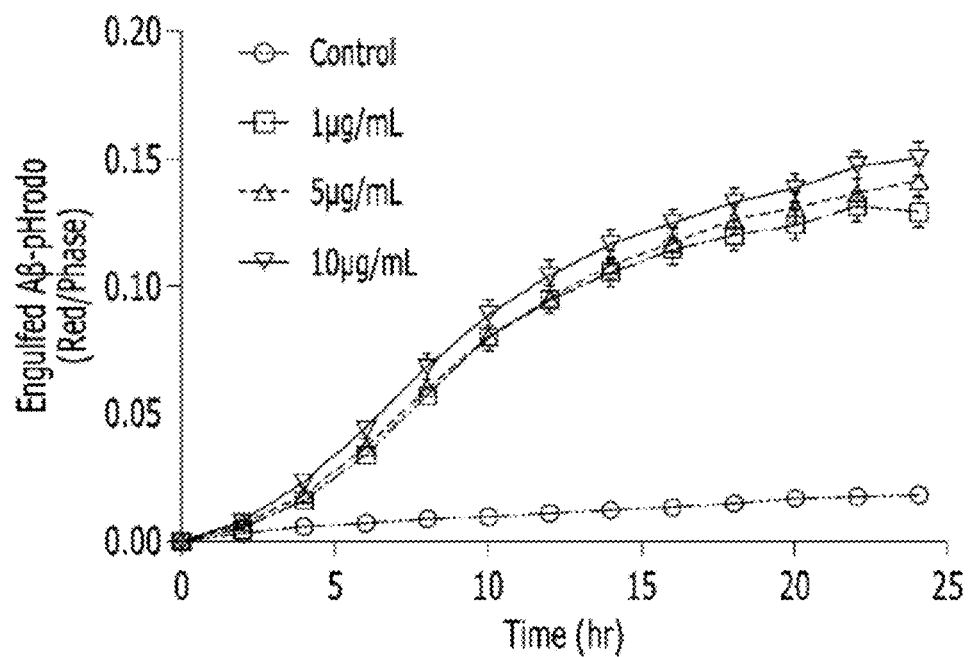

FIG. 17
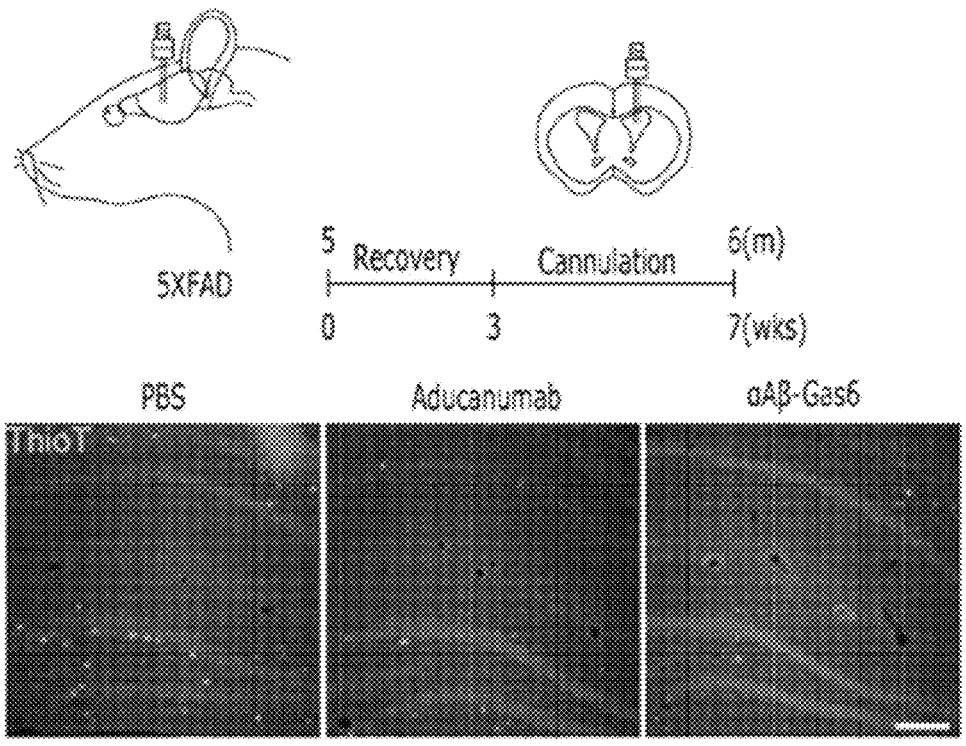
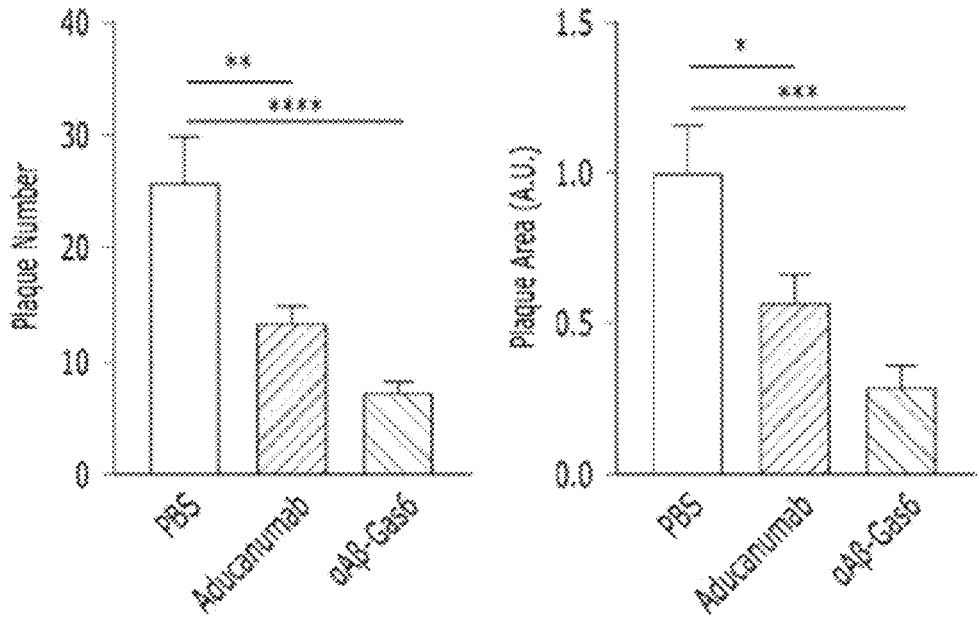

FIG. 18
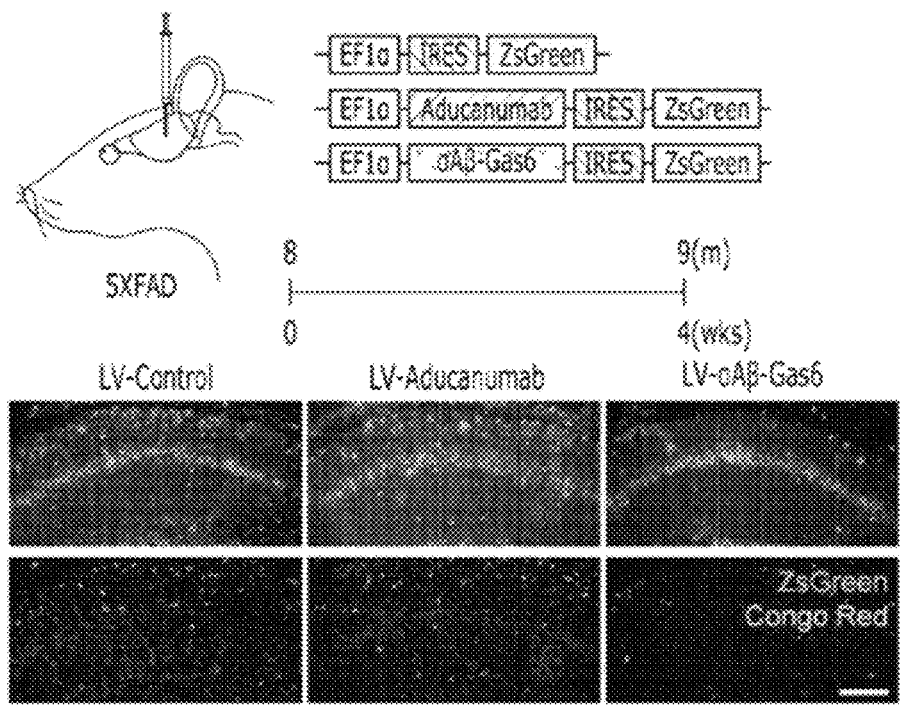
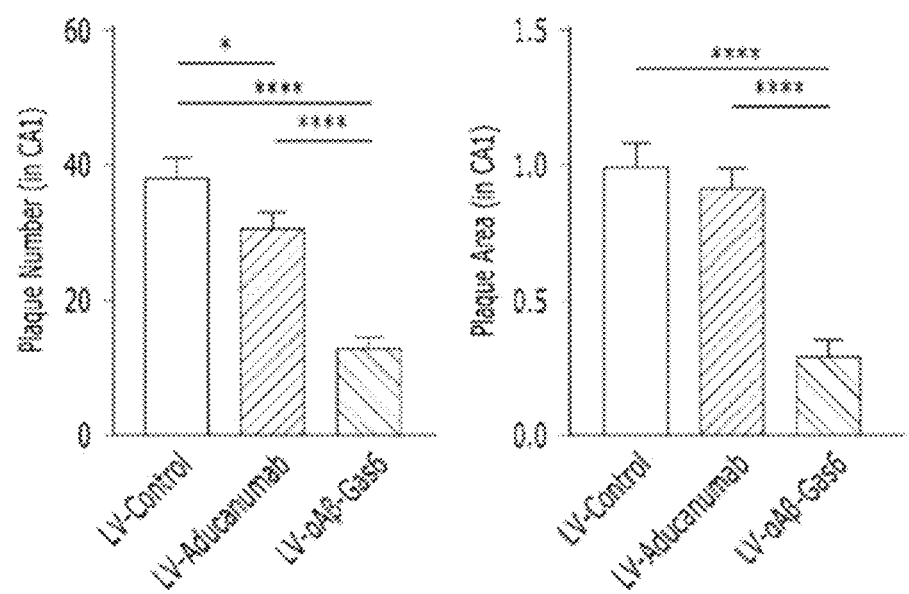

FIG. 19
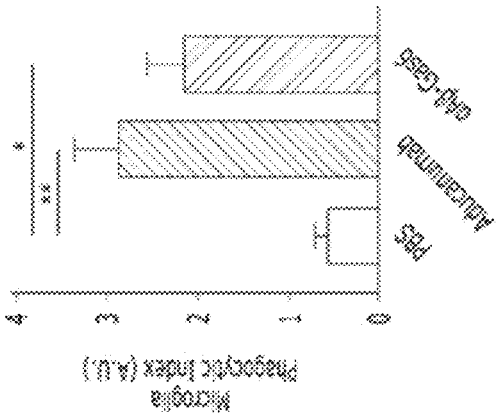
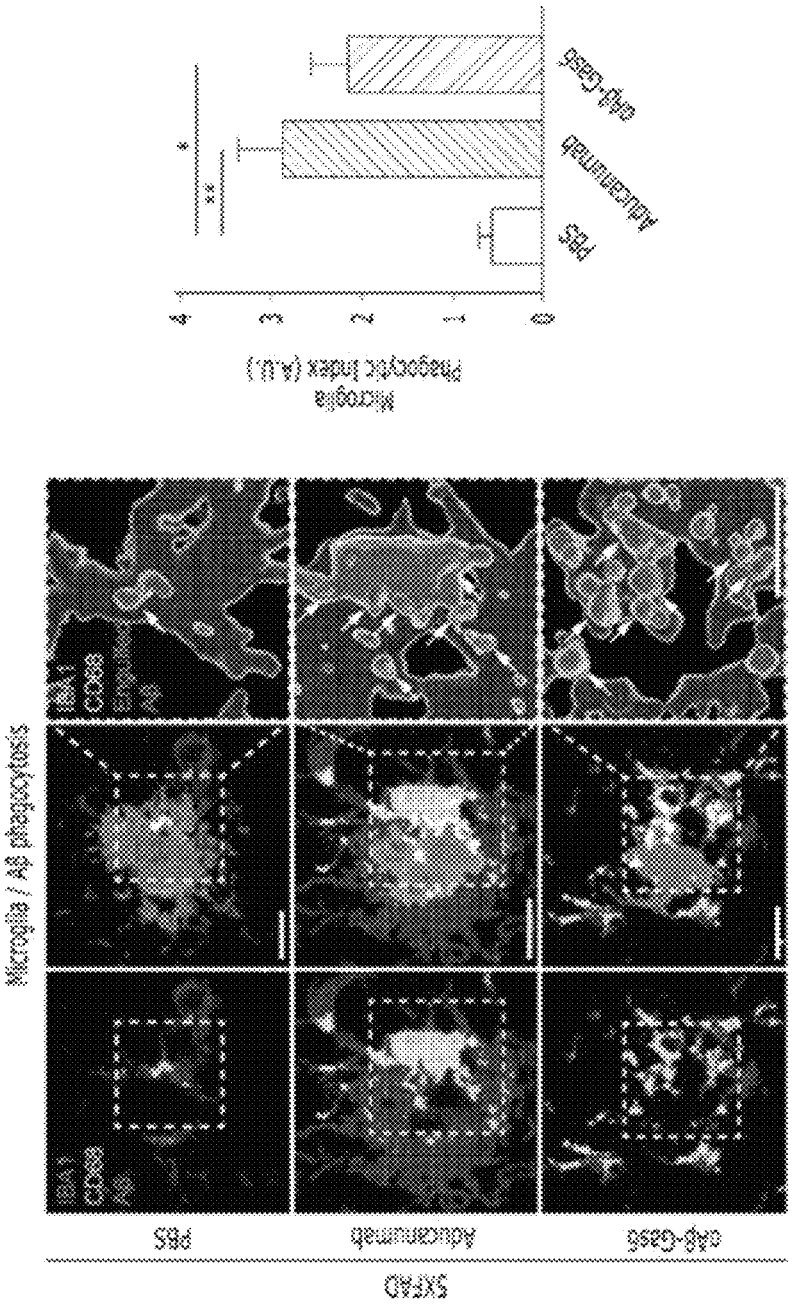

FIG. 23
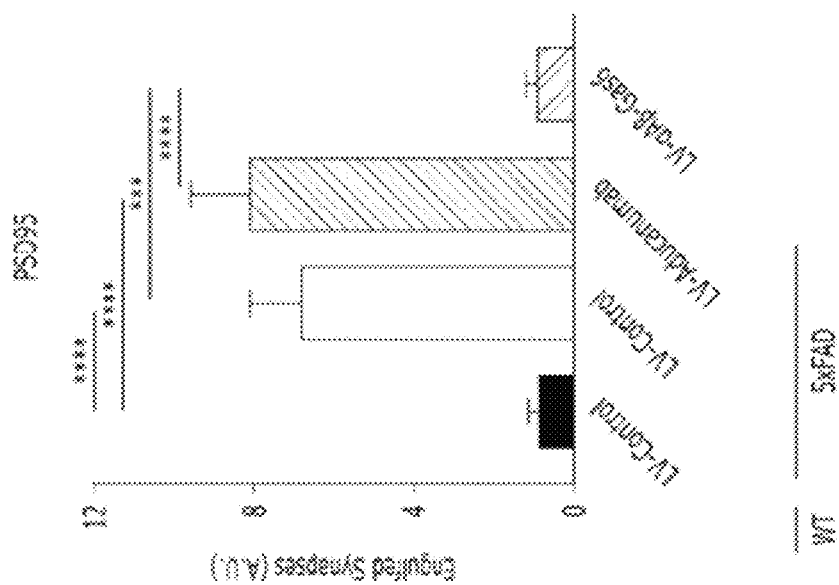
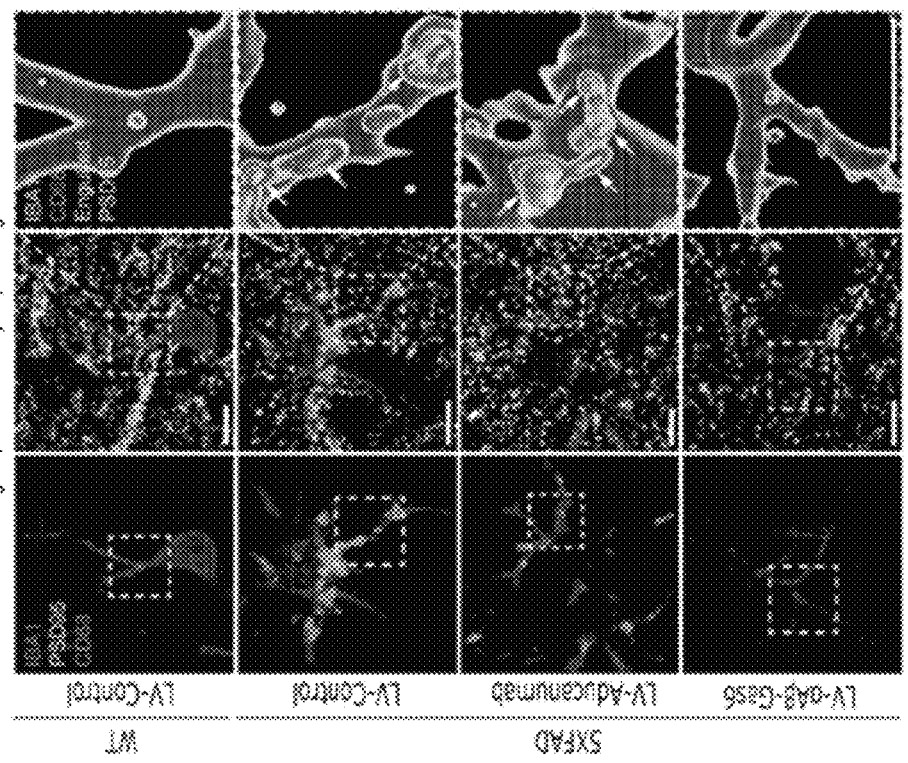

FIG. 25
Administration of vector carrying
αAβ-Gas6 -encoding gene
Novel Object Location Test
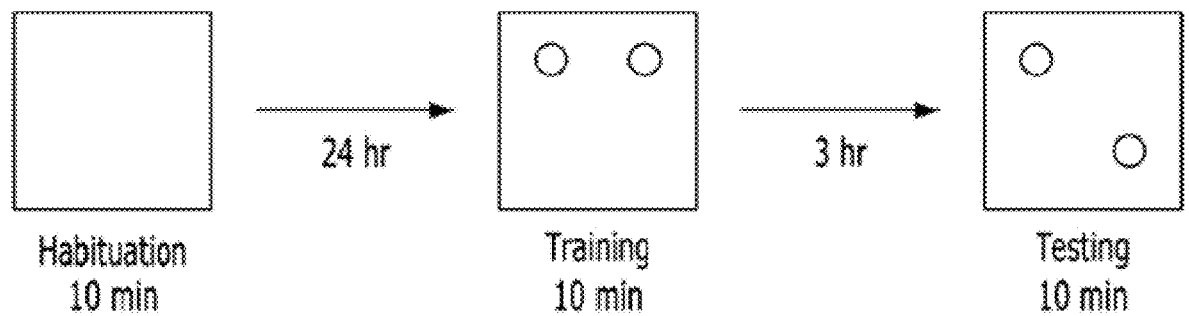
Novel Object Recognition Test
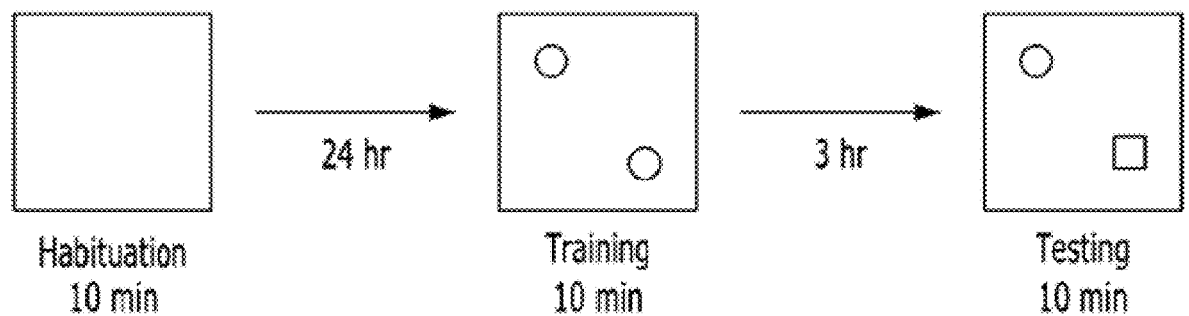

FIG. 27
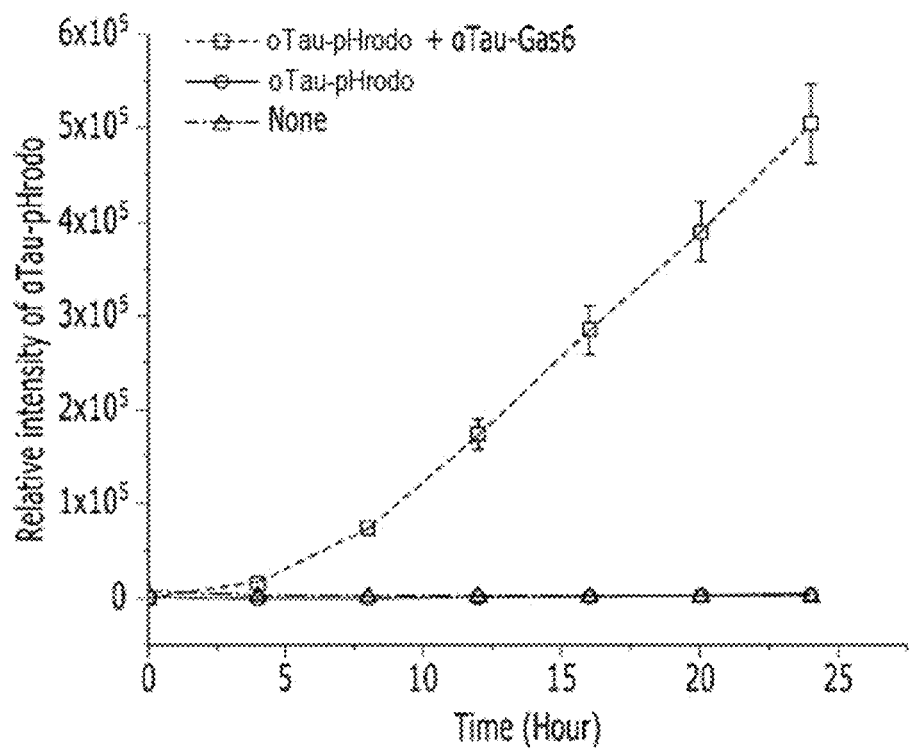
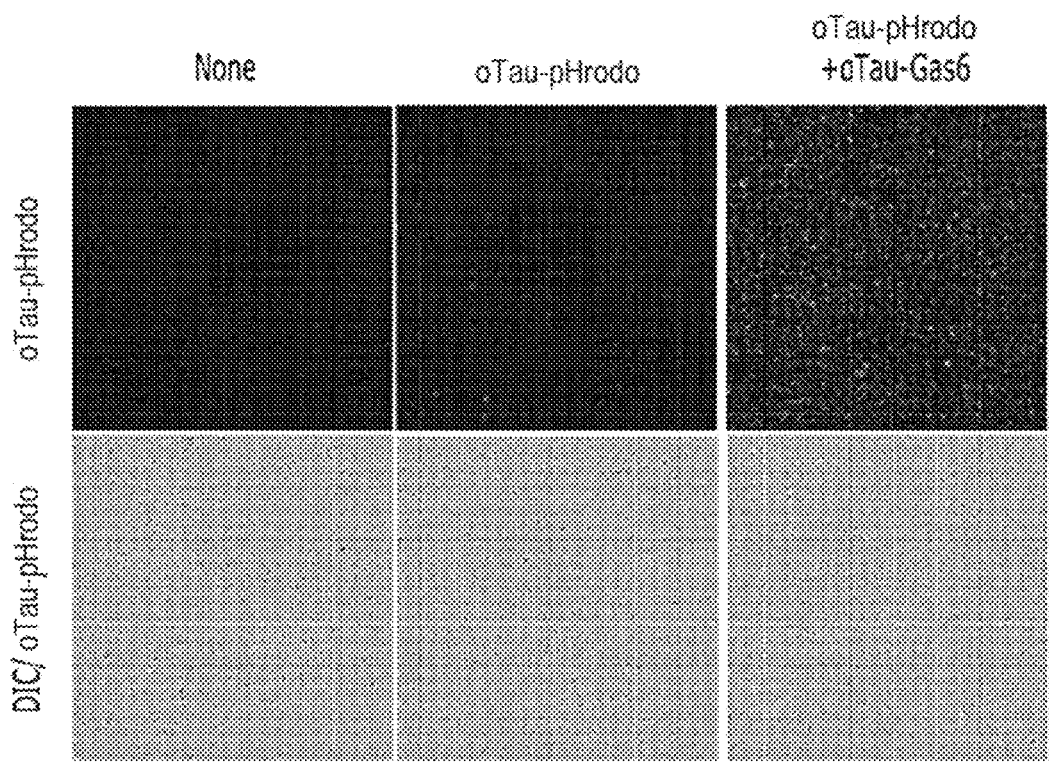

FIG. 30
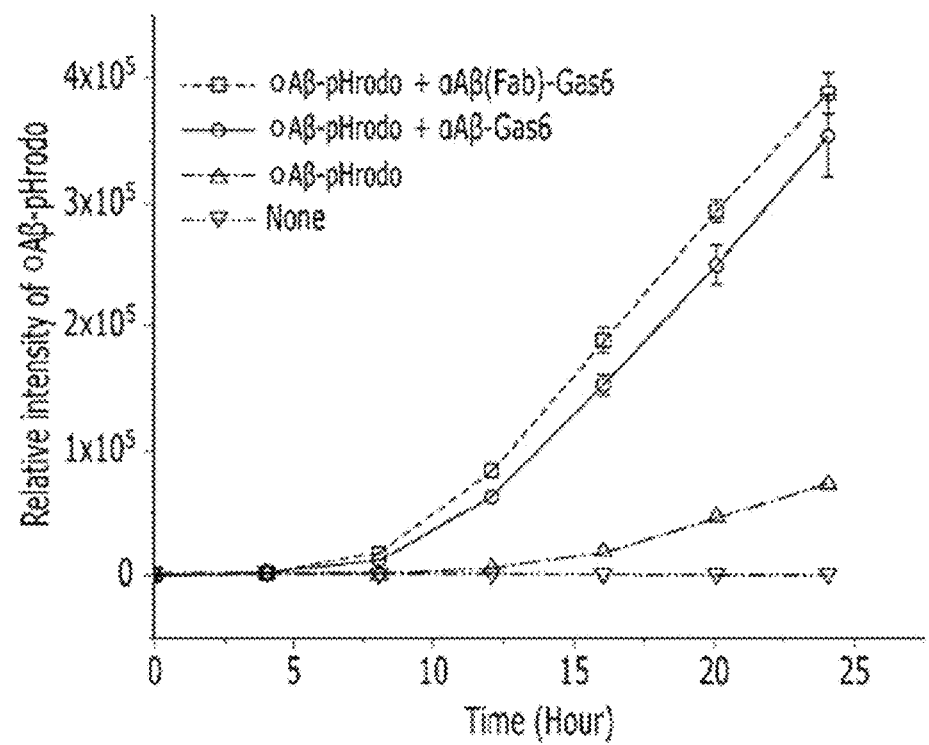
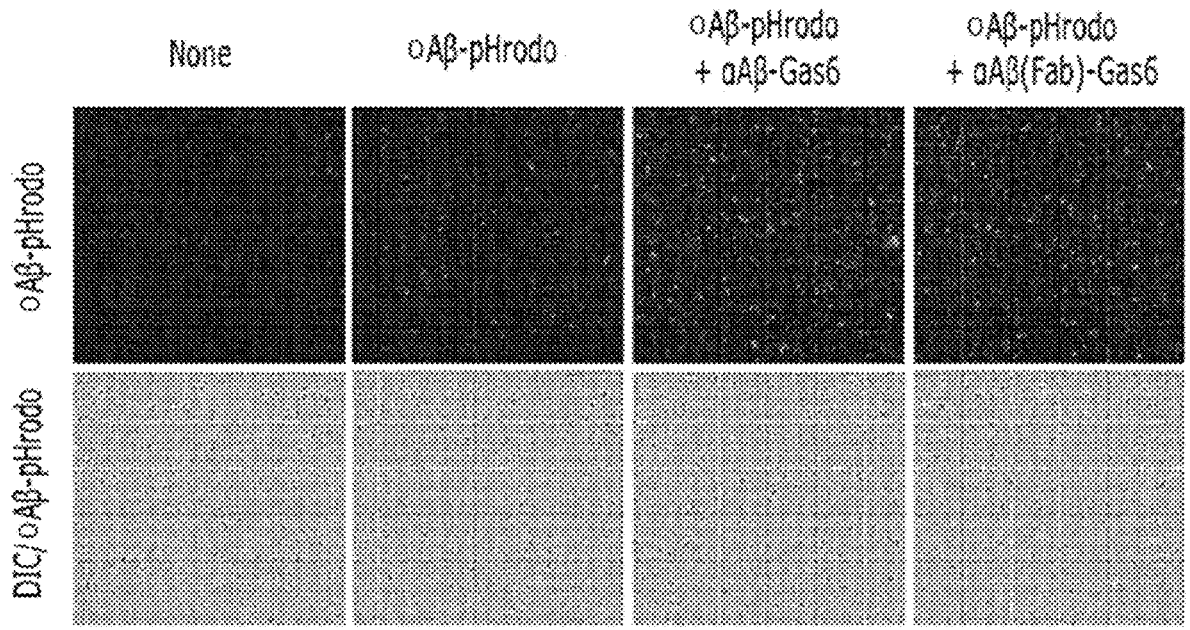

SEQUENCE LISTING

```
Sequence total quantity: 169
SEQ ID NO: 1            moltype = AA  length = 173
FEATURE                 Location/Qualifiers
REGION                  1..173
                        note = TAM(Axl)-binding sequence
source                  1..173
                        mol_type = protein
                        organism = synthetic construct
SEQUENCE: 1
GRMFSGTPVI RLRFKRLQPT RLVAEFDFRT FDPEGILLFA GGHQDSTWIV LALRAGRLEL   60
QLRYNGVGRV TSSGPVINHG MWQTISVEEL ARNLVIKVNR DAVMKIAVAG DLFQPERGLY  120
HLNLTVGGIP FHEKDLVQPI NPRLDGCMRS WNWLNGEDTT IQETVKVNTR MQC         173

SEQ ID NO: 2            moltype = AA  length = 194
FEATURE                 Location/Qualifiers
REGION                  1..194
                        note = TAM(Axl)-binding sequence
source                  1..194
                        mol_type = protein
```

```
                        organism = synthetic construct
SEQUENCE: 2
GSFYPGSGFA FYSLDYMRTP LDVGTESTWE VEVVAHIRPA ADTGVLFALW APDLRAVPLS    60
VALVDYHSTK KLKKQLVVLA VEHTALALME IKVCDGQEHV VTVSLRDGEA TLEVDGTRGQ   120
SEVSAAQLQE RLAVLERHLR SPVLTFAGGL PDVPVTSAPV TAFYRGCMTL EVNRRLLDLD   180
EAAYKHSDIT AHSC                                                    194

SEQ ID NO: 3               moltype = AA  length = 177
FEATURE                    Location/Qualifiers
REGION                     1..177
                           note = TAM(Axl)-binding sequence
source                     1..177
                           mol_type = protein
                           organism = synthetic construct
SEQUENCE: 3
LLYLAEQFAG VVLYLKFRLP EISRFSAEFD FRTYDSEGVI LYAESIDHSA WLLIALRGGK    60
IEVQLKNEHT SKITTGGDVI NNGLWNMVSV EELEHSISIK IAKEAVMDIN KPGPLFKPEN   120
GLLETKVYFA GFPRKVESEL IKPINPRLDG CIRSWNLMKQ GASGIKEIIQ EKQNKHC      177

SEQ ID NO: 4               moltype = AA  length = 183
FEATURE                    Location/Qualifiers
REGION                     1..183
                           note = TAM(Axl)-binding sequence
source                     1..183
                           mol_type = protein
                           organism = synthetic construct
SEQUENCE: 4
YYPGSGIAQF HIDYNNVSSA EGWHVNVTLN IRPSTGTGVM LALVSGNNTV PFAVSLVDST    60
SEKSQDILLS VENTVIYRIQ ALSLCSDQQS HLEFRVNRNN LELSTPLKIE TISHEDLQRQ   120
LAVLDKAMKA KVATYLGGLP DVPFSATPVN AFYNGCMEVN INGVQLDLDE AISKHNDIRA   180
HSC                                                                183

SEQ ID NO: 5               moltype = AA  length = 400
FEATURE                    Location/Qualifiers
REGION                     1..400
                           note = TAM(Axl)-binding sequence
source                     1..400
                           mol_type = protein
                           organism = synthetic construct
SEQUENCE: 5
DILPCVPFSV AKSVKSLYLG RMFSGTPVIR LRFKRLQPTR LVAEFDFRTF DPEGILLFAG    60
GHQDSTWIVL ALRAGRLELQ LRYNGVGRVT SSGPVINHGM WQTISVEELA RNLVIKVNRD   120
AVMKIAVAGD LFQPERGLYH LNLTVGGIPF HEKDLVQPIN PRLDGCMRSW NWLNGEDTTI   180
QETVKVNTRM QCFSVTERGS FYPGSGFAFY SLDMRTPLD VGTESTWEVE VVAHIRPAAD   240
TGVLFALWAP DLRAVPLSVA LVDYHSTKKL KKQLVVLAVE HTALALMEIK VCDGQEHVVT   300
VSLRDGEATL EVDGTRGQSE VSAAQLQERL AVLERHLRSP VLTFAGGLPD VPVTSAPVTA   360
FYRGCMTLEV NRRLLDLDEA AYKHSDITAH SCPPVEPAAA                         400

SEQ ID NO: 6               moltype = AA  length = 393
FEATURE                    Location/Qualifiers
REGION                     1..393
                           note = TAM(Axl)-binding sequence
source                     1..393
                           mol_type = protein
                           organism = synthetic construct
SEQUENCE: 6
VVSVCLPLNL DTKYELLYLA EQFAGVVLYL KFRLPEISRF SAEFDFRTYD SEGVILYAES    60
IDHSAWLLIA LRGGKIEVQL KNEHTSKITT GGDVINNGLW NMVSVEELEH SISIKIAKEA   120
VMDINKPGPL FKPENGLLET KVYFAGFPRK VESELIKPIN PRLDGCIRSW NLMKQGASGI   180
KEIIQEKQNK HCLVTVEKGS YYPGSGIAQF HIDYNNVSSA EGWHVNVTLN IRPSTGTGVM   240
LALVSGNNTV PFAVSLVDST SEKSQDILLS VENTVIYRIQ ALSLCSDQQS HLEFRVNRNN   300
LELSTPLKIE TISHEDLQRQ LAVLDKAMKA KVATYLGGLP DVPFSATPVN AFYNGCMEVN   360
INGVQLDLDE AISKHNDIRA HSCPSVWKKT KNS                                393

SEQ ID NO: 7               moltype = AA  length = 678
FEATURE                    Location/Qualifiers
REGION                     1..678
                           note = GAS6 protein
source                     1..678
                           mol_type = protein
                           organism = Homo sapiens
SEQUENCE: 7
MAPSLSPGPA ALRRAPQLLL LLLAAECALA ALLPAREATQ FLRPQRRRAF QVFEEAKQGH    60
LERECVEELC SREEAREVFE NDPETDFYP RYLDCINKYG SPYTKNSGFA TCVQNLPDQC   120
TPNPCDRKGT QACQDLMGNF FCLCKAGWGG RLCDKDVNEC SQENGGCLQI CHNKPGSFHC   180
SCHSGFELSS DGRTCQDIDE CADSEACGEA RCKNLPGSYS CLCDEGFAYS SQEKACRDVD   240
ECLQGRCEQV CVNSPGSYTC HCDGRGGLKL SQDMDTCEDI LPCVPFSVAK SVKSLYLGRM   300
FSGTPVIRLR FKRLQPTRLV AEFDFRTFDP EGILLFAGGH QDSTWIVLAL RAGRLELQLR   360
YNGVGRVTSS GPVINHGMWQ TISVEELARN LVIKVNRDAV MKIAVAGDLF QPERGLYHLN   420
```

-continued

```
LTVGGIPFHE KDLVQPINPR LDGCMRSWNW LNGEDTTIQE TVKVNTRMQC FSVTERGSFY  480
PGSGFAFYSL DYMRTPLDVG TESTWEVEVV AHIRPAADTG VLFALWAPDL RAVPLSVALV  540
DYHSTKKLKK QLVVLAVEHT ALALMEIKVC DGQEHVVTVS LRDGEATLEV DGTRGQSEVS  600
AAQLQERLAV LERHLRSPVL TFAGGLPDVP VTSAPVTAFY RGCMTLEVNR RLLDLDEAAY  660
KHSDITAHSC PPVEPAAA                                                678

SEQ ID NO: 8            moltype = AA  length = 173
FEATURE                 Location/Qualifiers
REGION                  1..173
                        note = TAM(Axl)-binding sequence
source                  1..173
                        mol_type = protein
                        organism = synthetic construct
SEQUENCE: 8
GRMFSGTPVI RLRFKRLQPT RLVAEFDFRT FDPEGILLFA GGHQDSTWIV LALRAGRLEL  60
QLRYNGVGRV TSSGPVINHG MWQTISVEEL ARNLVIKVNR DAVMKIAVAG DLFQPERGLY  120
HLNLTVGGIP FHEKDLVQPI NPRLDGCMRS WNWLNGEDTT IQETVKANTK MQC         173

SEQ ID NO: 9            moltype = AA  length = 173
FEATURE                 Location/Qualifiers
REGION                  1..173
                        note = TAM(Axl)-binding sequence
source                  1..173
                        mol_type = protein
                        organism = synthetic construct
SEQUENCE: 9
GRMFSGTPVI RLRFKRLQPT RLVAEFDFRT FDPEGILLFA GGHQDSTWIV LALRAGRLEL  60
QLRYNGVGRV TSSGPVINHG MWQTISVEEL ARNLVIKVNR DAVMKIAVAG DLFQPERGLY  120
HLNLTVGGIP FHEKDLVQPI NPRLDGCMRS WNWLNGEDTT IQETVKANTK MQC         173

SEQ ID NO: 10           moltype = AA  length = 172
FEATURE                 Location/Qualifiers
REGION                  1..172
                        note = TAM(Axl)-binding sequence
source                  1..172
                        mol_type = protein
                        organism = synthetic construct
SEQUENCE: 10
GRMFSGTPVI RLRFKRLQPT RLVAEFDFRT FDPEGILLFA GGHQDSTWIV LALRAGRLEL  60
QLRYNGVGRV TSSGPVINHG MWQTISVEEL ARNLVIKVNR DAVMKIAVAG DLFQPERGLY  120
HLNLTVGGIP FHEKDLVQPI NPRLDGCMRS WNWLNGEDTT IQETVKANTR MQ          172

SEQ ID NO: 11           moltype = AA  length = 173
FEATURE                 Location/Qualifiers
REGION                  1..173
                        note = TAM(Axl)-binding sequence
source                  1..173
                        mol_type = protein
                        organism = synthetic construct
SEQUENCE: 11
GRMFSGIPVI RLRFKRLQPT RLVAEFDFRT FDPEGVLFFA GGHQDSTWIV LALRAGRLEL  60
QLRYNGIGRV TSSGPVINHG MWQTISVEEL ERNLVIKVNK DAVMKIAVAG DLFQLDRGLY  120
HLNLTVGGIP FKEKDLIQPI NPRLDGCLRS WNWLNGEDTT IQETVKVNTK MQC         173

SEQ ID NO: 12           moltype = AA  length = 173
FEATURE                 Location/Qualifiers
REGION                  1..173
                        note = TAM(Axl)-binding sequence
source                  1..173
                        mol_type = protein
                        organism = synthetic construct
SEQUENCE: 12
GRMFSGTPVI RLRFKRLQPT RLVAEFDFRT FDPEGILLFA GGHQDSTWIV LALRAGRLEL  60
QLRYNGVGRV TSSGPVINHG MWQTISVEEL ARNLVIKVNR DAVMKIAVAG DLFQPERGLY  120
HLNLTVGGIP FHEKDLVQPI NPRLDGCMRS WNWLNGEDTT IQETVKANAK MQC         173

SEQ ID NO: 13           moltype = AA  length = 173
FEATURE                 Location/Qualifiers
REGION                  1..173
                        note = TAM(Axl)-binding sequence
source                  1..173
                        mol_type = protein
                        organism = synthetic construct
SEQUENCE: 13
GRMFSGTPVI RLRFKRLQPT RLVAEFDFRT FDPEGILLFA GGHQDSTWIV LALRAGRLEL  60
QLRYSGVGRV TSSGPVINHG MWQTISVEEL ARNLVIKVNR DAVMKIAVAG DLFQPERGLY  120
HLNLTVGGIP FHEKDLVQPI NPRLDGCMRS WNWLNGEDTT IHEAVKVNAR MQC         173

SEQ ID NO: 14           moltype = AA  length = 171
```

```
FEATURE                 Location/Qualifiers
REGION                  1..171
                        note = TAM(Axl)-binding sequence
source                  1..171
                        mol_type = protein
                        organism = synthetic construct
SEQUENCE: 14
GRMFSGTPVI RLRFKRLQPT RLVAEFDFRT FDPEGVLFFA GGHQDSAWIV LGLRAGRLEL    60
QLRYHGVSRV TSSGPVINHG MWQTISVEEL DRNLVVKVNR DAVMKIAVAG DLFQLDRGLY   120
HLNLTVGGIP FKERDLVQPI NPRLDGCVRS WNWLNGEDTT IQETVKANPK M            171

SEQ ID NO: 15           moltype = AA  length = 173
FEATURE                 Location/Qualifiers
REGION                  1..173
                        note = TAM(Axl)-binding sequence
source                  1..173
                        mol_type = protein
                        organism = synthetic construct
SEQUENCE: 15
GRMFSGTPVI RLRFKRLQPT RLVAEFDFRT FDPEGVLFFA GGHQDSTWIV LALRAGRLEL    60
QLRYGGVGRV TSSGPVINHG TWQTISVEEL ERNVVVKVNK DAVMKIAVAG DLFQRDRGLY   120
HLNLTVGGIP FKEKDLVQPI NPRLDGCMRS WNWLNGED -continued

```
GRMFSGTPVI RLRFKRLQPT RLVAEFDFRT FDPEGVLFFA GGHQDSTWIV LGLRAGRLEL  60
QLRYQGVGRV TSSGPVINHG MWQTISVEEL ERNLVIKVNK DAVMKIAVAG DLFQLDRGLY  120
HLNLTVGGIP FKEKDLVQPM NPRLDGCMRS WNWLNGEDTT IQETVKVNVK MQC         173

SEQ ID NO: 21          moltype = AA  length = 163
FEATURE                Location/Qualifiers
REGION                 1..163
                       note = TAM(Axl)-binding sequence
source                 1..163
                       mol_type = protein
                       organism = synthetic construct
SEQUENCE: 21
RLRFKRLQPT RLVAEFDFRT FDPEGVLFFA GGHQDSTWIV LGLRAGRLEL QLRYQGVGRV  60
TSSGPVINHG MWQTISVEEL ERNLVIKVNK DAVMKIAVAG DLFQLDRGLY HLNLTVGGIP  120
FKEKDLVQPM NPRLDGCMRS WNWLNGEDTT IQETVKVNVK MQC                    163

SEQ ID NO: 22          moltype = AA  length = 170
FEATURE                Location/Qualifiers
REGION                 1..170
                       note = TAM(Axl)-binding sequence
source                 1..170
                       mol_type = protein
                       organism = synthetic construct
SEQUENCE: 22
FSGTPVIRLR FKRLQPTRLV AEFDFRTFDP EGVLLFAGGH QDGTWVMLAL RAGRLELQLH  60
YNGVGRVTSS GPVINHGAWQ TISVEEMARS LVIKVNRDAV MKIAVAGDLF QPERGMFHLN  120
LTVGGIPFHE KDLVQPINPR LDGCIRSWNW MNGEDTTIQE TVKVNTKMQC            170

SEQ ID NO: 23          moltype = AA  length = 171
FEATURE                Location/Qualifiers
REGION                 1..171
                       note = TAM(Axl)-binding sequence
source                 1..171
                       mol_type = protein
                       organism = synthetic construct
SEQUENCE: 23
MFSGTPVIRL RFKRLQPTRL VAEFDFRTFD PEGVLFFAGG HQDSTWIVLG LRAGRLELQL  60
RYQGVGRVTS SGPVINHGMW QTISVEELER NLVIKVNKDA VMKIAVAGDL FQLDRGLYHL  120
NLTVGGIPFK EKDLVQPMNP RLDGCMRSWN WLNGEDTTIQ ETVKVNVKMQ C           171

SEQ ID NO: 24          moltype = AA  length = 194
FEATURE                Location/Qualifiers
REGION                 1..194
                       note = TAM(Axl)-binding sequence
source                 1..194
                       mol_type = protein
                       organism = synthetic construct
SEQUENCE: 24
GSFYPGSGFA FYSLDYMRTP LDIGTESTWE IEVVAHIRPA ADTGVLFALW VPDLRAVPLS  60
VALVDYHSTK KLKKQLVVLA VEHVALALME IKVCDGQEHM VTISLREGEA TLEVDGTRGQ  120
SEVSAAQLQE RLAVLEKHLR SPVLTFAGGL PDVPVTSAPV TAFYRGCMTL EVNRRLLDLD  180
EAAYKHSDIT AHSC                                                    194

SEQ ID NO: 25          moltype = AA  length = 194
FEATURE                Location/Qualifiers
REGION                 1..194
                       note = TAM(Axl)-binding sequence
source                 1..194
                       mol_type = protein
                       organism = synthetic construct
SEQUENCE: 25
GSFYPGSGFA FYSLDYMRTP LDIGTESTWE IEVVAHIRPA ADTGVLFALW VPDLRAVPLS  60
VALVDYHSTK KLKKQLVVLA VEHVALALME IKVCDGQEHV VTVSLRDGEA TLEVDGTRGQ  120
SEVSATQLQE RLAVLERHLR SPVLTFAGGL PDVPVTSAPV TAFYRGCMTL EVNRRLLDLD  180
EAAYKHSDIT AHSC                                                    194

SEQ ID NO: 26          moltype = AA  length = 189
FEATURE                Location/Qualifiers
REGION                 1..189
                       note = TAM(Axl)-binding sequence
source                 1..189
                       mol_type = protein
                       organism = synthetic construct
SEQUENCE: 26
GSFYPGSGFA FYSLDYMRTP LDIGTESTWE IEVVAHIRPA ADTGVLFALW VPDLRAVPLS  60
VALVDYHSTK KLKKQLVVLA VEHVALALME IKVCDGQEHV VTVSLRDSEA TLEVDGTRGQ  120
SEVSATQLQE RLAVLERHLR SPVLTFAGGL PDVPVTSAPV TAFYRGCMTL EVNRRLLDLD  180
EAAYKHSDI                                                          189
```

```
SEQ ID NO: 27              moltype = AA   length = 194
FEATURE                    Location/Qualifiers
REGION                     1..194
                           note = TAM(Axl)-binding sequence
source                     1..194
                           mol_type = protein
                           organism = synthetic construct
SEQUENCE: 27
GSFYPGSGFA FYSLDYMRTP LDVGTESAWE IEVVAHIRPA ADTGVLFALW VPDLRAVPLS    60
VALVDYHSTK KLKKQLVVLA VEHVALALME IKVCDGQEHV VTVSLRDGEA TLEVDGTRGQ   120
SEVSAAQLQE RLAVLERHLR SPVLTFAGGL PDVPVTSAPV TAFYRGCMTL EVNRRPLDLD   180
EAAYKHSDIT AHSC                                                    194

SEQ ID NO: 28              moltype = AA   length = 194
FEATURE                    Location/Qualifiers
REGION                     1..194
                           note = TAM(Axl)-binding sequence
source                     1..194
                           mol_type = protein
                           organism = synthetic construct
SEQUENCE: 28
GSFYPGSSFA FYSLDYVRTP LDVGTESTWE IDVVAHIRPA ADTGVLFALW VPDLRAVPLS    60
VALVDYHSTK KLKKQLVVLA VEHVALALME IKVCDGQEHV VTVSLRDGEA TLEVDGTRGQ   120
SEVSATQLQE RLAVLERHLR SPVLTFAGGL PDVPVTSAPV TAFYRGCMTL EVNRRLLDLD   180
EAAYKHGDIT AHSC                                                    194

SEQ ID NO: 29              moltype = AA   length = 194
FEATURE                    Location/Qualifiers
REGION                     1..194
                           note = TAM(Axl)-binding sequence
source                     1..194
                           mol_type = protein
                           organism = synthetic construct
SEQUENCE: 29
GSFYPGSGFA FYSLDYMRTP LDIRTESTWE IEVVAHIRPA ADTGVLFALW VPDLRAVPLS    60
VALVDYHSTK KLKKQLVVLA VEHVALALME IKVCDGQEHM VTISLREGEA TLEVDGTRGQ   120
SEVSAAQLQE RLAVLEKHLQ SPVLTFAGGL PDVPVTSAPV TAFYRGCMTL EVNRRLLDLD   180
EAAYKHSDIT AHSC                                                    194

SEQ ID NO: 30              moltype = AA   length = 190
FEATURE                    Location/Qualifiers
REGION                     1..190
                           note = TAM(Axl)-binding sequence
source                     1..190
                           mol_type = protein
                           organism = synthetic construct
SEQUENCE: 30
GSFYPGSGFA FYSLDYMRTP LDIRTESTWE IEVVAHIRPA ADTGVLFALW VPDLRAVPLS    60
VALVDYHSTK KLKKQLVVLA VEHVALALME IKVCDGQEHM VTISLREGEA TLEVDGTRGQ   120
SEVSAAQLQE RLAVLEKHLQ SSVLTFAGGL PDVPVTSAPV TAFYRGCMTL EVNRRLLDLD   180
EAAYKHSDIT                                                         190

SEQ ID NO: 31              moltype = AA   length = 191
FEATURE                    Location/Qualifiers
REGION                     1..191
                           note = TAM(Axl)-binding sequence
source                     1..191
                           mol_type = protein
                           organism = synthetic construct
SEQUENCE: 31
FYPGGFCLPS LDYMRTPLDI GTESTWEIEV VAHIRPAADT GVLFALWVPD LRAVPLSVAL    60
VDYHSTKKLK KQLVVLAVEH VALALMEIKV CDGQEHMVTI SLREGEATLE VDGTRGQSEV   120
SAAQLQERLA VLEKHLRSPV LTFAGGLPDV PVTSAPVTAF YRGCMTLEVN RRLLDLDEAA   180
YKHSDITAHS C                                                       191

SEQ ID NO: 32              moltype = AA   length = 195
FEATURE                    Location/Qualifiers
REGION                     1..195
                           note = TAM(Axl)-binding sequence
source                     1..195
                           mol_type = protein
                           organism = synthetic construct
SEQUENCE: 32
GRDRPASHGA QPVSPQAVRT PLDIGTESTW EIEVVAHIRP AADTGVLFAL WVPDLRAVPL    60
SVALVDYHST KKLKKQLVVL AVEHVALALM EIKVCDGQEH MVTVSLREGE ATLEVDGTRG   120
QSEVSAAQLQ ERLAVLEKHL QSPVLTFAGG LPDVPVTSAP VTAFYRGCMT LEVNRRLLDL   180
DEAAYKHSDI TAHSC                                                   195

SEQ ID NO: 33              moltype = AA   length = 194
```

-continued

```
FEATURE                Location/Qualifiers
REGION                 1..194
                       note = TAM(Axl)-binding sequence
source                 1..194
                       mol_type = protein
                       organism = synthetic construct
SEQUENCE: 33
GSFYPGNGFA FYSLNYMRTP LDVGTESTWE IEVVAHIRPA ADTGVLFALW AADLRAVPLS  60
VALVDYHSTK KLKKQLVVLA VERVALALME IKVCDGQEHV VTVSLREGEA TLAVDGTRGQ  120
SEVSAAQLQE RLATLHRHLQ SPVLTFAGGL PDVPVTSAPV TAFYRGCMTL EVNRRLLDLD  180
EAAYKHGDIT SHSC                                                    194

SEQ ID NO: 34          moltype = AA  length = 676
FEATURE                Location/Qualifiers
REGION                 1..676
                       note = Pro S protein
source                 1..676
                       mol_type = protein
                       organism = Homo sapiens
SEQUENCE: 34
MRVLGGRCGA PLACLLLVLP VSEANLLSKQ QASQVLVRKR RANSLLEETK QGNLERECIE  60
ELCNKEEARE VFENDPETDY FYPKYLVCLR SFQTGLFTAA RQSTNAYPDL RSCVNAIPDQ  120
CSPLPCNEDG YMSCKDGKAS FTCTCKPGWQ GEKCEFDINE CKDPSNINGG CSQICDNTPG  180
SYHCSCKNGF VMLSNKKDCK DVDECSLKPS ICGTAVCKNI PGDFECECPE GYRYNLKSKS  240
CEDIDECSEN MCAQLCVNYP GGYTCYCDGK KGFKLAQDQK SCEVVSVCLP LNLDTKYELL  300
YLAEQFAGVV LYLKFRLPEI SRFSAEFDFR TYDSEGVILY AESIDHSAWL LIALRGGKIE  360
VQLKNEHTSK ITTGGDVINN GLWNMVSVEE LEHSISIKIA KEAVMDINKP GPLFKPENGL  420
LETKVYFAGF PRKVESELIK PINPRLDGCI RSWNLMKQGA SGIKEIIQEK QNKHCLVTVE  480
KGSYYPGSGI AQFHIDYNNV SSAEGWHVNV TLNIRPSTGT GVMLALVSGN NTVPFAVSLV  540
DSTSEKSQDI LLSVENTVIY RIQALSLCSD QQSHLEFRVN RNNLELSTPL KIETISHEDL  600
QRQLAVLDKA MKAKVATYLG GLPDVPFSAT PVNAFYNGCM EVNINGVQLD LDEAISKHND  660
IRAHSCPSVW KKTKNS                                                  676

SEQ ID NO: 35          moltype = AA  length = 177
FEATURE                Location/Qualifiers
REGION                 1..177
                       note = TAM(Axl)-binding sequence
source                 1..177
                       mol_type = protein
                       organism = synthetic construct
SEQUENCE: 35
LLYLAEQFAG VVLYLKFRLP EISRFSAEFD FRTYDSEGVI LYAESIDHSA WFLIALRGGK  60
IEIQLKNEHT SKITTGGDVI NNGLWNMVSV EELEHSISIK IAKEAVMDIN KPGPLFKPEN  120
GLLETKVYFA GFPRKVESEL IKPINPRLDG CIRSWNLMKQ GASGIKEIIQ EKQNKHC     177

SEQ ID NO: 36          moltype = AA  length = 177
FEATURE                Location/Qualifiers
REGION                 1..177
                       note = TAM(Axl)-binding sequence
source                 1..177
                       mol_type = protein
                       organism = synthetic construct
SEQUENCE: 36
LLYLAEQFAG VVLYLKFRLP EISRFSAEFD FRTYDSQGVI LYAESIDHSA WLLIALRGGK  60
IEVQLKNEHT SKITTGGDII NNGLWNMVSV EELEHSISIK IAKEAVMDIN KPGPLFKPEN  120
GLLETKVYFA GFPRKVESEL IKPINPRLDG CIRSWNLMKQ GASGIKEIIQ EKQNKHC     177

SEQ ID NO: 37          moltype = AA  length = 177
FEATURE                Location/Qualifiers
REGION                 1..177
                       note = TAM(Axl)-binding sequence
source                 1..177
                       mol_type = protein
                       organism = synthetic construct
SEQUENCE: 37
LLYLAEQFAG VVLYLKFRLP EISRFSAEFD FRTYDSEGVI LYAESIDHSA WFLIALRGGK  60
IEIQLKNEHT SKITTGGDVI NNGLWNMVSV EELEHSISIK IAKEAVMDIN KPGPLFKPEN  120
GLLETKVYFA GFPRKVESEL IKPINPRLDG CIRSWNLMKQ GASGIKEIIQ EKQNKHC     177

SEQ ID NO: 38          moltype = AA  length = 177
FEATURE                Location/Qualifiers
REGION                 1..177
                       note = TAM(Axl)-binding sequence
source                 1..177
                       mol_type = protein
                       organism = synthetic construct
SEQUENCE: 38
LLYLAEQFAG VVLYLKFRLP EISRFSAEFD FRTYDSQGVI LYAESIDHSA WLLIALRGGK  60
IEVQLKNEHT SKITTGGDII NNGLWNMVSV EELEHSISIK IAKEAVMDIN KPGPLFKPEN  120
```

```
GLLETKVYFA GFPRKVESEL IKPINPRLDG CIRSWNLMKQ GASGIKEIIQ EKQNKHC     177

SEQ ID NO: 39          moltype = AA  length = 177
FEATURE                Location/Qualifiers
REGION                 1..177
                       note = TAM(Axl)-binding sequence
source                 1..177
                       mol_type = protein
                       organism = synthetic construct
SEQUENCE: 39
LLYLAEQFAG VVLYLKFRLP EISRFSAEFD FRTYDSQGVI LYAESIDHSA WLLIALRGGK  60
IEVQLKNEHT SKITTGGAII NNGLWNMVSV EELEHSISIK IAKEAVMDIN KPGPLFKPEN  120
GLLETKVYFA GFPRKVESEL IKPINPRLDG CIRSWNLMKQ GASGIKEIIQ EKQNKHC     177

SEQ ID NO: 40          moltype = AA  length = 177
FEATURE                Location/Qualifiers
REGION                 1..177
                       note = TAM(Axl)-binding sequence
source                 1..177
                       mol_type = protein
                       organism = synthetic construct
SEQUENCE: 40
LLYLAEQFAG VVLYLKFRLP EISRFTAEFD FRTYDSEGVV LYAESIDHSA WILIAVRDGK  60
FEVQLKNEQT SKITTGGGII NNGVWHTVSV EELEHSVSLK IAKEAVMNIN KLGPLFKPEH  120
GFLETKVYFA GFPRKVESQF IKPINPRLDG CIRGWNLMKQ GASGVKEIIQ EKQNKHC     177

SEQ ID NO: 41          moltype = AA  length = 177
FEATURE                Location/Qualifiers
REGION                 1..177
                       note = TAM(Axl)-binding sequence
source                 1..177
                       mol_type = protein
                       organism = synthetic construct
SEQUENCE: 41
LLYLAEQFVG VVLYLKFRLP EISRFSAEFD FRTYDSEGVI LYAESLDHSA WFLVALRDGK  60
IEIQFKNEHT TKITTGGKVI SNGLWNMVSV EELEHSISVK IAKEAVMNIN KPGSLFNPTN  120
GFLETKVYFA GFPRKVENAL IKPINPRLDG CIRGWNLMNQ GASGVKEIIQ EKQNKHC     177

SEQ ID NO: 42          moltype = AA  length = 177
FEATURE                Location/Qualifiers
REGION                 1..177
                       note = TAM(Axl)-binding sequence
source                 1..177
                       mol_type = protein
                       organism = synthetic construct
SEQUENCE: 42
LLYLAEQFAG VVLYLKFRLP EISRFTAEFD FRTYDSEGVV LYAESIDHSA WILIAVRDGK  60
FEVQLKNEQT SKITTGGGII NNGVWHTVSV EELEHSVSLK IAKEAVMNIN KLGPLFKPEH  120
GFLETKVYFA GFPRKVESQF IKPINPRLDG CIRGWNLMKQ GASGVKEIIQ EKQNKHC     177

SEQ ID NO: 43          moltype = AA  length = 177
FEATURE                Location/Qualifiers
REGION                 1..177
                       note = TAM(Axl)-binding sequence
source                 1..177
                       mol_type = protein
                       organism = synthetic construct
SEQUENCE: 43
LLYLAEQFAG VVLYLKFRLP EISRFTAEFD FRTYDSEGVV LYAESLDHSA WILIAVRDGK  60
FEVQLQNEQT SRITTGGGVV NNGVWHTVSV EELEHSVSLK IAKEAVMNIN KLGPLFKPEH  120
GFLETKVYFA GFPRQVESQF IKPINPRLDG CIRGWNLMKQ GASGVKEIIQ EKQNKHC     177

SEQ ID NO: 44          moltype = AA  length = 182
FEATURE                Location/Qualifiers
REGION                 1..182
                       note = TAM(Axl)-binding sequence
source                 1..182
                       mol_type = protein
                       organism = synthetic construct
VARIANT                42
                       note = X can be any amino acid
SEQUENCE: 44
LLYLAEQISG VVLYLKFHLP EISRFSAEFH FWTYDSEGMI LXAESVNHSA WLLIALRGGK  60
IEVQLKNEHT SKITTEGDVI NNGLWNELST SQVSVEELEH SISIKIAKEA VMDIDKPGPL  120
FKPENGLLET KVYFAGFPQK VESELIKPIN PCLDGCIRGW NLMKQGASGI KEIIQEKQNK  180
HC                                                                 182

SEQ ID NO: 45          moltype = AA  length = 177
FEATURE                Location/Qualifiers
```

-continued

```
REGION                  1..177
                        note = TAM(Axl)-binding sequence
source                  1..177
                        mol_type = protein
                        organism = synthetic construct
SEQUENCE: 45
LLYLAEQFVG VVLYLKFRLP EITRFSAEFD FRTYDSEGVI LYAESSDHSA WFLIALRDGK  60
IEIQFKNEHT TKITTGGRVI NDGLWNMVSV EELEQSISVK IAKEAVMNIN KPESLFKPTN  120
GFLETKVYFA GLPRKVENAL IKPINPRLDG CIRGWNLMNQ GASGVKEIIQ EKQNKHC     177

SEQ ID NO: 46           moltype = AA  length = 183
FEATURE                 Location/Qualifiers
REGION                  1..183
                        note = TAM(Axl)-binding sequence
source                  1..183
                        mol_type = protein
                        organism = synthetic construct
SEQUENCE: 46
YYPGSGIAQF HIDYNNVSSA EGWHVNVTLN IRPSTGTGVM LALVSGNNTV PFAVSLVDST  60
SEKSQDILLS VENTVIYRIQ ALSLCSDQQS HLEFRVNRNN LELSTPLKIE TISHEDLQRQ  120
LAILDKAMKA KVATYLGGLP DVPFSATPVN AFYNGCMEVN INGVQLDLDE AISKHNDIRA  180
HSC                                                               183

SEQ ID NO: 47           moltype = AA  length = 183
FEATURE                 Location/Qualifiers
REGION                  1..183
                        note = TAM(Axl)-binding sequence
source                  1..183
                        mol_type = protein
                        organism = synthetic construct
SEQUENCE: 47
YYPGSGIAQF HIDYNNVSGA EGWHVNVTLN IRPSTGTGVM LALVSGNNTV PFAVSLVDST  60
SEKSQDILLS VENTVIYRIQ ALSLCSDQQS HLEFRVNRNN LELSTPLKIE TISHEDLQRQ  120
LAVLDKAMKA KVATYLGGLP DVPFSATPVN AFYNGCMEVN INGVQLDLDE AISKHNDIRA  180
HSC                                                               183

SEQ ID NO: 48           moltype = AA  length = 183
FEATURE                 Location/Qualifiers
REGION                  1..183
                        note = TAM(axl)-binding sequence
source                  1..183
                        mol_type = protein
                        organism = synthetic construct
SEQUENCE: 48
YYPGSGIAQF HIDYNNVSSA EGWHINVTLN IRPSMGTGVM LALVSGNNTV PFAVSLVDST  60
SEKSQDILLS VENTVIYRIQ ALSLCSDQQS HLEFRVNRNN LELSTPLKIE TISHEDLQRQ  120
LAVLDKAMKA KVATYLGGLP DVPFSATPVN AFYNGCMEVN INGVQLDLDE AISKHNDIRA  180
HSC                                                               183

SEQ ID NO: 49           moltype = AA  length = 183
FEATURE                 Location/Qualifiers
REGION                  1..183
                        note = TAM(axl)-binding sequence
source                  1..183
                        mol_type = protein
                        organism = synthetic construct
SEQUENCE: 49
YYPGSGIAQF HIDYNNVSSA EGWHVNVTLN IRPSTGTGVM LALVSGNNTV PFAVSLVDST  60
SEKSQDILLS VENTVIYRIQ APSLCSDQQS HLEFRVNRNN LELSTPLKIE TISHEDLQRQ  120
LAVLDKAMKA KVATYLGGLP DVPFSATPVN AFYNGCMEVN INGVQLDLDE AISKHNDIRA  180
HSC                                                               183

SEQ ID NO: 50           moltype = AA  length = 183
FEATURE                 Location/Qualifiers
REGION                  1..183
                        note = TAM(axl)-binding sequence
source                  1..183
                        mol_type = protein
                        organism = synthetic construct
SEQUENCE: 50
YYPGSGIAQF HIDYNNVSSA EGWHINVTLN IRPSMGTGVM LALVSGNSTV PFAVSLVDST  60
SEKSQDILLS VENTVIYRIQ ALSLCSDQQS HLEFRVNRNN LELSTPLKIE TISHEDLQRQ  120
LAVLDKAMKA KVATYLGGLP DVPFSATPVN AFYNGCMEVN INGVQLDLDE AISKHNDIRA  180
HSC                                                               183

SEQ ID NO: 51           moltype = AA  length = 183
FEATURE                 Location/Qualifiers
REGION                  1..183
                        note = TAM(Axl)-binding sequence
```

```
source                  1..183
                        mol_type = protein
                        organism = synthetic construct
SEQUENCE: 51
YYPGSGIAEF HIDYNNGSNA EGWHINVTLN IRPSMGTGVM LALVSSNNTV PFAVSLVDST    60
SEKSQDIVLS VENTVIYRIQ ALSLCSNQRS HLEFRVNRNN LELLTPLKIE TISQEELQTQ   120
LAILDKAMKG KVATYLGGLP DVPFSATPVN AFYNGCMEVN VNGVELDLDE AISKHNDIRA   180
HSC                                                                 183

SEQ ID NO: 52           moltype = AA  length = 183
FEATURE                 Location/Qualifiers
REGION                  1..183
                        note = TAM(Axl)-binding sequence
source                  1..183
                        mol_type = protein
                        organism = synthetic construct
VARIANT                 80
                        note = X can be any amino acid
SEQUENCE: 52
YYPGFGIAQF HVDYNNVSSA EGWHINVTLN IHPSMGTGVM LALVSGNNTV PFAVSLVDST    60
SEKSQDILLS VENTVIYRIX ALSLCSDQQS HLEFRVNRNN LELLIPLKIE TISHEDLQRQ   120
LAILDKAMKA KVATYLGGLP DVPFSATPVN AFYNGCMEVN INGVQLDLDE AISKHNDIRA   180
HSC                                                                 183

SEQ ID NO: 53           moltype = AA  length = 183
FEATURE                 Location/Qualifiers
REGION                  1..183
                        note = TAM)Ax)-binding sequence
source                  1..183
                        mol_type = protein
                        organism = synthetic construct
SEQUENCE: 53
YYPGSGIAQF HIDYNNGSNA EGWHINVTLN IRPSMGTGVM LALVSSNNTV PFAVSLVDST    60
SEKSQDIVLS VENTVIYRIQ ALSLCSNQRS HLEFRVNRNN LELLTPLKIE TISHEELQRQ   120
LAILDKAMTG KVATYLGGLP DVPFSATPVN AFYNGCMEVN INGVQLDLDE AISKHNDIRA   180
HSC                                                                 183

SEQ ID NO: 54           moltype = AA  length = 183
FEATURE                 Location/Qualifiers
REGION                  1..183
                        note = TAM(Axl)-binding sequence
source                  1..183
                        mol_type = protein
                        organism = synthetic construct
SEQUENCE: 54
YYPGSGIAQF HIDYNNGSNA EGWHINVTLN IRPSMGTGVM LALVSGNNTV PFAVSLVDST    60
SEKSQDIVLS VENTVIYRIQ ALSLCSNQRS HLEFRVNRNN LELLTPLKIE TISDEELRRQ   120
LAILDKAMTG KVATYLGGLP DVPFSATPVN AFYNGCMEVN INDVQLDLDE AISKHNDIRA   180
HSC                                                                 183

SEQ ID NO: 55           moltype = AA  length = 183
FEATURE                 Location/Qualifiers
REGION                  1..183
                        note = TAM(Axl)-binding sequence
source                  1..183
                        mol_type = protein
                        organism = synthetic construct
SEQUENCE: 55
YYPGSGIAEF HIDYNNGSNA EGWHINVTLN IRPSMGTGVM LALVSSNNTV PFAVSLVDST    60
SEKSQDIVLS VENTVIYRIQ ALSLCSNQRS HLEFRANRNN LELLTPLKIE TISQEELQTQ   120
LAILDKAMKG KVATYLGGLP DVPFSATPVN AFYNGCMEVN INGVELDLDE AISKHNDIRA   180
HSC                                                                 183

SEQ ID NO: 56           moltype = AA  length = 183
FEATURE                 Location/Qualifiers
REGION                  1..183
                        note = TAM(Axl)-binding sequence
source                  1..183
                        mol_type = protein
                        organism = synthetic construct
VARIANT                 80
                        note = X can be any amino acid
SEQUENCE: 56
YYPSFGIAQF RIDYNNVSSV EGWHINVTLN IHPSMGTGVM LALVSGNNTV PFAVSLVDST    60
SEKSQDILLS VENTVIYLIX ALSLCSDQQS HLEFIVNRNN LELLTPLKIE TISHEDLQRQ   120
LAILDKAMKA KVATYLGGLP DVPFSATPVN ALYKGCMEVN INGVQLDLDE AISKHNDIIA   180
HSC                                                                 183

SEQ ID NO: 57           moltype = AA  length = 183
```

```
FEATURE                 Location/Qualifiers
REGION                  1..183
                        note = TAM(Axl)-binding sequence
source                  1..183
                        mol_type = protein
                        organism = synthetic construct
SEQUENCE: 57
YYPGSGIAKF IVDYNNVSSA EGWYVNVSLN IRPSKGTGVM LALVSHNNTV PFAVSLVDST    60
SEKLQDILLS VEKTVIYRIQ ALSLCSDQQF HLEFKVNRHN LEVSTPLKME TISHEDLQKQ   120
LAILDKAMQG EVVTYLGGLP DVPFSATPVN AFYNGCMEVN INGVLLDLDE AISKHNDIRA   180
HSC                                                                 183

SEQ ID NO: 58           moltype = AA   length = 183
FEATURE                 Location/Qualifiers
REGION                  1..183
                        note = TAM(Axl)-binding sequence
source                  1..183
                        mol_type = protein
                        organism = synthetic construct
SEQUENCE: 58
YYPGSGIAKF IIDYNNASNA EGWYVNVSLN IRPSTGTGVM LALVSRNNTV PFAVSLVDST    60
SEKLQDILLS VEKTVVCRIQ ALSLCSDQQS HLEFKVNRHN LEVLTPLKME TISHEDLQKQ   120
LAILDKAMQG DVVTYLGGLP DVPFSATPVN AFYNGCMEVN INGVLLDLDE AISKHNDIRA   180
HSC                                                                 183

SEQ ID NO: 59           moltype = AA   length = 183
FEATURE                 Location/Qualifiers
REGION                  1..183
                        note = TAM(Axl)-binding sequence
source                  1..183
                        mol_type = protein
                        organism = synthetic construct
SEQUENCE: 59
YYPGSGIAKF IIDYNNVSSA EGWHVNVSLN IRPSMGTGVM LALVSRNNTV PFAVSLVDST    60
SEKLQDILLS VEKTVIYRIE ALSLCSDQQS HLELKVNRHS LEVSTPLKME TVSHEDIQKE   120
LAILDKAMQG EVVTYLGGLP DVSFSATPAN AFYNGCMEVN MNGVLLDLDE AISKHNDIRA   180
HSC                                                                 183

SEQ ID NO: 60           moltype = AA   length = 176
FEATURE                 Location/Qualifiers
REGION                  1..176
                        note = TAM(Axl)-binding sequence
source                  1..176
                        mol_type = protein
                        organism = synthetic construct
SEQUENCE: 60
SGIAQFHIDY NNVSSAEGWH VNVTLNIRPS TGTGVMLALV SGNNTVPFAV SLVDSTSEKS    60
QDILLSVENT VIYRIQALSL CSDQQSHLEF RVNRNNLELS TPLKIETISH EDLQRQLAVL   120
DKAMKAKVAT YLGGLPDVPF SATPVNAFYN GCMEVNINGV QLDLDEAISK HNDIRA       176

SEQ ID NO: 61           moltype = AA   length = 173
FEATURE                 Location/Qualifiers
REGION                  1..173
                        note = TAM(Axl)-binding sequence
source                  1..173
                        mol_type = protein
                        organism = synthetic construct
SEQUENCE: 61
HIDYNNVSSA EGWHVNVTLN IRPSTGTGVM LALVSGNNTV PFAVSLVDST SEKSQDILLS    60
VENTVIYRIQ ALSLCSDQQS HLEFRVNRNN LELSTPLKIE TISHEDLQRQ LAVLDKAMKA   120
KVATYLGGLP DVPFSATPVN AFYNGCMEVN INGVQLDLDE AISKHNDIRA HSC          173

SEQ ID NO: 62           moltype = AA   length = 173
FEATURE                 Location/Qualifiers
REGION                  1..173
                        note = TAM(Axl)-binding sequence
source                  1..173
                        mol_type = protein
                        organism = synthetic construct
SEQUENCE: 62
YYPGSGIAQF HIDYNNVSSA EGWHVNVTLN IRPSTGTGVM LALVSGNNTV PFAVSLVDST    60
SEKSQDILLS VENTVIYRIQ ALSLCSDQQS HLEFRVNRNN LELSTPLKIE TISHEDLQRQ   120
LAVLDKAMKA KVATYLGGLP DVPFSATPVN AFYNGCMEVN INGVQLDLDE AIS          173

SEQ ID NO: 63           moltype = AA   length = 395
FEATURE                 Location/Qualifiers
REGION                  1..395
                        note = TAM(Axl)-binding sequence
source                  1..395
```

```
                         mol_type = protein
                         organism = synthetic construct
SEQUENCE: 63
VPFSVAKSVK SLYLGRMFSG TPVIRLRFKR LQPTRLVAEF DFRTFDPEGI LLFAGGHQDS    60
TWIVLALRAG RLELQLRYNG VGRVTSSGPV INHGMWQTIS VEELARNLVI KVNRDAVMKI   120
AVAGDLFQPE RGLYHLNLTV GGIPFHEKDL VQPINPRLDG CMRSWNWLNG EDTTIQETVK   180
VNTRMQCFSV TERGSFYPGS GFAFYSLDYM RTPLDVGTES TWEVEVVAHI RPAADTGVLF   240
ALWAPDLRAV PLSVALVDYH STKKLKKQLV VLAVEHTALA LMEIKVCDGQ EHVVTVSLRD   300
GEATLEVDGT RGQSEVSAAQ LQERLAVLER HLRSPVLTFA GGLPDVPVTS APVTAFYRGC   360
MTLEVNRRLL DLDEAAYKHS DITAHSCPPV EPAAA                             395

SEQ ID NO: 64            moltype = AA   length = 390
FEATURE                  Location/Qualifiers
REGION                   1..390
                         note = TAM(Axl)-binding sequence
source                   1..390
                         mol_type = protein
                         organism = synthetic construct
SEQUENCE: 64
DILPCVPFSV AKSVKSLYLG RMFSGTPVIR LRFKRLQPTR LVAEFDFRTF DPEGILLFAG    60
GHQDSTWIVL ALRAGRLELQ LRYNGVGRVT SSGPVINHGM WQTISVEELA RNLVIKVNRD   120
AVMKIAVAGD LFQPERGLYH LNLTVGGIPF HEKDLVQPIN PRLDGCMRSW NWLNGEDTTI   180
QETVKVNTRM QCFSVTERGS FYPGSGFAFY SLDYMRTPLD VGTESTWEVE VVAHIRPAAD   240
TGVLFALWAP DLRAVPLSVA LVDYHSTKKL KKQLVVLAVE HTALALMEIK VCDGQEHVVT   300
VSLRDGEATL EVDGTRGQSE VSAAQLQERL AVLERHLRSP VLTFAGGLPD VPVTSAPVTA   360
FYRGCMTLEV NRRLLDLDEA AYKHSDITAH                                   390

SEQ ID NO: 65            moltype = AA   length = 400
FEATURE                  Location/Qualifiers
REGION                   1..400
                         note = TAM(Axl)-binding sequence
source                   1..400
                         mol_type = protein
                         organism = synthetic construct
SEQUENCE: 65
DILPCVPFSV AKSVKSLYLG RMFSGTPVIR LRFKRLQPTR LVAEFDFRTF DPEGILLFAG    60
GHQDSTWIVL ALRAGRLELQ LRYNGVGRVT SSGPVINHGM WQTISVEELA RNLVIKVNKD   120
AVMKIAVAGD LFQPERGLYH LNLTVGGIPF HEKDLVQPIN PRLDGCMRSW NWLNGEDTTI   180
QETVKANTRM QCFSVTERGS FYPGSGFAFY SLDYMRTPLD IGTESTWEIE VVAHIRPAAD   240
TGVLFALWVP DLRAVPLSVA LVDYHSTKKL KKQLVVLAVE HVALALMEIK VCDGQEHVVT   300
VSLRDGEATL EVDGTRGQSE VSATQLQERL AVLERHLRSP VLTFAGGLPD VPVTSAPVTA   360
FYRGCMTLEV NRRLLDLDEA AYKHSDITAH SCPPVEPAAA                        400

SEQ ID NO: 66            moltype = AA   length = 400
FEATURE                  Location/Qualifiers
REGION                   1..400
                         note = TAM(Axl)-binding sequence
source                   1..400
                         mol_type = protein
                         organism = synthetic construct
SEQUENCE: 66
DILPCVPFSV AKSVKSLYLG RMFSGTPVIR LRFKRLQPTR LVAEFDFRTF DPEGILLFAG    60
GHQDSTWIVL ALRAGRLELQ LRYNGVGRVT SSGPVINHGM WQTISVEELA RNLVIKVNRD   120
AVMKIAVAGD LFQPERGLYH LNLTVGGIPF HEKDLVQPIN PRLDGCMRSW NWLNGEDTTI   180
QETVKVNTRM QCFSVTERGS FYPGSGFAFY SLDYMQTPLD IGTESTWEIE VVAHIRPAAD   240
TGVLFALWVP DLRAVPLSVA LVDYHSTKKL KKQLVVLAVE HVALALMEIK VCDGQEHVVT   300
VSLRDGEATL EVDGTRGQSE VSAAQLQERL AVLERHLRSP VLTFAGGLPD VPVTSAPVTA   360
FYRGCMTLEV NRRLLDLDEA AYKHSDITAH SCPPVEPTTA                        400

SEQ ID NO: 67            moltype = AA   length = 380
FEATURE                  Location/Qualifiers
REGION                   1..380
                         note = TAM(Axl)-binding sequence
source                   1..380
                         mol_type = protein
                         organism = synthetic construct
SEQUENCE: 67
RMFSGTPVIR LRFKRLQPTR LVAEFDFRTF DPEGILLFAG GHQDSTWIVL ALRAGRLELQ    60
LRYNGVGRVT SSGPVINHGM WQTISVEELA RNLVIKVNRD AVMKIAVAGD LFQPERGLYH   120
LNLTVGGIPF HEKDLVQPIN PRLDGCMRSW NWLNGEDTTI QETVKVNTRM QCFSVTERGS   180
FYPGSGFAFY SLDYMRTPLD VGTESTWEVE VVAHIRPAAD TGVLFALWAP DLRAVPLSVA   240
LVDYHSTKKL KKQLVVLAVE HTALALMEIK VCDGQEHVVT VSLRDGEATL EVDGTRGQSE   300
VSAAQLQERL AVLERHLRSP VLTFAGGLPD VPVTSAPVTA FYRGCMTLEV NRRLLDLDEA   360
AYKHSDITAH SCPPVEPAAA                                              380

SEQ ID NO: 68            moltype = AA   length = 400
FEATURE                  Location/Qualifiers
REGION                   1..400
                         note = TAM(Axl)-binding sequence
```

-continued

```
source                  1..400
                        mol_type = protein
                        organism = synthetic construct
SEQUENCE: 68
DILPCVPFSV AKSVKSLYLG RMFSGTPVIR LRFKRLQPTR LVAEFDFRTF DPEGILLFAG  60
GHQDSTWIVL ALRAGRLELQ LRYNGVGRVT SSGPVINHGM WQTISVEELA RNLVIKVNRD  120
AVMKIAVAGD LFQPERGLYH LNLTVGGIPF HEKDLVQPIN PRLDGCMRSW NWLNGEDTTI  180
QETVKVNTRM QCFSVTERGS FYPGSGFAFY SLDYMRTPLD VGTESAWEIE VVAHIRPAAD  240
TGVLFALWVP DLRAVPLSVA LVDYHSTKKL KKQLVVLAVE HVALALMEIK VCDGQEHVVT  300
VSLRDGEATL EVDGTRGQSE VSAAQLQERL AVLERHLRSP VLTFAGGLPD VPVTSAPVTA  360
FYRGCMTLEV NRRPLDLDEA AYKHSDITAH SCPPVEPAAA                        400

SEQ ID NO: 69           moltype = AA  length = 400
FEATURE                 Location/Qualifiers
REGION                  1..400
                        note = TAM(Axl)-binding sequence
source                  1..400
                        mol_type = protein
                        organism = synthetic construct
SEQUENCE: 69
DILPCVPFSV AKSVKSLYLG RMFSGTPVIR LRFKRLQPTR LVAEFDFRTF DPEGILLFAG  60
GHQDSTWIVL ALRAGRLELQ LRYNGVGRVT SSGPVINHGM WQTISVEELA RNLVIKVNRD  120
AVMKIAVAGD LFQPERGLYH LNLTVGGIPF HEKDLVQPIN PRLDGCMRSW NWLNGEDTTI  180
QETVKANTRM QCFSVTERGS FYPGSGFAFY SLDYMRTPLD IGTESTWEIE VVAHIRPAAD  240
TGVLFALWVP DLRAVPLSVA LVDYHSTKKL KKQLVVLAVE HVALALMEIK VCDGQEHVVT  300
VSLRDSEATL EVDGTRGQSE VSATQLQERL AVLERHLRSP VLTFAGGLPD VPVTSAPVTA  360
FYRGCMTLEV NRRLLDLDEA AYKHSDITAH SCPPVEPAAA                        400

SEQ ID NO: 70           moltype = AA  length = 400
FEATURE                 Location/Qualifiers
REGION                  1..400
                        note = TAM(Axl)-binding sequence
source                  1..400
                        mol_type = protein
                        organism = synthetic construct
SEQUENCE: 70
DILPCVPFSV AKSVKSLYLG RMFSGTPVIR LRFKRLQPTR LVAEFDFRTF DPEGILLFAG  60
GHQDSTWIVL ALRAGRLELQ LRYNGVGRVT SSGPVINHGM WQTISVEELA RNLVIKVNRD  120
AVMKIAVAGD LFQPERGLYH LNLTVGGIPF HEKDLVQPIN PRLDGCMRSW NWLNGEDTTI  180
QETVKVNTRM QCFSVTERGS FYPGSGFAFY SLDYMQTPLD IGTESTWEIE VVAHIRPAAD  240
TGVLFALWVP DLRAVPLSVA LVDYHSTKKL KKQLVVLAVE HVALALMEIK VCDGQEHVVT  300
VSLRDGEATL EVDGTRGQSE VSAAQLQERL AVLERHLRSP VLTFAGGLPD VPVTSAPVTA  360
FYRGCMTLEV NRRLLDLDEA AYKHSDITAH SCPPVEPTTA                        400

SEQ ID NO: 71           moltype = AA  length = 395
FEATURE                 Location/Qualifiers
REGION                  1..395
                        note = TAM(Axl)-binding sequence
source                  1..395
                        mol_type = protein
                        organism = synthetic construct
SEQUENCE: 71
LPCVPFSVAK SVKSLYLGRM FSGTPVIRLR FKRLQPTRLV AEFDFRTFDP EGILLFAGGH  60
QDSTWIVLAL RAGRLELQLR YNGVGRVTSS GPVINHGMWQ TISVEELARN LVIKVNRDAV  120
MKIAVAGDLF QPERGLYHLN LTVGGIPFHE KDLVQPINPR LDGCMRSWNW LNGEDTTIQE  180
TVKVNTRMQC FSVTERGSFY PGSGFAFYSL DYMRTPLDVG TESTWEVEVV AHIRPAADTG  240
VLFALWAPDL RAVPLSVALV DYHSTKKLKK QLVVLAVEHT ALALMEIKVC DGQEHVVTVS  300
LRDGEATLEV DGTRGQSEVS AAQLQERLAV LERHLRSPVL TFAGGLPDVP VTSAPVTAFY  360
RGCMTLEVNR RLLDLDEAAY KHSDITAHSC PPVEP                             395

SEQ ID NO: 72           moltype = AA  length = 400
FEATURE                 Location/Qualifiers
REGION                  1..400
                        note = TAM(Axl)-binding sequence
source                  1..400
                        mol_type = protein
                        organism = synthetic construct
SEQUENCE: 72
DILPCVPFSM AKSVKSLYLG RMFSGTPVIR LRFKRLQPTR LVAEFDFRTF DPEGILLFAG  60
GHQDSTWIVL ALRAGRLELQ LRYNGVGRVT SSGPVINHGM WQTISVEELA RNLVIKVNRD  120
AVMKIAVAGD LFQPERGLYH LNLTVGGIPF HEKDLVQPIN PRLDGCMRSW NWLNGEDTTI  180
QETVKANTKM QCFSVTERGS FYPGSGFAFY SLDYMRTPLD IGTESTWEIE VVAHIRPAAD  240
TGVLFALWVP DLRAVPLSVA LVDYHSTKKL KKQLVVLAVE HVALALMEIK VCDGQEHMVT  300
ISLREGEATL EVDGTRGQSE VSAAQLQERL AVLEKHLRSP VLTFAGGLPD VPVTSAPVTA  360
FYRGCMTLEV NRRLLDLDEA AYKHSDITAH SCPPVEPAAA                        400

SEQ ID NO: 73           moltype = AA  length = 400
FEATURE                 Location/Qualifiers
REGION                  1..400
```

```
                          note = TAM(Axl)-binding sequence
source                    1..400
                          mol_type = protein
                          organism = synthetic construct
SEQUENCE: 73
DILPCVPFSM AKSVKSLYLG RMFSGTPVIR LRFKRLQPTR LVAEFDFRTF DPEGILLFAG    60
GHQDSSWIVL ALRAGRLELQ LRYNGVGRVT SSGPVINHGM WQTISVEELA RNLVIKVNRD   120
AVMKIAVAGD LFQPERGLYH LNLTVGGIPF HEKDLVQPIN PRLDGCMRSW NWLNGEDTTI   180
QETVKANTKM QCFSVTERGS FYPGSGFAFY SLDYMRTPLD IGTESTWEIE VVAHIRPAAD   240
TGVLFALWVP DLRAVPLSVA LVDYHSTKKL KKQLVVLAVE HVALALMEIK VCDGQEHMVT   300
ISLREGEATL EVDGTRGQSE VSAAQLQERL AVLEKHLRSP VLTFAGGLPD VPVTSAPVTA   360
FYRGCMTLEV NRRLLDLDEA AYKHSDITAH SCPPVEPAAA                         400

SEQ ID NO: 74             moltype = AA   length = 400
FEATURE                   Location/Qualifiers
REGION                    1..400
                          note = TAM(Axl)-binding sequence
source                    1..400
                          mol_type = protein
                          organism = synthetic construct
SEQUENCE: 74
DILPCVPFSM AKSVKSLYLG RMFSGTPVIR LRFKRLQPTR LVAEFDFRTF DPEGILLFAG    60
GHQDSTWIVL ALRAGRLELQ LRYNGVGRVT SSGPVINHGM WQTISVEELA RNLVIKVNRD   120
AVMKIAVAGD LFQPERGLYH LNLTVGGIPF HEKDLVQPIN PRLDGCMRSW NWLNGEDTTI   180
QETVKANPKM QCFSVTERGS FYPGSGFAFY SLDYMRTPLD IGTESTWEIE VVAHIRPAAD   240
TGVLFALWVP DLRAVPLSVA LVDYHSTKKL KKQLVVLAVE HVALALMEIK VCDGQEHMVT   300
ISLREGEATL EVDGTRGQSE VSATQLQERL AVLEKHLRSP VLTFAGGLPD VPLTSAPVTA   360
FYRGCMTLEV NRRLLDLDEA AYKHSDITAH SCPPVEPTAA                         400

SEQ ID NO: 75             moltype = AA   length = 340
FEATURE                   Location/Qualifiers
REGION                    1..340
                          note = TAM(Axl)-binding sequence
source                    1..340
                          mol_type = protein
                          organism = synthetic construct
SEQUENCE: 75
DILPCVPFSL AKSVKSLYLG RMFSGTPVIR LRFKRLQPTR LVAEFDFRTF DPEGILLFAG    60
GHQDSTWIVL ALRAGRLELQ LRYNGVGRVT SSGPVINHGM WQTISVEELA RNLVIKVNRD   120
QETVKANAKM QCFSVTERGS FYPGSGFAFY SLDYMRTPLD IRTESTWEIE VVAHIRPAAD   180
TGVLFALWVP DLRAVPLSVA LVDYHSTKKL KKQLVVLAVE HVALALMEIK VCDGQEHMVT   240
ISLREGEATL EVDGTRGQSE VSAAQLQERL AVLEKHLQSP VLTFAGGLPD VSVTSAPVTA   300
FYRGCMTLEV NRRLLDLDEA AYKHSDITAH SCPPVEPATA                         340

SEQ ID NO: 76             moltype = AA   length = 400
FEATURE                   Location/Qualifiers
REGION                    1..400
                          note = TAM(Axl)-binding sequence
source                    1..400
                          mol_type = protein
                          organism = synthetic construct
VARIANT                   100
                          note = X can be A or T
SEQUENCE: 76
DILPCVPFSV AKSVKSLYLG RMFSGTPVIR LRFKRLQPTR LVAEFDFRTF DPEGVLLFAG    60
GHQDGTWVML ALRAGRLELQ LHYNGVGRVT SSGPVINHGX WQTISVEEMA RSLVIKVNRD   120
AVMKIAVAGD LFQPERGMFH LNLTVGGIPF HEKDLVQPIN PRLDGCIRSW NWMNGEDTTI   180
QETVKVNTKM QCFSVTERGS FYPGNGFAFY SLNYMRTPLD VGTESTWEIE VVAHIRPAAD   240
TGVLFALWAA DLRAVPLSVA LVDYHSTKKL KKQLVVLAVE RVALALMEIK VCDGQEHVVT   300
VSLREGEATL AVDGTRGQSE VSAAQLQERL ATLERHLQSP VLTFAGGLPD VPVTSAPVTA   360
FYRGCMTLEV NRRLLDLDEA AYKHGDITSH SCPTVEPAAA                         400

SEQ ID NO: 77             moltype = AA   length = 400
FEATURE                   Location/Qualifiers
REGION                    1..400
                          note = TAM(Axl)-binding sequence
source                    1..400
                          mol_type = protein
                          organism = synthetic construct
SEQUENCE: 77
DILPCVPFSM AKSVKSLYLG RMFSGTPVIR LRYRRLQPTR LVAEFDFRTF DPEGVLLFAG    60
GHQDGTWIML ALRAGRLELQ LRYNGVGRIT SSGPVINHGT WQTISVEELA RSLVIKVNRD   120
AVMKIAVAGD LFQPERGMFH LNLTVGGIPF HEEDLVQPIN PRLDGCIRSW NWMNGEDTTI   180
QETVKVNSKM QCFSVTERGS FYPGNGFAFY SLNYMRTPLD VGTESTWEIE VVAHIRPAAD   240
TGVLFALWAA DLRAVPLSVA LVDYHSTKKL KKQLVVLAVE RVALALMEIK VCDGQEHVVT   300
VSLREGEATL AVDGTRGQSE VSAAQLQERL ATLERHLQSP VLTFAGGLPD VPVTSAPVTA   360
FYRGCMTLEV NRRLLDLDEA AYKHGDITSH SCPTVEPAAA                         400

SEQ ID NO: 78             moltype = AA   length = 399
```

```
FEATURE                 Location/Qualifiers
REGION                  1..399
                        note = TAM(Axl)-binding sequence
source                  1..399
                        mol_type = protein
                        organism = synthetic construct
SEQUENCE: 78
DILPCVPFSV AKSLKSLYLG RMFSGTPVIR LRFKRLQPTR LVAEFDFRTF DPEGILFFAG  60
GHRDSTWIVL ALRAGRLELQ LLFNGVGRVT SSGPVINHGM WQTVSVEELE RNLVVKVNKD  120
AVMKIAVPGD LFQLDRGLYH LNLTVGGIPF KEKDLVQPIN PRLDGCMRSW NWLNGEDTTI  180
QETVKANAKM QCFSLTEKGS FFPGSGFAFY SLGYVRTSLD VGTETTWEIE VEARIRPAAD  240
TGVLLALWAP DHRAVPLSVA LVDYHSTKKL KKQLVVLAVE SVALALMEIK VCDGQEHVVS  300
VSVREDEATL EVDGTKGQSE VSAAQLQERL AALGRHLRDP VLTFIGGLPE VPVTSAPVTA  360
FYRGCMTLEV NRRPLDLDEA SYKHSDITAH SCPPVEPAA                        399

SEQ ID NO: 79           moltype = AA  length = 399
FEATURE                 Location/Qualifiers
REGION                  1..399
                        note = TAM(Axl)-binding sequence
source                  1..399
                        mol_type = protein
                        organism = synthetic construct
SEQUENCE: 79
DILPCVPFGV AKSVKSLYLG RMFSGTPVIR LRFKRLQPTR LVAEFDFRTF DPEGVLFFAG  60
GRQDSTWIVL ALRAGRLELQ LRYNGVGRVT SSGPVINHGT WQTISVEELE RNLVVKVNKD  120
AVMKIAVAGD LFQRDRGLYH LNLTVGGIPF KEKELVQPIN PRLDGCMRSW NWLNSEDTII  180
QETVKVNTKM QCFSVTEKGS FYPGTGFAFY SLNYMRTSLD TGTETTWEIK VMARIRPATD  240
TGVLLALCAP DHRTVPLSVA LVDYHSTKKL KKQLVVLAVE SVVLALVEIK ACDGQEHEVS  300
VSLKEGEATL EVDGTRGWSE ASATQLQERL DTLRRHLHDP VLTFTGGLPD VPVTAAPVTA  360
FYRGCMTLEV NRRLLDLDEA AYKHSDITSH SCPPVEPTA                        399

SEQ ID NO: 80           moltype = AA  length = 399
FEATURE                 Location/Qualifiers
REGION                  1..399
                        note = TAM(Axl)-binding sequence
source                  1..399
                        mol_type = protein
                        organism = synthetic construct
SEQUENCE: 80
DILPCVPFSV AKSVKSLYLG RMFSGTPVIR LRFKRLQPTR LVAEFDFRTF DPEGILLFAG  60
GHQDSTWIVL ALRAGRLELQ LRYNGVGRVT SSGPVINHGM WQTISVEELA RNLVIKVNRD  120
AVMKIAVAGD LFQPERGLYH LNLTVGGIPF HEKDLVQPIN PRLDGCMRSW NWLNGEDTTI  180
QETVKVNTRM QCFSVTERGS FYPGSGFAFY SLDYMRTPLD VGTESTWEVE VVAHIRPAAD  240
TGVLFALWAP DLRAVPLSVA LVDYHSTKKL KKQLVVLAVE HTALALMEIK VCDGQEHVVT  300
VSLRDGEATL EVDGTRGQSE VSAAQLQERL AVLERHLRSP VLTFAGGLPD VPVTSAPVTA  360
FYRGCMTLEV NRRLLDLDEA AYKHSDITAH SCPPVEPAA                        399

SEQ ID NO: 81           moltype = AA  length = 398
FEATURE                 Location/Qualifiers
REGION                  1..398
                        note = TAM(Axl)-binding sequence
source                  1..398
                        mol_type = protein
                        organism = synthetic construct
SEQUENCE: 81
DILPCVPFSV AKSMKSLYLG RMFSGTPVIR LRFKRLQPTR LVAEFDFRTF DPEGVLFFAG  60
GHQDSTWIVL ALRAGRLELQ LHYNGVGRVT SSGPVINHGM WQTISVEELE RNVVIKVNKD  120
AVMKIAVAGD LFQLDRGLYH LNLTVGGIPF KEKHLVQPIN PRLDGCMRSW SWLNGEDTTI  180
QETVKVNTRM QCFSVTERGS FYPGNGLAIY SLNYSRTPPD VGTETAWEVE VVARIRPATD  240
TGVLLALVGD GHTVPLSVAL VDYHSTKKLK KQLVVLAVEG MALALMEIKV CDGQEHVVAV  300
SLKAGEASLE VDGTKGQSEV SAAQLQERLA VLGRHLQGPL LTFIGGLPDV PVTSAPVTAF  360
YRGCMTLEVN QKRLDLDEAT YKHSDITSHS CPPVEHAA                         398

SEQ ID NO: 82           moltype = AA  length = 397
FEATURE                 Location/Qualifiers
REGION                  1..397
                        note = TAM(Axl)-binding sequence
source                  1..397
                        mol_type = protein
                        organism = synthetic construct
SEQUENCE: 82
DILPCVPFTM AKSVKSLYLG RMFSGTPVIR LRFKRLQPTR LLAEFDFRTF DPEGVLFFAG  60
GRSDSTWIVL GLRAGRLELQ LRYNGVGRIT SSGPVINHGM WQTISVEELE RNLVIKVNKD  120
AVMKIAVAGE LFQLERGLYH LNLTVGGIPF KEQDLVQPIN PRLDGCMRSW NWLNGEDSAI  180
QETVKANTKM QCFSVTERGS FFPGGAFAFY SLNYTRTSLD VGTETTWEVE IVAWIRPATD  240
TGVLLALVGD NHVVPLSVAL VDYHSTKKLK KQLVVLAVED VALALMEIKV CDSQEHVVTV  300
SLRDGEATLE VDGTKGQSEV SAAQLQERLD TLGEHLQGTV LTFVGGLPEV PVTSAPVTAF  360
YRGCMTLEVN QKTLDLDEAS YKHSDITSHS CPPVEHA                          397
```

```
SEQ ID NO: 83           moltype = AA  length = 398
FEATURE                 Location/Qualifiers
REGION                  1..398
                        note = TAM(Axl)-binding sequence
source                  1..398
                        mol_type = protein
                        organism = synthetic construct
SEQUENCE: 83
DILPCVPFSV AKSVKSLYLG RMFSGTPVIR LRFKRLQPTR LVAEFDFRTF DPEGILLFAG  60
GHQDSTWIVL ALRAGRLELQ LRYNGVGRVT SSGPVINHGM WQTISVEELA RNLVIKVNRD  120
AVMKIAVAGD LFQPERGLYH LNLTVGGIPF HEKDLVQPIN PRLDGCMRSW NWLNGEDTTI  180
QETVKVNTRM QCFSVTERGS FYPGSGFAFY SLDYMRTPLD VGTESTWEVE VVAHIRPAAD  240
TGVLFALWAP DLRAVPLSVA LVDYHSTKKL KKQLVVLAVE HTALALMEIK VCDGQEHVVT  300
VSLRDGEATL EVDGTRGQSE VSAAQLQERL AVLERHLRSP VLTFAGGLPD VPVTSAPVTA  360
FYRGCMTLEV NRRLLDLDEA AYKHSDITAH SCPPVEPA                          398

SEQ ID NO: 84           moltype = AA  length = 398
FEATURE                 Location/Qualifiers
REGION                  1..398
                        note = TAM(Axl)-binding sequence
source                  1..398
                        mol_type = protein
                        organism = synthetic construct
SEQUENCE: 84
DILPCVPFNV AKSVKSLYLG RMFSGTPVIR LRFKRLQPTR LLAEFDFRTF DPEGVLFFAG  60
GRQDSTWIVL GLRAGRLELQ LRYHGVGRVT SSGPVINHGM WQTISVEELD RNLVIKVNKD  120
AVMKIAVAGD LFQLDRGLYH LNLTVGGIPF KEKDLVQPIN PRLDGCMRSW NWLSGEDTTI  180
QETVKANSKM QCFSVTERGS FYPGTGFAFY SLDYTRTSTA VGTEATWEIE VVAQIRPATD  240
TGVLLALVAG DHVVALSVAL VDYHSTKKLK KQLVVLAVEG VTLALMEIKV CDGQEHRVAV  300
SVRKGEATLE VDGTRGQSEV TAAGLQESLA VLGRHLQASV LTFVGGLPDV PVTSAPVTAF  360
YRGCMTLEVN QQALDLDEAA YKHSDITSHS CPPVEQAG                          398

SEQ ID NO: 85           moltype = AA  length = 395
FEATURE                 Location/Qualifiers
REGION                  1..395
                        note = TAM(Axl)-binding sequence
source                  1..395
                        mol_type = protein
                        organism = synthetic construct
SEQUENCE: 85
DILPCVPFSV AKSVKSLYLG RMFSGTPVIR LRFKRLQPTR LVAEFDFRTF DPEGILLFAG  60
GHQDSTWIVL ALRAGRLELQ LRYNGVGRVT SSGPVINHGM WQTISVEELA RNLVIKVNRD  120
AVMKIAVAGD LFQPERGLYH LNLTVGGIPF HEKDLVQPIN PRLDGCMRSW NWLNGEDTTI  180
QETVKVNTRM QCFSVTERGS FYPGSGFAFY SLDYMRTPLD VGTESTWEVE VVAHIRPAAD  240
TGVLFALWAP DLRAVPLSVA LVDYHSTKKL KKQLVVLAVE HTALALMEIK VCDGQEHVVT  300
VSLRDGEATL EVDGTRGQSE VSAAQLQERL AVLERHLRSP VLTFAGGLPD VPVTSAPVTA  360
FYRGCMTLEV NRRLLDLDEA AYKHSDITAH SCPPV                             395

SEQ ID NO: 86           moltype = AA  length = 394
FEATURE                 Location/Qualifiers
REGION                  1..394
                        note = TAM(Axl)-binding sequence
source                  1..394
                        mol_type = protein
                        organism = synthetic construct
SEQUENCE: 86
DILPCVPFNV AKSVKSLYLG RMFSGTPVIR LRFKRLQPTR LVAEFDFRTF DPEGVLFFAG  60
GHQDSTWIVL ALRAGRLELQ LHYNGIGRVT SSGSVINHGM WQTISVEELE RNLVIKINKD  120
AVMKIAVAGD LFQLDRGLYH LNLTVGGIPF KDKDLVQPIN PRLDGCMRSW NWLNGEDSTI  180
QDTVKVNTKM QCFSVTEKGS FYPGNGFAFF SLNYVRTSLD VGTEMTWEIE VIARIRPATD  240
TGVLLALVAK NHTIPLSVAL VDYHSTKKLK KQLVILAIEN VALSLMEIKV CDGQEHVVTV  300
SVKEGEATLV VDGTKGQSEV SPTQLQERLA VLKRHLQDSV HTFVGGVPDV PVTSAPVTAF  360
YHGCMTLEVN KKALDLDEAV YKHSDITSHS CPPI                              394

SEQ ID NO: 87           moltype = AA  length = 398
FEATURE                 Location/Qualifiers
REGION                  1..398
                        note = TAM(Axl)-binding sequence
source                  1..398
                        mol_type = protein
                        organism = synthetic construct
SEQUENCE: 87
DILPCVPFNV AKSVKSLYLG RMFSGTPVIR LRFKRLQPTR LLAEFDFRTF DPEGVLFFAG  60
GHQDSAWIVL GLRAGRLELQ LRYGGVGRVT SSGPVINHGT WQTISVEELD RNLVIKVNKD  120
AVMKIAVAGD LFQLDRGLYH LNLTVGGIPF KEKDLVQPIN PRLDGCMRSW NWLSGEDTTI  180
QETVKANSKM QCFSVTERGS FYPGTGFAFY SLDYTRTSAA VGTEAAWEIE VVAWIRPATD  240
TGVLLALVGG DRVVALSVAL VDYHSTKKLK KQLVVLAVEG VTLALMEIKV CDGQEHRVAV  300
SVQKGEVTLE VDGTRGQSEV SAAGLQESLA VLERHLQGSV LTFVGGLPDV PVTSAPVTAF  360
YRGCMTLEVN QQTLDLDEAA YKHSDITSHS CPPVEQAS                          398
```

```
SEQ ID NO: 88          moltype = AA   length = 392
FEATURE                Location/Qualifiers
REGION                 1..392
                       note = TAM(Axl)-binding sequence
source                 1..392
                       mol_type = protein
                       organism = synthetic construct
SEQUENCE: 88
VSVCLPLNLD TKYELLYLAE QFAGVVLYLK FRLPEISRFS AEFDFRTYDS EGVILYAESI    60
DHSAWLLIAL RGGKIEVQLK NEHTSKITTG GDVINNGLWN MVSVEELEHS ISIKIAKEAV   120
MDINKPGPLF KPENGLLETK VYFAGFPRKV ESELIKPINP RLDGCIRSWN LMKQGASGIK   180
EIIQEKQNKH CLVTVEKGSY YPGSGIAQFH IDYNNVSSAE GWHVNVTLNI RPSTGTGVML   240
ALVSGNNTVP FAVSLVDSTS EKSQDILLSV ENTVIYRIQA LSLCSDQQSH LEFRVNRNNL   300
ELSTPLKIET ISHEDLQRQL AVLDKAMKAK VATYLGGLPD VPFSATPVNA FYNGCMEVNI   360
NGVQLDLDEA ISKHNDIRAH SCPSVWKKTK NS                                 392

SEQ ID NO: 89          moltype = AA   length = 388
FEATURE                Location/Qualifiers
REGION                 1..388
                       note = TAM(Axl)-binding sequence
source                 1..388
                       mol_type = protein
                       organism = synthetic construct
SEQUENCE: 89
LPLNLDTKYE LLYLAEQFAG VVLYLKFRLP EISRFSAEFD FRTYDSEGVI LYAESIDHSA    60
WLLIALRGGK IEVQLKNEHT SKITTGGDVI NNGLWNMVSV EELEHSISIK IAKEAVMDIN   120
KPGPLFKPEN GLLETKVYFA GFPRKVESEL IKPINPRLDG CIRSWNLMKQ GASGIKEIIQ   180
EKQNKHCLVT VEKGSYYPGS GIAQFHIDYN NVSSAEGWHV NVTLNIRPST GTGVMLALVS   240
GNNTVPFAVS LVDSTSEKSQ DILLSVENTV IYRIQALSLC SDQQSHLEFR VNRNNLELST   300
PLKIETISHE DLQRQLAVLD KAMKAKVATY LGGLPDVPFS ATPVNAFYNG CMEVNINGVQ   360
LDLDEAISKH NDIRAHSCPS VWKKTKNS                                      388

SEQ ID NO: 90          moltype = AA   length = 392
FEATURE                Location/Qualifiers
REGION                 1..392
                       note = TAM(Axl)-binding sequence
source                 1..392
                       mol_type = protein
                       organism = synthetic construct
SEQUENCE: 90
VVSVCLPLNL DTKYELLYLA EQFAGVVLYL KFRLPEISRF SAEFDFRTYD SEGVILYAES    60
IDHSAWLLIA LRGGKIEVQL KNEHTSKITT GGDVINNGLW NMVSVEELEH SISIKIAKEA   120
VMDINKPGPL FKPENGLLET KVYFAGFPRK VESELIKPIN PRLDGCIRSW NLMKQGASGI   180
KEIIQEKQNK HCLVTVEKGS YYPGSGIAQF HIDYNNVSSA EGWHVNVTLN IRPSTGTGVM   240
LALVSGNNTV PFAVSLVDST SEKSQDILLS VENTVIYRIQ ALSLCSDQQS HLEFRVNRNN   300
LELSTPLKIE TISHEDLQRQ LAVLDKAMKA KVATYLGGLP DVPFSATPVN AFYNGCMEVN   360
INGVQLDLDE AISKHNDIRA HSCPSVWKKT KN                                 392

SEQ ID NO: 91          moltype = AA   length = 390
FEATURE                Location/Qualifiers
REGION                 1..390
                       note = TAM(Axl)-binding sequence
source                 1..390
                       mol_type = protein
                       organism = synthetic construct
SEQUENCE: 91
VVSVCLPLNL DTKYELLYLA EQFAGVVLYL KFRLPEISRF SAEFDFRTYD SEGVILYAES    60
IDHSAWLLIA LRGGKIEVQL KNEHTSKITT GGDVINNGLW NMVSVEELEH SISIKIAKEA   120
VMDINKPGPL FKPENGLLET KVYFAGFPRK VESELIKPIN PRLDGCIRSW NLMKQGASGI   180
KEIIQEKQNK HCLVTVEKGS YYPGSGIAQF HIDYNNVSSA EGWHVNVTLN IRPSTGTGVM   240
LALVSGNNTV PFAVSLVDST SEKSQDILLS VENTVIYRIQ ALSLCSDQQS HLEFRVNRNN   300
LELSTPLKIE TISHEDLQRQ LAVLDKAMKA KVATYLGGLP DVPFSATPVN AFYNGCMEVN   360
INGVQLDLDE AISKHNDIRA HSCPSVWKKT                                    390

SEQ ID NO: 92          moltype = AA   length = 393
FEATURE                Location/Qualifiers
REGION                 1..393
                       note = TAM(Axl)-binding sequence
source                 1..393
                       mol_type = protein
                       organism = synthetic construct
SEQUENCE: 92
VVSVCLPLNL DTKYELLYLA EQFAGVVLYL KFRLPEISRF SAEFDFRTYD SEGVILYAES    60
IDHSAWFLIA LRGGKIEIQL KNEHTSKITT GGDVINNGLW NMVSVEELEH SISIKIAKEA   120
VMDINKPGPL FKPENGLLET KVYFAGFPRK VESELIKPIN PRLDGCIRSW NLMKQGASGI   180
KEIIQEKQNK HCLITVEKGS YYPGSGIAQF HIDYNNVSSA EGWHVNVTLN IRPSTGTGVM   240
LALVSGNNTV PFAVSLVDST SEKSQDILLS VENTVIYRIQ ALSLCSDQQS HLEFRVNRNN   300
LELSTPLKIE TISHEDLQRQ LAILDKAMKA KVATYLGGLP DVPFSATPVN AFYNGCMEVN   360
```

```
INGVQLDLDE AISKHNDIRA HSCPSVWKKT KNS                             393

SEQ ID NO: 93             moltype = AA   length = 393
FEATURE                   Location/Qualifiers
REGION                    1..393
                          note = TAM(Axl)-binding sequence
source                    1..393
                          mol_type = protein
                          organism = synthetic construct
SEQUENCE: 93
VVSVCLPLNL DTKYELLYLA EQFAGVVLYL KFRLPEISRF SAEFDFRTYD SEGVILYAES  60
IDHSAWLLIA LRGGKIEVQL KNEHTSKITT GGDVINNGLW NMVSVEELEH SISIKIAKEA 120
VMDINKPGPL FKPENGLLET KVYFAGFPRK VESELIKPIN PRLDGCIRSW NLMKQGASGI 180
KEIIQEKQNK HCLVTVEKGS YYPGSGIAQF HIDYNNVSSA EGWHINVTLN IRPSMGTGVM 240
LALVSGNNTV PFAVSLVDST SEKSQDILLS VENTVIYRIQ ALSLCSDQQS HLEFRVNRNN 300
LELSTPLKIE TISHEDLQRQ LAVLDKAMKA KVATYLGGLP DVPFSATPVN AFYNGCMEVN 360
INGVQLDLDE AISKHNDIRA HSCPSVWKKT KNS                             393

SEQ ID NO: 94             moltype = AA   length = 393
FEATURE                   Location/Qualifiers
REGION                    1..393
                          note = TAM(Axl)-binding sequence
source                    1..393
                          mol_type = protein
                          organism = synthetic construct
SEQUENCE: 94
VVSVCLPLNL DTKYELLYLA EQFAGVVLYL KFRLPEISRF SAEFDFRTYD SEGVILYAES  60
IDHSAWFLIA LRGGKIEIQL KNEHTSKITT GGDVINNGLW NMVSVEELEH SISIKIAKEA 120
VMDINKPGPL FKPENGLLET KVYFAGFPRK VESELIKPIN PRLDGCIRSW NLMKQGASGI 180
KEIIQEKQNK HCLITVEKGS YYPGSGIAQF HIDYNNVTLN EGWHVNVTLN IRPSTGTGVM 240
LALVSGNNTV PFAVSLVDST SEKSQDILLS VENTVIYRIQ ALSLCSDQQS HLEFRVNRNN 300
LELSTPLKIE TISHEDLQRQ LAILDKAMKA KVATYLGGLP DVPFSATPVN AFYNGCMEVN 360
INGVQLDLDE AISKHNDIRA HSCPSVWKKT KNS                             393

SEQ ID NO: 95             moltype = AA   length = 393
FEATURE                   Location/Qualifiers
REGION                    1..393
                          note = TAM(Axl)-binding sequence
source                    1..393
                          mol_type = protein
                          organism = synthetic construct
SEQUENCE: 95
VVSVCLPLNL DTKYELLYLA EQFAGVVLYL KFRLPEISRF SAEFDFRTYD SEGVILYAES  60
IYHSAWLLIA LRGGKIEVQL KNEHTSKITT GGDVINNGLW NMVSVEELEH SISIKIAKEA 120
VMDINKPGPL FKPENGLLET KVYFAGFPRK VESELIKPIN PRLDGCIRSW NLMKQGASGI 180
KEIIQEKQNK HCLVTVEKGS YYPGSGIAQF HIDYNNVSSA EGWHVNVTLN IRPSTGTGVM 240
LALVSGNNTV PFAVSLVDST SEKSQDILLS VENTVIYRIQ ALSLCSDQQS HLEFRVNRNN 300
LELSTPLKIE TISHEDLQRQ LAVLDKAMKA KVATYLGGLP DVPFSATPVN AFYNGCMEVN 360
INGVQLDLDE AISKHNDIRA HSCPSVWKKT KNS                             393

SEQ ID NO: 96             moltype = AA   length = 393
FEATURE                   Location/Qualifiers
REGION                    1..393
                          note = TAM(Axl)-binding sequence
source                    1..393
                          mol_type = protein
                          organism = synthetic construct
SEQUENCE: 96
VVSVCLPLNL DTKYELLYLA EQFAGVVLYL KFRLPEISRF SAEFDFRTYD SEGVILYAES  60
IDHSAWFLIA LRGGKIEIQL KNEHTSKITT GGDVINNGLW NMVSVEELEH SISIKIAKEA 120
VMDINKPGPL FKPENGLLET KVYFAGFPRK VESELIKPIN PRLDGCIRSW NLMKQGASGI 180
KEIIQEKQNK HCLITVEKGS YYPGSGIAQF HIDYNNVSSA EGWHVNVTLN IRPSTGTGVM 240
LALVSGNNTV PFAVSLVDST SEKSQDILLS VENTVIYRIQ ALSLCSDQQS HLEFRVNRNN 300
LELSTPLKIE TTSHEDLQRQ LAILDKAMKA KVATYLGGLP DVPFSATPVN AFYNGCMEVN 360
INGVQLDLDE AISKHNDIRA HSCPSVWKKT KNS                             393

SEQ ID NO: 97             moltype = AA   length = 393
FEATURE                   Location/Qualifiers
REGION                    1..393
                          note = TAM(Axl)-binding sequence
source                    1..393
                          mol_type = protein
                          organism = synthetic construct
SEQUENCE: 97
VVSVCLPLNL DTKYELLYLA EQFAGVVLYL KFRLPEISRF SAEFDFRTYD SEGVILYAES  60
IDHSAWFLIA LRGGKIEIQL KNEHTSKITT GGDVINNGLW NMVSVEELEH SISIKIAKEA 120
VMDINKPGPL FKPENGLLET KVYFAGFPRK VESELIKPIN PRLDGCIRSW NLMKQGASGI 180
KEIIQEKQNK HCLITVEKGS YYPGSGIAQF HIDYNNVSSA EGWHVNVTLN IRPSTGTGVM 240
LALVSGNNTV PFAVSLVDST SEKSQDILLS VENTVIYRIQ ALSLCSDQQS HLEFRVNRNN 300
```

```
LELSTPLKIE TISHEDLQRQ LAILDKAMKA KVATYLGGLP DVPFSATPVN AFYNGCMEVN    360
INGVQLDLDE AISKHNDIRA HSCPSVWKKT KNS                                393

SEQ ID NO: 98              moltype = AA  length = 393
FEATURE                    Location/Qualifiers
REGION                     1..393
                           note = TAM(Axl)-binding sequence
source                     1..393
                           mol_type = protein
                           organism = synthetic constru

```
LALVSSNNTV PFAVSLVDST SEKSQDIVLS VENTVIYRIQ ALSLCSNQRS HLEFRVNRNN  300
LELLTPLKIE TISHEELQRQ LAILDKAMTG KVATYLGGLP DVPFSATPVN AFYNGCMEVN  360
INGVQLDLDE AISKHNDIRA HSCPSVWKKT KNS                               393

SEQ ID NO: 103          moltype = AA  length = 393
FEATURE                 Location/Qualifiers
REGION                  1..393
                        note = tAM(Axl)-binding sequence
source                  1..393
                        mol_type = protein
                        organism = synthetic construct
SEQUENCE: 103
AVSVCLPLNL DTKYELLYLA EQFAGVVLYL KFRLPEISRF SAEFDFRTYD SQGVILYAES  60
IDHSAWLLIA LRGGKIEVQL KNEHTSKITT GGDIINNGLW NMVSVEELEH SISIKIAKEA  120
VMDINKPGPL FKPENGLLET KVYFAGFPRK VESELIKPIN PRLDGCIRSW NLMKQGASGI  180
KEIIQEKQNK HCLVTVEKGS YYPGSGIAEF HIDYNNGSNA EGWHINVTLN IRPSMGTGVM  240
LALVSSNNTV PFAVSLVDST SEKSQDIVLS VENTVIYRIQ ALSLCSNQRS HLEFRVNRNN  300
LELLTPLKIE TISQEELQTQ LAILDKAMKG KVATYLGGLP DVPFSATPVN AFYNGCMEVN  360
INGVELDLDE AISKHNDIRA HSCPSVWKKT KNS                               393

SEQ ID NO: 104          moltype = AA  length = 393
FEATURE                 Location/Qualifiers
REGION                  1..393
                        note = TAM(Axl)-binding sequence
source                  1..393
                        mol_type = protein
                        organism = synthetic construct
SEQUENCE: 104
AVSVCLPLNL DTKYELLYLA EQFAGVVLYL KFRLPEISRF SAEFDFRTYD SQGVILYAES  60
IDHSAWLLIA LRGGKIEVQL KNEHTSKITT GGDIINNGLW NMVSVEELEH SISIKIAKEA  120
VMDINKPGPL FKPENGLLET KVYFAGFPRK VESELIKPIN PRLDGCIRSW NLMKQGASGI  180
KEIIQEKQNK HCLVTVEKGS YYPGSGIAEF HIDYNNGSNA EGWHINVTLN IRPSMGTGVM  240
LALVSSNNTV PFAVSLVDST SEKSQDIVLS VENTVIYRIQ ALSLCSNQRS HLEFRVNRNN  300
LELLTPLKIE TISQEELQTQ LAILDKAMKG KVATYLGGLP DVPFSATPVN AFYNGCMEVN  360
INGVELDLDE AISKHNDIRA HSCPSIWKKT KNS                               393

SEQ ID NO: 105          moltype = AA  length = 393
FEATURE                 Location/Qualifiers
REGION                  1..393
                        note = TAM(Axl)-binding sequence
source                  1..393
                        mol_type = protein
                        organism = synthetic construct
SEQUENCE: 105
AVSVCLPLNL DTKYELLYLA EQFAGVVLYL KFRLPEISRF SAEFDFRTYD SQGVILYAES  60
IDHSAWLLIA LRGGKIEVQL KNEHTSKITT GGDIINNGLW NMVSVEELEH SISIKIAKEA  120
VMDINKPGPL FKPENGLLET KVYFAGFPRK VESELIKPIN PRLDGCIRSW NLMKQGASGI  180
KEIIQEKQNK HCLVTVEKGS YYPGSGIAEF HIDYNNGSNA EGWHINVTLN IRPSMGTGVM  240
LALVSSNNTV PFAVSLVDST SEKSQDIVLS VENTVIYRIQ ALSLCSNQRS HLEFRANRNN  300
LELLTPLKIE TISQEELQTQ LAILDKAMKG KVATYLGGLP DVPFSATPVN AFYNGCMEVN  360
INGVELDLDE AISKHNDIRA HSCPSIWKKT KNS                               393

SEQ ID NO: 106          moltype = AA  length = 393
FEATURE                 Location/Qualifiers
REGION                  1..393
                        note = TAM(Axl)-binding sequence
source                  1..393
                        mol_type = protein
                        organism = synthetic construct
SEQUENCE: 106
AVSVCLPLNL DTKYELLYLA EQFAGVVLYL KFRLPEISRF SAEFDFRTYD SQGVILYAES  60
IDHSAWLLIA LRGGKIEVQL KNEHTSKITT GGDIINNGLW NMVSVEELEH SISIKIAKEA  120
VMDINKPGPL FKPENGLLET KVYFAGFPRK VESELIKPIN PRLDGCIRSW NLMKQGASGI  180
KEIIQEKQNK HCLVTVEKGS YYPGSGIAEF HIDYNNGSNA EGWHINVTLN IRPSMDTGVM  240
LALVSSNSTV PFAVSLVDST SEKSQDIVLS VENTVIYRIQ ALSLCSSQRS HLEFRVNRNN  300
LELLTPLKIE TISHEELQTQ LAILDKAMKG KVATYLGGLP DVPFSATPVN AFYNGCMEVN  360
INGVELDLDE AISKHNDIRA HSCPSVWEKT KNS                               393

SEQ ID NO: 107          moltype = AA  length = 393
FEATURE                 Location/Qualifiers
REGION                  1..393
                        note = TAM(Axl)-binding sequence
source                  1..393
                        mol_type = protein
                        organism = synthetic construct
SEQUENCE: 107
AVSVCLPLDL DTKYELLYLA EQFAGVVLYL KFRLPEISRF SAEFDFRTYD SQGVILYAES  60
IDHSAWLLIA LRGGKIEVQL KNEHTSKITT GGAIINNGLW NMVSVEELEH SISIKIAKEA  120
VMDINKPGPL FKPENGLLET KVYFAGFPRK VESELIKPIN PRLDGCIRSW NLMKQGASGI  180
```

```
KEIIQEKQNK HCLVTVEKGS YYPGSGIAEF HIDYNNGSNA EGWHINVTLN IRPSMGTGVM    240
LALVSSNNTV PFAVSLVDST SEKSQDIVLS VENTVIYRIQ ALSLCSNQRS HLEFRVNRNN    300
LELLTPLKIE TISQEELQTQ LAILDKAMKG KVATYLGGLP DVPFSATPVN AFYNGCMEVN    360
INGVELDLDE AISKHNDIRA HSCPSVWKKT KNS                                 393

SEQ ID NO: 108          moltype = AA   length = 398
FEATURE                 Location/Qualifiers
REGION                  1..398
                        note = TAM(Axl)-binding sequence
source                  1..398
                        mol_type = protein
                        organism = synthetic construct
VARIANT                 57
                        note = X can be any amino acid
VARIANT                 285
                        note = X can be any amino acid
SEQUENCE: 108
VVSVCLPLNL DTQYELLYLA EQISGVVLYL KFHLPEISRF SAEFHFWTYD SEGMILXAES     60
VNHSAWLLIA LRGGKIEVQL KNEHTSKTTT EGDVINNGLW NELSTSQVSV EELEHSISIK    120
IAKEAVMDID KPGPLFKPEN GLLETKVYFA GYPQKVESEL IKPINPCLDG CIRGWNLMKQ    180
GASGIKEIIQ EKQNKHCLVT VEKGSYYPGF GIAQFHVDYN NVSSAEGWHI NVTLNIHPSM    240
GTGVMLALVS GNNTVPFAVS LVDSTSEKSQ DILLSVENTV IYRIXALSLC SDQQSHLEFR    300
VNRNNLELLI PLKIETISHE DLQRQLAILD KAMKAKVATY LGGLPDVPFS ATPVNAFYNG    360
CMEVNINGVQ LDLDEAISKH NDIRAHSCPS FWKKTKNS                            398

SEQ ID NO: 109          moltype = AA   length = 393
FEATURE                 Location/Qualifiers
REGION                  1..393
                        note = TAM(Axl)-binding sequence
source                  1..393
                        mol_type = protein
                        organism = synthetic construct
SEQUENCE: 109
AVPVCLPLNL DTKSELLYLA EQFAGVVLYL KFRLPEISRF TAEFDFRTYD SEGVVLYAES     60
IDHSAWILIA VRDGKFEVQL KNEQTSKITT GGGIINNGVW HTVSVEELEH SVSLKIAKEA    120
VMNINKLGPL FKPEHGFLET KVYFAGFPRK VESQFIKPIN PRLDGCIRGW NLMKQGASGV    180
KEIIQEKQNK HCLVTVEKGS YYPGSGIAKF IIDYNNVSSA EGWYVNVSLN IRPSMGTGVM    240
LALVSHNNTV PFAVSLVDST SEKSQDILLS VEKTVVYRIQ ALSLCSDQQS HLEFRVNRRN    300
LEVSTPLKME TISHEDLQKQ LAILDKAMQG EVVTYLGGLP DVPFSAAPAN AFYNGCMEVN    360
INGVLLDLDE AISKHNDIRA HSCPSVWKKT KSS                                 393

SEQ ID NO: 110          moltype = AA   length = 416
FEATURE                 Location/Qualifiers
REGION                  1..416
                        note = TAM(Axl)-binding sequence
source                  1..416
                        mol_type = protein
                        organism = synthetic construct
VARIANT                 57
                        note = X can be any amino acid
VARIANT                 303
                        note = X can be any amino acid
SEQUENCE: 110
VVSVCLPLNL DTQYELFYLA EQFAGVVLYL KFHLPEISRF SAEFHFWTYD SEGMILXAES     60
VNHSAWLLIA LRGGKIEVQL ENEHTSKITT GGDVINNGLW NVFKIITFLK NVMNAKIVQQ    120
IFCVYVSVEE LEHSISIKIA KEAVMDINKP GPLFKPENGL LETKVYFAGF PQKAEGELIK    180
PINPCLDGCI RGWNLMKQGA SGIKEIIQEK QNKHCLVTVE KGSYYPSFGI AQFRIDYNNV    240
SSVEGWHINV TLNIHPSMGT GVMLALVSGN NTVPFAVSLV DSTSEKSQDI LLSVENTVIY    300
LIXALSLCSD QQSHLEFIVN RNNLELLTPL KIETISHEDL QRQLAILDKA MKAKVATYLG    360
GLPDVPFSAT PVNALYKGCM EVNINGVQLD LDEAISKHND IIAHSCPSFW KKTKNS        416

SEQ ID NO: 111          moltype = AA   length = 393
FEATURE                 Location/Qualifiers
REGION                  1..393
                        note = TAM(Axl)-binding sequence
source                  1..393
                        mol_type = protein
                        organism = synthetic construct
SEQUENCE: 111
AVPVCLLLNL DTKSELLYLA EQFAGVVLYL KFRLPEISRF TAEFDFRTYD SEGVVLYAES     60
IDHSAWILIA VRDGKFEVQL KNEQTSKITT GGGIINNGVW HTVSVEELEH SVSLKIAKEA    120
VMNINKLGPL FKPEHGFLET KVYFAGFPRK VESQFIKPIN PRLDGCIRGW NLMKQGASGV    180
KEIIQEKQNK HCLVTVEKGS YYPGSGIAKF IIDYNNASNA EGWYVNVSLN IRPSTGTGVM    240
LALVSRNNTV PFAVSLVDST SEKLQDILLS VEKTVVYRIQ ALSLCSDQQS HLEFKVNRHN    300
LEVSTPLKME TISHEDLQKQ LAILDKAMQG DVVTYLGGLP DVPFSATPVN AFYNGCMEVN    360
INGVLLDLDE AISKHNDIRA HSCPSVWKKT KSS                                 393

SEQ ID NO: 112          moltype = AA   length = 393
FEATURE                 Location/Qualifiers
```

```
REGION                      1..393
                            note = TAM(Axl)-binding sequence
source                      1..393
                            mol_type = protein
                            organism = synthetic construct
SEQUENCE: 112
AIPVCLPLNL DTKSELLYLA EQFAGVVLYL KFRLPEISRF TAEFDFRTYD SEGVVLYAES    60
LDHSAWILIA VRDGKFEVQL QNEQTSRITT GGGVVNNGVW HTVSVEELEH SVSLKIAKEA   120
VMNINKLGPL FKPEHGFLET KVYFAGFPRQ VESQFIKPIN PRLDGCIRGW NLMKQGASGV   180
KEIIQEKQNK HCLVTVEKGS YYPGSGIAKF IIDYNNVSSA EGWHVNVSLN IRPSMGTGVM   240
LALVSRNNTV PFAVSLVDST SEKLQDILLS VEKTVIYRIE ALSLCSDQQS HLELKVNRHS   300
LEVSTPLKME TVSHEDIQKE LAILDKAMQG EVVTYLGGLP DVSFSATPAN AFYNGCMEVN   360
MNGVLLDLDE AISKHNDIRA HSCPSVWRKT KSS                                393

SEQ ID NO: 113              moltype = AA  length = 388
FEATURE                     Location/Qualifiers
REGION                      1..388
                            note = TAM(Axl)-binding sequence
source                      1..388
                            mol_type = protein
                            organism = synthetic construct
SEQUENCE: 113
VVSVCLPLNL DTKYELLYLA EQFAGVVLYL KFRLPEISRF SAEFDFRTYD SEGVILYAES    60
IDHSAWLLIA LRGGKIEVQL KNEHTSKITT GGDVINNGLW NMVSVEELEH SISIKIAKEA   120
VMDINKPGPL FKPENGLLET KVYFAGFPRK VESELIKPIN PRLDGCIRSW NLMKQGASGI   180
KEIIQEKQNK HCLVTVEKGS YYPGSGIAQF HIDYNNVSSA EGWHVNVTLN IRPSTGTGVM   240
LALVSGNNTV PFAVSLVDST SEKSQDILLS VENTVIYRIQ ALSLCSDQQS HLEFRVNRNN   300
LELSTPLKIE TISHEDLQRQ LAVLDKAMKA KVATYLGGLP DVPFSATPVN AFYNGCMEVN   360
INGVQLDLDE AISKHNDIRA HSCPSVWK                                      388

SEQ ID NO: 114              moltype = AA  length = 894
FEATURE                     Location/Qualifiers
source                      1..894
                            mol_type = protein
                            organism = Homo sapiens
SEQUENCE: 114
MAWRCPRMGR VPLAWCLALC GWACMAPRGT QAEESPFVGN PGNITGARGL TGTLRCQLQV    60
QGEPPEVHWL RDGQILELAD STQTQVPLGE DEQDDWIVVS QLRITSLQLS DTGQYQCLVF   120
LGHQTFVSQP GYVGLEGLPY FLEEPEDRTV AANTPFNLSC QAQGPPEPVD LLWLQDAVPL   180
ATAPGHGPQR SLHVPGLNKT SSFSCEAHNA KGVTTSRTAT ITVLPQQPRN LHLVSRQPTE   240
LEVAWTPGLS GIYPLTHCTL QAVLSDDGMG IQAGEPDPPE EPLTSQASVP PHQLRLGSLH   300
PHTPYHIRVA CTSSQGPSSW THWLPVETPE GVPLGPPENI SATRNGSQAF VHWQEPRAPL   360
QGTLLGYRLA YQGQDTPEVL MDIGLRQEVT LELQGDGSVS NLTVCVAAYT AAGDGPWSLP   420
VPLEAWRPGQ AQPVHQLVKE PSTPAFSWPW WYVLLGAVVA AACVLILALF LVHRRKKETR   480
YGEVFEPTVE RGELVVRYRV RKSYSRRTTE ATLNSLGISE ELKEKLRDVM VDRHKVALGK   540
TLGEGEFGAV MEGQLNQDDS ILKVAVKTMK IAICTRSELE DFLSEAVCMK EFDHPNVMRL   600
IGVCFQGSER ESFPAPVVIL PFMKHGDLHS FLLYSRLGDQ PVYLPTQMLV KFMADIASGM   660
EYLSTKRFIH RDLAARNCML NENMSVCVAD FGLSKKIYNG DYYRQGRIAK MPVKWIAIES   720
LADRVYTSKS DVWSFGVTMW EIATRGQTPY PGVENSEIYD YLRQGNRLKQ PADCLDGLYA   780
LMSRCWELNP QDRPSFTELR EDLENTLKAL PPAQEPDEIL YVNMDEGGGY PEPPGAAGGA   840
DPPTQPDPKD SCSCLTAAEV HPAGRYVLCP STTPSPAQPA DRGSPAAPGQ EDGA          894

SEQ ID NO: 115              moltype = AA  length = 888
FEATURE                     Location/Qualifiers
source                      1..888
                            mol_type = protein
                            organism = Mus musculus
SEQUENCE: 115
MGRVPLAWWL ALCCWGCAAH KDTQTEAGSP FVGNPGNITG ARGLTGTLRC ELQVQGEPPE    60
VVWLRDGQIL ELADNTQTQV PLGEDWQDEW KVVSQLRISA LQLSDAGEYQ CMVHLEGRTF   120
VSQPGFVGLE GLPYFLEEPE DKAVPANTPF NLSCQAQGPP EPVTLLWLQD AVPLAPVTGH   180
SSQHSLQTPG LNKTSSFSCE AHNAKGVTTS RTATITVLPQ RPHHLHVVSR QPTELEVAWT   240
PGLSGIYPLT HCNLQAVLSD DGVGIWLGKS DPPEDPLTLQ VSVPPHQLRL EKLLPHTPYH   300
IRISCSSSQG PSPWTHWLPV ETTEGVPLGP PENVSAMRNG SQVLVRWQEP RVPLQGTLLG   360
YRLAYRGQDT PEVLMDIGLT REVTLELRGD RPVANLTVSV TAYTSAGDGP WSLPVPLEPW   420
RPGQGQPLHH LVSEPPPRAF SWPWWYVLLG ALVAAACVLI LALFLVHRRK KETRYGEVFE   480
PTVERGELVV RYRVRKSYSR RTTEATLNSL GISEELKEKL RDVMVDRHKV ALGKTLGEGE   540
FGAVMEGQLN QDDSILKVAV KTMKIAICTR SELEDFLSEA VCMKEFDHPN VMRLIGVCFQ   600
GSDREGFPEP VVILPFMKHG DLHSFLLYSR LGDQPVFLPT QMLVKFMADI ASGMEYLSTK   660
RFIHRDLAAR NCMLNENMSV CVADFGLSKK IYNGDYYRQG RIAKMPVKWI AIESLADRVY   720
TSKSDVWSFG VTMWEIATRG QTPYPGVENS EIYDYLRQGN RLKQPVDCLD GLYALMSRCW   780
ELNPRDRPSF AELREDLENT LKALPPAQEP DEILYVNMDE GGSHLEPRGA AGGADPPTQP   840
DPKDSCSCLT AADVHSAGRY VLCPSTAPGP TLSADRGCPA PPGQEDGA                888

SEQ ID NO: 116              moltype = AA  length = 5
FEATURE                     Location/Qualifiers
source                      1..5
                            mol_type = protein
                            organism = synthetic construct
```

```
REGION                  1..5
                        note = The entire sequence of amino acids 1-5 can be
                         repeated one or more times
SEQUENCE: 116
GGGGS                                                                    5

SEQ ID NO: 117          moltype =   length =
SEQUENCE: 117
000

SEQ ID NO: 118          moltype = AA  length = 6
FEATURE                 Location/Qualifiers
source                  1..6
                        mol_type = protein
                        organism = synthetic construct
REGION                  1..6
                        note = The entire sequence of amino acids 1-6 can be
                         repeated one or more times
SEQUENCE: 118
GSSGGS                                                                   6

SEQ ID NO: 119          moltype = AA  length = 18
FEATURE                 Location/Qualifiers
source                  1..18
                        mol_type = protein
                        organism = synthetic construct
SEQUENCE: 119
KESGSVSSEQ LAQFRSLD                                                     18

SEQ ID NO: 120          moltype = AA  length = 14
FEATURE                 Location/Qualifiers
source                  1..14
                        mol_type = protein
                        organism = synthetic construct
SEQUENCE: 120
EGKSSGSGSE SKST                                                         14

SEQ ID NO: 121          moltype = AA  length = 12
FEATURE                 Location/Qualifiers
source                  1..12
                        mol_type = protein
                        organism = synthetic construct
SEQUENCE: 121
GSAGSAAGSG EF                                                           12

SEQ ID NO: 122          moltype = AA  length = 5
FEATURE                 Location/Qualifiers
source                  1..5
                        mol_type = protein
                        organism = synthetic construct
REGION                  1..5
                        note = The entire sequence of amino acids 1-5 can be
                         repeated one or more times
SEQUENCE: 122
EAAAK                                                                    5

SEQ ID NO: 123          moltype = AA  length = 12
FEATURE                 Location/Qualifiers
source                  1..12
                        mol_type = protein
                        organism = synthetic construct
SEQUENCE: 123
CRRRRREAE AC                                                            12

SEQ ID NO: 124          moltype = AA  length = 46
FEATURE                 Location/Qualifiers
source                  1..46
                        mol_type = protein
                        organism = synthetic construct
SEQUENCE: 124
AEAAAKEAAA KEAAKEAAA KALEAEAAAK EAAAKEAAAK EAAAKA                        46

SEQ ID NO: 125          moltype = AA  length = 8
FEATURE                 Location/Qualifiers
source                  1..8
                        mol_type = protein
                        organism = synthetic construct
SEQUENCE: 125
GGGGGGGG                                                                 8
```

```
SEQ ID NO: 126          moltype = AA  length = 6
FEATURE                 Location/Qualifiers
source                  1..6
                        mol_type = protein
                        organism = synthetic construct
SEQUENCE: 126
GGGGGG                                                                    6

SEQ ID NO: 127          moltype = AA  length = 13
FEATURE                 Location/Qualifiers
source                  1..13
                        mol_type = protein
                        organism = synthetic construct
SEQUENCE: 127
AEAAAKEAAA AKA                                                           13

SEQ ID NO: 128          moltype = AA  length = 5
FEATURE                 Location/Qualifiers
source                  1..5
                        mol_type = protein
                        organism = synthetic construct
SEQUENCE: 128
PAPAP                                                                     5

SEQ ID NO: 129          moltype = AA  length = 17
FEATURE                 Location/Qualifiers
source                  1..17
                        mol_type = protein
                        organism = synthetic construct
SEQUENCE: 129
VSQTSKLTRA ETVFPDV                                                       17

SEQ ID NO: 130          moltype = AA  length = 6
FEATURE                 Location/Qualifiers
source                  1..6
                        mol_type = protein
                        organism = synthetic construct
SEQUENCE: 130
PLGLWA                                                                    6

SEQ ID NO: 131          moltype = AA  length = 10
FEATURE                 Location/Qualifiers
source                  1..10
                        mol_type = protein
                        organism = synthetic construct
SEQUENCE: 131
TRHRQPRGWE                                                               10

SEQ ID NO: 132          moltype = AA  length = 10
FEATURE                 Location/Qualifiers
source                  1..10
                        mol_type = protein
                        organism = synthetic construct
SEQUENCE: 132
AGNRVRRSVG                                                               10

SEQ ID NO: 133          moltype = AA  length = 8
FEATURE                 Location/Qualifiers
source                  1..8
                        mol_type = protein
                        organism = synthetic construct
SEQUENCE: 133
RRRRRRRR                                                                  8

SEQ ID NO: 134          moltype = AA  length = 4
FEATURE                 Location/Qualifiers
source                  1..4
                        mol_type = protein
                        organism = synthetic construct
SEQUENCE: 134
GFLG                                                                      4

SEQ ID NO: 135          moltype = AA  length = 31
FEATURE                 Location/Qualifiers
source                  1..31
                        mol_type = protein
                        organism = synthetic construct
SEQUENCE: 135
```

```
GSSGGSGSSG GSGGGDEADG SRGSQKAGVD E                                 31

SEQ ID NO: 136           moltype = AA  length = 898
FEATURE                  Location/Qualifiers
source                   1..898
                         mol_type = protein
                         organism = synthetic construct
SIGNAL                   1..30
SEQUENCE: 136
MAPSLSPGPA ALRRAPQLLL LLLAAECALA DIQMTQSPSS LSASVGDRVT ITCRASQSIS   60
SYLNWYQQKP GKAPKLLIYA ASSLQSGVPS RFSGSGSGTD FTLTISSLQP EDFATYYCQQ  120
SYSTPLTFGG GTKVEIKRGG GGSGGGGSGG GGSEVQLVES GGGVVQPGRS LRLSCAASGF  180
AFSSYGMHWV RQAPGKGLEW VAVIWFDGTK KYYTDSVKGR FTISRDNSKN TLYLQMNTLR  240
AEDTAVYYCA RDRGIGARRG PYYMDVWGKG TTVTVSSGGG GSGGGGSCIN KYGSPYTKNS  300
GFATCVQNLP DQCTPNPCDR KGTQACQDLM GNFFCLCKAG WGGRLCDKDV NECSQENGGC  360
LQICHNKPGS FHCSCHSGFE LSSDGRTCQD IDECADSEAC GEARCKNLPG SYSCLCDEGF  420
AYSSQEKACR DVDECLQGRC EQVCVNSPGS YTCHCDGRGG LKLSQDMDTC EDILPCVPFS  480
VAKSVKSLYL GRMFSGTPVI RLRFKRLQPT RLVAEFDFRT FDPEGILLFA GGHQDSTWIV  540
LALRAGRLEL QLRYNGVGRV TSSGPVINHG MWQTISVEEL ARNLVIKVNR DAVMKIAVAG  600
DLFQPERGLY HLNLTVGGIP FHEKDLVQPI NPRLDGCMRS WNWLNGEDTT IQETVKVNTR  660
MQCFSVTERG SFYPGSGFAF YSLDYMRTPL DVGTESTWEV EVVAHIRPAA DTGVLFALWA  720
PDLRAVPLSV ALVDYHSTKK LKKQLVVLAV EHTALALMEI KVCDGQEHVV TVSLRDGEAT  780
LEVDGTRGQS EVSAAQLQER LAVLERHLRS PVLTFAGGLP DVPVTSAPVT AFYRGCMTLE  840
VNRRLLDLDE AAYKHSDITA HSCPPVEPAA AQGSRADYKD HDGDYKDHDI DYKDDDDK    898

SEQ ID NO: 137           moltype = AA  length = 902
FEATURE                  Location/Qualifiers
source                   1..902
                         mol_type = protein
                         organism = synthetic construct
SEQUENCE: 137
MAPSLSPGPA ALRRAPQLLL LLLAAECALA QVQLVESGGN LVQPGGSLRL SCAASGFTFG   60
SFSMSWVRQA PGGGLEWVAG LSARSSLTHY ADSVKGRFTI SRDNAKNSVY LQMNSLRVED  120
TAVYYCARRS YDSSGYWGHF YSYMDVWGQG TLVTVSGGGG SGGGGSGGGG SSVLTQPSSV  180
SAAPGQKVTI SCSGSTSNIG NNYVSWYQQH PGKAPKLMIY DVSKRPSGVP DRFSGSKSGN  240
SASLDISGLQ SEDEADYYCA AWDDSLSEFL FGTGTKLTVL GGGGGSGGGG SCINKYGSPY  300
TKNSGFATCV QNLPDQCTPN PCDRKGTQAC QDLMGNFFCL CKAGWGGRLC DKDVNECSQE  360
NGGCLQICHN KPGSFHCSCH SGFELSSDGR TCQDIDECAD SEACGEARCK NLPGSYSCLC  420
DEGFAYSSQE KACRDVDECL QGRCEQVCVN SPGSYTCHCD GRGGLKLSQD MDTCEDILPC  480
VPFSVAKSVK SLYLGRMFSG TPVIRLRFKR LQPTRLVAEF DFRTFDPEGI LLFAGGHQDS  540
TWIVLALRAG RLELQLRYNG VGRVTSSGPV INHGMWQTIS VEELARNLVI KVNRDAVMKI  600
AVAGDLFQPE RGLYHLNLTV GGIPFHEKDL VQPINPRLDG CMRSWNWLNG EDTTIQETVK  660
VNTRMQCFSV TERGSFYPGS GFAFYSLDYM RTPLDVGTES TWEVEVVAHI RPAADTGVLF  720
ALWAPDLRAV PLSVALVDYH STKKLKKQLV VLAVEHTALA LMEIKVCDGQ EHVVTVSLRD  780
GEATLEVDGT RGQSEVSAAQ LQERLAVLER HLRSPVLTFA GGLPDVPVTS APVTAFYRGC  840
MTLEVNRRLL DLDEAAYKHS DITAHSCPPV EPAAAQGSRA DYKDHDGDYK DHDIDYKDDD  900
DK                                                                902

SEQ ID NO: 138           moltype = AA  length = 714
FEATURE                  Location/Qualifiers
source                   1..714
                         mol_type = protein
                         organism = synthetic construct
SIGNAL                   1..30
SEQUENCE: 138
MAPSLSPGPA ALRRAPQLLL LLLAAECALA DIQMTQSPSS LSASVGDRVT ITCRASQSIS   60
SYLNWYQQKP GKAPKLLIYA ASSLQSGVPS RFSGSGSGTD FTLTISSLQP EDFATYYCQQ  120
SYSTPLTFGG GTKVEIKRGG GGSGGGGSGG GGSEVQLVES GGGVVQPGRS LRLSCAASGF  180
AFSSYGMHWV RQAPGKGLEW VAVIWFDGTK KYYTDSVKGR FTISRDNSKN TLYLQMNTLR  240
AEDTAVYYCA RDRGIGARRG PYYMDVWGKG TTVTVSSGGG GSGGGGSDIL PCVPFSVAKS  300
VKSLYLGRMF SGTPVIRLRF KRLQPTRLVA EFDFRTFDPE GILLFAGGHQ DSTWIVLALR  360
AGRLELQLRY NGVGRVTSSG PVINHGMWQT ISVEELARNL VIKVNRDAVM KIAVAGDLFQ  420
PERGLYHLNL TVGGIPFHEK DLVQPINPRL DGCMRSWNWL NGEDTTIQET VKVNTRMQCF  480
SVTERGSFYP GSGFAFYSLD YMRTPLDVGT ESTWEVEVVA HIRPAADTGV LFALWAPDLR  540
AVPLSVALVD YHSTKKLKKQ LVVLAVEHTA LALMEIKVCD GQEHVVTVSL RDGEATLEVD  600
GTRGQSEVSA AQLQERLAVL ERHLRSPVLT FAGGLPDVPV TSAPVTAFYR GCMTLEVNRR  660
LLDLDEAAYK HSDITAHSCP PVEPAAAQGS RADYKDHDGD YKDHDIDYKD DDDK         714

SEQ ID NO: 139           moltype = AA  length = 718
FEATURE                  Location/Qualifiers
source                   1..718
                         mol_type = protein
                         organism = synthetic construct
SEQUENCE: 139
MAPSLSPGPA ALRRAPQLLL LLLAAECALA QVQLVESGGN LVQPGGSLRL SCAASGFTFG   60
SFSMSWVRQA PGGGLEWVAG LSARSSLTHY ADSVKGRFTI SRDNAKNSVY LQMNSLRVED  120
TAVYYCARRS YDSSGYWGHF YSYMDVWGQG TLVTVSGGGG SGGGGSGGGG SSVLTQPSSV  180
SAAPGQKVTI SCSGSTSNIG NNYVSWYQQH PGKAPKLMIY DVSKRPSGVP DRFSGSKSGN  240
SASLDISGLQ SEDEADYYCA AWDDSLSEFL FGTGTKLTVL GGGGGSGGGG SDILPCVPFS  300
```

```
VAKSVKSLYL GRMFSGTPVI RLRFKRLQPT RLVAEFDFRT FDPEGILLFA GGHQDSTWIV    360
LALRAGRLEL QLRYNGVGRV TSSGPVINHG MWQTISVEEL ARNLVIKVNR DAVMKIAVAG    420
DLFQPERGLY HLNLTVGGIP FHEKDLVQPI NPRLDGCMRS WNWLNGEDTT IQETVKVNTR    480
MQCFSVTERG SFYPGSGFAF YSLDYMRTPL DVGTESTWEV EVVAHIRPAA DTGVLFALWA    540
PDLRAVPLSV ALVDYHSTKK LKKQLVVLAV EHTALALMEI KVCDGQEHVV TVSLRDGEAT    600
LEVDGTRGQS EVSAAQLQER LAVLERHLRS PVLTFAGGLP DVPVTSAPVT AFYRGCMTLE    660
VNRRLLDLDE AAYKHSDITA HSCPPVEPAA AQGSRADYKD HDGDYKDHDI DYKDDDDK     718

SEQ ID NO: 140         moltype = AA  length = 708
FEATURE                Location/Qualifiers
source                 1..708
                       mol_type = protein
                       organism = synthetic construct
SIGNAL                 1..30
SEQUENCE: 140
MAPSLSPGPA ALRRAPQLLL LLLAAECALA DIQMTQSPSS LSASVGDRVT ITCRASQSIS     60
SYLNWYQQKP GKAPKLLIYA ASSLQSGVPS RFSGSGSGTD FTLTISSLQP EDFATYYCQQ    120
SYSTPLTFGG GTKVEIKRGG GGSGGGGSGG GGSEVQLVES GGGVVQPGRS LRLSCAASGF    180
AFSSYGMHWV RQAPGKGLEW VAVIWFDGTK KYYTDSVKGR FTISRDNSKN TLYLQMNTLR    240
AEDTAVYYCA RDRGIGARRG PYYMDVWGKG TTVTVSSGGG GSGGGGSDIL PCVPFSVAKS    300
VKSLYLGRMF SGTPVIRLRF KRLQPTRLVA EFDFRTFDPE GILLFAGGHQ DSTWIVALR    360
AGRLELQLRY NGVGRVTSSG PVINHGMWQT ISVEELARNL VIKVNRDAVM KIAVAGDLFQ    420
PERGLYHLNL TVGGIPFHEK DLVQPINPRL DGCMRSWNWL NGEDTTIQET VKVNTRMQCF    480
SVTERGSFYP GSGFAFYSLD YMRTPLDVGT ESTWEVEVVA HIRPAADTGV LFALWAPDLR    540
AVPLSVALVD YHSTKKLKKQ LVVLAVEHTA LALMEIKVCD GQEHVVTVSL RDGEATLEVD    600
GTRGQSEVSA AQLQERLAVL ERHLRSPVLT FAGGLPDVPV TSAPVTAFYR GCMTLEVNRR    660
LLDLDEAAYK HSDITAHSCP PVEPAAAGSG SGSGSGSGSY PYDVPDYA                 708

SEQ ID NO: 141         moltype = AA  length = 727
FEATURE                Location/Qualifiers
source                 1..727
                       mol_type = protein
                       organism = synthetic construct
SEQUENCE: 141
MGWSCIILFL VATATGDIQM TQSPSSLSAS VGDRVTITCR ASQSISSYLN WYQQKPGKAP     60
KLLIYAASSL QSGVPSRFSG SGSGTDFTLT ISSLQPEDFA TYYCQQSYST PLTFGGGTKV    120
EIKRKRTVAA PSVIFPPSD EQLKSGTASV VCLLNNFYPR EAKVQWKVDN ALQSGNSQES     180
VTEQDSKDST YSLSSTLTLS KADYEKHKVY ACEVTHQGLS SPVTKSFNRG ECRRKRGSGE    240
GRGSLLTCGD VEENPGPMGW SCIILFLVAT ATGEVQLVES GGGVVQPGRS LRLSCAASGF    300
AFSSYGMHWV RQAPGKGLEW VAVIWFDGTK KYYTDSVKGR FTISRDNSKN TLYLQMNTLR    360
AEDTAVYYCA RDRGIGARRG PYYMDVWGKG TTVTVSSAST KGPSVFPLAP SSKSTSGGTA    420
ALGCLVKDYF PEPVTVSWNS GALTSGVHTF PAVLQSSGLY SLSSVVTVPS SSLGTQTYIC    480
NVNHKPSNTK VDKKVEPKSS DKTHTSPPCP APELLGGPSV FLFPPKPKDT LMISRTPEVT    540
CVVVDVSHED PEVKFNWYVD GVEVHNAKTK PREEQYNSTY RVVSVLTVLH QDWLNGKEYK    600
CKVSNKALPA PIEKTISKAK GQPREPQVYT LPPSRDELTK NQVSLTCLVK GFYPSDIAVE    660
WESNGQPENN YKTTPPVLDS DGSFFLYSKL TVDKSRWQQG NVFSCSVMHE ALHNHYTQKS    720
LSLSPGK                                                              727

SEQ ID NO: 142         moltype = AA  length = 705
FEATURE                Location/Qualifiers
source                 1..705
                       mol_type = protein
                       organism = synthetic construct
SEQUENCE: 142
MAPSLSPGPA ALRRAPQLLL LLLAAECALA ALLPAREATQ FLRPRQRRAF QVFEEAKQGH     60
LERECVEELC SREEAREVFE NDPETDYFYP RYLDCINKYG SPYTKNSGFA TCVQNLPDQC    120
TPNPCDRKGT QACQDLMGNF FCLCKAGWGG RLCDKDVNEC SQENGGCLQI CHNKPGSFHC    180
SCHSGFELSS DGRTCQDIDE CADSEACGEA RCKNLPGSYS CLCDEGFAYS SQEKACRDVD    240
ECLQGRCEQV CVNSPGSYTC HCDGRGGLKL SQDMDTCEDI LPCVPFSVAK SVKSLYLGRM    300
FSGTPVIRLR FKRLQPTRLV AEFDFRTFDP EGILLFAGGH QDSTWIVLAL RAGRLELQLR    360
YNGVGRVTSS GPVINHGMWQ TISVEELARN LVIKVNRDAV MKIAVAGDLF QPERGLYHLN    420
LTVGGIPFHE KDLVQPINPR LDGCMRSWNW LNGEDTTIQE TVKVNTRMQC FSVTERGSFY    480
PGSGFAFYSL DYMRTPLDVG TESTWEVEVV AHIRPAADTG VLFALWAPDL RAVPLSVALV    540
DYHSTKKLKK QLVVLAVEHT ALALMEIKVC DGQEHVVTVS LRDGEATLEV DGTRGQSEVS    600
AAQLQERLAV LERHLRSPVL TFAGGLPDVP VTSAPVTAFY RGCMTLEVNR RLLDLDEAAY    660
KHSDITAHSC PPVEPAAAQG SRADYKDHDG DYKDHDIDYK DDDDK                    705

SEQ ID NO: 143         moltype = DNA  length = 2697
FEATURE                Location/Qualifiers
source                 1..2697
                       mol_type = other DNA
                       organism = synthetic construct
SEQUENCE: 143
atggcccctt cgctctcgcc cgggcccgcc gccctgcgcc gcgcgccgca gctgctgctg     60
ctgctgctgg ccgcggagtg cgcgcttgcc gacattcaga tgactcaatc tcctagctct    120
ctgagcgcct ccgttggaga tagagtcact attacctgca gagccagcca atccatcagc    180
tcttatctaa attggtacca acagaagccc ggcaaagcgc caaagctgct catctacgct    240
gcaagctcct tacagagcgg agtacccagc agattctcag cagtgggcag tgggactgac    300
ttcacattga cgattagctc tctgcagcct gaagactttg ccacatacta ttgtcagcag    360
```

```
agctatagca ccccgctgac gtttggaggc ggaactaagg tggaaatcaa gagaggaggc    420
ggggggctccg gcggggggtgg ctcgggggga ggaggctcag aggttcagct tgtcgagtct   480
ggggggggag tcgttcagcc aggtagaagc ctcagactga gctgtgccgc aagtgggttt    540
gctttttcat cttacggtat gcactgggtg agacaggctc ctggcaaagg actcgagtgg    600
gtcgctgtaa tatggttcga tggtacaaag aaatactata ccgatagtgt gaaaggaaga    660
ttcaccattt cacgagacaa cagtaaaaat accttgtacc ttcagatgaa caccctgaga    720
gcagaagaca cagccgtgta ctactgcgcc agagatagag gtatcggagc aaggcgtggt    780
ccctattata tggatgtgtg ggggaaggga acaacagtga ctgtgagctc tggcgggggc    840
ggcagcggcc gcggtggcag ctgcatcaac aagtatgggt ctccgtacac caaaaactca    900
ggcttcgcca cctgcgtgca aaacctgcct gaccagtgca cgcccaaccc ctgcgataggg   960
aaggggaccc aagcctgcca ggacctcatg gcaacttct tctgcctgtg taaagctggc   1020
tgggggggcc ggctctgcga caaagatgtc aacgaatgca gccaggagaa cggggggctgc  1080
ctccagatct gccacaacaa gccgggtagc ttccactgtt cctgccacag cggcttcgag  1140
ctctcctctg atggcaggac ctgccaagac atagacgagt gcgcagactc ggaggcctgc  1200
ggggaggcgc gctgcaagaa cctgcccggc tcctactcct gcctctgtga cgagggcttc  1260
gcgtacagct cccaggagaa ggcttgccga gatgtggacg agtgtctgca gggccgctgt  1320
gagcaggtct gcgtgaactc cccagggagc tacacctgcc actgtgacgg cgtgggggc   1380
ctcaagctgt cccaggacat ggacacctgt gaggacatct tgccgtgcgt gcccttcagc  1440
gtggccaaga gtgtgaagtc cttgtacctg ggcggatgt tcagtgggac ccccgtgatc   1500
cgactgcgct tcaagaggct gcagcccacc aggctggtag ctgagtttga cttccggacc  1560
tttgacccccg agggcatcct cctctttgcc ggaggccacc aggacagcac ctggatcgtg  1620
ctggccctga gagccggccg gctggagctg cagctgcgct acaacggtgt ggccgtgtc   1680
accagcagcg gcccggtcat caaccatggc atgtggcaga caatctctgt tgaggagctg  1740
gcgcggaatc tggtcatcaa ggtcaacagg gatgctgtca tgaaaatcgc ggtggccggg  1800
gacttgttcc aaccggagcg aggactgtat catctgaacc tgaccgtggg aggtattccc  1860
ttccatgaga aggacctcgt gcagcctata aaccctcgtc tggatggctg catgaggac   1920
tggaactggc tgaacggaga agacaccacc atccaggaaa cggtgaaagt gaacacgagg  1980
atgcagtgct ctcggtgac ggagagaggc tctttctacc ccgggagcgg cttcgccttc   2040
tacagcctgg actacatgcg gacccctctg gacgtcggga ctgaatcaac ctgggaagta  2100
gaagtcgtgg ctcacatccg cccagccgca gacacaggcc tgctgtttgc gctctgggcc  2160
cccgacctcc gtgccgtgcc tctctctgtg gcactggtag actatcactc cacgaagaaa  2220
ctcaagaagc agctggtggt cctggccgtg gagcatacgg ccttggccct aatggagatc  2280
aaggtctgcg acgccaaga gcacgtggtc accgtctcgc tgagggacgg tgaggccacc  2340
ctggaggtgg acggcaccag gggccagagc gaggtgagcc ccgcgcagct gcaggagagg  2400
ctggccctga tcgagaggca cctgcggagc ccgtgctca ccttgctgg cggcctgcca   2460
gatgtgccgg tgacttcagc gccagtcacc cgcgttctacc gcggctgcat gacactggag  2520
gtcaaccgga ggctgctgga cctggacgag gcggcgtaca agcacagcga catcacggcc  2580
cactcctgcc ccccgtgga gcccgccgca gcccaaggat cccgggctga ctacaaagac  2640
catgacggtg attataaaga tcatgacatc gactacaagg atgacgatga caagtga     2697

SEQ ID NO: 144        moltype = DNA  length = 2709
FEATURE               Location/Qualifiers
source                1..2709
                      mol_type = other DNA
                      organism = synthetic construct
SEQUENCE: 144
atggcccctt cgctctcgcc cgggcccgcc gccctgcgcc gcgcgccgca gctgctgctg     60
ctgctgctgg ccgcggagtg cgcgcttgcc caggttcagc tggttgagag cggaggcaat    120
ctggttcagc ccggtggtag tctgcgtctg tcttgtgcgg cgtcagggtt cactttcggt    180
agttttcaa tgagctgggt ccgtcaggca ccaggcggtg ggctgaatg ggtggcaggt    240
ctgtctgcac gtagctccct gacccactat gcagatagtg ttaaagggcg gttcacaatt    300
tcacgcgaca acgctaagaa tagcgtctac ctgcaaatga actccctgcg ggtcgaggat    360
accgcagtgt attactgcgc tcgccgttct tatgactcta gtggatactg gggccattt    420
tatagctaca tggatgtgtg gggacagggc actctggtga ccgtttccgg aggcggtggg    480
tctggaggcg gtggagtgg aggcggtggg tcaagcgttc tgacccagcc gtcctctgla    540
agcgccgcgc caggccagaa agtgacaatt tcctgttctg gaagtactfc aaacatcggc    600
aacaattatg tttcctggta tcagcagcac ccgggcaaag cgcccaagct gatgatttat    660
gatgtgtcta aacgtccaag tggtgttcct gaccggttca gcggttccaa gtctgggaat    720
agtgcctcac tggacatctc aggcctgcaa agcgaagatg aggcggacta ttactgcgca    780
gcttgggatg acagcctgtc cgaatttctg ttcggcaccg ggacaaagct gaccgtgctg    840
ggcggcgggg gcggcagcgg cggcggtggc agctgcatca acaagtatgg gtctccgtac    900
accaaaaact caggcttcgc cacctgcgtg caaaacctgc ctgaccagtg cacgcccaac    960
ccctgcgata ggaaggggac ccaagcctgc caggacctca tgggcaactt cttctgcctg   1020
tgtaaagctg gctgggggg ccggctctgc gacaaagatg tcaacgaatg cagccaggaa  1080
aacgggggct gcctcagat ctgccacaac aagccgggta gcttccactg ttcctgccac   1140
agcggcttcg agctctcctc tgatggcagg acctgccaag acatagacga gtgcgcagac   1200
tcggaggcct gcggggaggc gcgctgcaag aacctgcccg ctcctactc ctgcctctgt   1260
gacgagggct ttgcgtacag ctcccaggag aaggcttgcc gagatgtgga cgagtgtctg  1320
cagggccgct gtgagcaggt ctgcgtgaac tcccagggga gctacacctg ccactgtgac   1380
gggcgtgggg gcctcaagct gtcccaggac atggacacct gtgaggacat cttgccgtgc  1440
gtgcccttca gcgtggccaa gagtgtgaag tccttgtacc tgggccggat gttcagtggg   1500
acccccgtga tccgactgcg cttcaagagg ctgcagccca ccaggctggt agctgagttt   1560
gacttccgga ccttttgaccc cgagggcatc ctcctctttg ccggaggcca ccaggacagc  1620
acctggatcg tgctggccct gagagccggc cggctggagc tgcagctgcg ctacaacggt   1680
gtcggccgtg tcaccagcag cggcccggtc atcaaccatg gcatgtggca gacaatctct   1740
gttgaggagc tggcgcggaa tctggtcatc aaggtcaaca gggatgctgt catgaaaatc   1800
gcggtggccg ggaccttgtt ccaaccggag cgaggactgt atcatctgaa cctgaccgtg  1860
ggaggtattc ccttccatga gaaggacctc gtgcagccta taaaccctcg tctggatggc   1920
tgcatgagga gctggaactg gctgaacgga gaagacacca ccatccagga aacggtgaaa  1980
```

```
gtgaacacga ggatgcagtg cttctcggtg acggagagag gctctttcta ccccgggagc   2040
ggcttcgcct tctacagcct ggactacatg cggaccsctc tggacgtcgg gactgaatca   2100
acctgggaag tagaagtcgt ggctcacatc cgcccagccg cagacacagg cgtgctgttt   2160
gcgctctggg cccccgacct ccgtgccgtg cctctctctg tggcactggt agactatcac   2220
tccacgaaga aactcaagaa gcagctggtg gtcctggcta ccgagcatac ggccttggcc   2280
ctaatggaga tcaaggtctg cgacggccaa gagcacgtgg tcaccgtctc gctgagggac   2340
ggtgaggcca ccctggaggt ggacggcacc aggggccaga gcgaggtgag cgccgcgcag   2400
ctgcaggaga ggctggccgt gctcgagagg cacctgcgga ccccgtgct cacctttgct    2460
ggcggcctgc cagatgtgcc ggtgacttca gcgccagtca gcgcgtttcta ccgcggctgc   2520
atgacactgg aggtcaaccg gaggcgctg gacctggacg aggcggcgta caagcacagc    2580
gacatcacgg cccactcctg ccccccgtg gagcccgccg cagcccaagg atcccgggct    2640
gactacaaag accatgacgg tgattataaa gatcatgaca tcgactacaa ggatgacgat   2700
gacaagtga                                                          2709

SEQ ID NO: 145          moltype = DNA  length = 2145
FEATURE                 Location/Qualifiers
source                  1..2145
                        mol_type = other DNA
                        organism = synthetic construct
SEQUENCE: 145
atggcccctt cgctctcgcc cgggcccgcc gccctgcgcc gcgcgccgca gctgctgctg    60
ctgctgctgg ccgcggagtg cgcgcttgcc gacattcaga tgactcaatc tcctagctct   120
ctgagcgcct ccgttggaga tagagtcact attaccgtca gagccagcca atccatcagc   180
tcttatctaa attggtacca acagaagccc ggcaaagcgc caaagctgct catctacgct   240
gcaagctcct tacagagcgg agtacccagc agattctcag gcagtggcag tgggactgac   300
ttcacattga cgattagctc tctgcagcct gaagactttg ccacatacta ttgtcagcag   360
agctatagca ccccgctgac gtttggaggc ggaactaagg tggaaatcaa gagaggaggc   420
gggggctccg gcggggggtgg ctcggggga ggaggctcag aggttcagct tgtcgagtct    480
ggggggggag tcgttcagcc aggtagaagc ctcagactga gctgtgccgc aagtgggttt   540
gcttttttcat cttacggtat gcactgggtg agacaggtc ctggcaaagg actcgagtgg   600
gtcgctgtaa tatggttcga tggtacaaag aaatactata ccgatagtgt gaaaggaaga   660
ttcaccattt cacgagacaa cagtaaaaat acctgtacc ttcagatgaa cacccctgaga   720
gcagaagaca cagccgtgta ctactgcgcc agagatagag gtatcggagc aaggcgtggt   780
ccctattata tggatgtgtg ggggaaggga acaacagtga ctgtgagctc tggcggggc    840
ggcagcggcg gcggtggcag cgacatcttg ccgtgcgtgc cctcagcgt ggccaagagt    900
gtgaagtcct tgtacctggg ccggatgttc agtgggaccc ccgtgatccg actgcgcttc   960
aagaggctgc agccaccag gctggtagct gagtttgact tccggacctt tgaccccgag   1020
ggcatcctcc tctttgccgg aggccaccag gacagcacct ggatcgtgct ggccctgaga   1080
gccggccgc tggagctgca gctcgcgtac aacggtgtcg gccgtgtcac cagcagcggc   1140
ccggtcatca accatggcat gtggcagaca atctctgttg aggagctggc gcggaatctg   1200
gtcatcaagg tcaacaggga tgctgtcatg aaaatcgcgg tggccgggga cttgttccaa   1260
ccggagcgag gactgtatca tctgaacctg accgtgggag gtattccctt ccatgagaag   1320
gacctcgtgc agcctataaa ccctcgtctg gatggctgca tgaggacgtg gaactggctg   1380
aacggagaag acaccaccat ccaggaaacg gtgaaagtga acacgaggat gcagtgcttc   1440
tcggtgacga agagaggctc tttctacccc gggagcggct tcgccttcta cagcctggac   1500
tacatgcgga cccctctgga cgtcgggact gaatcaacct gggaagtaga agtcgtggct   1560
cacatccgcc cagccgcaga cacaggcgtg tgtttgcgc tctgggcccc cgacctccgt   1620
gccgtgcctc tctctgtggc actggtagac tatcactcca cgaagaaact caagaagcag   1680
ctggtggtcc tggccgtgga gcatacggcc ttgccctaa tggagatcaa ggtctgcgac   1740
ggccaagagc acgtggtcac cgtctcgctg agggacggtg aggccaccct ggaggtggac   1800
ggcaccaggg gccagagcga ggtgagcgcc gcgcagctgc agagaggct ggccgtgctc    1860
gagaggcacc tgcggagccc cgtgctcacc tttgctggcg gcctgccaga tgtgccggtg   1920
acttcagcgc cagtcaccgc gttctaccgc ggctgcatga cactggaggt caaccggagg   1980
ctgctgacc tggacgaggc ggcgtacaag cacagcgaca tcacgcccca ctcctgcccc    2040
cccgtggagc ccgccgcagc ccaaggatcc cgggctgact acaaagacca tgacggtgat   2100
tataaagatc atgacatcga ctacaaggat gacgatgaca agtga                  2145

SEQ ID NO: 146          moltype = DNA  length = 2157
FEATURE                 Location/Qualifiers
source                  1..2157
                        mol_type = other DNA
                        organism = synthetic construct
SEQUENCE: 146
atggcccctt cgctctcgcc cgggcccgcc gccctgcgcc gcgcgccgca gctgctgctg    60
ctgctgctgg ccgcggagtg cgcgcttgcc caggttcagc tggttgagag cggaggcaat   120
ctggttcagc ccgtggtag tctgcgtctg tcttgtgcgg cgtcagggtt cactttcggt   180
agttttcaa tgagctgggt ccgtcaggca ccaggcggtg gctgaatg gtggcaggt      240
ctgtctgcac gtagctccct gacccactat gcagatagtg ttaaagggcg gttcacaatt   300
tcacgcgaca acgctaagaa tagcgtctac ctgcaaatga actccctgcg tgccgaggat   360
accgcagtgt attactgcgc tcgccgttct tatgactcta gtggatactg ggccattttt   420
tatagctaca tggatgtgtg gggacagggc actctggtga ccgttccgg aggcggtggg   480
tctgaggcg gtgggagtgg aggcggtggg tcagcgttc tgacccagcc gtcctctgtc   540
agcgccgcgc caggccagaa agtgacaatt tcctgttctg gaagtacttc aaacatcggc   600
aacaattatg tttctggta tcagcagcac ccggggcaaa gcccaaagct gatgatttat   660
gatgtgtcta aacgtccaag tggtgttcct gaccggttca gcggttccaa gtctgggaat   720
agtgcctcac tggacatctc aggcctgcaa agcgaagatg aggcggacta ttactgcgca   780
gcttgggatg acagcctgtc cgaatttctg ttcggcaccg ggacaaagct gaccgtgctg   840
ggcggcgggg gcgcagcgg cggcggtggc agcgacatct gccgtgcgt gcccttcagc     900
gtggccaaga gtgtgaagtc cttgtacctg gccggatgt tcagtgggac cccgtgatc    960
```

-continued

```
cgactgcgct tcaagaggct gcagcccacc aggctggtag ctgagtttga cttccggacc   1020
tttgacccg  agggcatcct cctctttgcc ggaggccacc aggacagcac ctggatcgtg   1080
ctggccctga gagccggccg gctggagctg cagctgcgct acaacggtgt cggccgtgtc   1140
accagcagcg gcccggtcat caaccatggc atgtggcaga caatctctgt tgaggagctg   1200
gcgcggaatc tggtcatcaa ggtcaacagg gatgctgtca tgaaaatgcc ggtggccggg   1260
gacttgttcc aaccggagcg aggactgtat catctgaacc tcaccgtggg aggtattccc   1320
ttccatgaga aggaccgtcgt gcagcctata aaccctcgtc tggatggctg tatgaggagc   1380
tggaactggc tgaacggaga agacaccacc atccaggaaa cggtgaaagt gaacacgagg   1440
atgcagtgct tctcggtgac ggagagaggc tctttctacc ccgggagcgg cttcgccttc   1500
tacagcctgg actacatgcg gaccctctg  gacgtcggga ctgaatcaac ctgggaagta   1560
gaagtcgtgg ctcacatccg cccagccgca gacacaggcg tgctgtttgc gctctgggcc   1620
cccgacctcc gtgccgtgcc tctctctgtg gcactggtag actatcactc cacgaagaaa   1680
ctcaagaagc agctggtggt cctggccgtg gagcatacgg ccttggccct aatggagatc   1740
aaggtctgcg acggccaaga gcacgtggtc accgtctgtc tgagggacgg tgaggccacc   1800
ctggaggtgg acggcaccag gggccagagc gaggtgagcg ccgcgcagct gcaggagagg   1860
ctggccgtgc tcgagaggca cctgcggagc ccgtgctca  cctttgccgg cggcctgcca   1920
gatgtgccgg tgacttcagc gccagtcacc gcgttctacc gcggctgcat gacactggag   1980
gtcaaccgga ggctgctgga cctggaacgag gcggcgtaca agcacagcga catcacggcc   2040
cactcctgcc ccccgtgga  gcccgccgca gcccaaggat cccgggctga ctacaaagac   2100
catgacggtg attataaaga tcatgacatc gactacaagg atgacgatga caagtga      2157

SEQ ID NO: 147           moltype = DNA  length = 2127
FEATURE                  Location/Qualifiers
source                   1..2127
                         mol_type = other DNA
                         organism = synthetic construct
SEQUENCE: 147
atggccccttc gctctcgcc  cgggcccgcc gccctgcgcc gcgcgccgca gctgctgctg    60
ctgctgctgg ccgcggagtg cgcgcttgcc gacattcaga tgactcaatc tcctagctct  120
ctgagcgcct ccgttggaga tagagtcact attacctgca gagccagcca atccatcagc  180
tcttatctaa attggtacca acagaagccc ggcaaagcgc caaagctgct catctacgct  240
gcaagctcct tacagagcgg agtcccagc  agattctcag gcagtggcag tgggactgac  300
ttcacattga cgattagctc tctgcagcct gaagactttg ccacatacta ttgtcagcag  360
agctatagca cccgctgac  gtttggaggc ggaactaagg tggaaatcaa gagaggaggc  420
ggggctccg  gcgggtgg   ctcgggggga ggaggctcag aggttcagct tgtcgagtct  480
ggggggggag tcgttcagcc aggtagaagc ctcagactga gctgtgccgc aagtgggttt  540
gcttttcat  cttacggtat gcactgggtg agacaggctc ctggcaaagg actcgagtgg  600
gtcgctgtaa tatggttcga tggtaaaag  aaatactata ccgatagtgt gaaggaagga  660
ttcaccattt cacgagacaa cagtaaaaat accttgtacc ttcagatgaa caccctgaga  720
gcagaagaca cagccgtgta ctactgcgcc agagatagag gtatcggagc aaggcgtggt  780
ccctattata tggatgtgtg ggggaaggga acaacagtga ctgtgagctc tggcggggc   840
ggcagcggcg gcggtggcag cgacatcttg ccgtgcgtgc ccttcagcgt ggccaagagt  900
gtgaagtcct tgtacctggg ccggatgttc agtgggaccc actgcgcttc              960
aagaggctgc agcccaccag gctggtagct gagtttgact tccggaccgtt tgaccccgag 1020
ggcatcctcc tctttgccgg aggccaccag gacagcacct ggatcgtgct ggccctgaga 1080
gccggccgg  tggagctgca gctgcgctac aacggtgtcg gccgtgtcac cagcagcggc 1140
ccggtcatca accatggcat gtggcagaca atctctgttg aggagctgg  gcggaatctg 1200
gtcatcaagg tcaacaggga tgctgtcatg aaaatgcgg tggccgggga cttgttccaa 1260
ccggagcgag gactgtatca tctgaacctg accgtgggag gtattccctt ccatgagaag 1320
gacctcgtgc agcctataaa ccctcgtctg gatggctgca tgaggagctg gaactggctg 1380
aacggagaag acaccaccat ccaggaaacg gtgaaagtga acacggagg tgcagtgctc 1440
tcggtgacgg agagaggctc tttctacccc gggagcggct tcgccttcta cagcctggac 1500
tacatgcgga ccctctgga  cgtcgggact gaatcaacct gggaagtaga agtcgtggct 1560
cacatccgcc cagccgcaga cacaggcgtg ctgtttgcgc tctgggcccc cgacctccgt 1620
gccgtgcctc tctctgtggc actggtagac tatcactcca cgaagaaact caagaagcag 1680
ctggtggtcc tggccgtgga gcatacggcc ttggccctaa tggagatcaa ggtctgcgac 1740
ggccaagagc acgtggtcac cgtctcgctg agggacggtg aggccaccct ggaggtggac 1800
ggcaccaggg gccagagcga ggtgagcgcc gcgcagctgc aggagaggct ggccgtgctc 1860
gagaggcacc tgcggagccc cgtgctcacc tttgctggcg gcctgccaga tgtgccggtg 1920
acttcagcgc cagtcaccgc gttctaccgc ggctgcatga cactggaggt caaccggagg 1980
ctgctggacc tggacgaggc ggcgtacaag cacagcgaca tcacggccca ctcctgcccc 2040
cccgtggagc ccgccgcagc cggcagcgg  agcggcagcg gcagcggcag cggcagctac 2100
ccatacgatg ttccagatta cgcttga                                      2127

SEQ ID NO: 148           moltype = DNA  length = 2190
FEATURE                  Location/Qualifiers
source                   1..2190
                         mol_type = other DNA
                         organism = synthetic construct
SEQUENCE: 148
ggatccatgg gctggtcctg catcatcctg ttcctggtgg ccaccgccac cggcgacatt    60
cagatgactc aatctcctag ctctctgagc gcctccgttg gagatagagt cactattacc  120
tgcagagcca gccaatccat cagctcttat ctaaattggt accaacagaa gcccggcaaa  180
gcgccaaagc tgctcatcta cgctgcaagc tccttacaga gcggagtccc agcagattc   240
tcaggcagtg gcagtgggac tgacttcaca ttgacgatta gctctctgca gcctgaagac  300
tttgccacat actattgtca gcagagctat agcacccgc  tgacgtttgg aggcggaact  360
aaggtggaaa tcaagagaaa acgaactgtg gctgcaccat ctgtcttcat cttcccgcca  420
tctgatgagc agttgaaatc tggaactgcc tctgtcgtgt gcctgctgaa taacttctat  480
cccagagagg ccaaagtaca gtggaaggtg gataacgccc tccaatcggg taactcccag  540
```

```
gagagtgtca cagagcagga cagcaaggac agcaccctaca gcctcagcag caccctgacg    600
ctgagcaaag cagactacga gaaacacaaa gtctacgcct gcgaagtcac ccatcagggc    660
ctgtcctcgc ccgtcacaaa gagcttcaac aggggagagt gtcgcagaaa acgcggaagc    720
ggagagggca gaggaagtct tctaacatgc ggtgacgtgg aggagaatcc cggccctatg    780
ggctggtcct gcatcatcct gttcctggtg gccaccgcca ccggcgaggt tcagcttgtc    840
gagtctgggg ggggagtcgt tcagccaggt agaagcctca gactgagctg tgccgcaagt    900
gggtttgctt tttcatctta cggtatgcac tgggtgagac aggctcctgg caaaggactc    960
gagtgggtcg ctgtaatatg gttcgatggt acaaagaaat actataccga tagtgtgaaa   1020
ggaagattca ccatttcacg agacaacagt aaaaatacct tgtaccttca gatgaacacc   1080
ctgagagcag aagacacagc cgtgtactac tgcgccagag atagaggtat cggagcaagg   1140
cgtggtccct attatatgga tgtgtggggg aagggaacaa cagtgactgt gagctctgcc   1200
tccaccaagg gcccatcggt cttccccctg cacccctcct ccaagagcac ctctgggggc   1260
acagcggccc tgggctgcct ggtcaaggac tacttccccg aaccggtgac ggtgtcgtgg   1320
aactcaggcg ccctgaccag cggcgtgcac accttcccgg ctgtcctaca gtcctcagga   1380
ctctactccc tcagcagcgt ggtgactgtg ccctctagca gcttgggcac ccagacctac   1440
atctgcaacg tgaatcacaa gcccagcaac accaaggtgg acaagaaagt tgagcccaaa   1500
tctagcgaca aaactcacac aagcccaccg tgcccagcac ctgaactcct gggggggaccg   1560
tcagtcttcc tcttcccccc aaaacccaag gacaccctca tgatctcccg gacccctgag   1620
gtcacatgcg tggtggtgga cgtgagccac gaagaccctg aggtcaagtt caactggtac   1680
gtggacggcg tggaggtgca taatgccaag acaaagccgc gggaggagca gtacaacagc   1740
acgtaccgtg tggtcagcgt cctcaccgtc ctgcaccagg actggctgaa tggcaaggag   1800
tacaagtgca aggtctccaa caaagccctc ccagccccca tcgagaaaac catctccaaa   1860
gccaaagggc agccccgaga accacaggtg tacaccctgc ccccatcccg ggatgagctg   1920
accaagaacc aggtcagcct gacctgcctg gtcaaaggct tctatcccag cgacatcgcc   1980
gtggagtggg agagcaatgg gcagccggag aacaactaca agaccacgcc tcccgtgctg   2040
gactccgacg gctccttctt cctctacagc aagctcaccg tggacaagag caggtggcag   2100
caggggaacg tcttctcatg ctccgtgatg catgaggctc tgcacaacca ctacacgcag   2160
aagagcctct ccctgtcccc gggtaaatga                                     2190

SEQ ID NO: 149         moltype = DNA  length = 2118
FEATURE                Location/Qualifiers
source                 1..2118
                       mol_type = other DNA
                       organism = synthetic construct
SEQUENCE: 149
atggccccctt cgctctcgcc cgggcccgcc gccctgcgcc gcgcgccgca gctgctgctg     60
ctgctgctgg ccgcggagtg cgcgcttgcc gcgctgttgc cggcgcgcga ggccacgcag    120
ttcctgcgcg ccaggcagcg ccgcgccttt caggtcttcg aggaggccaa gcaggccac     180
ctggagaggg agtgcgtgga ggagctgtgc agccgcgagg aggcgcggga ggtgttcgag    240
aacgaccccg agacggatta ttttacccca agatacttag actgcatcaa caagtatggg    300
tctccgtaca ccaaaaactc aggcttcgcc acctgcgtgc aaaacctgcc tgaccagtgc    360
acgcccaacc cctgcgatag aagggggacc caagcctgcc aggacctcat gggcaacttc    420
ttctgcctgt gtaaagctgg ctgggggggc cggctctgca aacaagatgt caacgaatgc    480
agccaggaga acgggggctg cctccagatc tgccacaaca gccgggtag cttccactgt    540
tcctgccaca gcgcgcttcga gctctcctct gatggcagga cctgccaaga catagacgag    600
tgcgcagact cggaggcctg cggggaggcg cgctgcaaga acctgccgg ctcctactcc    660
tgcctctgtg acgagggctt tgcgtacagc tcccaggaga aggcttgccg agatgtggac    720
gagtgtctgc agggccgctg tgagcaggtc tgcgtgaact ccccagggag ctacacctgc    780
cactgtgacg ggcgtggggg cctcaagctg tcccaggaca tggacacctg tgaggacatc    840
ttgccgtgcg tgcccttcag cgtggccaag agtgtgaagt ccttgtacct gggccggatg    900
ttcagtggga ccccccgtgat ccgactgcgc ttcaaggagc tgcagcccac caggctgtg    960
gctgagtttg acttccggac cttttgaccc cgagggcatcc tcctctttgc cggaggccca   1020
caggacagca cctggatcgt gctggccctg agagccggcc ggctggagct gcagctgcgc   1080
tacaacggtg tcggccgtgt caccagcagc ggcccggtca tcaaccatgg catgtggcag   1140
acaatctctg ttgaggagct ggcgcggaat ctggtcatca aggtcaacag ggatgctgtc   1200
atgaaaatcg cggtgccgg ggacttgttc caaccggagc gaggactgta tcatctgaac   1260
ctgaccgtgg gaggtattcc cttccatgag aaggacctcg tgcagcctat aaaccctcgt   1320
ctggatggct gcatgaggag ctggaactgg ctgaacggag aagacaccac catccaggaa   1380
acggtgaaag tgaacacgag gatgcagtgc ttctcggtga cggagagagg ctcttttctac   1440
cccggggagcg gcttcgcctt ctacagcctg gactacatgc ggacccctct ggacgtcggg   1500
actgaatcaa cctgggaagt agaagtcgtg gctcacatcc gcccagccgc agacacaggc   1560
gtgctgtttg cgctctgggc ccccgacctc gtgccgtgc ctctctctgt ggcactggta   1620
gactatcact ccacgaagaa actcaagaag cagctggtgg tcctggccgt ggagcatacg   1680
gcccttggccc taatggagat caaggtctgc acgggccaag agccgtgtg caccgtctcg   1740
ctgagggacg gtgaggccac cctggaggtg gacggcacca ggggccagag cgaggtgagc   1800
gccgcgcagc tgcaggagag gctggccgtg ctcgagaggc acctgcggag cccgtgctc   1860
acctttgctg gcggcctgcc agatgtgccg gtgacttcag cgccagtcac cgcgttctac   1920
cgcggctgca tgaacactga ggtcaaccgg aggctgctgg acctggacga ggcggcgtac   1980
aagcacacgc acatcacggc ccactcctgc cccccgtgg agcccgccgc agcccaagga   2040
tccggctg actacaaaga ccatgacggt gattataaag atcatgacat cgactacaag   2100
gatgacgatg acaagtga                                                 2118

SEQ ID NO: 150         moltype = AA   length = 961
FEATURE                Location/Qualifiers
source                 1..961
                       mol_type = protein
                       organism = synthetic construct
SIGNAL                 1..30
SEQUENCE: 150
```

```
MAPSLSPGPA ALRRAPQLLL LLLAAECALA DDVLTQTPLS LPVTPGQPAS ISCRSSQSIV    60
HSNGNTYLEW YLQKPGQSPQ LLIYKVSNRF SGVPDRFSGS GSGTDFTLKI SRVEAEDVGV   120
YYCFQGSLVP WTFGQGTKVE IKGGGSGGG GSGGGGSEVQ LVESGGGLVQ PGGSLRLSCA   180
ASGLIFRSYG MSWVRQAPGK GLEWVATINS GGTYTYYPDS VKGRFTISRD NSKNTLYLQM   240
NSLRAEDTAV YYCANSYSGA MDYWGQGTLV TVSSGGGGSG GGGSDILPCV PFSVAKSVKS   300
LYLGRMFSGT PVIRLRFKRL QPTRLVAEFD FRTFDPEGIL LFAGGHQDST WIVLALRAGR   360
LELQLRYNGV GRVTSSGPVI NHGMWQTISV EELARNLVIK VNRDAVMKIA VAGDLFQPER   420
GLYHLNLTVG GIPFHEKDLV QPINPRLDGC MRSWNWLNGE DTTIQETVKV NTRMQCFSVT   480
ERGSFYPGSG FAFYSLDYMR TPLDVGTEST WEVEVVAHIR PAADTGVLFA LWAPDLRAVP   540
LSVALVDYHS TKKLKKQLVV LAVEHTALAL MEIKVCDGQE HVVTVSLRDG EATLEVDGTR   600
GQSEVSAAQL QERLAVLERH LRSPVLTFAG GLPDVPVTSA PVTAFYRGCM TLEVNRRLLD   660
LDEAAYKHSD ITAHSCPPVE PAAAGSGSGS GSGSGSYPYD VPDYAEGRGS LLTCGDVEEN   720
PGPVSKGEEL FTGVVPILVE LDGDVNGHKF SVSGEGEGDA TYGKLTLKFI CTTGKLPVPW   780
PTLVTTLTYG VQCFSRYPDH MKQHDFFKSA MPEGYVQERT IFFKDDGNYK TRAEVKFEGD   840
TLVNRIELKG IDFKEDGNIL GHKLEYNYNS HNVYIMADKQ KNGIKVNFKI RHNIEDGSVQ   900
LADHYQQNTP IGDGPVLLPD NHYLSTQSAL SKDPNEKRDH MVLLEFVTAA GITLGMDELY   960
K                                                                 961

SEQ ID NO: 151           moltype = DNA   length = 2886
FEATURE                  Location/Qualifiers
source                   1..2886
                         mol_type = other DNA
                         organism = synthetic construct
SEQUENCE: 151
atggcccctt cgctctcgcc cgggcccgcc gccctgcgcc gcgcgccgca gctgctgctg     60
ctgctgctgg ccgcggagtg cgcgcttgcc gacgatgtat taacacaaac tcccctatca    120
ttgccggtga ccccgggcca accagcttcg atcagctgcc gtagctctca gagcatcgtg    180
cacagcaacg gtaataccta cctggaatgg tatttgcaaa aaccgggtca atccccgcag    240
ttgctgattt ataaagtttc gaatcgtttc agcggtgttc cggatcgttt cagcggctct    300
ggctccggca ccgattttac gctgaagatc agtcgctggg aagcggagga cgtgggtgtc    360
tactactgct ttcagggtag tttggtgccg tggacctttg gtcagggtac taaggtggaa    420
attaagggtg gtggggatc aggtggcggc ggcagcggcg gtggcgggag cgaggtacaa    480
ctagttgaat caggtggagg gttggttcag ccaggtggtt cgctgcgtct gagttgtgcg    540
gcaagcggtt tgatcttccg cagctatggt atgagctggg ttcgtcaggc gccgggcaag    600
ggtctggagt gggtggcgac cattaactct ggcggcacgt acacctacta tcccgactcc    660
gtgaaaggcc gtttccacca tctcccgcga caatagcaaaa acaccctgta tttgcagatg    720
aactcgctcc gcgcagagga caccgctgtg tactactgcg ccaattccta cagcggtgct    780
atggattatt ggggtcaggg cacattggtg actgtaagca gcggcggggg cggcagcggc    840
ggcggtggca gcgacatctt gccgtgcgtg cccttcagtg tggccaagag tgtgaagtcc    900
ttgtacctgg gccggatgtt cagtgggacc cccgtgatcc gactgcgctt caagaggctg    960
cagcccacca ggctggtagc tgagtttgac ttccggacct ttgaccccga gggcatcctc   1020
ctctttgccg gaggccacca ggacagcacc tggatcgtgc tggccctgag agccggccgg   1080
ctggagctgc agctgcgcta caacggtgtc ggccgtgtca ccagcagcgg ccccgtgatc   1140
aaccatggca tgtggcagac aatctctgtt gaggagctgg cgcggaatct ggtcatcaag   1200
gtcaacaggg atgctgtcat gaaaatcgcg gtggccgggg acttgttcca accggagcga   1260
ggactgtatc atctgaacct gaccgtggga ggtattcccc tccatgagaa ggacctcgtg   1320
cagcctataa accctcgtct ggatggctgc atgaggagct ggaactggct gaacggagaa   1380
gacaccacca tccaggaaac ggtgaaagtg aacacgagga tgcagtgctt ctcggtgacg   1440
gagagaggct ctttctaccc cggagcggg ttcgccttct acagcctgga ctacatgcgg   1500
acccctctgg acgtcgggac tgaatcaacc tgggaagtag aagtcgtggc tcacatccgc   1560
ccagcgcag acacaggcgt gctgtttgcg tctgggccg ccgacctccg tgccgtgcct   1620
ctctctgtgg cactggtaga ctatcactcc acgaagaaac tcaagaagca gctggtggtc   1680
ctggccgtgg agcatacggc cttgccccta atggagatca aggtctgcga cggccaagag   1740
cacgtggtca ccgtctcgct gagggacggt gaggccaccc tggaggtgga cggcaccagg   1800
ggccagagcg aggtgagcgc cgcgcagctg caggagagcc tggccgtgct cgagaggcac   1860
ctgcggagcc ccgtgctcac ctttgctggc ggcctgccag atgtgccggt gacttcagcg   1920
ccagtcaccg cgttctaccg cggctgcatg acactggagg tcaaccggag gctgctggac   1980
ctggacgagg cggcgtacaa gcacagcgac atcacggccc actcctgccc ccccgtggag   2040
cccgccgcag ccggcagcgg cagcggcagc ggcagcggca gcggcagcta cccatacgat   2100
gttccagatt acgctgaggg cagaggaagt ctgctaacat gtggtgacgt cgaggagaat   2160
cctggcccag tgagcaaggg cgaggagctg ttcaccgggg tggtgcccat cctggtcgag   2220
ctggacggcg acgtaaacgg ccacaagttc agcgtgtccg gcgagggcga gggcgatgcc   2280
acctacggca agctgaccct gaagttcatc tgcaccaccg gcaagctgcc cgtgccctgg   2340
cccaccctcg tgaccaccct gacctacggc gtgcagtgct tcagccgcta cccgaccac   2400
atgaagcagc acgacttctt caagtccgcc atgcccgaag gctacgtcca ggagcgcacc   2460
atcttcttca aggacgacgg caactacaag acccgcgccg aggtgaagtt cgagggcgac   2520
accctggtga accgcatcga gctgaagggc atcgacttca aggaggacgg caacatcctg   2580
gggcacaagc tggagtacaa ctacaacagc cacaacgtct atatcatggc cgacaagcag   2640
aagaacggca tcaaggtgaa cttcaagatc cgccacaaca tcgaggacgg cagcgtgcag   2700
ctcgccgacc actaccagca gaacacccc atcggcgacg gccccgtgct gctgcccgac   2760
aaccactacc tgagcaccca gtccgccctg agcaaagacc ccaacgagaa gcgcgatcac   2820
atggtcctgc tggagttcgt gaccgccgcc gggatcactc tcggcatgga cgagctgtac   2880
aagtaa                                                              2886

SEQ ID NO: 152           moltype = AA    length = 953
FEATURE                  Location/Qualifiers
source                   1..953
                         mol_type = protein
                         organism = synthetic construct
```

```
SIGNAL                  1..30
SEQUENCE: 152
MAPSLSPGPA ALRRAPQLLL LLLAAECALA SYELTQPPSV SVSPGQTARI TCSGEALPMQ    60
FAHWYQQRPG KAPVIVVYKD SERPSGVPER FSGSSSGTTA TLTITGVQAE DEADYYCQSP   120
DSTNTYEVFG GGTKLTVLGG GGSGGGGSGG GGSEVQLVES GGGLVEPGGS LRLSCAVSGF   180
DFEKAWMSWV RQAPGQGLQW VARIKSTADG GTTSYAAPVE GRFIISRDDS RNMLYLQMNS   240
LKTEDTAVYY CTSAHWGQGT LVTVSSGGGG SGGGGSDILP CVPFSVAKSV KSLYLGRMFS   300
GTPVIRLRFK RLQPTRLVAE FDFRTFDPEG ILLFAGGHQD STWIVLALRA GRLELQLRYN   360
GVGRVTSSGP VINHGMWQTI SVEELARNLV IKVNRDAVMK IAVAGDLFQP ERGLYHLNLT   420
VGGIPFHEKD LVQPINPRLD GCMRSWNWLN GEDTTIQETV KVNTRMQCFS VTERGSFYPG   480
SGFAFYSLDY MRTPLDVGTE STWEVEVVAH IRPAADTGVL FALWAPDLRA VPLSVALVDY   540
HSTKKLKKQL VVLAVEHTAL ALMEIKVCDG QEHVVTVSLR DGEATLEVDG TRGQSEVSAA   600
QLQERLAVLE RHLRSPVLTF AGGLPDVPVT SAPVTAFYRG CMTLEVNRRL LDLDEAAYKH   660
SDITAHSCPP VEPAAGSGS  GSGSGSGSYP YDVPDYAEGR GSLLTCGDVE ENPGPVSKGE   720
ELFTGVVPIL VELDGDVNGH KFSVSGEGEG DATYGKLTLK FICTTGKLPV PWPTLVTTLT   780
YGVQCFSRYP DHMKQHDFFK SAMPEGYVQE RTIFFKDDGN YKTRAEVKFE GDTLVNRIEL   840
KGIDFKEDGN ILGHKLEYNY NSHNVYIMAD KQKNGIKVNF KIRHNIEDGS VQLADHYQQN   900
TPIGDGPVLL PDNHYLSTQS ALSKDPNEKR DHMVLLEFVT AAGITLGMDE LYK          953

SEQ ID NO: 153          moltype = DNA   length = 2862
FEATURE                 Location/Qualifiers
source                  1..2862
                        mol_type = other DNA
                        organism = synthetic construct
SEQUENCE: 153
atggcccctt cgctctcgcc cgggcccgcc gccctgcgcc gcgcgccgca gctgctgctg    60
ctgctgctgg ccgcggagtg cgcgcttgcc tcctatgagc tgactcagcc accctcggtg   120
tcagtgtccc caggacagac ggccaggatc acctgctctg gagaagcatt gccaatgcaa   180
tttgctcatt ggtaccaaca gaggccaggc aaggccccag tgatagtggt gtacaaagac   240
agtgagagac cgtcaggtgt ccctgagcga ttctctggct ccagctcagg gacaacagcc   300
acgttgacca tcactggagt ccaggcagaa gatgaggctg actattactg ccagtcgcca   360
gacagcacta cacttatga agtcttcggc ggagggacca agctgaccgt cctaggtggt   420
gggggatcag gtggcggcgg cagcggcggt ggcgggagcg aggtgcagct ggtggagtct   480
gggggaggtc tggtcgagcc ggggggggtcc ctaagactct cctgtgcagt ctccggattc   540
gatttcgaaa aagcctggat gagttgggtc cgccaggctc cagggcaggg gctacagtgg   600
gttgcccgta tcaagagcac agctgatggt gggacaacaa gctacgccgc ccccgtggaa   660
ggcaggttca tcatctcaag agatgattcg agaaacatgc tttatctgca aatgaacagt   720
ctgaaaactg aagacacagc cgtctattat tgtacatcag cccactgggg ccaggaaccc   780
ctggtcaccg tctcctcggg cgggggcggc agcggcggtg gtggcagcga catcttgccg   840
tgcgtgccct tcagcgtggc caagagtgtg aagtccttgt acctgggccg gatgttcagt   900
gggacccccg tgatccgact gcgcttcaag aggctgcagc ccaccaggct ggtagctgag   960
tttgacttcc ggacctttga ccccgagggc atcctcctct ttgccggagg ccaccaggac  1020
agcacctgga tcgtgctggc cctgagagcc ggcggctgga gctgcagct gcgctacaac  1080
ggtgtcggcc gtgtcaccag cagcggcccg gtcatcaacc atggcatgtg gcagacaatc  1140
tctgttgagg agctggcgcg gaatctggtc atcaaggtca caggggatgc tgtcatgaaa  1200
atcgcggtgg ccggggactt gttccaaccg gagcgaggac tgtatcatct gaacctgacc  1260
gtgggaggta ttcccttcca tgagaaggac ctcgtgcagc ctataaaacc tcgtctggat  1320
ggctgcatga ggagctggaa ctggctgaac ggagaagaca ccaccatcca ggaaacggtg  1380
aaagtgaaca cgaggatgca gtgcttctcg gtgacggaga gggctctttt ctaccccggg  1440
agcggcttcg ccttctacag cctggactac atgcggaccc ctctgacgt cgggactgaa  1500
tcaacctggg aagtagaagt cgtggctcac atccgccacg ccgcagacac aggcgtgctg  1560
tttgcgctct gggcccccga cctccgtgcc gtgcctctct ctgtggcact ggtagactat  1620
cactccacga agaaactcaa gaagcagctg gtggtcctgg ccgtgagca tacggccttg  1680
gccctaatgg agatcaaggt ctgcgacggc aagagcacg tggtcaccgt ctcgctgagg  1740
gacggtgagg ccaccctgga ggtggacggc accaggggcc agagcgaggt gagcgccgcg  1800
cagctgcagg agaggctggc cgtgctcgag aggcaccgcc ggagcccgt gctcaccttt  1860
gctggcggcc tgccagatgt gccgtgact cagcgccag tcaccgcgtt ctaccgcggc  1920
tgcatgacac tggaggtcaa ccggaggctg ctggacctgg acgaggcgg gtacaagcac  1980
agcgacatca cggcccactc ctgcccccc ctggagcccg ccgcagccgg cagcggcagc  2040
ggcagcggca gcggcagcgg cagctaccca tacgatgttc cagattacgc tgagggcgaa  2100
ggaagtctgc taacatgcgg tgacgtcgag gagaatcctg gccagtgag caagggcgag  2160
gagctgttca ccggggtgt gcccatcctg gtcgagctgg acggcgacgt aaacggccac  2220
aagttcagcg tgtccggcga gggcgagggc gatgccacct acggcaagct gaccctgaag  2280
ttcatctgca ccaccggcaa gctgcccgtg ccctggccca cccttgtcacc  2340
tacggcgtgc agtgcttcag ccgctacccc gaccacatga gcagcacga cttcttcaag  2400
tccgccatgc ccgaaggcta cgtccaggag cgcaccatct tcttcaagga cgacggcaac  2460
tacaagaccc gcgccgaggt gaagttcgag ggcgacaccc tggtgaaccg catcgagctg  2520
aagggcatcg acttcaagga ggacggcaac atcctggggc acaagctgga gtacaactac  2580
aacagccaca acgtctatat catggccgac aagcagaaga cggcatcaa gtgaacttc  2640
aagatccgcc acaacatcga ggacggcagc gtgcagctcg ccgaccacta ccagcagaac  2700
acccccatcg gcgacggccc cgtgctgctg cccgacaacc actacctgag cacccagtcc  2760
gccctgagca agaccccaa cgagaagcgc gatcacatgg tcctgctgga gttcgtgacc  2820
gccgccggga tcactctcgg catggacgag ctgtacaagt aa                     2862

SEQ ID NO: 154          moltype = AA   length = 701
FEATURE                 Location/Qualifiers
source                  1..701
                        mol_type = protein
                        organism = synthetic construct
```

```
SIGNAL                     1..24
SEQUENCE: 154
MRVLGGRCGA LLACLLLVLP VSEADIQMTQ SPSSLSASVG DRVTITCRAS QSISSYLNWY    60
QQKPGKAPKL LIYAASSLQS GVPSRFSGSG SGTDFTLTIS SLQPEDFATY YCQQSYSTPL   120
TFGGGTKVEI KRGGGGSGGG GSGGGGSEVQ LVESGGGVVQ PGRSLRLSCA ASGFAFSSYG   180
MHWVRQAPGK GLEWVAVIWF DGTKKYYTDS VKGRFTISRD NSKNTLYLQM NTLRAEDTAV   240
YYCARDRGIG ARRGPYYMDV WGKGTTVTVS SGGGGSGGGG SVVSVCLPLN LDTKYELLYL   300
AEQFAGVVLY LKFRLPEISR FSAEFDFRTY DSEGVILYAE SIDHSAWLLI ALRGGKIEVQ   360
LKNEHTSKIT TGGDVINNGL WNMVSVEELE HSISIKIAKE AVMDINKPGP LFKPENGLLE   420
TKVYFAGFPR KVESELIKPI NPRLDGCIRS WNLMKQGASG IKEIIQEKQN KHCLVTVEKG   480
SYYPGSGIAQ FHIDYNNVSS AEGWHVNVTL NIRPSTGTGV MLALVSGNNT VPFAVSLVDS   540
TSEKSQDILL SVENTVIYRI QALSLCSDQQ SHLEFRVNRN NLELSTPLKI ETISHEDLQR   600
QLAVLDKAMK AKVATYLGGL PDVPFSATPV NAFYNGCMEV NINGVQLDLD EAISKHNDIR   660
AHSCPSVWKK TKNSQGSRAD YKDHDGDYKD HDIDYKDDDD K                       701

SEQ ID NO: 155             moltype = DNA   length = 2106
FEATURE                    Location/Qualifiers
source                     1..2106
                           mol_type = other DNA
                           organism = synthetic construct
SEQUENCE: 155
atgagggtcc tgggtgggcg ctgcggggcg ctgctggcgt gtctcctcct agtgcttccc    60
gtctcagagg cagacattca gatgactcaa tctcctagct ctctgagcgc tccgttgga   120
gatagagtca ctattacctg cagagccagc caatccatca gctcttatct aaattggtac   180
caacagaagc ccgcaaagc gccaaagctg ctcatctacg ctgcaagctc cttacagagc   240
ggagtaccca gcagattctc aggcagtggc agtgggacag acttcacatt gacgattagc   300
tctctgcagc ctgaagactt tgccacatac tattgtcagc agagctatag caccccgctg   360
acgtttggag gcgggactaa ggtggaaatc aagagaggag gcgggggctc cggcggggt   420
ggctcggggg gaggaggctc agaggttcag cttgtcgagt ctggggggg agtcgttcag   480
ccaggtagaa gcctcagact gagctgtgcc gcaagtgggt tgcttttttc atcttacggt   540
atgcactggg tgagacaggc tcctggcaaa ggactgggt gggtcgctgt aatatggttc   600
gatggtacaa agaatactta accgatagt gtgaaggaa gattcaccat ttcacgagac   660
aacagtaaaa atacccttgta ccttcagatg aacacccctga gagcagaaga cacagccgtg   720
tactactgcg ccagagatag aggtatcgga gcaaggcgtg gtcccctata tatggatgtg   780
tggggaagg gaacaacagt gactgtgagc tctggcgggg gcggcagcgg cggcggtgc   840
agcgttgttt cagtgtgcct tcccttgaac cttgacacaa gtatgaatt actttacttg   900
gcggagcagt tgcaggggt tgtttttatt ttaaaatttc gtttgccaga aatcagcaga   960
ttttcagcag aatttgattt ccggacatat gattcagaag cgtggatact gtacgcagaa  1020
tctatcgatc actcagcgtg gctcatcgatt gcacttcgtg gtggaaagat tgaagttcag  1080
cttaagaatg aacatacatc caaaatcaca actggaggtg atgttattaa taatggtcta  1140
tggaatatgg tgtctgtgga agaattagaa catagtatta gcattaaaat agctaaagaa  1200
gctgtgatgg atataaataa acctggaccc ttttttaagc cggaaaatgg attgctggaa  1260
accaaagtat actttgcagg attccctcgg aaagtggaaa gtgaactact taaaccgatt  1320
aaccctcgtc tagatggatg tatacgaagc tggaatttga tgaagcaagg agcttctgga  1380
ataaaggaaa ttattcaaga aaaacaaaat aagcattgcc tggttactgt ggagaagggc  1440
tcctactatc ctggttctgg aattgctcaa tttcacatag attataataa tgtatccagt  1500
gctgagggt ggcatgtaaa tgtgacccttg aatattcgtc catccaccgg cactggtgtt  1560
atgcttgcct tggtttctgg taacaacaca gtgcccttg ctgtgtcctt ggtggactcc  1620
acctctgaaa aatcacagga tattctgtta tctgttgaaa atactgtaat atatcggata  1680
caggccctaa gtctatgttc cgatcaacaa tctcatctgg aatttagagt caacagaaac  1740
aatctggagt tgtcgacacc acttaaaata gaaaccatcc cccatgaaga ccttcaaaga  1800
caacttgccg tcttggacaa agcaatgaaa gcaaaagtgg ccacatacct gggtggcctt  1860
ccagatgttc cattcagtgc cacaccagtg aatgccttt ataatggctg catgaagtg  1920
aatattaatg gtgtacagtt ggatctggat gaagccattt ctaaacataa tgatattaga  1980
gctcactcat gtccatcagt ttggaaaaag acaaagaatt ctcaaggatc ccgggctgac  2040
tacaaagacc atgacggtga ttataaagat catgacatcg actacaagga tgacgatgac  2100
aagtga                                                             2106

SEQ ID NO: 156             moltype = AA   length = 684
FEATURE                    Location/Qualifiers
source                     1..684
                           mol_type = protein
                           organism = synthetic construct
SIGNAL                     1..21
SEQUENCE: 156
METDTLLLWV LLLWVPGSTG DEVQLVESGG GVVQPGRSLR LSCAASGFAF SSYGMHWVRQ    60
APGKGLEWVA VIWFDGTKKY YTDSVKGRFT ISRDNSKNTL YLQMNTLRAE DTAVYYCARD   120
RGIGARRGPY YMDVWGKGTT VTVSSASTKG PSVFPLAPSS KSTSGGTAAL GCLVKDYFPE   180
PVTVSWNSGA LTSGVHTFPA VLQSSGLYSL SSVVTVPSSS LGTQTYICNV NHKPSNTKVD   240
KKVEPKSCDK THGGGGSGGG GSDILPCVPF SVAKSVKSLY LGRMFSGTPV IRLRFKRLQP   300
TRLVAEFDFR TFDPEGILLF AGGHQDSTWI VLALRAGRLE LQLRYNGVGR VTSSGPVINH   360
GMWQTISVEE LARNLVIKVN RDAVMKIAVA GDLFQPERGL YHLNLTVGGI PFHEKDLVQP   420
INPRLDGCMR SWNWLNGEDT TIQETVKVNT RMQCFSVTER GSFYPGSGFA FYSLDYMRTP   480
LDVGTESTWE VEVVAHIRPA ADTGVLFALW APDLRAVPLS VALVDYHSTK KLKKQLVVLA   540
VEHTALALME IKVCDGQEHV VTVSLRDGEA TLEVDGTRGQ SEVSAAQLQE RLAVLERHLR   600
SPVLTFAGGL PDVPVTSAPV TAFYRGCMTL EVNRRLLDLD EAAYKHSDIT AHSCPPVEPA   660
AADYKDHDGD YKDHDIDYKD DDDK                                          684

SEQ ID NO: 157             moltype = DNA   length = 2055
```

```
FEATURE              Location/Qualifiers
source               1..2055
                     mol_type = other DNA
                     organism = synthetic construct
SEQUENCE: 157
atggagacag acacactcct gctatgggta ctgctgctct ggttccagg  ttccactggt   60
gacgaggttc agcttgtcga gtctgggggg ggagtcgttc agccaggtag aagcctcaga  120
ctgagctgtg ccgcaagtgg gtttgctttt tcatcttacg gtatgcactg ggtgagacag  180
gctcctggca aaggactcga gtgggtcgct gtaatatggt tcgatggtac aaagaaatac  240
tataccgata gtgtgaaagg aagattcacc atttcacgag acaacagtaa aaataccttg  300
taccttcaga tgaacaccct gagagcagaa gacacagccg tgtactactg cgccagagat  360
agaggtatcg gagcaaggcg tggtccctat tatatggatg tgtggggaa  gggaacaaca  420
gtgactgtga gctctgcctc caccaagggc ccatcggtct tccccctggc accctcctcc  480
aagagcacct ctggggggca agcggccctg ggctgcctgg tcaaggacta cttccccgaa  540
ccggtgacgg tgtcgtggaa ctcaggcgcc ctgaccagcg gcgtgcacac cttcccggct  600
gtcctacagt cctcaggact ctactccctc agcagcgtgg tgactgtgcc ctctagcagc  660
ttgggcaccc agacctacat ctgcaacgtg aatcacaagc ccagcaacac caaggtggac  720
aagaaagttg agcccaaatc ttgtgacaaa actcacgcg  aggatgaag  cggaggcgg   780
ggaagcgaca tcttgccgtg cgtgccttc  agcgtggcca agagtgtgaa gtccttgtac  840
ctgggccgga tgttcagtgg gacccccgtg atccgactgc gcttcaagag gctgcagccc  900
accaggctgg tagctgagtt tgacttccgg acctttgacc ccgagggcat cctcctcttt  960
gccggagccc accaggacag cacctggatc gtgctgaccc tgagagccgg ccggctggag 1020
ctgcagctgc gctacaacgg tgtcggccgt gtcaccagca gcggcccggt catcaaccat 1080
ggcatgtggc agaatctct  gttgaggag  ctggcgcgga atctggtcat caaggtcaac 1140
agggatgctg tcatgaaaat cgcggtggcc ggggacttgt tccaaccgga gcgaggactg 1200
tatcatctga acctcaccgt gggaggtatt cccttccatg agaaggacct cgtgcagcct 1260
ataaaccctc gtctgatgg  ctgtatgagg agctggaact ggctgaacgg agaagcacc  1320
accatccagg aaacggtgaa agtgaacacg aggatgcagt gcttctcggt gacggagaga 1380
ggctcttttc accccgggag cggcttcgcc ttctacagcc tggactacat gcggacccct 1440
ctggacgtcg ggactgaatc aacctgggaa gtagaagtcg tggctcacat ccgccccagc 1500
gcagacacag gcgtgctgtt tgcgctctgg gcccccgacc tccgtgccgt gcctctctct 1560
gtggcactgg tagactatca ctccacgaag aaactcaaga agcagctggt ggtcctggcc 1620
gtggagcata cggccttggc cctaatggag atcaaggtct gcgacggcca agagcacgtg 1680
gtcaccgtct cgctgaggga cggtgaggcc accctggagg tggacggcac caggggccag 1740
agcgaggtga gcgccgcgca gctgcaggag aggctggccg tgctcgagag gcacctgcgg 1800
agccccgtgc tcacctttgc cggcggcctg ccagatgtgc cggtgacttc agcgccagtc 1860
accgcgttct accgcggctg catgactgtg gaggtcaacc ggaggctgct ggacctggac 1920
gaggcggcgt acaagcacag cgacatcacg gcccactcct gccccccgt  ggagcccgcc 1980
gcagccgact acaaagacca tgacggtgat tataaagatc atgacatcga ctacaaggat 2040
gacgatgaca agtga                                                  2055
```

```
SEQ ID NO: 158       moltype = AA   length = 907
FEATURE              Location/Qualifiers
source               1..907
                     mol_type = protein
                     organism = synthetic construct
SIGNAL               1..21
SEQUENCE: 158
METDTLLLWV LLLWVPGSTG DEVQLVESGG GVVQPGRSLR LSCAASGFAF SSYGMHWVRQ   60
APGKGLEWVA VIWFDGTKKY YTDSVKGRFT ISRDNSKNTL YLQMNTLRAE DTAVYYCARD  120
RGIGARRGPY YMDVWGKGTT VTVSSASTKG PSVFPLAPSS KSTSGGTAAL GCLVKDYFPE  180
PVTVSWNSGA LTSGVHTFPA VLQSSGLYSL SSVVTVPSSS LGTQTYICNV NHKPSNTKVD  240
KKVEPKSCDK THTCPPCPAP ELLGGPSVFL FPPKPKDTLM ISRTPEVTCV VVDVSHEDPE  300
VKFNWYVDGV EVHNAKTKPR EEQYNSTYRV VSVLTVLHQD WLNGKEYKCK VSNKALPAPI  360
EKTISKAKGQ PREPQVYTLP PSRDELTKNQ VSLTCLVKGF YPSDIAVEWE SNGQPENNYK  420
TTPPVLDSDG SFFLYSKLTV DKSRWQQGNV FSCSVMHEAL HNHYTQKSLS LSPGKGGGGS  480
GGGGSDILPC VPFSVAKSVK SLYLGRMFSG TPVIRLRFKR LQPTRLVAEF DPRTFDPEGI  540
LLFAGGHQDS TWIVLALRAG RLELQLRYNG VGRVTSSGPV INHGMWQTIS VEELARNLVI  600
KVNRDAVMKI AVAGDLFQPE RGLYHLNLTV GGIPFHEKDL VQPINPRLDG CMRSWNWLNG  660
EDTTIQETVK VNTRMQCFSV TERGSFYPGS GFAFYSLDYM RTPLDVGTES TWEVEVVAHI  720
RPAADTGVLF ALWAPDLRAV PLSVALVDYH STKKLKKQLV VLAVEHTALA LMEIKVCDGQ  780
EHVVTVSLRD GEATLEVDGT RGQSEVSAAQ LQERLAVLER HLRSPVLTFA GGLPDVPVTS  840
APVTAFYRGC MTLEVNRRLL DLDEAAYKHS DITAHSCPPV EPAAADYKDH DGDYKDHDID  900
YKDDDDK                                                            907
```

```
SEQ ID NO: 159       moltype = DNA   length = 2724
FEATURE              Location/Qualifiers
source               1..2724
                     mol_type = other DNA
                     organism = synthetic construct
SEQUENCE: 159
atggagacag acacactcct gctatgggta ctgctgctct ggttccagg  ttccactggt   60
gacgaggttc agcttgtcga gtctgggggg ggagtcgttc agccaggtag aagcctcaga  120
ctgagctgtg ccgcaagtgg gtttgctttt tcatcttacg gtatgcactg ggtgagacag  180
gctcctggca aaggactcga gtgggtcgct gtaatatggt tcgatggtac aaagaaatac  240
tataccgata gtgtgaaagg aagattcacc atttcacgag acaacagtaa aaataccttg  300
taccttcaga tgaacaccct gagagcagaa gacacagccg tgtactactg cgccagagat  360
agaggtatcg gagcaaggcg tggtccctat tatatggatg tgtggggaa  gggaacaaca  420
gtgactgtga gctctgcctc caccaagggc ccatcggtct tccccctggc accctcctcc  480
```

```
aagagcacct ctgggggcac agcggccctg ggctgcctgg tcaaggacta cttccccgaa    540
ccggtgacgg tgtcgtggaa ctcaggcgcc ctgaccagcg gcgtgcacac cttcccggct    600
gtcctacagt cctcaggact ctactccctc agcagcgtgg tgactgtgcc ctctagcagc    660
ttgggcaccc agacctacat ctgcaacgtg aatcacaagc ccagcaacac caaggtggac    720
aagaaagttg agcccaaatc ttgtgacaaa actcacacat gcccaccgtg cccagcacct    780
gaactcctgg ggggaccgtc agtcttcctc ttccccccaa aacccaagga caccctcatg    840
atctcccgga cccctgaggt cacatgcgtg gtggtggacg tgagccacga agaccctgag    900
gtcaagttca actggtacgt ggacggcgtg gaggtgcata atgccaagac aaagccgcgg    960
gaggagcagt acaacagcac gtaccgtgtg gtcagcgtcc tcaccgtcct gcaccaggac   1020
tggctgaatg gcaaggagta caagtgcaag gtctccaaca aagccctccc agcccccatc   1080
gagaaaacca tctccaaagc caagggcagc cccgagaacc acaggtgta caccctgccc   1140
ccatcccggg atgagctgac caagaaccag gtcagcctga cctgcctggt caaaggcttc   1200
tatcccagcg acatcgccgt ggagtgggag agcaatgggc agccggagaa caactacaag   1260
accacgcctc ccgtgctgga ctccgacggc tccttcttcc tctacagcaa gctcaccgtg   1320
gacaagagca ggtggcagca ggggaacgtc ttctcatgct ccgtgatgca tgaggctctg   1380
cacaaccact acacgcagaa gagcctctcc ctgtccccgg gtaaaggcgg aggtggaagc   1440
ggaggcggtg gaagcgacat cttgccgtgc gtgcccttca gcgtggccaa gagtgtgaag   1500
tccttgtacc tgggcggat gttcagtggg accccgtga tccgactgcg cttcaagagg   1560
ctgcagccca ccaggctggt agctgagttt gacttccgga cctttgaccc cgagggcatc   1620
ctcctctttg ccggaggcca ccaggacagc acctggatcg tgctggccct gagagccggc   1680
cggctggagc tgcagctgcg ctacaacggt gtcggccgtg tcaccagcag cggccccgtc   1740
atcaaccatg gcatgtggca gacaatctct gttgaggagc tggcgggaa tctggtcatc   1800
aaggtcaaca gggatgctgt catgaaaatc gcggtggccg gggacttgtt ccaaccggaa   1860
cgaggactgt atcatctgaa cctcaccgtg gaggtattcc ccttccatga aggacctc    1920
gtgcagccta taaaccctcg tctggatggc tgtatgagga gctggaactg ctgaacgga    1980
gaagacacca ccatccagga aacggtgaaa gtgaacacga ggatgcagtg cttctcggtg    2040
acggagagag gctcttttcta ccccgggagc ggcttcgcct tctacagcct ggactacatg    2100
cggacccctc tggacgtcgg gactgaatca acctgggaag tagaagtcgt ggctcacatc    2160
cgcccagccg cagacacagg cgtgctgttt gcgctctggg ccccccgacct ccgtgccgtg    2220
cctctctctg tggcactggt agactatcac tccacgaaga aactcaagaa gcagctggtg    2280
gtcctggccg tggagcatac ggccttggcc ctaatgagaa tcaaggtctg cgacggccaa    2340
gagcacgtgg tcaccgtctc gctgagggac ggtgaggcca cctgaggt ggacggcacc     2400
aggggccaga gcgaggtgag cgccgcgcag ctgcaggaga ggctgccgt gctcgagagg    2460
cacctgcgga gccccgtgct cacctttgcc ggcggcctgc cagatgtgcc ggtgacttca    2520
gcgccagtca ccgcgttcta ccgcggctgc atgacactgg aggtcaaccg gaggctgctg    2580
gacctggacg aggcggcgta caagcacagc gacatcacgg cccactcctg ccccccgtg    2640
gagcccgccg cagccgacta caaagaccat gacggtgatt ataaagatca tgacatcgac    2700
tacaaggatg acgatgacaa gtga                                          2724

SEQ ID NO: 160         moltype = AA   length = 5
FEATURE                Location/Qualifiers
source                 1..5
                       mol_type = protein
                       organism = synthetic construct
SEQUENCE: 160
GGGGS                                                                5

SEQ ID NO: 161         moltype = AA   length = 232
FEATURE                Location/Qualifiers
source                 1..232
                       mol_type = protein
                       organism = synthetic construct
SIGNAL                 1..16
SEQUENCE: 161
MGWSCIILFL VATATGDIQM TQSPSSLSAS VGDRVTITCR ASQSISSYLN WYQQKPGKAP     60
KLLIYAASSL QSGVPSRFSG SGSGTDFTLT ISSLQPEDFA TYYCQQSYST PLTFGGGTKV    120
EIKRKRTVAA PSVFIFPPSD EQLKSGTASV VCLLNNFYPR EAKVQWKVDN ALQSGNSQES    180
VTEQDSKDST YSLSSTLTLS KADYEKHKVY ACEVTHQGLS SPVTKSFNRG EC            232

SEQ ID NO: 162         moltype = AA   length = 914
FEATURE                Location/Qualifiers
source                 1..914
                       mol_type = protein
                       organism = synthetic construct
SIGNAL                 1..21
SEQUENCE: 162
METDTLLLWV LLLWVPGSTG DDIQMTQSPS SLSASVGDRV TITCRASQSI SSYLNWYQQK     60
PGKAPKLLIY AASSLQSGVP SRFSGSGSGT DFTLTISSLQ PEDFATYYCQ QSYSTPLTFG    120
GGTKVEIKGG GGSGGGGSGG GGSEVQLVES GGGVVQPGRS LRLSCAASGF AFSSYGMHWV    180
RQAPGKGLEW VAVIWFDGTK KYYTDSVKGR FTISRDNSKN TLYLQMNTLR AEDTAVYYCA    240
RDRGIGARRG PYYMDVWGKG TTVTVSSGGG GSGGGGSAPE FLGGPSVFLF PPKPKDTLYI    300
TREPEVTCVV VDVSQEDPEV QFNWYVDGVE VHNAKTKPRE EQFNSTYRVV SVLTVLHQDW    360
LNGKEYKCKV SNKGLPSSIE KTISKAKGQP REPQVYTFPP EQEEMTKNQV SLRCLVKGFY    420
PSDIAVEWES NGQPENNYKT TKPVLDSDGS FRLESRLTVD KSRWQEGNVF SCSVMHEACS    480
WHLCKSLSLS LGKGGGGSGG GGSGGGGSDI LPCVPFSVAK SVKSLYLGRM FSGTPVIRLR    540
FKRLQPTRLV AEFDFRTFDP EGILLFAGGH QDSTWIVLAL RAGRLELQLR YNGVGRVTSS    600
GPVINHGMWQ TISVEELARN LVIKVNRDAV MKIAVAGDLF QPERGLYHLN LTVGGIPFHE    660
KDLVQPINPR LDGCMRSWNW LNGEDTTIQE TVKVNTRMQC FSVTERGSFY PGSGFAFYSL    720
DYMRTPLDVG TESTWEVEVV AHIRPAADTG VLFALWAPDL RAVPLSVALV DYHSTKKLKK    780
```

```
QLVVLAVEHT ALALMEIKVC DGQEHVVTVS LRDGEATLEV DGTRGQSEVS AAQLQERLAV    840
LERHLRSPVL TFAGGLPDVP VTSAPVTAFY RGCMTLEVNR RLLDLDEAAY KHSDITAHSC    900
PPVEPAAAHH HHHH                                                      914

SEQ ID NO: 163              moltype = AA   length = 925
FEATURE                     Location/Qualifiers
source                      1..925
                            mol_type = protein
                            organism = synthetic construct
SIGNAL                      1..21
SEQUENCE: 163
METDTLLLWV LLLWVPGSTG DDIQMTQSPS SLSASVGDRV TITCRASQSI SSYLNWYQQK     60
PGKAPKLLIY AASSLQSGVP SRFSGSGSGT DFTLTISSLQ PEDFATYYCQ QSYSTPLTFG    120
GGTKVEIKGG GGSGGGGSGG GGSEVQLVES GGGVVQPGRS LRLSCAASGF AFSSYGMHWV    180
RQAPGKGLEW VAVIWFDGTK KYYTDSVKGR FTISRDNSKN TLYLQMNTLR AEDTAVYYCA    240
RDRGIGARRG PYYMDVWGKG TTVTVSSGGG GSGGGGSDKT HTCPPCPAPE LLGGPSVFLF    300
PPKPKDTLYI TREPEVTCVV VDVSHEDPEV KFNWYVDGVE VHNAKTKPRE EQYASTYRVV    360
SVLTVLHQDW LNGKEYKCKV SNKALPAPIE KTISKAKGQP REPQVYTLPP SREEMTKNQV    420
SLTCLVKGFY PSDIAVEWES NGQPENNYDT TPPVLDSDGS FFLYSDLTVD KSRWQQGNVF    480
SCSVMHEALH NHYTQKSLSL SPGKGGGGSG GGGSGGGGSD ILPCVPFSVA KSVKSLYLGR    540
MFSGTPVIRL RFKRLQPTRL VAEFDFRTFD PEGILLFAGG HQDSTWIVLA LRAGRLELQL    600
RYNGVGRVTS SGPVINHGMW QTISVEELAR NLVIKVNRDA VMKIAVAGDL FQPERGLYHL    660
NLTVGGIPFH EKDLVQPINP RLDGCMRSWN WLNGEDTTIQ ETVKVNTRMQ CFSVTERGSF    720
YPGSGFAFYS LDYMRTPLDV GTESTWEVEV VAHIRPAADT GVLFALWAPD LRAVPLSVAL    780
VDYHSTKKLK KQLVVLAVEH TALALMEIKV CDGQEHVVTV SLRDGEATLE VDGTRGQSEV    840
SAAQLQERLA VLERHLRSPV LTFAGGLPDV PVTSAPVTAF YRGCMTLEVN RRLLDLDEAA    900
YKHSDITAHS CPPVEPAAAH HHHH                                           925

SEQ ID NO: 164              moltype = AA   length = 504
FEATURE                     Location/Qualifiers
source                      1..504
                            mol_type = protein
                            organism = synthetic construct
SIGNAL                      1..21
SEQUENCE: 164
METDTLLLWV LLLWVPGSTG DDIQMTQSPS SLSASVGDRV TITCRASQSI SSYLNWYQQK     60
PGKAPKLLIY AASSLQSGVP SRFSGSGSGT DFTLTISSLQ PEDFATYYCQ QSYSTPLTFG    120
GGTKVEIKGG GGSGGGGSGG GGSEVQLVES GGGVVQPGRS LRLSCAASGF AFSSYGMHWV    180
RQAPGKGLEW VAVIWFDGTK KYYTDSVKGR FTISRDNSKN TLYLQMNTLR AEDTAVYYCA    240
RDRGIGARRG PYYMDVWGKG TTVTVSSGGG GSGGGGSDKT HTCPPCPAPE LLGGPSVFLF    300
PPKPKDTLYI TREPEVTCVV VDVSHEDPEV KFNWYVDGVE VHNAKTKPRE EQYASTYRVV    360
SVLTVLHQDW LNGKEYKCKV SNKALPAPIE KTISKAKGQP REPQVYTLPP SRKEMTKNQV    420
SLTCLVKGFY PSDIAVEWES NGQPENNYKT TPPVLKSDGS FFLYSKLTVD KSRWQQGNVF    480
SCSVMHEALH NHYTQKSLSL SPGK                                           504

SEQ ID NO: 165              moltype = AA   length = 925
FEATURE                     Location/Qualifiers
source                      1..925
                            mol_type = protein
                            organism = synthetic construct
SIGNAL                      1..21
SEQUENCE: 165
METDTLLLWV LLLWVPGSTG DDIQMTQSPS SLSASVGDRV TITCRASQSI SSYLNWYQQK     60
PGKAPKLLIY AASSLQSGVP SRFSGSGSGT DFTLTISSLQ PEDFATYYCQ QSYSTPLTFG    120
GGTKVEIKGG GGSGGGGSGG GGSEVQLVES GGGVVQPGRS LRLSCAASGF AFSSYGMHWV    180
RQAPGKGLEW VAVIWFDGTK KYYTDSVKGR FTISRDNSKN TLYLQMNTLR AEDTAVYYCA    240
RDRGIGARRG PYYMDVWGKG TTVTVSSGGG GSGGGGSDKT HTCPPCPAPE LLGGPSVFLF    300
PPKPKDTLYI TREPEVTCVV VDVSHEDPEV KFNWYVDGVE VHNAKTKPRE EQYASTYRVV    360
SVLTVLHQDW LNGKEYKCKV SNKALPAPIE KTISKAKGQP REPQVYTLPP SREEMTKNQV    420
SLTCLVKGFY PSDIAVEWES NGQPENNYKT TPPVLDSDGS FFLYSKLTVD KSRWQQGNVF    480
SCSVMHEALH NHYTQKSLSL SPGKGGGGSG GGGSGGGGSD ILPCVPFSVA KSVKSLYLGR    540
MFSGTPVIRL RFKRLQPTRL VAEFDFRTFD PEGILLFAGG HQDSTWIVLA LRAGRLELQL    600
RYNGVGRVTS SGPVINHGMW QTISVEELAR NLVIKVNRDA VMKIAVAGDL FQPERGLYHL    660
NLTVGGIPFH EKDLVQPINP RLDGCMRSWN WLNGEDTTIQ ETVKVNTRMQ CFSVTERGSF    720
YPGSGFAFYS LDYMRTPLDV GTESTWEVEV VAHIRPAADT GVLFALWAPD LRAVPLSVAL    780
VDYHSTKKLK KQLVVLAVEH TALALMEIKV CDGQEHVVTV SLRDGEATLE VDGTRGQSEV    840
SAAQLQERLA VLERHLRSPV LTFAGGLPDV PVTSAPVTAF YRGCMTLEVN RRLLDLDEAA    900
YKHSDITAHS CPPVEPAAAH HHHH                                           925

SEQ ID NO: 166              moltype = AA   length = 730
FEATURE                     Location/Qualifiers
source                      1..730
                            mol_type = protein
                            organism = synthetic construct
SEQUENCE: 166
METDTLLLWV LLLWVPGSTG DEVQLVESGG GVVQPGRSLR LSCAASGFAF SSYGMHWVRQ     60
APGKGLEWVA VIWFDGTKKY YTDSVKGRFT ISRDNSKNTL YLQMNTLRAE DTAVYYCARD    120
RGIGARRGPY YMDVWGKGTT VTVSSASTKG PSVFPLAPSS KSTSGGTAAL GCLVKDYFPE    180
PVTVSWNSGA LTSGVHTFPA VLQSSGLYSL SSVVTVPSSS LGTQTYICNV NHKPSNTKVD    240
```

```
KKVEPKSCDK THTCPPCPAP ELLGGPSVFL FPPKPKDTLM ISRTPEVTCV VVDVSHEDPE  300
VKFNWYVDGV EVHNAKTKPR EEQYASTYRV VSVLTVLHQD WLNGKEYKCK VSNKALPAPI  360
EKTISKAKGQ PREPQVYTLP PSRDELTKNQ VSLTCLVKGF YPSDIAVEWE SNGQPENNYK  420
TTPPVLDSDG SFFLYSKLTV DKSRWQQGNV FSCSVMHEAL HNHYTQKSLS LSPGKGGGGS  480
GGGGSEVKLV ESGGDLVKPG GSLKLSCAAS GFTFSSYGMS WVRQTPDKRL EWVATISSGG  540
SYTYYPDSVK GRFTISRDNA KNTLYLQMSS LKSEDTAMYY CARHPIYYTY DDTMDYWGQG  600
TSVTVSSGGG GSGGGGSGGG GSDIVLTQSP AIMAASPGEK VTMTCSASSS VSSGNFHWYQ  660
QKPGTSPKLW IYRTSNLASG VPARFSGSGS GTSYSLTISS MEAEDAATYY CQQWSGYPWT  720
FGGGTKLEIK                                                        730

SEQ ID NO: 167      moltype = AA  length = 730
FEATURE             Location/Qualifiers
source              1..730
                    mol_type = protein
                    organism = synthetic construct
SEQUENCE: 167
METDTLLLWV LLLWVPGSTG DEVQLVESGG GVVQPGRSLR LSCAASGFAF SSYGMHWVRQ  60
APGKGLEWVA VIWFDGTKKY YTDSVKGRFT ISRDNSKNTL YLQMNTLRAE DTAVYYCARD  120
RGIGARRGPY YMDVWGKGTT VTVSSASTKG PSVFPLAPSS KSTSGGTAAL GCLVKDYFPE  180
PVTVSWNSGA LTSGVHTFPA VLQSSGLYSL SSVVTVPSSS LGTQTYICNV NHKPSNTKVD  240
KKVEPKSCDK THTCPPCPAP ELLGGPSVFL FPPKPKDTLM ISRTPEVTCV VVDVSHEDPE  300
VKFNWYVDGV EVHNAKTKPR EEQYASTYRV VSVLTVLHQD WLNGKEYKCK VSNKALPAPI  360
EKTISKAKGQ PREPQVYTLP PSRDELTKNQ VSLTCLVKGF YPSDIAVEWE SNGQPENNYK  420
TTPPVLDSDG SFFLYSKLTV DKSRWQQGNV FSCSVMHEAL HNHYTQKSLS LSPGKGGGGS  480
GGGGSEVKLV ESGGDLVKPG GSLKLSCAAS GFTFSSYGMS WVRQTPDKRL EWVATISSGG  540
SYTYYPDSVK GRFTISRDNA KNTLYLQMSS LKSEDTAMYY CARHPIYYTY DDTMDYWGQG  600
TSVTVSSGGG GSGGGGSGGG GSDIVLTQSP AIMAASPGEK VTMTCSASSS VSSGNFHWYQ  660
QKPGTSPKLW IYRTSNLASG VPARFSGSGS GTSYSLTISS MEAEDAATYY CQQWSGYPWT  720
FGGGTKLEIK                                                        730

SEQ ID NO: 168      moltype = AA  length = 730
FEATURE             Location/Qualifiers
source              1..730
                    mol_type = protein
                    organism = synthetic construct
SEQUENCE: 168
METDTLLLWV LLLWVPGSTG DEVQLVESGG GVVQPGRSLR LSCAASGFAF SSYGMHWVRQ  60
APGKGLEWVA VIWFDGTKKY YTDSVKGRFT ISRDNSKNTL YLQMNTLRAE DTAVYYCARD  120
RGIGARRGPY YMDVWGKGTT VTVSSASTKG PSVFPLAPSS KSTSGGTAAL GCLVKDYFPE  180
PVTVSWNSGA LTSGVHTFPA VLQSSGLYSL SSVVTVPSSS LGTQTYICNV NHKPSNTKVD  240
KKVEPKSCDK THTCPPCPAP ELLGGPSVFL FPPKPKDTLM ISRTPEVTCV VVDVSHEDPE  300
VKFNWYVDGV EVHNAKTKPR EEQYASTYRV VSVLTVLHQD WLNGKEYKCK VSNKALPAPI  360
EKTISKAKGQ PREPQVYTLP PSRDELTKNQ VSLTCLVKGF YPSDIAVEWE SNGQPENNYK  420
TTPPVLDSDG SFFLYSDLTV DKSRWQQGNV FSCSVMHEAL HNHYTQKSLS LSPGKGGGGS  480
GGGGSEVKLV ESGGDLVKPG GSLKLSCAAS GFTFSSYGMS WVRQTPDKRL EWVATISSGG  540
SYTYYPDSVK GRFTISRDNA KNTLYLQMSS LKSEDTAMYY CARHPIYYTY DDTMDYWGQG  600
TSVTVSSGGG GSGGGGSGGG GSDIVLTQSP AIMAASPGEK VTMTCSASSS VSSGNFHWYQ  660
QKPGTSPKLW IYRTSNLASG VPARFSGSGS GTSYSLTISS MEAEDAATYY CQQWSGYPWT  720
FGGGTKLEIK                                                        730

SEQ ID NO: 169      moltype = AA  length = 475
FEATURE             Location/Qualifiers
source              1..475
                    mol_type = protein
                    organism = synthetic construct
SEQUENCE: 169
METDTLLLWV LLLWVPGSTG DEVQLVESGG GVVQPGRSLR LSCAASGFAF SSYGMHWVRQ  60
APGKGLEWVA VIWFDGTKKY YTDSVKGRFT ISRDNSKNTL YLQMNTLRAE DTAVYYCARD  120
RGIGARRGPY YMDVWGKGTT VTVSSASTKG PSVFPLAPSS KSTSGGTAAL GCLVKDYFPE  180
PVTVSWNSGA LTSGVHTFPA VLQSSGLYSL SSVVTVPSSS LGTQTYICNV NHKPSNTKVD  240
KKVEPKSCDK THTCPPCPAP ELLGGPSVFL FPPKPKDTLM ISRTPEVTCV VVDVSHEDPE  300
VKFNWYVDGV EVHNAKTKPR EEQYASTYRV VSVLTVLHQD WLNGKEYKCK VSNKALPAPI  360
EKTISKAKGQ PREPQVYTLP PSRKELTKNQ VSLTCLVKGF YPSDIAVEWE SNGQPENNYK  420
TTPPVLKSDG SFFLYSKLTV DKSRWQQGNV FSCSVMHEAL HNHYTQKSLS LSPGK       475
```

TAM RECEPTOR-BINDING FUSION MOLECULE HAVING NON-INFLAMMATORY PHAGOCYTOSIS INDUCING ACTIVITY

CROSS REFERENCE TO RELATED APPLICATIONS

This application is a continuation-in-part of and claims the benefit of PCT Application No. PCT/KR2022/001671 filed Jan. 28, 2022, which claims priority based on Korean Patent Application No. 10-2021-0013056 filed Jan. 29, 2021, of which the entire contents are incorporated by reference herein.

INCORPORATION BY REFERENCE OF SEQUENCE LISTING

The content of the electronically submitted sequence listing, file name: Q289305_SEQ_LIST_ST26.xml; size: 268,800 bytes; and date of creation: Jul. 16, 2023, filed herewith, is incorporated herein by reference in its entirety.

FILED

The present disclosure relates to fusion molecules that are capable of inducing phagocytosis without inducing inflammatory reaction, their uses, and manufacturing method. The fusion molecules are useful for prevention or treatment of diseases that are caused by or characterized by abnormal accumulation of substances in the body, such as proteopathy. The present disclosure also relates to nucleic acid molecules encoding the fusion molecules. The present disclosure further relates to methods of suppressing abnormal accumulation of substances, promoting clearance of aggregates of substances, and/or treating disorders or diseases that are caused by or characterized by abnormal accumulation of substances, without inducing inflammatory reaction.

BACKGROUND

Numerous degenerative diseases are characterized by aberrant folding, polymerization and accumulation of proteins. These proteopathies include various types of amyloidosis.

Amyloidosis is a disease in which abnormal proteins called amyloid accumulate in tissues. Amyloid is a protein aggregate that has a diameter of 7-13 nm and a beta-sheet structure and exhibits a fibrous morphology when viewed under a microscope, and it is characterized by being stained with Thioflavin T (ThioT) and Congo red. Amyloid is not normally found in the body, and to date, 36 proteins have been identified as being amyloidogenic (Picken, *Acta Haematol.* (2020), 143:322-334). Representative examples of amyloidosis diseases include neurological diseases such as Alzheimer's disease, Parkinson's disease, Huntington's disease and prion disease. In addition, there are a number of amyloid diseases having various aspects depending on amyloid-causing proteins and affected organs.

Alzheimer's disease is the biggest cause of dementia and is a fatal disease accompanied by learning and memory impairment. 130 million people are expected to suffer from Alzheimer's disease by 2050 worldwide, and 1 in 9 people among the population above 65 years old have already been diagnosed with Alzheimer's disease.

A hallmark of Alzheimer's disease is that beta-amyloid (Aβ) protein caused by abnormal degradation of amyloid precursor protein (APP), deposits and accumulates around the brain cell membrane. Another hallmark is abnormal hyperphosphorylation of microtubule-associated tau protein.

It has recently been reported that beta-amyloid oligomers and fibrils cause synaptic dysfunction and cytotoxicity through various pathways, and create a vicious cycle that adversely affects nerve cells through functional changes in astrocytes and microglia, which are responsible for immunity in the brain.

Therapeutic drugs for Alzheimer's disease approved by the FDA to date inhibit acetylcholine degradation or inhibit the activity of NMDA receptors, and, thus, provide temporary relief of symptoms, but do not treat the underlying cause or the disease itself. Therefore, there is a need for the development of new treatments for treating Alzheimer's disease and other diseases characterized by aberrant accumulation or deposit of beta-amyloid.

For a therapeutic treatment of Alzheimer's disease, drug development has been conducted for decades with a focus on inhibiting formation of and eliminating beta-amyloid. Unfortunately, however, most of the therapeutic drugs for Alzheimer's disease developed to inhibit formation of and eliminate beta-amyloid failed during the clinical stage due to ineffectiveness or insufficient efficacy. For example, in the case of BACE (β-site amyloid precursor protein cleaving enzyme) inhibitors for reducing beta-amyloid, strategies that prevent additional beta-amyloid production are largely ineffective, because in Alzheimer's patients with cognitive decline, beta-amyloid plaques have already accumulated and neuronal cell death is taking place.

Since the recent studies reporting that monoclonal antibodies which specifically bind to beta-amyloid oligomers and fibrils induced beta-amyloid clearance and restored cognitive function in Alzheimer's disease patients, a strategy to treat Alzheimer's disease through anti-beta-amyloid antibodies has emerged as a new hope.

The mechanisms of action of beta-amyloid monoclonal antibodies proposed to date include inhibition of aggregation of beta-amyloid oligomers and fibrils by binding thereto, or the induction of microglial phagocytosis of beta-amyloid through Fc receptors that recognize the monoclonal antibodies.

However, despite the advances in the development of therapeutic drugs for Alzheimer's disease, current immunotherapy using anti-beta-amyloid monoclonal antibodies shows amyloid-related imaging abnormalities (ARIAs) accompanied by severe edema in 55% of patients treated with the antibodies, and for this reason, about 35% of the ARIA patients were dropped from clinical trials. The ARIA phenomenon is known to be due to synaptotoxicity and cytotoxicity caused by inflammatory responses that are inevitably activated when anti-beta-amyloid monoclonal antibodies stimulate Fc receptors of microglia cells.

Since synapses and neurons in the brain respond sensitively to inflammatory cytokines, treatment using anti-beta-amyloid monoclonal antibodies has an inherent problem in that it inevitably causes damages to neurons and synapses, even if it clears beta-amyloid to some extent. In addition to monoclonal antibodies, companies such as Alector and Denali presented strategies to improve the microglia's ability to clear beta-amyloid by activating targets such as TREM2 that regulate the immunological mechanism of microglia, and these strategies have received a lot of attention. However, even in these strategies, when microglia are excessively activated, synaptic damage due to an increase in overall phagocytotic capacity is expected.

Therefore, an important task in the treatment of Alzheimer's disease is to develop therapeutic modalities to selectively clear only beta-amyloid oligomers and fibrils without causing inflammatory responses and synaptic damage, and these drugs are expected to make a significant contribution to the treatment of Alzheimer's disease.

Furthermore, there is a need to selectively clear only a substance of which abnormal accumulation causes disorders or accumulates thereof as a target, for example, abnormally accumulated proteins causing proteopathy, without causing inflammatory responses and consequent additional tissue damage reported in conventional experimental drugs. The present disclosure meets this need by providing therapeutic modalities for selectively clearing abnormally accumulated proteins that cause or characterize certain disease.

SUMMARY

The present disclosure relates to fusion molecules having phagocytosis-inducing activity without inducing inflammatory responses. One aspect of the present disclosure provides a fusion molecule having phagocytosis-inducing activity, the fusion molecule comprising: a first region that is capable of binding to a TAM (Tyro3, Axl and MerTK) receptor; and a second region that specifically binds to a target substance to be cleared or decreased, and the fusion molecule does not induce inflammatory responses. In embodiments, the fusion molecule does not have an effector function and does not induce Fc-mediated inflammatory responses.

In some embodiments, the TAM receptor may be any one selected from the group consisting of Tyro3, Axl, MerTK, or a combination thereof, which are capable of inducing phagocytosis by binding to a laminin G-like domain (or LG domain) of a phagocytic cell including, but not limited to, macrophages or microglial cells. In embodiments, the TAM receptor may be Axl receptor.

In embodiments, the first region may comprise Gas6, ProS1, Tubby, Tulp1, Gal3, or an active fragment thereof, which each is capable of specifically binding to a TAM receptor. The first region may be selected from Gas6, ProS1, or an active fragment thereof, which each is capable of specifically binding to a TAM receptor. In embodiments, the first region may comprise or consist essentially of Gas6 or an active fragment thereof that is capable of binding to TAM receptor. In embodiments, the first region comprising or consisting essentially of Gas6 or an active fragment thereof is capable of binding to Axl receptor.

In certain embodiments, the first region may comprise a laminin G-like domain of Gas6 or ProS1, or an active fragment thereof, which contains a laminin G-like domain as a phagocytosis-related bridging molecule which is abundantly expressed in various tissue, and thus is able to induce phagocytosis through a TAM receptor. In embodiments, the laminin G-like domain may comprise an LG1 domain, an LG2 domain, or a combination thereof, and may preferably include both an LG1 domain and an LG2 domain, which are able to induce phagocytosis by binding to the TAM receptor.

Exemplary embodiments are directed to a binding molecule or fusion molecule comprising a first region capable of binding to a TAM receptor and a second region capable of specifically binding to a target substance, said target substance being a substance of which aberrant accumulation in a living tissue is characteristic of or associated with a disease, wherein the first region and the second region are coupled to each other directly or via a linker, wherein the first region comprises
   (a) a TAM receptor ligand;
   (b) an anti-Axl antibody or an antigen-binding fragment thereof;
   (c) an anti-Tyro3 antibody or an antigen-binding fragment thereof; or
   (d) an anti-MerTK antibody or an antigen-binding fragment thereof, with proviso that when the first region comprises an anti-MerTK antibody or an antigen-binding fragment thereof, the molecule is not a bispecific antibody; or
   (e) combinations thereof.

According to some embodiments, the binding molecule may further comprise a scaffold bound to the first region, to the second, or to both of the first region and the second region at different positions.

In embodiments, the first region is a TAM receptor ligand and the TAM receptor ligand comprises a sequence selected from the group consisting of SEQ ID NOS: 1-113 or a sequence having at least 85% of sequence identity thereto.

In still some embodiments, the first region is capable of binding to an Axl receptor the first region capable of binding to an Axl receptor comprises one or more sequences selected from the group consisting of SEQ ID NO: 1, SEQ ID NO: 2, SEQ ID NO: 5, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, and SEQ ID NO: 87, or a sequence having at least 85% of sequence identity thereto.

In still some embodiments, the first region is capable of binding to an Axl receptor the first region capable of binding to an Axl receptor comprises the sequence of SEQ ID NO: 1 or a sequence having at least 85% of sequence identity thereto, and/or the sequence of SEQ ID NO: 2 or a sequence having at least 85% of sequence identity thereto.

In still another embodiment, the first region capable of binding to an Axl receptor the first region capable of binding to an Axl receptor comprises the sequence of SEQ ID NO: 5 or a sequence having at least 85% of sequence identity thereto.

In still some embodiments, the first region is capable of binding to an Axl receptor the first region capable of binding to an Axl receptor comprises one or more sequences selected from the group consisting of SEQ ID NO: 3, SEQ ID NO: 4, SEQ ID NO: 6, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO: 60, SEQ ID NO: 61, SEQ ID NO: 62, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO:

100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, and SEQ ID NO: 113, or a sequence having at least 85% of sequence identity thereto.

In still some embodiments, the first region is capable of binding to an Axl receptor the first region capable of binding to an Axl receptor comprises the sequence of SEQ ID NO: 3 or a sequence having at least 85% of sequence identity thereto, and/or the sequence of SEQ ID NO: 4 or a sequence having at least 85% of sequence identity thereto.

In still another embodiment, the first region capable of binding to an Axl receptor the first region capable of binding to an Axl receptor comprises the sequence of SEQ ID NO: 6 or a sequence having at least 85% of sequence identity thereto.

In embodiments, the fusion molecule (or binding molecule) may comprise the first region comprising the sequence of SEQ ID NO: 1, SEQ ID NO: 2, or a combination thereof, or a sequence having at least 85% sequence identity thereto. In an embodiment, the combination of the sequence of SEQ ID NO: 1 and SEQ ID NO: 2 may comprise the sequence of SEQ ID NO: 5 or a sequence having at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to SEQ ID NO: 5.

In embodiments, the fusion molecule (or binding molecule) may comprise the first region comprising the sequence of SEQ ID NO: 3, SEQ ID NO: 4, or a combination thereof, or a sequence having at least 85% sequence identity thereto. In an embodiment, the combination of the sequence of SEQ ID NO: 3 and SEQ ID NO: 4 may comprise the sequence of SEQ ID NO: 6 or a sequence having at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to SEQ ID NO: 6.

In embodiments, the fusion molecule (or binding molecule) may comprise the sequence of amino acid residues 31-871 of SEQ ID NO: 136, amino acid residues 31-687 of SEQ ID NO:138, amino acid residues 31-697 of SEQ ID NO:140, amino acid residues 31-684 of SEQ ID NO: 150, amino acid residues 31-676 of SEQ ID NO: 152, amino acid residues 25-673 of SEQ ID NO: 154, amino acid residues 22-662 of SEQ ID NO: 156, or amino acid residues 22-885 of SEQ ID NO: 158, amino acid residues 22-908 of SEQ ID NO: 162, amino acid residues 22-919 of SEQ ID NO: 163, amino acid residues 22-919 of SEQ ID NO: 165, or a sequence having at least 90% sequence identity thereto (wherein a different linker can be used in place the linkers as shown in Tables 3 and 5-10.

In embodiments, the first region comprising a laminin G-like domain of Gas6 or ProS1, or an active fragment thereof, does not comprise a Gla domain. Without being bound to a particular theory, it is expected that the lacking of Gla domain in the first region may make the fusion molecule not be able to recognize phosphatidylserine (PS) of TAM receptor, while the second region is able to induce phagocytosis by recognizing a target substance.

In some embodiments, the first region comprising a laminin G-like domain of Gas6 or ProS1, or an active fragment thereof, does not comprise a Gla domain and does not comprise an EGF domain. The lacking of EGF domain in the first region provides an advantage in the manufacturing process of the fusion molecule to increase the yield by suppressing an aggregation of the fusion molecule during the purification step. In some embodiments, the fusion molecule (or binding molecule) may form a homomultimer or a heteromultimer, or form a linear multimer as a single chain.

According to embodiments, the target substance that is to be cleared or decreased and to which the second region specifically binds, may be a substance that accumulates in living tissue, causing a disease. For example, it may be a substance accumulated in an affected (i.e., diseased) tissue of a patient or circulating in blood of a patient. The substance may be protein. That is, the disease may be, but not limited thereto, proteopathy. In certain embodiments, the target substance may be amyloid. That is, the proteopathy may be amyloidosis. The target substance may be one or more of the amyloid substances listed in Table 1 below or APOE or apoptosis-associated spec-like protein containing a caspase activating recruitment domain (ASC-speck), of which abnormal accumulation or deposit is associated with or characteristic of a disease, and in this case, the disease may be a disease in which each abnormally accumulated substance is detected. For example, the proteopathy may be Alzheimer's disease, Parkinson's disease, Huntington's disease, and Prion disease, and in this case, target substances may be β-amyloid, tau, α-synuclein, huntingtin, and prion proteins, respectively, which are identified as proteins of which abnormal accumulation causes the diseases. Aberrant accumulation of APOE is associated with Alzheimer's disease, cerebral amyloid angiopathy, and/or cardiovascular disease. Aberrant accumulation of apoptosis-associated spec-like protein containing a caspase activating recruitment domain (ASC-speck) is associated with Alzheimer's Disease, Parkinson's Disease, Huntington's disease, Multiple System Atrophy, Amyotrophic Lateral Sclerosis, Sinocerebellar ataxia. Frontotemporal Dementia, Frontotemporal Lobar Degeneration, Mild Cognitive Impairment, Parkinson-plus syndromes, Pick disease, Progressive isolated aphasia, Grey-matter degeneration [Alpers], Subacute necrotizing encephalopathy, and Lewy body dementia.

TABLE 1

| Target Substance | Abbreviation | Diseases associated with or characterized by aberrant accumulation of target substance |
|---|---|---|
| β-Amyloid | Aβ | Alzheimer's disease, Hereditary cerebral haemorrhage with amyloidosis, etc. |
| Amyloid precursor protein-derived β-amyloid | Aβ | Alzheimer's disease, Hereditary cerebral haemorrhage with amyloidosis, etc. |
| α-Synuclein | α-Syn | Parkinson's disease, Parkinson's dementia, dementia with Lewy bodies, multiple system atrophy, etc. |

TABLE 1-continued

| Target Substance | Abbreviation | Diseases associated with or characterized by aberrant accumulation of target substance |
|---|---|---|
| Prp$^{Sc}$ | PrP | Transmissible spongiform encephalopathy (fatal familial insomnia, Gerstmann-Straussler-Scheinker disease, Creutzfeldt-Jacob disease, new variant Creutzfeldt-Jacob disease, etc.), etc. |
| Microtubule-associated protein tau | Tau | Tauopathies (Pick's disease, progressive supranuclear palsy, corticobasal degeneration, frontotemporal dementia with parkinsonism linked to chromosome 17, argyrophilic grain disease, etc.), Alzheimer's disease, Parkinson's disease, etc. |
| Huntingtin exon 1 | HTT exon 1 | Huntington's disease, etc. |
| TAR DNA-binding protein 43 | TDP43 | Frontotemporal dementia, amyotrophic lateral sclerosis (ALS), etc. |
| Superoxide dismutase 1 | SOD1 | Amyotrophic lateral sclerosis (ALS), etc. |
| ABri peptide | bri | Familial British dementia |
| ADan peptide | dan | Familial Danish dementia |
| Immunoglobulin light-chain fragment | AL | Light-chain amyloidosis |
| Immunoglobulin heavy-chain fragment | AH | Heavy-chain amyloidosis |
| N-terminal fragment of serum amyloid A protein | AA | AA amyloidosis |
| Transthyretin | ATTR | Senile systemic amyloidosis, familial amyloid polyneuropathy, familial amyloid cardiomyopathy, leptomeningeal amyloidosis |
| β-2 microglobulin | Aβ2M | Dialysis-related amyloidosis, hereditary visceral amyloidosis |
| N-terminal fragment of apolipoprotein AI | AApoAI | ApoAI amyloidosis |
| C-terminally extended apolipoprotein AII | AApoAII | ApoAII amyloidosis |
| N-terminal fragment of apolipoprotein AIV | AApoAIV | ApoAIV amyloidosis |
| apolipoprotein C-II | AApoCII | ApoCII amyloidosis |
| apolipoprotein C-III | AApoCIII | ApoCIII amyloidosis |
| Gelsoliin fragment | AGel | Familial amyloidosis, Finnish type, Hereditary gelsolin amyloidosis |
| Lysozyme | ALys | Hereditary non-neuropathic systemic amyloidosis |
| Fibrinogen alpha chain fragment | AFib | Fibrinogen amyloidosis |
| N-terminally truncated cystatin C | ACys | Hereditary cerebral hemorrhage with amyloidosis, Icelandic type |
| Amylin, IAPP | IAPP | Diabetes mellitus type 2, insulinoma |
| Calcitonin | Cal | Medullary carcinoma of the thyroid |
| Atrial natriuretic factor | AANF | Cardiac arrhythmias, isolated atrial amyloidosis |
| Prolactin | PRL | Pituitary prolactinoma |
| Insulin | AIns | Localized amyloidosis at insulin injection sites |
| Lactadherin or medin | AMed | Aortic medial amyloidosis |
| Lactotransferrin or lactoferrin | LTF | Gelatinous drop-like corneal dystrophy |
| Odontogenic ameloblast-associated protein | ODAM | Calcifying epithelial odontogenic tumors |
| pulmonary surfactant-associated protein C | SPC | Pulmonary alveolar proteinosis |
| Leukocyte cell-derived chemotaxin-2 | ALECT2 | Renal LECT2 amyloidosis |
| Galectin-7 | Agal7 | Lichen amyloidosis, macular amyloidosis |
| Corneodesmosin | Cor | Hypotrichosis simplex of the scalp |
| C-terminal fragment of TGFBI (or keratoepithelin) | Ker | Lattice corneal dystrophy; type I, 3A or Avellino |
| SGI (Semenogelin-1) | ASem1 | Seminal vesicle amyloidosis |
| S100 protein (A8 or A9) | (no abbreviation) | Prostate cancer |
| Enfuvirtide | AEnf | Injection-localized amyloidosis |
| Apolipoprotein E | APOE | Alzheimer's disease, cerebral amyloid angiopathy, cardiovascular disease |

TABLE 1-continued

| Target Substance | Abbreviation | Diseases associated with or characterized by aberrant accumulation of target substance |
| --- | --- | --- |
| Apoptosis-associated Spec-like protein containing a Caspase Activating Recruitment Domain | ASC | Alzheimer's Disease, Parkinsons's Disease, Huntington's disease, Multiple System Atrophy, Amyotrophic Lateral Sclerosis, Sinocerebellar ataxia. Frontotemporal Dementia, Frontotemporal Lobar Degeneration, Mild Cognitive Impairment, Parkinson-plus syndromes, Pick disease, Progressive isolated aphasia, Grey-matter degeneration [Alpers], Subacute necrotizing encephalopathy, and Lewy body dementia |

In embodiments, the present disclosure is directed to a nucleic acid or polynucleotide encoding the fusion proteins described above.

In embodiments, the present disclosure is directed to a vector containing the nucleic acid or polynucleotide.

Embodiments are directed to a host cell containing the vector.

Another aspect of the present disclosure provides a method of producing a therapeutic fusion molecule for treatment of a disease or disorder associated with or characterized by aberrant accumulation of substance in a subject, comprising expressing the fusion molecule by culturing a host cell under a condition for expressing the fusion molecule.

In embodiments, the present disclosure is directed to a method of reducing or enhancing a reduction of aberrant deposit of substance that causes or characterizes certain disorder or diseases in a subject, which method comprises administering to the subject an effective amount of a fusion molecule or a polynucleotide encoding the fusion molecule, wherein the fusion molecule comprises a first region that is capable of binding to a TAM (Tyro3, Axl and MerTK) receptor on surface of a cell in the subject; and a second region that specifically binds to the substance. In non-limiting embodiments, the substance and the disease or disorder may be one or more of those listed in Table 1. In non-limiting embodiments, the fusion molecule does not have an effector function and does not induce Fc-mediated inflammatory responses. For example, the fusion molecule does not comprise a moiety to bind to an Fc receptor, and preferably may comprise an Fc region variant that does not bind to an Fc receptor (particularly an Fcγ receptor).

In embodiments, the present disclosure is directed to a method of removing or clearing or enhancing clearance of aberrant deposit of substance that causes or characterizes certain disorder or diseases in a subject, which method comprises administering to the subject an effective amount of a fusion molecule or a polynucleotide encoding the fusion molecule, wherein the fusion molecule comprises a first region that is capable of binding to a TAM (Tyro3, Axl and MerTK) receptor on surface of a cell in the subject; and a second region that specifically binds to the substance. In non-limiting embodiments, the substance and the disease or disorder may be one or more of those listed in Table 1. In non-limiting embodiments, the fusion molecule does not have an effector function and does not induce inflammatory responses. For example, the fusion molecule does not comprise a moiety to bind to an Fc receptor, and may comprise an Fc region variant that does not bind to an Fc receptor (particularly an Fcγ receptor).

In embodiments, the present disclosure is directed to a method of suppressing formation of aberrant accumulations of substance in a subject. The method comprises administering to the subject an effective amount of a fusion molecule or a polynucleotide encoding the fusion molecule, wherein the fusion molecule comprises a first region that is capable of binding to a TAM (Tyro3, Axl and MerTK) receptor on surface of a cell in the subject and a second region that specifically binds to the substance. In non-limiting embodiments, the substance and the disease or disorder may be one or more of those listed in Table 1. In non-limiting embodiments, the fusion molecule does not have an effector function and does not induce Fc-mediated inflammatory responses. For example, the fusion molecule does not comprise a moiety to bind to an Fc receptor, and preferably may comprise an Fc region variant that does not bind to an Fc receptor (particularly an Fcγ receptor).

In embodiments, the present disclosure is directed to a method of treating or preventing a disorder or disease in a subject, wherein the disorder or disease is characterized by or caused by aberrant accumulation of substance. The method comprises administering to the subject an effective amount of a fusion molecule or a polynucleotide encoding the fusion molecule, wherein the fusion molecule comprises a first region that is capable of binding to a TAM (Tyro3, Axl and MerTK) receptor on surface of a cell in the subject; and a second region that specifically binds to the substance. In non-limiting embodiments, the substance and the disease or disorder may be one or more of those listed in Table 1. In non-limiting embodiments, the fusion molecule does not have an effector function and does not induce Fc-mediated inflammatory responses. For example, the fusion molecule does not comprise a moiety to bind to an Fc receptor, and preferably may comprise an Fc region variant that does not bind to an Fc receptor (particularly an Fcγ receptor).

In embodiments, the present disclosure is directed to a method of delaying development of a symptom associated with a disease that is characterized by, associated with, or caused by aberrant accumulation of substance, in a subject. The method comprises administering to the subject an effective amount of a fusion molecule or a polynucleotide encoding the fusion molecule, a vector comprising the polynucleotide, wherein the fusion molecule comprises a first region that is capable of binding to a TAM (Tyro3, Axl and MerTK) receptor on surface of a cell in the subject; and a second region that specifically binds to the substance. In non-limiting embodiments, the substance and the disease or disorder may be one or more of those listed in Table 1. In non-limiting embodiments, the fusion molecule does not have an effector function and does not induce Fc-mediated inflammatory responses. For example, the fusion molecule does not comprise a moiety to bind to an Fc receptor, and preferably may comprise an Fc region variant that does not bind to an Fc receptor (particularly an Fcγ receptor).

In embodiments, the present disclosure provides a method of reducing a substance of which aberrant accumulation is associated with or characteristic of a disease or disorder, in a subject. The method comprises administering to the subject an effective amount of a fusion molecule or a polynucleotide encoding the fusion molecule, wherein the fusion molecule comprises a first region that is capable of binding to a TAM (Tyro3, Axl and MerTK) receptor on surface of a cell in the subject, and a second region that specifically binds to the substance. The substance may be soluble, oligomeric, or aggregated form. In some embodiments, the toxic effects of accumulated substance are inhibited and/or reduced. Thus, the method of the disclosure can be used to treat any disease in which accumulation of a substance is present or suspected. In non-limiting embodiments, the substance and the disease or disorder may be one or more of those listed in Table 1. In non-limiting embodiments, the fusion molecule does not have an effector function and does not induce Fc-mediated inflammatory responses. For example, the fusion molecule does not comprise a moiety to bind to an Fc receptor, and preferably may comprise an Fc region variant that does not bind to an Fc receptor (particularly an Fcγ receptor).

In the above methods, according to embodiments thereof, the aberrant deposits of substance are in the brain (brain tissue) of the subject. In some embodiments, the aberrant deposits of substance are in the cerebral vasculature. In some embodiments, the aberrant accumulation of substance is in the circulatory system. In some embodiments, the aberrant accumulation of substance is in various tissues such as heart, kidney, liver, and the like.

In embodiments, the present disclosure is directed to a pharmaceutical composition comprising an effective amount of any of the above-disclosed fusion molecule or polynucleotides encoding the fusion molecule, and a pharmaceutical acceptable excipient. In non-limiting embodiments, the fusion molecule does not have an effector function and does not induce Fc-mediated inflammatory responses. For example, the fusion molecule does not comprise a moiety to bind to an Fc receptor, and preferably may comprise an Fc region variant that does not bind to an Fc receptor (particularly an Fcγ receptor).

In embodiments, the present disclosure is directed to kits comprising an effective amount of any of the above-disclosed fusion molecule or polynucleotides encoding the fusion molecule. The kits are generally in suitable packaging and provided with appropriate instructions, are useful for any of the methods described herein.

These and other aspects, objects, features and advantages of the example embodiments will become apparent to those having ordinary skill in the art upon consideration of the following detailed description of illustrated example embodiments.

BRIEF DESCRIPTION OF DRAWINGS

In FIG. 1A, EGF stands for epidermal growth factor, Ig stands for immunoglobulin, LG stands for laminin G, and SHBG stands for sex hormone-binding globulin.

FIG. 1C through FIG. 1M schematically show non-limiting exemplary embodiments of the structure of the fusion molecules.

FIG. 13 shows results indicating that the beta-amyloid clearing ability of microglia was significantly increased by αAβ-Gas6.

FIG. 14 shows results indicating that the beta-amyloid clearing ability of astrocytes was significantly increased by αAβ-Gas6.

FIG. 17 shows the evaluation results for beta-amyloid plaque clearing ability of αAβ-Gas6 through administration of αAβ-Gas6 protein in 5×FAD Alzheimer's disease model mice.

FIG. 18 shows the evaluation results for beta-amyloid plaque clearing ability of αAβ-Gas6 through administration of αAβ-Gas6 virus in 5×FAD Alzheimer's disease model mice.

FIG. 19 shows results indicating that beta-amyloid contained in lysosomes were increased by microglia-mediated clearance in 5×FAD Alzheimer's disease model mice upon administration of αAβ-Gas6 protein.

FIG. 23 shows results indicating that microglia-mediated synapse engulfment that abnormally increased in 5×FAD Alzheimer's disease model mice due to the side effect of aducanumab was significantly restored upon administration of αAβ-Gas6 virus.

FIG. 25 shows an experimental protocol for evaluating cognitive and memory abilities in 5×FAD Alzheimer's disease model mice upon administration of αAβ-Gas6 virus.

FIG. 27 shows the evaluation results for tau clearing ability of αTau-Gas6 in the HMC3 cell line by in vitro tau engulfment assay.

FIG. 30 shows the evaluation results for beta-amyloid clearing ability of αAβ(Fab)-Gas6 in the HMC3 cell line by in vitro tau engulfment assay.

DETAILED DESCRIPTION

Figure 1A:
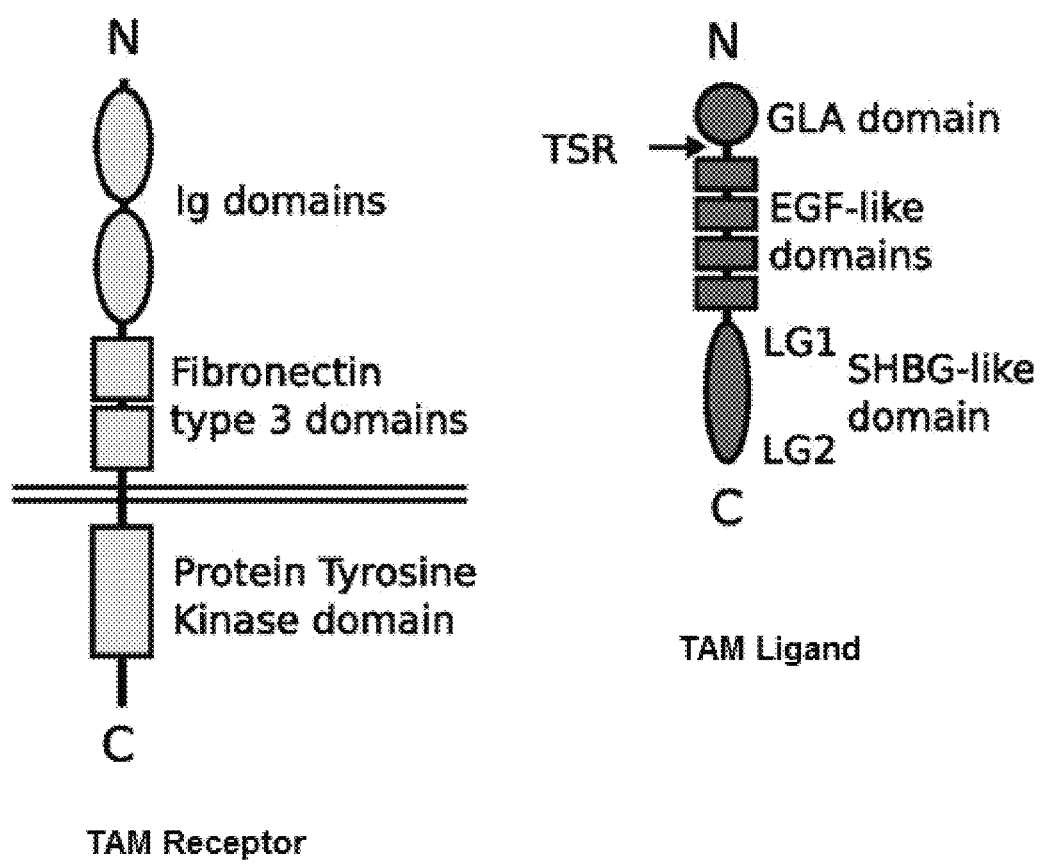
FIG. 1A schematically illustrates the structure of TAM receptors and TAM ligands. In the structure of TAM receptors: the N-terminal starts with 2 Ig-like domains, followed by 2 fibronectin type 3 domains, followed by a single-pass transmembrane domain and a protein tyrosine kinase at the C-terminal. In the structure of the TAM ligands protein S (Pros1) and Gas6, the N-terminal contains a GLA domain, followed by a thrombin-sensitive region (TSR), followed by 4 EGF-like domains, followed by a C-terminal (SHBG-like domain, consisting of 2 LG repeats.

Methods and compositions are provided for reducing or suppressing formation of or clearing a target substance of which accumulation is associated with or characteristic of a disorder or disease via a phagocytosis, preventing or treating an individual having a disease or disorder characterized by an aberrant accumulation of a substance, improving symptoms of a disease or disorder characterized by an aberrant accumulation of a substance, and/or a target substance of which accumulation is associated with or characteristic of a disorder or disease via a phagocytosis.

Where a range of values is provided, it is understood that each intervening value, to the tenth of the unit of the lower limit unless the context dearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Definitions

As used herein, the singular forms "a," "an," and "the," refer to both the singular as well as plural, unless the context clearly indicates otherwise. Therefore, for example, reference to "a cell" includes a plurality of such cells and reference to "the peptide" includes reference to one or more peptides and equivalents thereof, e.g. polypeptides, known to those skilled in the art, and so forth.

As used herein, the terms "about" and "consisting essentially of" refers to a value or composition that is within an acceptable error range for the particular value or composition as determined by one of ordinary skill in the art, which will depend in part on how the value or composition is measured or determined, i.e., the limitations of the measurement system. For example, "about" or "consisting essentially of" can mean within 1 or more than 1 standard deviation per the practice in the art. Alternatively, "about" or "consisting essentially of" can mean a range of up to 10% (i.e., ±10%). For example, "about 5 mg" can include any number between 4.5 mg and 5.5 mg (for 10%), between 4.75 mg and 6.25 mg (for 5%), between 4.8 mg and 6.2 mg (for 4%), between 4.85 mg and 6.15 mg (for 3%), between 4.9 mg and 6.1 mg (for 2%), or between 4.95 mg and 6.05 mg (for 1%). Furthermore, particularly with respect to biological systems or processes, the terms can mean up to an order of magnitude or up to 5-fold of a value. When particular values or compositions are provided in the application and claims, unless otherwise stated, the meaning of "about" or "consisting essentially of" should be assumed to be within an acceptable error range for that particular value or composition.

As used herein, "administration" or "administering" refers to the introduction of a composition into a subject by a chosen route. For example, if the chosen route is intravenous, the composition is administered by introducing the composition into a vein of the subject. In some examples, the peptides and antibodies disclosed herein are administered to a subject.

As used herein, "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

As used herein, "polypeptide," "oligopeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

As used herein, "polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5 and 3 terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, a-anomeric sugars, epimeric sugars such as arabinose, xyloses or lyxoses, pyranose sugars, furanose sugars, sedoheptulose, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S ("thiolate"), P(S)S ("dithioate"), "(O)NR$_2$ ("amidate"), P(O)R, P(O)OR', CO or CH$_2$ ("formacetyl"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

As used herein, "recipient", "individual", "subject", "host", and "patient", are used interchangeably herein and refer to any mammalian subject for whom diagnosis, treatment, or therapy is desired, particularly humans. "Mammal" for purposes of treatment refers to any animal classified as a mammal, including humans, domestic and farm animals, and zoo, sports, or pet animals, such as dogs, horses, cats, cows, sheep, goats, pigs, etc. In embodiments, the mammal is human.

As used herein, "antibody" refers to single chain, two-chain, and multi-chain proteins and glycoproteins belonging to the classes of polyclonal, monoclonal, chimeric and hetero immunoglobulins (monoclonal antibodies being preferred); it also includes synthetic and genetically engineered variants of these immunoglobulins.

As used herein, "specific binding," "specifically binds," and the like, refer to non-covalent or covalent preferential binding to a molecule relative to other molecules or moieties in a solution or reaction mixture (e.g., an antibody specifically binds to a particular polypeptide or epitope relative to other available polypeptides/epitopes). In some embodiments, the affinity of one molecule for another molecule to which it specifically binds is characterized by a KD (dissociation constant) of $10^{-5}$ M or less (e.g., $10^{-6}$ M or less, $10^{-7}$ M or less, $10^{-8}$ M or less, $10^{-9}$ M or less, $10^{-10}$ M or less, $10^{-11}$ M or less, $10^{-12}$ M or less, $10^{-13}$ M or less, $10^{-14}$ M or less, $10^{-15}$ M or less, or $10^{-16}$ M or less). "Affinity" refers to the strength of binding, increased binding affinity being correlated with a lower KD. As used herein, the "binding" and "specific binding" of the first region to TAM receptor and the second region to a target substance do not require modulating, changing, affecting, or modifying activity of the bound TAM receptor or the target substance.

As used herein, "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

"Fv" is the minimum antibody fragment, which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The term "complementarity determining region" or "CDR," as used herein, refers to the sequences of amino acids within antibody variable regions which confer antigen specificity and binding affinity. For example, in general, there are three CDRs in each heavy chain variable region (e.g., HCDR1, HCDR2, and HCDR3) and three CDRs in each light chain variable region (LCDR1, LCDR2, and LCDR3). The precise amino acid sequence boundaries of a given CDR can be determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273,927-948 ("Chothia" numbering scheme), or a combination thereof. Under the Kabat numbering scheme, in some embodiments, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under the Chothia numbering scheme, in some embodiments, the CDR amino acids in the VH are numbered 26-32 (HCDR1), 52-56 (HCDR2), and 95-102 (HCDR3); and the CDR amino acid residues in the VL are numbered 26-32 (LCDR1), 50-52 (LCDR2), and 91-96 (LCDR3). In a combined Kabat and Chothia numbering scheme, in some embodiments, the CDRs correspond to the amino acid residues that are part of a Kabat CDR, a Chothia CDR, or both. For instance, in some embodiments, the CDRs correspond to amino acid residues 26-35 (HCDR1), 50-65 (HCDR2), and 95-102 (HCDR3) in a VH, e.g., a mammalian VH, e.g., a human VH; and amino acid residues 24-34 (LCDR1), 50-56 (LCDR2), and 89-97 (LCDR3) in a VL, e.g., a mammalian VL, e.g., a human VL.

The "Fab fragment" also contains the constant domain of the light chain and the first constant domain (CH1) of the heavy chain. Fab fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab fragments which have hinge cysteines between them. Other chemical couplings of antibody fragments are also known.

As used herein, the term "antibody fragment" or "antigen-binding fragment" or "active fragment" is defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')2, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules, (2) single chain polypeptides containing only one light chain variable domain, or a fragment thereof that contains the three CDRs of the light chain variable domain, without an associated heavy chain moiety, (3) single chain polypeptides containing only one heavy chain variable region, or a fragment thereof containing the three CDRs of the heavy chain variable region, without an associated light chain moiety, (4) nanobodies comprising single Ig domains from non-human species or other specific single-domain binding modules; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s), and (5) an isolated complementarity determining region (CDR).

The terms "phagocytic cells" and "phagocytes" are used interchangeably herein to refer to a cell that is capable of phagocytosis. There are four main categories of phagocytes: macrophages, mononuclear cells (histiocytes and monocytes), polymorphonuclear leukocytes (neutrophils), and dendritic cells.

As used herein "chimeric" refers to a molecule that includes sequences derived from two different molecules.

The term "Fc region" is used to define a C-terminal region of an immunoglobulin heavy chain. The "Fc region" may be a native sequence Fc region or a variant Fc region. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The numbering of the residues in the Fc region is that of the EU index as in Kabat. Kabat et al., Sequences of Proteins of Immunological Interest, 5th Ed. Public Health Service, National Institutes of Health, Bethesda, Md., 1991. The Fc region of an immunoglobulin generally comprises two constant domains, CH2 and CH3, and when the Fc region is employed as a scaffold according to embodiments of the present disclosure, the Fc region may comprise CH2, CH3, or combinations thereof. The Fc region as a scaffold or in a heavy chain of an antibody may contain mutations. For example, heavy chain constant region or Fc region may contain substitutions selected from T250Q/M428L; M252Y/S254T/T256E+H433K/N434F; E233P/L234V/L235A/G236A+A327G/A330S/P331S; E333A; S239D/A330L/I332E; P257I/Q311; K326W/E333S; S239D/I332E/G236A; N297A; L234A/L235A; N297A+M252Y/S254T/T256E; K322A and K444A, wherein the numbering is according to the EU numbering (Edelman, G. M. et al., Proc. Natl. Acad. USA, 63, 78-85 (1969); www.imgt.org/IMGTScientific-Chart/Numbering/Hu_IGHGnber.html#refs).

As used herein, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIM (an "inhibiting receptor"), which have similar amino acid sequences that differ primarily in the cytoplasmic domains thereof.

A "native sequence Fc region" or "wile-type Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, at least about 91%, at least about 92%, at least about 93%, at least about 94%, at least about 95%, at least about 96%, at least about 97%, at least about 98%, at least about 99% sequence identity therewith.

A polynucleotide or polypeptide having a certain percent "sequence identity" to another polynucleotide or polypeptide, means that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web (www) at ncbi.nlm.nih.gov/BLAST. See, e.g., Altschul et al. (1990), J. Mol. Biol. 215:403-10. Another alignment algorithm is FASTA, available in the Genetics Computing Group (GCG) package. See also at ebi.ac.uk/Tools/sss/fasta/. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See Meth. Mol. Biol. 70:173-187 (1997). Also, the GAP program using the Needleman and Wunsch alignment method can be utilized to align sequences. See J. Mol. Biol. 48:443-453 (1970), doi: 10.1016/0022-2836 (70) 90057-4.

As used herein, an "effective dosage" or "effective amount" drug, compound, or pharmaceutical composition is an amount sufficient to effect beneficial or desired results. For prophylactic use, beneficial or desired results include results such as eliminating or reducing the risk, lessening the severity, or delaying the outset of the disease, including biochemical, histological and/or behavioral symptoms of the disease, its complications and intermediate pathological phenotypes presenting during development of the disease. For therapeutic use, beneficial or desired results include clinical results such as inhibiting, suppressing or reducing the formation of substance accumulation (non-limiting example may include amyloid plaques), reducing, removing, clearing amyloid plaques, improving cognition, reversing or slowing cognitive decline, sequestering or increasing soluble substance circulating in biological fluids, decreasing one or more symptoms resulting from the disease (biochemical, histological and/or behavioral), including its complications and intermediate pathological phenotypes presenting during development of the disease, increasing the quality of life of those suffering from the disease, decreasing the dose of other medications required to treat the disease, enhancing effect of another medication, delaying the progression of the disease, and/or prolonging survival of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "treatment" or "treating" is an approach for obtaining beneficial or desired results including clinical results. For purposes of this invention, beneficial or desired clinical results include, but are not limited to, one or more of the following: inhibiting, suppressing or reducing the formation of deposit of substance, reducing, removing, or clearing amyloid deposits, improving cognition, reversing or slowing cognitive decline, sequestering soluble substance circulating in biological fluids, reducing a substance (including soluble, oligomeric and deposited) in a tissue, inhibiting, slowing and/or reducing accumulation of substance in the tissue, inhibiting, slowing and/or reducing toxic effects of a substance peptide in a tissue, decreasing symptoms resulting from the disease, increasing the quality of life of those suffering from the disease, decreasing the dose of other medications required to treat the disease, delaying the progression of the disease, and/or prolonging survival of patients. The tissue may include brain of an individual.

The term "development" of a disease means the onset and/or progression of the disease within an individual. A disease development can be detectable using standard clinical techniques as described herein. However, development also refers to disease progression that may be initially undetectable. For purposes of this invention, progression refers to the biological course of the disease state, in this case, as determined by a standard neurological examination, patient interview, or may be determined by more specialized testing. A variety of these diagnostic tests include, but not limited to, neuroimaging, detecting alterations of levels of specific proteins in the serum or cerebrospinal fluid (e.g., amyloid peptides and Tau), computerized tomography (CT), and magnetic resonance imaging (MRI). "Development" includes occurrence, recurrence, and onset. As used herein "onset" or "occurrence" of a disease includes initial onset and/or recurrence.

As used herein, "delaying" development of a disease means to defer, hinder, slow, retard, stabilize, and/or postpone development of the disease. This delay can be of varying lengths of time, depending on the history of the disease and/or individual being treated. As is evident to one skilled in the art, a sufficient or significant delay can, in effect, encompass prevention, in that the individual does not develop the disease. For example, a method that delays development of a disease is a method that reduces probability of disease development in a given time frame and/or reduces extent of the disease in a given time frame, when compared to not using the method. Such comparisons are typically based on clinical studies, using a statistically significant number of subjects.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" includes any material which, when combined with an active ingredient, allows the ingredient to retain biological activity and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well-known conventional methods.

TAM Receptor

TAM receptors (Tyro3, Axl, and Mer) belong to a family of receptor tyrosine kinases that have important effects on homeostasis and inflammation. Also, they affect cell proliferation, survival, adhesion, and migration. TAM receptors comprise 2 immunoglobulin-like and 2 fibronectin type III repeats in their extracellular domains in tandem. This is connected to a single-pass transmembrane domain and a cytoplasmic protein tyrosine kinase. Left figure of FIG. 1A.

TAM receptors enhance phagocytosis of apoptotic cells, also known as efferocytosis.

The Axl protein contains 894 amino acids with a glycine-rich loop (Gly543-Gly548), a catalytic loop (His670-Asn677), and a DFG motif (Asp690-Phe691-Gly692). Although the molecular weight of the full-length Axl is 104 kDa, post-translational modifications of the extracellular domains give rise to two modified forms with molecular weights 120 and 140 kDa. Potential N-linked glycosylation sites include Asn43, Asn157, Asn198, Asn339, Asn345, and Asn401. In various embodiments of the present disclosure, the term "Axl" or "Axl receptor" or "Axl protein" includes the full-length Axl of 104 kDa, post-translational modified Axl, and glycosylated Axl. In some embodiments, the human Axl polypeptide corresponds to Genbank accession no. NP_068713 or NP_068713.2 (isoform 1 precursor), SEQ ID NO: 114, or UniProt accession no. P30530.4, Q8N5L2, or Q9UD27, or their mature forms. Amino acid residues 1-32 of SEQ ID NO: 114 is reported as signal sequence, and regions ranging amino acid residues 26 to 92 of SEQ ID NO: 114 is reported as interaction with Gas6. In one embodiment, the nucleic acid encoding the human Axl polypeptide corresponds to Genbank accession no. NM_021913, version no. NM_021913.5. Murine Axl refers to the Axl member of the murine TAM family of receptor tyrosine kinases. In some embodiments, the murine Axl polypeptide corresponds to Genbank accession no. AAH46618, version no. AAH46618.1, SEQ ID NO: 115. In one embodiment, the nucleic acid encoding the murine Axl polypeptide corresponds to Genbank accession no. BC046618, version no. BC046618.1. Various natural variants and mutations, and posttranslational variants and mutants of Axl as well as orthologues of Axl have been reported. For example, human Axl proteins under accession nos. NP_001265528.1 (626 amino acid residues), NP_001690.2 (885 amino acid residues, isoform 2 precursor), EAW57022 (885 amino acid residues, isoform CRA_a), EAW57023.1 (894 amino acid residues, isoform CRA_b), AAH32229.1 (894 amino acid residues), AAH32229.1 (885 amino acid residues), and the like are considered as "Axl" or "Axl receptor" or "Axl protein" according to the embodiments of the present disclosure.

The cells expressing the TAM receptor(s) may be at least one type of professional phagocytes, at least one type of non-professional phagocytes, or a combination thereof. Here, the professional phagocytes refer to cells whose main role is to remove dead cells and accumulated debris through phagocytosis, and examples thereof include macrophages, neutrophils, dendritic cells, and mast cells. Macrophages usually stay in each tissue that can become a path of infection, and in many cases, they are called different names for tissues, including, for example, adipose tissue macrophages, bone marrow or blood monocytes, hepatic Kupffer cells, lymph node sinus histiocytes, alveolar macrophages, connective tissue histiocytes or giant cells, microglia of the central nervous system, placental Hofbauer cells, renal intraglomerular mesangial cells, bone osteoclasts, epithelioid cells of granulomas, red pulp macrophages of the spleen, peritoneal macrophage of the peritoneal cavity, LysoMac of Peyer's patch, and the like. On the other hand, the non-professional phagocytes refer to cells that mainly perform functions specific to the tissue in which the phagocytes reside, but can perform phagocytosis when necessary, and examples thereof epithelial cells, endothelial cells, fibroblasts, mesenchymal cells, some tissue-specific cells, for example, astrocytes or oligodendrocyte of the central nervous system, retinal Muller glia, hepatocytes, muscular satellite cells, testicular Sertoli cells, etc., and some lymphocytes such as natural killer cells, large granular lymphocytes, eosinophils, basophils, B cells, etc. The fusion molecule according to the present disclosure is able to induce phagocytosis in phagocytes specific to a tissue in which a target substance to be cleared accumulates. For example, when abnormal proteins accumulated in the brain are to be cleared, the phagocytosis may be induced in astrocytes, microglia, oligodendrocytes, or combinations thereof. It may be induced, for example, by topically administering the fusion molecule according to the present disclosure to this tissue or by manipulating cells in the tissue to express and secrete the fusion molecule.

First Region Comprising a Sequence Capable of Binding to TAM Receptor

TAM receptors can be activated via their ligands, growth arrest specific 6 protein (Gas6) and Protein S (Pros1), which are members of the family of vitamin K-dependent proteins.

In exemplary embodiments, the first region that is capable of binding to TAM receptors may comprise, consist of, or consist essentially of one or more TAM ligands.

A TAM ligand, protein S contains an amino terminal γ carboxyglutamic acid (GLA) domain, followed by a thrombin-sensitive loop region and 4 epidermal growth factor-like domains ending with the carboxy-terminal (C-terminal), consisting of 2 laminin G repeats that together comprise the sex hormone-binding globulin domain (right figure of FIG. 1A). The C-terminal region is sufficient for TAM receptor binding and phosphorylation. Gas6 is a 75-kDa vitamin K-dependent protein and has high structural homology (~42%) with protein S and the modular composition is the same as shown in FIG. 1A.

In addition to Gas6 (SEQ ID NO: 7) and ProS1 (SEQ ID NO: 34), tubby (accession nos. P50607, U54644.1, AAB53494.1, U82467.1, AAB53699.1, CH471064.2, EAW68634.1, BC075031.2, AAH75031.1, BC075032.2, AAH75032.1, NP_003311.2, NP_813977.1, 1S31_A), tubby-like protein 1 (Tulp1) (accession nos. AAB53700.1, AAH32714.1, AAH65261.1, NP_001276324.1, AAB97966.1, EAX03840.1, EAX03839.1, BAJ84064.1, BAJ84063.1, AKU84911.1, NP_813977.1, NP_003311.2), and galectin-3 (Gal3) (accession nos. NP_002297, NP_002297.1) are reported as TAM receptor ligands. Tubby and Gal-3 specifically bind to Mer, whereas Tulp1 can activate all 3 of the TAM receptors.

Gas6, one of the ligands for TAM receptors, is reported to show the highest affinity for Axl compared to Tyro3 or Mer. Human Gas6 contains 678 amino acids (SEQ ID NO: 7), with gamma-carboxyglutamic acid (Gla) domains, four epidermal growth factor (EGF)-like domains, and two laminin G-like (LG) domains (FIG. 1A, right figure). Various isoforms of GAS6 are reported. For example, S6L, G8R, G8V, R14H, L18Q isoforms have been reported and these isoforms are included in the present disclosure.

In embodiments, the first region that is capable of binding to TAM receptor may comprise, consist of, or consist essentially of Gas6 protein or an active fragment thereof. The term "active fragment" as used herein denotes a fragment that is capable of binding to TAM receptor, in particular, Axl receptor. For example, an active fragment of Gas6 protein may comprise, consist of, or consist essentially of the sequence of SEQ ID NO: 1, 2, 5, 8, 9, 10, 11, 12, 13, 14, 15, 16, 17, 18, 19, 20, 21, 22, 23, 24, 25, 26, 27, 28, 29, 30, 31, 32, 33, 63, 64, 65, 66, 67, 68, 69, 70, 71, 72, 73, 74, 75, 76, 77, 78, 79, 80, 81, 82, 83, 84, 85, 86, or 87. For example, an active fragment of ProS protein may comprise, consist of, or consist essential of the sequence of SEQ ID NO: 3, 4, 6, 35, 36, 37, 38, 39, 40, 41, 42, 43, 44, 45, 46, 47, 48, 49, 50, 51, 52, 53, 54, 55, 56, 57, 58, 59, 60, 61, 62, 88, 89, 90, 91, 92, 93, 94, 95, 96, 97, 98, 99, 100, 101, 102, 103, 104, 105, 106, 107, 108, 109, 110, 111, 112, or 113. The present disclosure encompass the sequences having sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the sequence of any one of SEQ ID NOs. Sequences of SEQ ID NOS: 8-23 show sequence identity of at least 85% to SEQ ID NO: 1 (LG-1 domain of Gas6). Sequences of SEQ ID NOS: 24-33 show sequence identity of at least 85% to SEQ ID NO: 2 (LG-2 domain of Gas6). Sequences of SEQ ID NOS: 35-45 show sequence identity of at least 85% to SEQ ID NO: 3 (LG-1 domain of ProS). Sequences of SEQ ID NOS: 46-62 show sequence identity of at least 85% to SEQ ID NO: 4 (LG-2 domain of ProS). Sequences of SEQ ID NOS: 63-87 show sequence identity of at least 85% to SEQ ID NO: 5 (LG domains of Gas6). Sequences of SEQ ID NOS: 88-113 show sequence identity of at least 84% to SEQ ID NO: 6 (LG domains of ProS).

In other embodiments, the first region may comprise, consist, or consist essentially of variable region or CDRs of an anti-Axl antibody or a full-length anti-Axl antibody of which the effector function, in particular, Fc receptor-binding function is abolished or removed. The antibody or antigen-binding fragments may bind to extracellular domain of Axl, for example expressed on surface of phagocytic cells and induce internalization and phagocytosis without involving inflammatory reaction, in particular Fc-mediated inflammatory reaction. Non-limiting examples of anti-Axl antibody may include those described in, for example, WO2017200493A1, WO2015193430A1, WO2011159980A1, WO2016097370A1, WO2012175691A1, WO2015193428A1, WO2010131733A1, WO2017220695A1, WO2010130751A1, WO2016166302A1, WO2017009258A1, WO2016005593A1, and the like, all of which the contents are incorporated by reference herein in their entireties. According to embodiments of the present disclosure, whole antibody, variable region, CDRs, or scFv, F(ab), or F(ab') of those anti-Axl antibodies may be employed as the first region of the fusion molecule. In certain embodiments, anti-Axl antibody may be anti-Axl agonistic antibodies or antigen-binding fragments thereof. The antibody or an antigen-binding fragment thereof may be selected from among, for example, i) immunoglobulins such as IgG1, IgG2, IgG3 and IgG4; ii) native antibody fragments such as Fv, Fab, Fab', F(ab')2, VHH, VNAR, etc.; and iii) engineered antibodies such as scFv, dsFv, ds-scFv, (scFv)2, diabody, triabody, tetrabody, pentabody, etc. The antibody or antigen-binding fragment thereof may be, for example, a Mab, Fab, or single-chain variable fragment (scFv) based on an antibody that specifically binds to a corresponding target substance, or six complementarity-determining regions (CDRs) derived from the antibody.

In other embodiments, the first region may comprise, consist, or consist essentially of variable region or CDRs of an anti-MerTK (Mer Tyrosine Kinase) antibody or a full-length anti-MerTK antibody of which the effector function, in particular, Fc receptor-binding function is abolished or removed. The antibody or antigen-binding fragments may bind to extracellular domain of MerTK, for example expressed on surface of phagocytic cells and induce internalization and phagocytosis without involving inflammatory reaction, in particular Fc-mediated inflammatory reaction. Non-limiting examples of anti-MerTK antibody may include those described in, for example, WO2016106221A1, WO2020076799A1, WO2020176497A1, and the like, all of which the contents are incorporated by reference herein in their entireties. According to embodiments of the present disclosure, whole antibody, variable region, CDRs, or scFv, F(ab), or F(ab') of those anti-MerTK antibodies may be employed as the first region of the fusion molecule. The antibody or an antigen-binding fragment thereof may be selected from among, for example, i) immunoglobulins such as IgG1, IgG2, IgG3 and IgG4; ii) native antibody fragments such as Fv, Fab, Fab', F(ab')2, VHH, VNAR, etc.; and iii) engineered antibodies such as scFv, dsFv, ds-scFv, (scFv)2, diabody, triabody, tetrabody, pentabody, etc. The antibody or antigen-binding fragment thereof may be, for example, a Mab, Fab, or single-chain variable fragment (scFv) based on an antibody that specifically binds to a corresponding target substance, or six complementarity-determining regions (CDRs) derived from the antibody.

In other embodiments, the first region may comprise, consist, or consist essentially of variable region or CDRs of an anti-Tyro3 antibody or a full-length anti-Tyro3 antibody of which the effector function, in particular, Fc receptor-binding function is abolished or removed. The antibody or antigen-binding fragments may bind to extracellular domain of Tyro3, for example expressed on surface of phagocytic cells and induce internalization and phagocytosis without involving inflammatory reaction, in particular Fc-mediated inflammatory reaction. Non-limiting examples of anti-Tyro3 antibody may include those described in, for example, WO2016166348A1, and the like, all of which the contents are incorporated by reference herein in their entireties. According to embodiments of the present disclosure, whole antibody, variable region, CDRs, or scFv, F(ab), or F(ab') of those anti-Tyro3 antibodies may be employed as the first region of the fusion molecule. The antibody or an antigen-binding fragment thereof may be selected from among, for example, i) immunoglobulins such as IgG1, IgG2, IgG3 and IgG4; ii) native antibody fragments such as Fv, Fab, Fab', F(ab')2, VHH, VNAR, etc.; and iii) engineered antibodies such as scFv, dsFv, ds-scFv, (scFv)2, diabody, triabody, tetrabody, pentabody, etc. The antibody or antigen-binding fragment thereof may be, for example, a Mab, Fab, or single-chain variable fragment (scFv) based on an antibody that specifically binds to a corresponding target substance, or six complementarity-determining regions (CDRs) derived from the antibody.

The peptide comprising the sequence of any one of SEQ ID Nos above includes not only the amino acid sequence of the peptide but also an amino acid sequence variant thereof. The term "sequence variant" refers to a protein having a sequence in which one or more amino acid residues differ from the amino acid sequence. As long as the activity of the fusion molecule is maintained, any truncation, deletion, insertion, substitution, or a combination thereof in the final structure of the protein is possible. One example of the sequence variant is a form in which amino acid residues at sites not essential for activity are truncated or deleted, or amino acid residues at sites important for autoinhibition are substituted. In some cases, it may also be modified by phosphorylation, glycosylation, methylation, farnesylation, or the like. These sequence variations and modifications are more preferable when the function and/or stability (thermal stability, pH stability, structural stability, etc.) and/or solubility of the protein are increased by mutation in the amino acid sequence.

The method for mutagenesis of the amino acid sequence is based on a method of producing a nucleic acid molecule comprising a nucleotide sequence corresponding to the amino acid sequence to be mutated by mutating a nucleotide sequence encoding the protein, and a method for obtaining the gene encoding the protein may be performed in vivo or in vitro using any mutagenesis technique well known in the art, for example, site-directed mutagenesis (Hutchinson et al., *J. Biol. Chem.*, 253:6551, 1978; Zoller and Smith, *DNA*, 3:479-488, 1984; Oliphant et al., *Gene*, 44:177, 1986; Hutchinson et al., Proc. Natl. Acad. Sci. U.S.A., 83:710, 1986), TAB linker (Pharmacia), PCR technique (Higuchi, 1989, "Using PCR to Engineer DNA" in *PCR Technology: Principles and Applications for DNA Amplification*, H. Erlich, ed., Stockton Press, Chapter 6, pp. 61-70), or the like.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the serum half-life of the antibody.

Examples of modified polypeptides include polypeptides with conservative substitutions of amino acid residues, one or more deletions or additions of amino acids which do not significantly deleteriously change the functional activity, or use of chemical analogs.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 2 under the heading of "conservative substitutions". If such substitutions result in a change in biological activity, then more substantial changes, denominated "exemplary substitutions" in Table 2, or as further described below in reference to amino acid classes, may be introduced and the products screened.

TABLE 2

Amino acid substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Leu | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

Non-polar: Norleucine, Met, Ala, Val, Leu, Ile;
Polar without charge: Cys, Ser, Thr, Asn, Gln;
Acidic (negatively charged): Asp, Glu;
Basic (positively charged): Lys, Arg;
Residues that influence chain orientation: Gly, Pro; and
Aromatic: Trp, Tyr, Phe, His.

Non-conservative substitutions are made by exchanging a member of one of these classes for another class. Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR domain. In still other embodiments, the CDR domain is CDR H3 and/or CDR L3.

Target Substances and Diseases Characterized by Aberrant Accumulation or Deposit of Target Substances The target substance may be a substance that accumulates in living tissue, causing a disease. For example, it may be a substance accumulated in an affected (i.e., diseased) tissue of a patient. The substance accumulated in a disease may be protein. That is, the disease may be proteopathy, without being limited thereto. For example, the target substance may be amyloid. That is, the proteopathy may be amyloidosis. The target substance may be selected from abnormally accumulated substances listed in Table 1 above, and in this case, the disease may be a disease in which each abnormally accumulated substance is detected. In some embodiments, the target substance, of which aberrant accumulation is associated with proteopathy and which is desired to be cleared or reduced or suppressed, may be APOE or apoptosis-associated spec-like protein containing a caspase activating recruitment domain (ASC-speck). For example, the proteopathy may be selected from Alzheimer's disease, Parkinson's disease, Huntington's disease, and Prion disease, and in this case, target substances may be abnormally accumulated proteins that cause the diseases. That is, the target substances may be β-amyloid, tau, α-synuclein, huntingtin, and prion proteins, respectively.

Aberrant accumulation of APOE is associated with Alzheimer's disease, cerebral amyloid angiopathy, and/or cardiovascular disease. Aberrant accumulation of apoptosis-associated spec-like protein containing a caspase activating recruitment domain (ASC-speck) is associated with Alzheimer's Disease, Parkinson's Disease, Huntington's disease, Multiple System Atrophy, Amyotrophic Lateral Sclerosis, Sinocerebellar ataxia. Frontotemporal Dementia, Frontotemporal Lobar Degeneration, Mild Cognitive Impairment, Parkinson-plus syndromes, Pick disease, Progressive isolated aphasia, Grey-matter degeneration [Alpers], Subacute necrotizing encephalopathy, and Lewy body dementia.

Second Region of Fusion Molecule

The second region that specifically binds to the target substance may be selected from among an antibody, an antigen-binding fragment thereof, an antibody-like protein, a peptide, an aptamer, and a soluble receptor, and is not particularly limited as long as it specifically binds to the target substance.

Here, the antibody or an antigen-binding fragment thereof may be selected from among, for example, i) immunoglobulins such as IgG1, IgG2, IgG3 and IgG4; ii) native antibody fragments such as Fv, Fab, Fab', F(ab')2, VHH, VNAR, etc.; and iii) engineered antibodies such as scFv, dsFv, ds-scFv, (scFv)2, diabody, triabody, tetrabody, pentabody, etc. The antibody or antigen-binding fragment thereof may be, for example, a Mab, Fab, or single-chain variable fragment (scFv) based on an antibody that specifically binds to a corresponding target substance, or six complementarity-determining regions (CDRs) derived from the antibody. That is, the protein or antigen-binding fragment thereof that specifically binds to the target substance comprises a portion necessary for an activity that specifically binds to the target substance, and the type or range thereof is not particularly limited as long as the protein or antigen-binding fragment thereof is linked to the first region and does not cause an inflammatory response and synaptic damage. For example, the target substance may be beta-amyloid, and in this case, the protein or antigen-binding fragment thereof that specifically binds to the target substance may comprise aducanumab or a single-chain variable fragment thereof. The second region comprise a Mab, Fab, or single-chain variable fragment based on based on six complementarity determining regions (CDRs) derived from commercially available antibodies such as aducanumab, semorinemab, and cinpanemab.

In non-limiting exemplary embodiments, the sequence information of the target substance can be obtained from public database and the target substance-binding sequences can be obtained from the publications or public database. By way of exemplary embodiments, some sequences from the public database are exemplified below. One skilled art should understand that sequences of target substance or a second region capable of binding to the target substance are not limited to the specific sequences exemplified below, but encompass isomers, orthologues, variants, and mutants. For example, when Amyloid precursor protein-derived β-amyloid is a target substance, the target subject may have the sequence available under GenBank accession no. AAB29908.1 or a fragment thereof (e.g., beta-amyloid (29-40) or a Chain A (Accession No. 1BJC_A)), and the second region that is capable of binding to the target substance can have a light chain variable region of SEQ ID NO: SEQ ID NO: 161 and a heavy chain variable region of SEQ ID NO: 162. When the target substance is α-Synuclein, it can have the sequence available under UniProtKB/Swiss-Prot: P37840.1 or a fragment thereof, and the second region capable of binding to the target substance may have light chain variable region of SEQ DI NO: 163 and a heavy chain variable region of SEQ ID NO: 164. When the target substance is Microtubule-associated protein tau, it can have the sequence available under UniProtKB/Swiss-Prot: P10636.5 or a fragment thereof, and the second region capable of binding to the target substance may have light chain variable region of SEQ DI NO: 165 and a heavy chain variable region of SEQ ID NO: 166. When the target substance is PrP$^{Sc}$, it can have the sequence available under GenBank Accession No. NP_001073592.1 or a fragment thereof, and the second region capable of binding to the target substance may be the sequences disclosed in US 2021/0070870 A1. When the target substance is Huntingtin exon 1, it can have the sequence available under GenBank Accession No. NP_001375421.1 or a fragment thereof, and the second region capable of binding to the target substance may be the sequences disclosed in US 2022/0332808 A1. When the target substance is TAR DNA-binding protein 43

(TDP43), it can have the sequence available under UniProtKB/Swiss-Prot: Q13148.1 or a fragment thereof, and the second region capable of binding to the target substance may be the sequences disclosed in U.S. Pat. No. 9,587,014 B2. When the target substance is superoxide dismutase 1 (SOD1), it can have the sequence available under GenBank: CAG46542.1 or a fragment thereof, and the second region capable of binding to the target substance may be the sequences disclosed in U.S. Pat. No. 9,283,271 B2. When the target substance is an immunoglobulin light-chain fragment, it can have the sequence available under PDB: 6Z1O_A or a fragment thereof, and the second region capable of binding to the target substance may be the sequences disclosed in U.S. Pat. No. 8,268,973 B2. When the target substance is an N-terminal fragment of serum amyloid A protein, it can have the sequence available under GenBank: AAB24060.1, GenBank: AAA85338.1, NCBI NP_001372595.1, or NCBI Reference Sequence: NP_110381.2 or a fragment thereof, and the second region capable of binding to the target substance may be the sequences disclosed in U.S. Pat. No. 8,268,973 B2. When the target substance is a transthyretin, it can have the sequence available under UniProtKB/Swiss-Prot: P02766.1 or a fragment thereof, and the second region capable of binding to the target substance may be the sequences disclosed in U.S. Pat. No. 11,267,877 B2. When the target substance is an amylin, IAPP (AIAPP), it can have the sequence available under UniProtKB/Swiss-Prot:P10997 or a fragment thereof, and the second region capable of binding to the target substance may be the sequences disclosed in U.S. Pat. No. 10,882,902. When the target substance is an APOE, it can have the sequence available under UniProtKB/Swiss-Prot:P02649.1 or a fragment thereof, and the second region capable of binding to the target substance may be the sequences disclosed in US 2022/0411485A. When the target substance is an Apoptosis-associated Spec-like protein containing a Caspase Activating Recruitment Domain (ASC-speck), it can have the sequence available under UniProtKB/Swiss-Prot:Q9ULZ3.2 or a fragment thereof (e.g., US 2021/0079075A), and the second region capable of binding to the target substance may be the sequences disclosed in US No. 10,961,3-6 B22021/0079075A.

The antibody or antigen-binding fragment thereof may not comprise an Fc region, and preferably may comprise an Fc region variant that does not bind to an Fc receptor (particularly an Fcγ receptor). This Fc region variant may serve to improve properties such as purification. Fc variants with a reduced affinity to the human FcγRIIIA and/or FcγRIIA and/or FcγRI compared to a IgG Fc region by way of amino acid substitution are disclosed for example, WO2012130831 and U.S. Pat. No. 8,753,628, of which entire content is incorporated by reference herein. Fc regions may be aglycosylated or deglycosylated.

The antibody-like protein refers to a protein scaffold capable of specifically binding to a target substance, like an antibody. Antibody-like proteins may be designed to have a size of about 2 to 20 kDa, which is smaller than antibodies (about 150 kDa on average), and thus target a binding site that antibodies cannot reach. It is known that antibody-like proteins are more stable at high temperatures than antibodies and are much easier to synthesize using non-mammalian cells such as viruses and yeast or synthesize chemically, compared to antibodies.

As used herein, the term "aptamer" refers to a single-stranded DNA (ssDNA) or RNA having high specificity and affinity for a specific substance. Aptamers have a very high affinity for specific substances, are stable, may be synthesized in a relatively simple way, may be modified in various ways to increase the binding affinity thereof, and can target cells, proteins, and even small organic substances. Thus, the aptamers are characterized by having very high specificity and stability compared to antibodies that have already been developed. In addition, the aptamer may be produced through a known SELEX (Systematic Evolution of Ligands by Exponential enrichment) method. As this aptamer, an aptamer that specifically binds to, for example, beta-amyloid, tau, or alpha-synuclein, may be produced through a known SELEX (Systematic Evolution of Ligands by Exponential enrichment) method and then linked to the first region, thereby producing the fusion molecule according to the present invention.

The aptamer of the present disclosure is not limited as long as it is able to specifically bind to beta-amyloid, tau, or alpha-synuclein, and bases that are used for the aptamer may be selected from among A, G, C, U, and deoxy forms thereof, unless otherwise specified.

In addition, the aptamer may be modified by linkage of at least one, selected from the group consisting of polyethylene glycol (PEG), inverted deoxythymidine (idT), locked nucleic acid (LNA), 2'-methoxy nucleoside, 2'-amino nucleoside, 2'F-nucleoside, amine linker, thiol linker, and cholesterol, at the 5'-end region, intermediate region, 3'-end region, or both ends thereof in order to increase the stability thereof. Inverted deoxythymidine (idT) is a molecule that is generally used to prevent nuclease degradation of an aptamer having weak nuclease resistance. In the case of a nucleic acid unit, the 3'-OH of the previous nucleotide is attached to the 5'-OH of the next nucleotide to form a chain, but in the case of idT, the 3'-OH of the previous nucleotide to attached the 3'-OH of the next unit so that 5'-OH, not 3'-OH, is exposed. Thus, idT is a molecule that has the effect of inhibiting degradation by 3' exonuclease, a type of nuclease. In exemplary embodiments, aptamers against beta-amyloid include, but are not limited to, those reported in Yan Zheng, Advances in aptamers against Aβ and applications in Aβ detection and regulation for Alzheimer's disease, Theranostics, 2022; 12(5): 2095-2114, of which the content is incorporated by reference herein in its entirety.

The soluble receptor of the present disclosure comprises a domain having an activity capable of binding to a target substance, that is, an endogenous ligand, wherein the domain may be one derived from an endogenous membrane receptor or an intracellular receptor, or a derivative thereof. In this case, the soluble receptor comprised in the second region of the fusion molecule of the present disclosure may preferably be one in which regions having activities other than binding to a target substance have been removed from the endogenous receptor. Exemplary soluble receptors that bind to beta-amyloid are reported by John E. Donahue et al., RAGE, LRP-1, and amyloid-beta protein in Alzheimer's disease, Acta Neuropathol (2006) 112:405-415, of which the content is incorporated by reference herein in its entirety.

In the embodiments, the peptide as a second region, means an entity other than the antibody or an active fragment thereof, antibody-like protein or soluble receptor among polypeptides having amino acids as monomers capable of binding specifically to a target substance. Various peptides that bind to beta amyloid are reported in, for example, Alexander L. Schwarzman, Selection of peptides binding to the amyloid b-protein reveals potential inhibitors of amyloid formation, Amyloid, December 2005; 12(4): 199-209, of which the content is incorporated by reference herein in its entirety.

Since the fusion molecule according to the present disclosure induces phagocytosis through interaction with the TAM receptor(s), the phagocytosis may be induced in cells expressing the TAM receptor(s). Phagocytosis generally means ingestion of cells or particles of 0.5 μm or more in size, and includes a process of tethering, engulfing, and degrading the cells or particles. In this case, phagocytosis forms a phagosome that surrounds the internalized cell or particle, and includes degradation within the phagolysosome by fusion of the phagosome and the lysosome. In phagocytosis, the process of cell death by apoptosis or necrosis is also referred to as efferocytosis.

Fusion Molecule or Binding Molecule

The induction of phagocytosis by the fusion molecule according to the present disclosure may not involve an inflammatory response. This enables clearance of the target substance without inducing an inflammatory response and tissue damage caused by an inflammatory response to be suppressed so that tissue dysfunction caused by accumulation of the target substance can be treated more safely than conventional techniques.

According to the embodiments, the fusion molecule or the binding molecule does not contain the target substance or a fragment thereof, to which the first region binds.

The first region and the second regions, described above, are coupled to each other directly or via a linker, to form a fusion molecule. Embodiments of the fusion molecule according to the present disclosure encompass monomers of a polypeptide comprising the first region and the second region in a single chain as well as multimers composed of two or more polypeptide chains. Multimers encompass various forms of multimers such as homo-multimers and hetero-multimers. Therefore, according to the embodiments, the fusion molecule may have a monovalent first region (i.e., having one binding site to a single TAM receptor) or a multivalent first region(s) (i.e., having multiple first regions or having one single first region capable of binding to two or more TAM receptors). Embodiments of the fusion molecule according to the present disclosure may have a monovalent second region (i.e., having one binding site to a single target substance) or a multivalent second region(s) (i.e., having multiple second regions each binding different target substances or having one single second region capable of binding to two or more target substances). Embodiments of the fusion molecule according to the present disclosure may a monovalent first region and a monovalent second region; a monovalent first region and a multivalent second region; or a multivalent first region and a multivalent second region.

Schematic depiction of non-limiting exemplary embodiments of the fusion molecules are shown in FIGS. 1C through 1M.

Figure 1B:
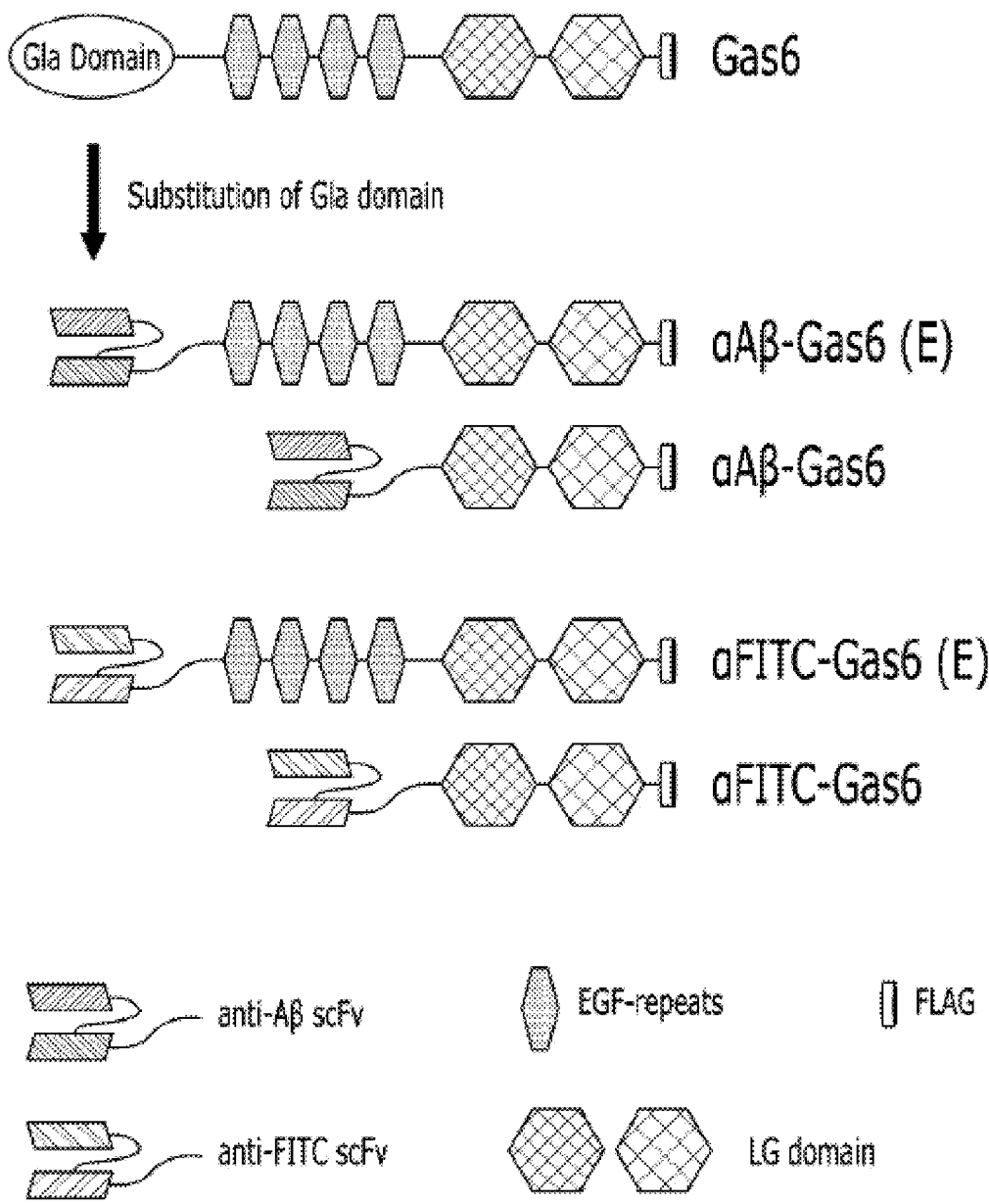
FIG. 1B schematically shows beta-amyloid- and FITC-binding phagocytosis inducing fusion molecule comprising Gas6 as a non-limiting example of first region of the fusion molecule.
Figure 1C:
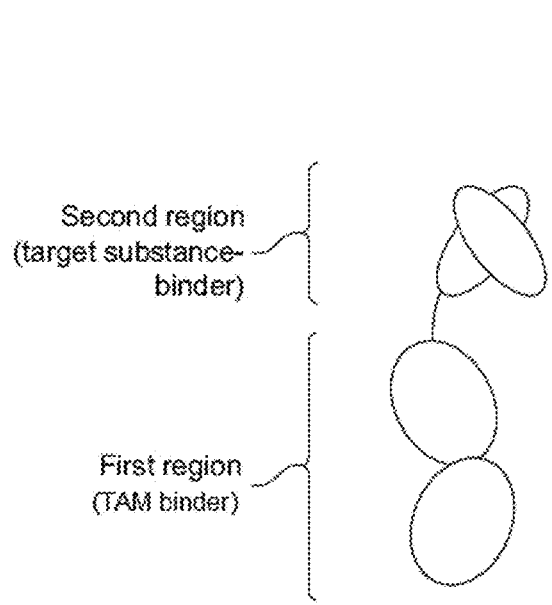

FIG. 1C depicts fusion molecules comprising a first region and a second region coupled to each other. The first region of FIG. 1C may be any one of the first region described above, which is capable of binding to a TAM receptor. The first region may be a single TAM ligand or an antibody or antigen-binding fragment thereof. The first region may be of a plurality of same or different TAM binders. Similarly, the second region of FIG. 1C may be any one of the second region described above, which is capable of binding to a target substance. The second region may be a single target substance binder. The second region may be of a plurality of same or different target substance binders. A fusion molecule may comprise a scFv, Fab, nanobody, or antibody as a first region and a scFv, Fab, nanobody, or antibody as a second region, a TAM ligand or a fragment thereof as a first region and a scFv, Fab, nanobody, or antibody as a second region, a scFv, Fab, nanobody, or antibody as a first region and a ligand or receptor or an aptamer as a second region, and the like. For example, a scFv, Fab, or nanobody as a first region or a second region may be a part of an antibody as a second region or a first region, forming a bispecific or multispecific antibody as a fusion molecule. A single or tandem of a scFv, Fab, or nanobody as a first or a second region may be linked to a whole antibody as a second or a first region. When the fusion molecule is a form of bispecific antibody, the first region is not an anti-MerTK antibody or a fragment thereof. The fusion molecule may be of a monomeric structure, a tandem structure where the first region, the second region, or the entire fusion molecule are repeated, or a multimeric structure containing two or more peptide chains. In case of multimeric fusion molecules, individual peptide chain may have a same sequence (homomultimer) or different sequences (heteromultimer), For heteromultimeric fusion molecules, the first region and the second region may present in all of the plural peptide chains forming the multimeric structure, or in different peptide chains, respectively, or a part of the plural peptide chains has both the first and the second region and the other(s) of the plural peptide chains has only either of the first region or the second region. While not shown in FIG. 1C, the fusion molecule may comprise one or more linker to couple the first region and the second region.

FIGS. 1D-1M depict fusion molecules comprising a first region and a second region as well as a scaffold. The first region, second region, and scaffold are as those described in this disclosure. As depicted in FIGS. 1D-1M, the scaffold may be bond to the first region and/or second region at different positions. The first region of FIGS. 1D-1M may be any one of the first region described above, which is capable of binding to a TAM receptor. The first region may be a single TAM ligand or an antibody or antigen-binding fragment thereof. The first region may be of a plurality of same or different TAM binders. Similarly, the second region of FIGS. 1C-1M may be any one of the second region described above, which is capable of binding to a target substance. The second region may be a single target substance binder. The second region may be of a plurality of same or different target substance binders. A fusion molecule may comprise a scFv, Fab, nanobody, or antibody as a first region and a scFv, Fab, nanobody, or antibody as a second region, a TAM ligand or a fragment thereof as a first region and a scFv, Fab, nanobody, or antibody as a second region, a scFv, Fab, nanobody, or antibody as a first region and a ligand or receptor or an aptamer as a second region, and the like. For example, a scFv, Fab, or nanobody as a first region or a second region may be a part of an antibody as a second region or a first region, forming a bispecific or multispecific antibody as a fusion molecule. A single or tandem of a scFv, Fab, or nanobody as a first or a second region may be linked to a whole antibody as a second or a first region. When the fusion molecule is a form of bispecific antibody, the first region is not an anti-MerTK antibody or a fragment thereof. The fusion molecule may be of a monomeric structure, a tandem structure, or a multimeric structure containing two or more peptide chains. In case of multimeric fusion molecules, individual peptide chains may have a same sequence (homomultimer) or different sequences (heteromultimer). In case of heteromultimeric fusion molecules, the first region and the second region may present in all of the plural peptide chains forming the multimeric structure, or in different peptide chains, respectively, or a part of the plural peptide chains has both the first and the second region and the other(s) of the plural peptide chains has only either of the first region or the second region. While not shown in FIGS. 1D-1M, the fusion molecule may comprise one or more linker to couple the first region, the second region, and/or the scaffold.

The fusion molecule may further comprise a tag. When such a label is added to the fusion molecule, it may be used to check the purification, expression, action or mechanism of action of the fusion molecule.

Examples of the tag include, but are not limited to, His-tag, T7-tag, S-tag, FLAG-tag, Strep-tag, thioredoxin (Trx)-tag, His-patch thioredoxin-tag, lacZ (L-galactosidase)-tag, chloramphenicol acetyltransferase-tag, trpE-tag, avidin/streptavidin/Strep-tag, T7gene10-tag, staphylococcal protein A-tag, streptococcal protein G-tag, glutathione-S-transferase (GST)-tag, dihydrofolate reductase (DHFR)-tag, cellulose binding domains (CBDs)-tag, maltose binding protein (MBP)-tag, galactose-binding protein-tag, calmodulin binding protein (CBP)-tag, hemagglutinin influenza virus (HAI)-tag, HSV-tag, B-(VP7 protein region of bluetongue virus)-tag, polycysteine-tag, polyphenylanine-tag, (Ala-Trp-Trp-Pro)$_n$-tag, polyaspartic acid-tag, c-myc-tag, lac repressor-tag, and the like. The tag may be located at the N-terminus, C-terminus or internally of the target protein.

The fusion molecule may further comprise a signal peptide or leader sequence at the N-terminus. It is known that a signal peptide is a short peptide present at the N-terminus at the initial stage of protein synthesis toward the secretory pathway, and directs the intracellular localization of the corresponding protein, membrane topology (in the case of a membrane protein), and the like. The signal peptide may be cleaved during expression and extracellular secretion of the fusion molecule.

The above-mentioned first region, second region, tag, signal peptide, or regions having minimal functionality (e.g., LG1 and LG2 regions or scFv heavy chain variable region and light chain variable region) included in the fusion molecule may be linked together directly or by a linker comprising a short oligopeptide or polypeptide. In general, the linker may comprise 2 to 500 amino acid residues. The length or type of the linker is not particularly limited as long as the linker can link the above-described regions together so as to have the intended activity, thereby forming the fusion molecule. An example of the linker may be the commonly used oligopeptide linker (GGGGS)n (SEQ ID NO: 116), that is, a linker in which one or more Gly-Gly-Gly-Gly-Ser (SEQ ID NO: 117) units are repeated. Other examples of the linker include, but are not limited to, (GSSGGS)n (SEQ ID NO: 118), KESGSVSSE-QLAQFRSLD (SEQ ID NO: 119), EGKSSGSGSESKST (SEQ ID NO: 120), GSAGSAAGSGEF (SEQ ID NO: 121), (EAAAK)n (SEQ ID NO: 122), CRRRRRREAEAC (SEQ ID NO: 123), A(EAAAK)$_4$ALEA(EAAAK)$_4$A (SEQ ID NO: 124), GGGGGGGG (SEQ ID NO: 125), GGGGGG (SEQ ID NO: 126), AEAAAKEAAAAKA (SEQ ID NO: 127), PAPAP (SEQ ID NO: 128), (Ala-Pro)n, VSQTSKL-TRAETVFPDV (SEQ ID NO: 129), PLGLWA (SEQ ID NO: 130), TRHRQPRGWE (SEQ ID NO: 131), AGNRVRRSVG (SEQ ID NO: 132), RRRRRRRR (SEQ ID NO: 133), GFLG (SEQ ID NO: 134), and GSSGGSGSSGGSGGGDEADGSRGSQKAGVDE (SEQ ID NO: 135). Other suitable linkers comprise the sequences described in WO2012/088461A, of which the content is incorporated by reference herein in its entirety.

Figure 1D:
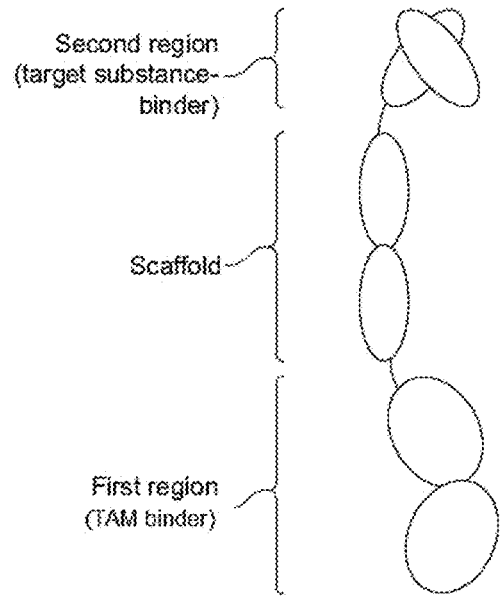
Figure 1E:
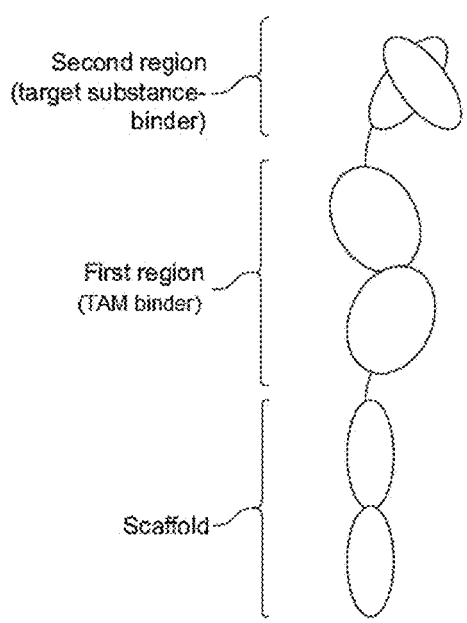
Figure 1F:
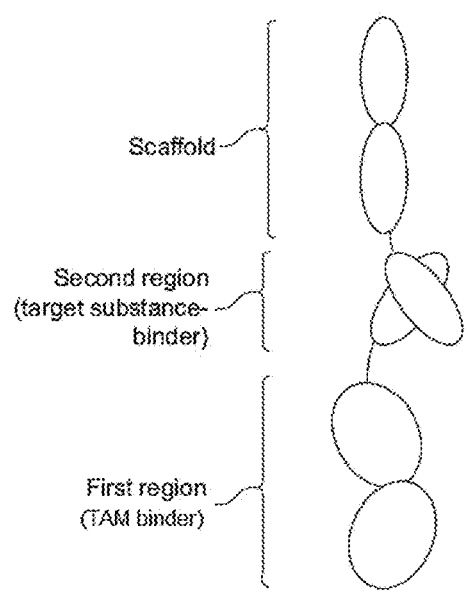
Figure 1I:
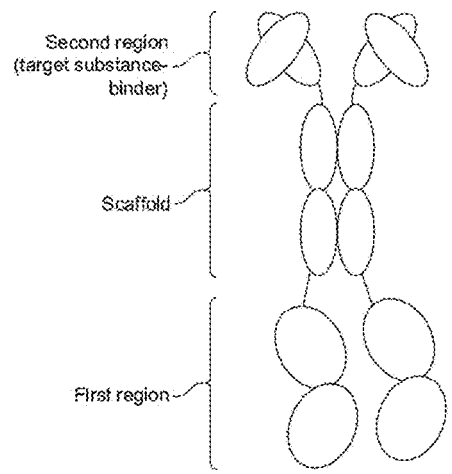
Figure 1J:
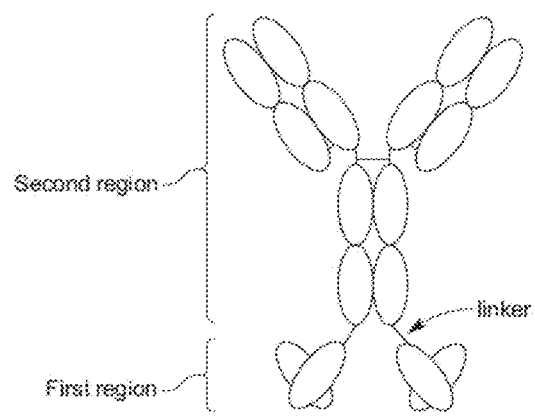
Figure 1K:
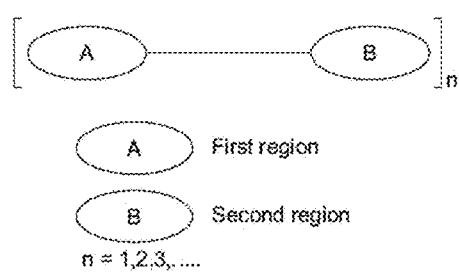
Figure 1L:
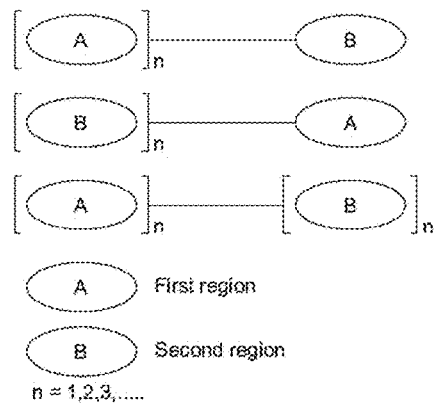
Figure 1M:
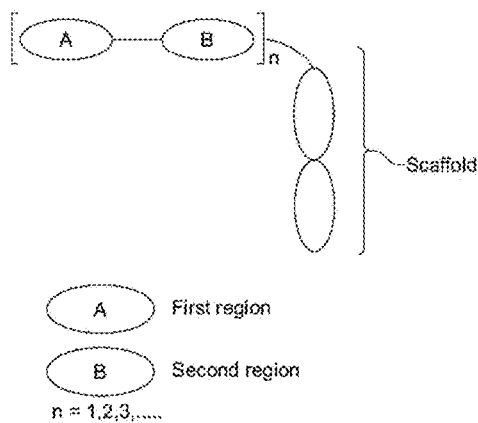

The fusion molecule according to embodiments of the present disclosure may further comprise a scaffold bound to the first region, to the second, or to both of the first region and the second region at different positions of the scaffold, as schematically depicted in FIGS. 1D-1D-1M. The scaffold refers to a protein or peptide, when incorporated into a protein or peptide of interest, improves properties of the total protein such as PK, enhances stability and/or in vivo half-life, or enhances productivity of the protein. In some embodiments, blood-brain barrier (BBB) permeable scaffold may optimize BBB permeability and/or optimizing distribution of the protein of interest (e.g., the fusion molecules according to the present disclosure) in the brain.

The scaffold may include, but not limited thereto, a single chain Fc region with reduced or abolished Fc receptor binding affinity, a multimer Fc region with reduced or abolished Fc receptor binding affinity, an antibody without variable region, or an Fc-hinge region with reduced or abolished Fc receptor binding affinity. In some embodiments, the scaffold may include albumin. The first region may be linked or fused to one position of the scaffold and the second region may be linked or fused to another position of the scaffold. The link or fusion between the first/the second region and the scaffold may be a direct bond or via a linker described above. It is known that heavy chain constant region or Fc region may contain mutations selected among T250Q/M428L; M252Y/S254T/T256E+H433K/N434F; E233P/L234V/L235A/G236A+A327G/A330S/P331S; E333A; S239D/A330L/I332E; P257I/Q311; K326W/E333S; S239D/I332E/G236A; N297A; L234A/L235A; N297A+M252Y/S254T/T256E; K322A and K444A, wherein the numbering is according to the EU numbering (Edelman, G. M. et al., Proc. Natl. Acad. USA, 63, 78-85 (1969); imgt.org/IMGTScientificChart/Numbering/Hu IGHGnber.html #refs).

The fusion molecules according to aspects of the present disclosure may have a structure as schematically shown in non-limiting exemplary illustrations of, for example, FIG. 1B and FIGS. 1C through 1D-1M.

Structures of non-limiting exemplary fusion molecules (including signal sequences, optional linkers, and tags) are illustrated in Tables 3 and 5-13 and SEQ ID NOs: 136, 138, 140, 142, 150, 152, 154, 156, 158, 162-169. Non-limiting exemplary fusion molecules may comprise, consist of, or consist essentially of the fusion molecule (or binding molecule) of the sequence of amino acid residues 31-871 of SEQ ID NO: 136, amino acid residues 31-687 of SEQ ID NO:138, amino acid residues 31-697 of SEQ ID NO:140, amino acid residues 31-684 of SEQ ID NO: 150, amino acid residues 31-676 of SEQ ID NO: 152, amino acid residues 25-673 of SEQ ID NO: 154, amino acid residues 22-662 of SEQ ID NO: 156, or amino acid residues 22-885 of SEQ ID NO: 158, or a sequence having at least 90% sequence identity thereto, wherein a different linker can be used in place the linkers as shown in Tables 3 and 5-Another aspect of the present disclosure provides a nucleic acid molecule encoding the fusion molecule, and an expression vector containing the same.

As described above, the nucleic acid molecule sequence encoding the fusion molecule may be mutated by substitution, deletion, insertion, or a combination thereof, of one or more nucleotide residues, as long as it encodes a protein having an activity equivalent thereto. The nucleic acid molecule sequence encoding the fusion molecule may be isolated from nature or artificially produced through synthesis or genetic recombination. The nucleic acid molecule sequence encoding the fusion molecule is operatively linked to an expression vector capable of expressing the same.

The term "expression vector" is a vector capable of expressing a protein or RNA of interest by introducing a nucleic acid sequence encoding a gene of interest into a suitable host cell, and refers to a gene construct containing essential regulatory elements operably linked to express the gene insert. Such expression vectors include all vectors such as plasmid vectors, cosmid vectors, bacteriophage vectors, and viral vectors.

A suitable expression vector has expression control elements such as a promoter, a start codon, a stop codon, a polyadenylation signal and an enhancer. The start codon and the stop codon are generally considered to be part of a nucleic acid sequence encoding a protein, and the sequence encoding the protein is designed to be in frame so as to be operable in the vector. The promoter may be constitutive or inducible. In addition, a conventional expression vector contains a selectable marker. Operational linkage with the expression vector can be performed using genetic recombination techniques well known in the art, and site-specific DNA cleavage and ligation can be performed using enzymes generally known in the art.

The expression vector may preferably be configured to express the fusion molecule in a host cell for isolation and purification of the fusion molecule or such that the vector may be introduced into a cell in vivo and the corresponding cell may express and secrete the fusion molecule. For the purpose of introducing into cells in vivo, the vector may preferably be a non-integrating vector, that is, a vector that is not integrated into the genome of a host cell.

Still another aspect of the present disclosure provides a cell expressing the fusion molecule.

The cells may be transformed to contain the nucleic acid molecule or an expression vector containing the same, and the "transformation" may be performed using suitable standard techniques selected depending on the host cell as known in the art, including any method of introducing the nucleic acid molecule into an organism, cell, tissue, or organ. These methods include, but are not limited to, electroporation, protoplast fusion, calcium phosphate ($CaPO_4$) precipitation, calcium chloride ($CaCl_2$) precipitation, agitation using silicon carbide fibers, agrobacterium-mediated transformation, PEG-, dextran sulfate-, lipofectamine-, and desiccation/inhibition-mediated transformation methods.

Examples of the host cells include, but are not limited to, prokaryotic host cells such as *Escherichia coli, Bacillus subtilis, Streptomyces, Pseudomonas* (e.g., *Pseudomonas putida*), *Proteus mirabilis*, or *Staphylococcus* (e.g., *Staphylocus carnosus*). Other examples of the host cell include fungal cells such as *Aspergillus*, yeast cells, including *Pichia pastoris, Saccharomyces cerevisiae, Schizosaccharomyces*, and *Neurospora crassa*, lower eukaryotic cells, or cells derived from higher eukaryotes including insect cells, plant cells, or mammalian cells.

After the fusion molecule is expressed in the cells, it may be isolated and purified using conventional biochemical isolation techniques, such as treatment with a protein precipitating agent (salting out method), centrifugation, sonication, ultrafiltration, dialysis, or various chromatography such as molecular sieve chromatography (gel filtration), adsorption chromatography, ion exchange chromatography, and affinity chromatography, which are generally used in combination in order to isolate proteins with high purity (Sambrook et al., Molecular Cloning: A laboratory Manual, 2nd Ed., Cold Spring Harbor Laboratory Press(1989); Deuscher, M., Guide to Protein Purification Methods Enzymology, Vol. 182. Academic Press. Inc., San Diego, CA (1990)).

Pharmaceutical Composition

Yet another aspect of the present disclosure provides a pharmaceutical composition for preventing or treating a disease caused by accumulation of the target substance in living tissue, the pharmaceutical composition containing the fusion molecule or the expression vector. Here, the composition may be administered topically to a site where the substance that causes the disease, that is, the target substance, accumulates.

A further aspect of the present disclosure provides the use of the fusion molecule for manufacture of a medicament for preventing or treating proteopathy.

The fusion molecule, which is an active ingredient in the pharmaceutical composition, is contained in a "pharmaceutically effective amount".

The pharmaceutical composition may be administered orally or parenterally, preferably parenterally. More preferably, it may be administered topically to a tissue in which the target substance to be cleared accumulates.

As used herein, the term "parenteral administration" includes subcutaneous injection, intravenous, intramuscular, intrasternal injection or infusion techniques.

When the pharmaceutical composition is prepared as an injectable formulation, it may be prepared as the injectable formulation a conventional method known in the art. The injectable formulation may be in a form dispersed in a sterile medium so that it may be administered directly to a patient or may be in a form that may be administered after being dispersed in distilled water for injection at an appropriate concentration.

When the pharmaceutical composition is formulated for oral administration, it may contain one or more carriers selected from among diluents, lubricants, binders, disintegrants, sweeteners, stabilizers, and preservatives, and may contain one or more additives selected from among flavorings, vitamins, and antioxidants.

Techniques necessary for formulation of the pharmaceutical composition, and pharmaceutically acceptable carriers, additives, etc. are widely known to those skilled in the art (see, for example, the Handbook of Pharmaceutical Excipients, 4$^{th}$ edition, Rowe et al., Eds., American Pharmaceuticals Association (2003); Remington: the Science and Practice of Pharmacy, 20$^{th}$ edition, Gennaro, Ed., Lippincott Williams & Wilkins (2000); Remington's Pharmaceutical Sciences (19$^{th}$ ed., 1995)).

The appropriate dosage of the pharmaceutical composition may vary depending on factors such as formulation method, administration mode, patient's age, weight, sex, medical condition, diet, administration time, administration route, excretion rate, and response sensitivity. The dosage of the pharmaceutical composition of the present disclosure is 0.0001 to 1,000 μg/kg body weight for an adult.

Advantageous Effects

The present disclosure relates to a fusion molecule having phagocytosis-inducing activity, which can solve the problem of tissue damage caused by activation of an inflammatory response, which occurs in the prior art. Accordingly, the fusion molecule is able to effectively clear abnormally accumulated substances such as beta-amyloid, tau, alpha-synuclein, huntingtin or prion protein, and thus may be used to prevent or treat diseases caused by these abnormally accumulated substances, for example, Alzheimer's disease, Parkinson's disease, Huntington's disease, or prion disease. The fusion molecule may be administered to a patient in the form of a purified fusion molecule or a gene therapy vector capable of expressing and secreting the fusion molecule when introduced into a cell.

However, it should be understood that effects of the present disclosure are not limited to the above effects, and include all effects that may be inferred from the configuration of the invention described in the detailed description or claims.

EXAMPLES

Hereinafter, the present disclosure will be described in more detail with reference to examples and experimental examples. However, the following examples and experimental examples are illustrative only, and the scope of the invention is not limited thereto.

Preparation Example 1. Preparation of Gas6-Based Fusion Molecule Having Beta-Amyloid Clearance Activity (I): Beta-Amyloid Binding Region in the Form of scFv To prepare a beta-amyloid (Aβ)-specific chimeric phagocytosis inducer based on Gas6 protein, the Gla domain, which recognizes PS (phosphatidylserine) in apoptotic cells, was first removed, and a single-chain variable fragment (scFv) of aducanumab, an amyloid-specific antibody, was introduced at that position [αAβ-Gas6(E)].

In addition, for the efficiency of protein production, the EGF repeat domain present in the internal residues of the Gas6 protein was also removed and an scFv of aducanumab was introduced at that position, thereby preparing αAβ-Gas6 (FIG. 1B).

In addition, as controls for verifying beta-amyloid-specific binding of the scFv of aducanumab, αFITC-Gas6(E) and αFITC-Gas6, each introduced with an E2 scFv that selectively recognizes FITC, instead of the scFv of aducanumab, were prepared.

Table 3 below shows amino acid sequences related to the preparation of the fusion molecules, and Table 4 below shows nucleotide sequences related to the preparation of the fusion molecules (the underlined sequences are flag tags). In Table 3, information for sequences constituting the final binding molecules are included within parenthesis. The full length sequences contain, from the N-terminal to the C-terminal direction, as an example, signal sequence (SS), first region, linker (when applicable), second region, and flag or his tags, which are linked consecutively. The sequence identifiers are intended for the full length sequences.

TABLE 3

```
1. αAβ-Gas6(E) (FLAG tag, Gla delete, G-/-) SEQ ID NO: 136
MAPSLSPGPAALRRAPQLLLLLLAAECALA (SS)
DIQMTQSPSSLSASVGDRVTITCRASQSISSYLNWYQQKPGKAPKLLIYAASSLQSGV
PSRFSGSGSGTDFTLTISSLQPEDFATYYCQQSYSTPLTFGGGTKVEIKRGGGSGGG
GSGGGGSEVQLVESGGGVVQPGRSLRLSCAASGFAFSSYGMHWVRQAPGKGLEWV
AVIWFDGTKKYYTDSVKGRFTISRDNSKNTLYLQMNTLRAEDTAVYYCARDRGIGA
RRGPYYMDVWGKGTTVTVSS (Adu-scFv)
GGGGSGGGGS (Linker)
CINKYGSPYTKNSGFATCVQNLPDQCTPNPCDRKGTQACQDLMGNFFCLCKAGWG
GRLCDKDVNECSQENGGCLQICHNKPGSFHCSCHSGFELSSDGRTCQDIDECADSEA
CGEARCKNLPGSYSCLCDEGFAYSSQEKACRDVDECLQGRCEQVCVNSPGSYTCHC
DGRGGLKLSQDMDTCEDILPCVPFSVAKSVKSLYLGRMFSGTPVIRLRFKRLQPTRL
VAEFDFRTFDPEGILLFAGGHQDSTWIVLALRAGRLELQLRYNGVGRVTSSGPVINH
GMWQTISVEELARNLVIKVNRDAVMKIAVAGDLFQPERGLYHLNLTVGGIPFHEKD
LVQPINPRLDGCMRSWNWLNGEDTTIQETVKVNTRMQCFSVTERGSFYPGSGFAFY
SLDYMRTPLDVGTESTWEVEVVAHIRPAADTGVLFALWAPDLRAVPLSVALVDYH
STKKLKKQLVVLAVEHTALALMEIKVCDGQEHVVTVSLRDGEATLEVDGTRGQSE
VSAAQLQERLAVLERHLRSPVLTFAGGLPDVPVTSAPVTAFYRGCMTLEVNRRLLD
LDEAAYKHSDITAHSCPPVEPAAA(Gas6-Gla deleted)
QGSRADYKDHDGDYKDHDIDYKDDDDK* (FLAG)

2. αFITC-Gas6(E) (FLAG tag, Gla delete, G-/-) SEQ ID NO: 137
MAPSLSPGPAALRRAPQLLLLLLAAECALA(SS)
QVQLVESGGNLVQPGGSLRLSCAASGFTFGSFSMSWVRQAPGGGLEWVAGLSARSS
LTHYADSVKGRFTISRDNAKNSVYLQMNSLRVEDTAVYYCARRSYDSSGYWGHFY
SYMDVWGQGTLVTVSGGGGSGGGGSGGGGSSVLTQPSSVSAAPGQKVTISCSGSTS
NIGNNYVSWYQQHPGKAPKLMIYDVSKRPSGVPDRFSGSKSGNSASLDISGLQSEDE
ADYYCAAWDDSLSEFLFGTGTKLTVLG (aFITC-scFv)
GGGGSGGGGS (Linker)
CINKYGSPYTKNSGFATCVQNLPDQCTPNPCDRKGTQACQDLMGNFFCLCKAGWG
GRLCDKDVNECSQENGGCLQICHNKPGSFHCSCHSGFELSSDGRTCQDIDECADSEA
CGEARCKNLPGSYSCLCDEGFAYSSQEKACRDVDECLQGRCEQVCVNSPGSYTCHC
DGRGGLKLSQDMDTCEDILPCVPFSVAKSVKSLYLGRMFSGTPVIRLRFKRLQPTRL
VAEFDFRTFDPEGILLFAGGHQDSTWIVLALRAGRLELQLRYNGVGRVTSSGPVINH
GMWQTISVEELARNLVIKVNRDAVMKIAVAGDLFQPERGLYHLNLTVGGIPFHEKD
LVQPINPRLDGCMRSWNWLNGEDTTIQETVKVNTRMQCFSVTERGSFYPGSGFAFY
SLDYMRTPLDVGTESTWEVEVVAHIRPAADTGVLFALWAPDLRAVPLSVALVDYH
STKKLKKQLVVLAVEHTALALMEIKVCDGQEHVVTVSLRDGEATLEVDGTRGQSE
VSAAQLQERLAVLERHLRSPVLTFAGGLPDVPVTSAPVTAFYRGCMTLEVNRRLLD
LDEAAYKHSDITAHSCPPVEPAAA(Gas6-Gla deleted)
QGSRADYKDHDGDYKDHDIDYKDDDDK* (FLAG)

3. αAβ-Gas6 (FLAG tag, Gla EGF delete, GE-/-) SEQ ID NO: 138
MAPSLSPGPAALRRAPQLLLLLLAAECALA(SS)
DIQMTQSPSSLSASVGDRVTITCRASQSISSYLNWYQQKPGKAPKLLIYAASSLQSGV
PSRFSGSGSGTDFTLTISSLQPEDFATYYCQQSYSTPLTFGGGTKVEIKRGGGSGGG
```

TABLE 3-continued

```
GSGGGGSEVQLVESGGGVVQPGRSLRLSCAASGFAFSSYGMHWVRQAPGKGLEWV
AVIWFDGTKKYYTDSVKGRFTISRDNSKNTLYLQMNTLRAEDTAVYYCARDRGIGA
RRGPYYMDVWGKGTTVTVSS (Adu-scFv)
GGGGSGGGGS (Linker)
DILPCVPFSVAKSVKSLYLGRMFSGTPVIRLRFKRLQPTRLVAEFDFRTFDPEGILLFA
GGHQDSTWIVLALRAGRLELQLRYNGVGRVTSSGPVINHGMWQTISVEELARNLVI
KVNRDAVMKIAVAGDLFQPERGLYHLNLTVGGIPFHEKDLVQPINPRLDGCMRSWN
WLNGEDTTIQETVKVNTRMQCFSVTERGSFYPGSGFAFYSLDYMRTPLDVGTESTW
EVEVVAHIRPAADTGVLFALWAPDLRAVPLSVALVDYHSTKKLKKQLVVLAVEHT
ALALMEIKVCDGQEHVVTVSLRDGEATLEVDGTRGQSEVSAAQLQERLAVLERHLR
SPVLTFAGGLPDVPVTSAPVTAFYRGCMTLEVNRRLLDLDEAAYKHSDITAHSCPPV
EPAAA (Gas6-Gla EGF deleted)
QGSRADYKDHDGDYKDHDIDYKDDDDK* (FLAG)

4. αFITC-Gas6 (FLAG tag, Gla EGF delete, GE-/-) SEQ ID NO: 139
MAPSLSPGPAALRRAPQLLLLLLAAECALA(SS)
QVQLVESGGNLVQPGGSLRLSCAASGFTFGSFSMSWVRQAPGGGLEWVAGLSARSS
LTHYADSVKGRFTISRDNAKNSVYLQMNSLRVEDTAVYYCARRSYDSSGYWGHFY
SYMDVWGQGTLVTVSGGGGSGGGGSGGGGSSVLTQPSSVSAAPGQKVTISCSGSTS
NIGNNYVSWYQQHPGKAPKLMIYDVSKRPSGVPDRFSGSKSGNSASLDISGLQSEDE
ADYYCAAWDDSLSEFLFGTGTKLTVLG (aFITC-scFv)
GGGGSGGGGS (Linker)
DILPCVPFSVAKSVKSLYLGRMFSGTPVIRLRFKRLQPTRLVAEFDFRTFDPEGILLFA
GGHQDSTWIVLALRAGRLELQLRYNGVGRVTSSGPVINHGMWQTISVEELARNLVI
KVNRDAVMKIAVAGDLFQPERGLYHLNLTVGGIPFHEKDLVQPINPRLDGCMRSWN
WLNGEDTTIQETVKVNTRMQCFSVTERGSFYPGSGFAFYSLDYMRTPLDVGTESTW
EVEVVAHIRPAADTGVLFALWAPDLRAVPLSVALVDYHSTKKLKKQLVVLAVEHT
ALALMEIKVCDGQEHVVTVSLRDGEATLEVDGTRGQSEVSAAQLQERLAVLERHLR
SPVLTFAGGLPDVPVTSAPVTAFYRGCMTLEVNRRLLDLDEAAYKHSDITAHSCPPV
EPAAA (Gas6-Gla EGF deleted)
QGSRADYKDHDGDYKDHDIDYKDDDDK* (FLAG)

5. αAβ-Gas6 (HA tag, Gla EGF delete, GE-/-) SEQ ID NO: 140
MAPSLSPGPAALRRAPQLLLLLLAAECALA(SS)
DIQMTQSPSSLSASVGDRVTITCRASQSISSYLNWYQQKPGKAPKLLIYAASSLQSGV
PSRFSGSGSGTDFTLTISSLQPEDFATYYCQQSYSTPLTFGGGTKVEIKRGGGGSGGG
GSGGGGSEVQLVESGGGVVQPGRSLRLSCAASGFAFSSYGMHWVRQAPGKGLEWV
AVIWFDGTKKYYTDSVKGRFTISRDNSKNTLYLQMNTLRAEDTAVYYCARDRGIGA
RRGPYYMDVWGKGTTVTVSS (Adu-scFv)
GGGGSGGGGS (Linker)
DILPCVPFSVAKSVKSLYLGRMFSGTPVIRLRFKRLQPTRLVAEFDFRTFDPEGILLFA
GGHQDSTWIVLALRAGRLELQLRYNGVGRVTSSGPVINHGMWQTISVEELARNLVI
KVNRDAVMKIAVAGDLFQPERGLYHLNLTVGGIPFHEKDLVQPINPRLDGCMRSWN
WLNGEDTTIQETVKVNTRMQCFSVTERGSFYPGSGFAFYSLDYMRTPLDVGTESTW
EVEVVAHIRPAADTGVLFALWAPDLRAVPLSVALVDYHSTKKLKKQLVVLAVEHT
ALALMEIKVCDGQEHVVTVSLRDGEATLEVDGTRGQSEVSAAQLQERLAVLERHLR
SPVLTFAGGLPDVPVTSAPVTAFYRGCMTLEVNRRLLDLDEAAYKHSDITAHSCPPV
EPAAA (Gas6-Gla EGF deleted)
GSGSGSGSGSGSYPYDVPDYA* (HA)

6. Lentiviral Aducanumab IgG_IRES Zsgreen deleted SEQ ID NO: 141
MGWSCIILFLVATATG (SS)
DIQMTQSPSSLSASVGDRVTITCRASQSISSYLNWYQQKPGKAPKLLIYAASSLQSGV
PSRFSGSGSGTDFTLTISSLQPEDFATYYCQQSYSTPLTFGGGTKVEIKRKRTVAAPSV
FIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC (Adu-Light chain)
RRKRGSGEGRGSLLTCGDVEENPGP (T2A)
MGWSCIILFLVATATG (SS)
EVQLVESGGGVVQPGRSLRLSCAASGFAFSSYGMHWVRQAPGKGLEWVAVIWFDG
TKKYYTDSVKGRFTISR
DNSKNTLYLQMNTLRAEDTAVYYCARDRGIGARRGPYYMDVWGKGTTVTVSSA
STKGPSVFPLAPSSKSTSGGTAALGCLVKDYFPEPVTVSWNSGALTSGVHTFPAVL
QSSGLYSLSSVVTVPSSSLGTQTYICNVNHKPSNTKVDKKVEPKSSDKTHTSPPCPA
PELLGGPSVFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIEKTISKAKG
QPREPQVYTLPPSRDELTKNQVSLTCLVKGFYPSDIAVEWESNGQPENNYKTTPPV
LDSDGSFFLYSKLTVDKSRWQQGNVFSCSVMHEALHNHYTQKSLSLSPGK* (Adu-
Heavy chain)

7. Endogenous full sequence human Gas6 protein SEQ ID NO: 142
MAPSLSPGPAALRRAPQLLLLLLAAECALAALLPAREATQFLRPRQRRAFQVFEEAK
QGHLERECVEELCSREEAREVFENDPETDYFYPRYLDCINKYGSPYTKNSGFATCVQ
NLPDQCTPNPCDRKGTQACQDLMGNFFCLCKAGWGGRLCDKDVNECSQENGGCL
QICHNKPGSFHCSCHSGFELSSDGRTCQDIDECADSEACGEARCKNLPGSYSCLCDE
GFAYSSQEKACRDVDECLQGRCEQVCVNSPGSYTCHCDGRGGLKLSQDMDTCEDIL
PCVPFSVAKSVKSLYLGRMFSGTPVIRLRFKRLQPTRLVAEFDFRTFDPEGILLFAGG
HQDSTWIVLALRAGRLELQLRYNGVGRVTSSGPVINHGMWQTISVEELARNLVIKV
NRDAVMKIAVAGDLFQPERGLYHLNLTVGGIPFHEKDLVQPINPRLDGCMRSWNW
LNGEDTTIQETVKVNTRMQCFSVTERGSFYPGSGFAFYSLDYMRTPLDVGTESTWE
VEVVAHIRPAADTGVLFALWAPDLRAVPLSVALVDYHSTKKLKKQLVVLAVEHTA
```

TABLE 3-continued

```
LALMEIKVCDGQEHVVTVSLRDGEATLEVDGTRGQSEVSAAQLQERLAVLERHLRS
PVLTFAGGLPDVPVTSAPVTAFYRGCMTLEVNRRLLDLDEAAYKHSDITAHSCPPVE
PAAA (full-length human Gas6)
QGSRADYKDHDGDYKDHDIDYKDDDDK* (FLAG)
```

TABLE 4

```
1. αAβ-Gas6(E) (FLAG tag, Gla delete, G-/-) SEQ ID NO: 143
ATGGCCCCTTCGCTCTCGCCCGGGCCCGCCGCCCTGCGCCGCGCCGCAGCTGC
TGCTGCTGCTGGCCGCGGAGTGCGCGCTTGCC (SS)
GACATTCAGATGACTCAATCTCCTAGCTCTCTGAGCGCCTCCGTTGGAGATAGAG
TCACTATTACCTGCAGAGCCAGCCAATCCATCAGCTCTTATCTAAATTGGTACCA
ACAGAAGCCCGGCAAAGCGCCAAAGCTGCTCATCTACGCTGCAAGCTCCTTACA
GAGCGGAGTACCCAGCAGATTCTCAGGCAGTGGCAGTGGGACTGACTTCACATT
GACGATTAGCTCTCTGCAGCCTGAAGACTTTGCCACATACTATTGTCAGCAGAGC
TATAGCACCCCGCTGACGTTTGGAGGCGGAACTAAGGTGGAAATCAAGAGAGG
AGGCGGGGCTCCGGCGGGGGTGGCTCGGGGGGAGGAGGCTCAGAGGTTCAGC
TTGTCGAGTCTGGGGGGGAGTCGTTCAGCCAGGTAGAAGCCTCAGACTGAGCT
GTGCCGCAAGTGGGTTTGCTTTTTCATCTTACGGTATGCACTGGGTGAGACAGGC
TCCTGGCAAAGGACTCGAGTGGGTCGCTGTAATATGGTTCGATGGTACAAAGAA
ATACTATACCGATAGTGTGAAAGGAAGATTCACCATTTCACGAGACAACAGTAA
AAATACCTTGTACCTTCAGATGAACACCCTGAGAGCAGAAGACACAGCCGTGTA
CTACTGCGCCAGAGATAGAGGTATCGGAGCAAGGCGTGGTCCCTATTATATGGA
TGTGTGGGGAAGGGAACAACAGTGACTGTGAGCTCT (Adu-scFv)
GGCGGGGGCGGCAGCGGCGGCGGTGGCAGC (Linker)
TGCATCAACAAGTATGGGTCTCCGTACACCAAAAACTCAGGCTTCGCCACCTGC
GTGCAAAACCTGCCTGACCAGTGCACGCCCAACCCCTGCGATAGGAAGGGGACC
CAAGCCTGCCAGGACCTCATGGGCAACTTCTTCTGCCTGTGTAAAGCTGGCTGGG
GGGGCCGGCTCTGCGACAAAGATGTCAACGAATGCAGCCAGGAGAACGGGGGC
TGCCTCCAGATCTGCCACAACAAGCCGGGTAGCTTCCACTGTTCCTGCCACAGCG
GCTTCGAGCTCTCCTCTGATGGCAGGACCTGCCAAGACATAGACGAGTGCGCAG
ACTCGGAGGCCTGCGGGAGGCGCGCTGCAAGAACCTGCCCGGCTCCTACTCCT
GCCTCTGTGACGAGGGCTTTGCGTACAGCTCCCAGGAGAAGGCTTGCCGAGATG
TGGACGAGTGTCTGCAGGGCCGCTGTGAGCAGGTCTGCGTGAACTCCCCAGGGA
GCTACACCTGCCACTGTGACGGGCGTGGGGGCCTCAAGCTGTCCCAGGACATGG
ACACCTGTGAGGACATCTTGCCGTGCGTGCCCTTCAGCGTGGCCAAGAGTGTGA
AGTCCTTGTACCTGGGCCGGATGTTCAGTGGGACCCCCGTGATCCGACTGCGCTT
CAAGAGGCTGCAGCCCACCAGGCTGGTAGCTGAGTTTGACTTCCGGACCTTTGA
CCCCGAGGGCATCCTCCTCTTTGCCGGAGGCCACCAGGACAGCACCTGGATCGT
GCTGGCCCTGAGAGCCGGCCGGCTGGAGCTGCAGCTGCGCTACAACGGTGTCGG
CCGTGTCACCAGCAGCGGCCCGGTCATCAACCATGGCATGTGGCAGACAATCTC
TGTTGAGGAGCTGGCCGCGGAATCTGGTCATCAAGGTCAACAGGGATGCTGTCAT
GAAAATCGCGGTGGCCGGGGACTTGTTCCAACCGGAGCGAGGACTGTATCATCT
GAACCTGACCGTGGGAGGTATTCCCTTCCATGAGAAGGACCTCGTGCAGCCTAT
AAACCCTCGTCTGGATGGCTGCATGAGGAGCTGGAACTGGCTGAACGGAGAAGA
CACCACCATCCAGGAAACGGTGAAAGTGAACACGAGGATGCAGTGCTTCTCGGT
GACGGAGAGAGGCTCTTTCTACCCCGGGAGCGGCTTCGCCTTCTACAGCCTGGA
CTACATGCGGACCCCTCTGGACGTCGGGACTGAATCAACCTGGGAAGTAGAAGT
CGTGGCTCACATCCGCCCAGCCGCAGACACAGGCGTGCTGTTTGCGCTCTGGGC
CCCCGACCTCCGTGCCGTGCCTCTCTCTGTGGCACTGGTAGACTATCACTCCACG
AAGAAACTCAAGAAGCAGCTGGTGGTCCTGGCCGTGGAGCATACGGCCTTGGCC
CTAATGGAGATCAAGGTCTGCGACGGCCAAGAGCACGTGGTCACCGTCTCGCTG
AGGGACGGTGAGGCCACCCTGGAGGTGGACGGCACCAGGGGCCAGAGCGAGGT
GAGCGCCGCGCAGCTGCAGGAGAGGCTGGCCGTGCTCGAGAGGCACCTGCGGA
GCCCCGTGCTCACCTTTGCTGGCGGCCTGCCAGATGTGCCGGTGACTTCAGCGCC
AGTCACCGCGTTCTACCGCGGCTGCATGACACTGGAGGTCAACCGGAGGCTGCT
GGACCTGGACGAGGCGGCGTACAAGCACAGCGACATCACGGCCCACTCCTGCCC
CCCCGTGGAGCCCGCCGCAGCC (Gas6-Gla deleted)
caagGATCCCGGGCTGACTACAAAGACCATGACGGTGATTATAAAGATCATGACA
TCGACTACAAGGATGACGATGACAAGtga (FLAG)

2. αFITC-Gas6(E) (FLAG tag, Gla delete, G-/-) SEQ ID NO: 144
ATGGCCCCTTCGCTCTCGCCCGGGCCCGCCGCCCTGCGCCGCGCCGCAGCTGC
TGCTGCTGCTGGCCGCGGAGTGCGCGCTTGCC (SS)
CAGGTTCAGCTGGTTGAGAGCGGAGGCAATCTGGTTCAGCCCGGTGGTAGTCTG
CGTCTGTCTTGTGCGGCGTCAGGGTTCACTTTCGGTAGTTTTTCAATGAGCTGGG
TCCGTCAGGCACCAGGCGGTGGGCTGGAATGGGTGGCAGGTCTGTCTGCACGTA
GCTCCCTGACCCACTATGCAGATAGTGTTAAAGGGCGGTTCACAATTTCACGCG
ACAACGCTAAGAATAGCGTCTACCTGCAAATGAACTCCCTGCGGGTCGAGGATA
CCGCAGTGTATTACTGCGCTCGCCGTTCTTATGACTCTAGTGGATACTGGGGCCA
TTTTTATAGCTACATGGATGTGTGGGGACAGGGCACTCTGGTGACCGTTTCGGA
GGCGGTGGGTCTGGAGGCGGTGGGAGTGGAGGCGGTGGGTCAAGCGTTCTGACC
CAGCCGTCCTCTGTCAGCGCCGCGCCAGGCCAGAAAGTGACAATTTCCTGTTCTG
GAAGTACTTCAAACATCGGCAACAATTATGTTTCCTGGTATCAGCAGCACCCGG
```

TABLE 4-continued

```
GCAAAGCGCCCAAGCTGATGATTTATGATGTGTCTAAACGTCCAAGTGGTGTTCC
TGACCGGTTCAGCGGTTCCAAGTCTGGGAATAGTGCCTCACTGGACATCTCAGG
CCTGCAAAGCGAAGATGAGGCGGACTATTACTGCGCAGCTTGGGATGACAGCCT
GTCCGAATTTCTGTTCGGCACCGGGACAAAGCTGACCGTGCTGGGC (aFITC-scFv)
GGCGGGGGCGGCAGCGGCGGCGGTGGCAGC (Linker)
TGCATCAACAAGTATGGGTCTCCGTACACCAAAAACTCAGGCTTCGCCACCTGC
GTGCAAAACCTGCCTGACCAGTGCACGCCCAACCCCTGCGATAGGAAGGGGACC
CAAGCCTGCCAGGACCTCATGGGCAACTTCTTCTGCCTGTGTAAAGCTGGCTGGG
GGGGCCGGCTCTGCGACAAAGATGTCAACGAATGCAGCCAGGAGAACGGGGGC
TGCCTCCAGATCTGCCACAACAAGCGGGTAGCTTCCACTGTTCCTGCCACAGCG
GCTTCGAGCTCTCCTCTGATGGCAGGACCTGCCAAGACATAGACGAGTGCGCAG
ACTCGGAGGCCTGCGGGGAGGCGCGCTGCAAGAACCTGCCCGGCTCCTACTCCT
GCCTCTGTGACGAGGGCTTTGCGTACAGCTCCCAGGAGAAGGCTTGCCGAGATG
TGGACGAGTGTCTGCAGGGCCGCTGTGAGCAGGTCTGCGTGAACTCCCCAGGGA
GCTACACCTGCCACTGTGACGGGCGTGGGGGCCTCAAGCTGTCCCAGGACATGG
ACACCTGTGAGGACATCTTGCCGTGCGTGCCCTTCAGCGTGGCCAAGAGTGTGA
AGTCCTTGTACCTGGGCCGGATGTTCAGTGGGACCCCCGTGATCCGACTGCGCTT
CAAGAGGCTGCAGCCCACCAGGCTGGTAGCTGAGTTTGACTTCCGGACCTTTGA
CCCCGAGGGCATCCTCCTCTTTGCCGGAGGCCACCAGGACAGCACCTGGATCGT
GCTGGCCCTGAGAGCCGGCCGGCTGGAGCTGCAGCTGCGCTACAACGGTGTCGG
CCGTGTCACCAGCAGCGGCCCGGTCATCAACCATGGCATGTGGCAGACAATCTC
TGTTGAGGAGCTGGCGCGGAATCTGGTCATCAAGGTCAACAGGGATGCTGTCAT
GAAAATCGCGGTGGCCGGGGACTTGTTCCAACCGGAGCGAGGACTGTATCATCT
GAACCTGACCGTGGGAGGTATTCCCTTCCATGAGAAGGACCTCGTGCAGCCTAT
AAACCCTCGTCTGGATGGCTGCATGAGGAGCTGGAACTGGCTGAACGGAGAAGA
CACCACCATCCAGGAAACGGTGAAAGTGAACACGAGGATGCAGTGCTTCTCGGT
GACGGAGAGAGGCTCTTTCTACCCCGGGAGCGGCTTCGCCTTCTACAGCCTGGA
CTACATGCGGACCCCTCTGGACGTCGGGACTGAATCAACCTGGGAAGTAGAAGT
CGTGGCTCACATCCGCCCAGCCGCAGACACAGGCGTGCTGTTTGCGCTCTGGGC
CCCCGACCTCCGTGCCGTGCCTCTCTCTGTGGCACTGGTAGACTATCACTCCACG
AAGAAACTCAAGAAGCAGCTGGTGGTCCTGGCCGTGGAGCATACGGCCTTGGCC
CTAATGGAGATCAAGGTCTGCGACGGCCAAGAGCACGTGGTCACCGTCTCGCTG
AGGGACGGTGAGGCCACCCTGGAGGTGGACGGCACCAGGGGCCAGAGCGAGGT
GAGCGCCGCGCAGCTGCAGGAGAGGCTGGCCGTGCTCGAGAGGCACCTGCGGA
GCCCCGTGCTCACCTTTGCTGGCGGCCTGCCAGATGTGCCGGTGACTTCAGCGCC
AGTCACCGCGTTCTACCGCGGCTGCATGACACTGGAGGTCAACCGGAGGCTGCT
GGACCTGGACGAGGCGGCGTACAAGCACAGCGACATCACGGCCCACTCCTGCCC
CCCCGTGGAGCCCGCCGCAGCC (Gas6-Gla deleted)
caagGATCCCGGGCTGACTACAAAGACCATGACGGTGATTATAAAGATCATGACA
TCGACTACAAGGATGACGATGACAAGtga (FLAG)
```

3. αAβ-Gas6 (FLAG tag, Gla EGF delete, GE-/-) SEQ ID NO: 145

```
ATGGCCCCTTCGCTCTCGCCCGGGCCCGCCGCCCTGCGCCGCGCGCCGCAGCTGC
TGCTGCTGCTGGCCGCGGAGTGCGCGCTTGCC (SS)
GACATTCAGATGACTCAATCTCCTAGCTCTCTGAGCGCCTCCGTTGGAGATAGAG
TCACTATTACCTGCAGAGCCAGCCAATCCATCAGCTCTTATCTAAATTGGTACCA
ACAGAAGCCCGGCAAAGCGCCAAAGCTGCTCATCTACGCTGCAAGCTCCTTACA
GAGCGGAGTACCCAGCAGATTCTCAGGCAGTGGCAGTGGGACTGACTTCACATT
GACGATTAGCTCTCTGCAGCCTGAAGACTTTGCCACATACTATTGTCAGCAGAGC
TATAGCACCCCGCTGACGTTTGGAGGCGGAACTAAGGTGGAAATCAAGAGAGG
AGGCGGGGGCTCCGGCGGGGGTGGCTCGGGGGAGGAGGCTCAGAGGTTCAGC
TTGTCGAGTCTGGGGGGGGAGTCGTTCAGCCAGGTAGAAGCCTCAGACTGAGCT
GTGCCGCAAGTGGGTTTGCTTTTTCATCTTACGGTATGCACTGGGTGAGACAGGC
TCCTGGCAAAGGACTCGAGTGGGTCGCTGTAATATGGTTCGATGGTACAAAGAA
ATACTATACCGATAGTGTGAAAGGAAGATTCACCATTTCACGAGACAACAGTAA
AAATACCTTGTACCTTCAGATGAACACCCTGAGAGCAGAAGACACAGCCGTGTA
CTACTGCGCCAGAGATAGAGGTATCGGAGCAAGGCGTGGTCCCTATTATATGGA
TGTGTGGGGGAAGGGAACAACAGTGACTGTGAGCTCT (Adu-scFv)
GGCGGGGGCGGCAGCGGCGGCGGTGGCAGC (Linker)
GACATCTTGCCGTGCGTGCCCTTCAGCGTGGCCAAGAGTGTGAAGTCCTTGTACC
TGGGCCGGATGTTCAGTGGGACCCCCGTGATCCGACTGCGCTTCAAGAGGCTGC
AGCCCACCAGGCTGGTAGCTGAGTTTGACTTCCGGACCTTTGACCCCGAGGGCA
TCCTCCTCTTTGCCGGAGGCCACCAGGACAGCACCTGGATCGTGCTGGCCCTGAG
AGCCGGCCGGCTGGAGCTGCAGCTGCGCTACAACGGTGTCGGCCGTGTCACCAG
CAGCGGCCCGGTCATCAACCATGGCATGTGGCAGACAATCTCTGTTGAGGAGCT
GGCGCGGAATCTGGTCATCAAGGTCAACAGGGATGCTGTCATGAAAATCGCGGT
GGCCGGGGACTTGTTCCAACCGGAGCGAGGACTGTATCATCTGAACCTGACCGT
GGGAGGTATTCCCTTCCATGAGAAGGACCTCGTGCAGCCTATAAACCCTCGTCTG
GATGGCTGCATGAGGAGCTGGAACTGGCTGAACGGAGAAGACACCACCATCCA
GGAAACGGTGAAAGTGAACACGAGGATGCAGTGCTTCTCGGTGACGGAGAGAG
GCTCTTTCTACCCCGGGAGCGGCTTCGCCTTCTACAGCCTGGACTACATGCGGAC
CCCTCTGGACGTCGGGACTGAATCAACCTGGGAAGTAGAAGTCGTGGCTCACAT
CCGCCCAGCCGCAGACACAGGCGTGCTGTTTGCGCTCTGGGCCCCCGACCTCCGT
GCCGTGCCTCTCTCTGTGGCACTGGTAGACTATCACTCCACGAAGAAACTCAAG
AAGCAGCTGGTGGTCCTGGCCGTGGAGCATACGGCCTTGGCCTAATGGAGATC
AAGGTCTGCGACGGCCAAGAGCACGTGGTCACCGTCTCGCTGAGGGACGGTGAG
GCCACCCTGGAGGTGGACGGCACCAGGGGCCAGAGCGAGGTGAGCGCCGCGCA
GCTGCAGGAGAGGCTGGCCGTGCTCGAGAGGCACCTGCGGAGCCCCGTGCTCAC
CTTTGCTGGCGGCCTGCCAGATGTGCCGGTGACTTCAGCGCCAGTCACCGCGTTC
TACCGCGGCTGCATGACACTGGAGGTCAACCGGAGGCTGCTGGACCTGGACGAG
```

TABLE 4-continued

```
GCGGCGTACAAGCACAGCGACATCACGGCCCACTCCTGCCCCCCCGTGGAGCCC
GCCGCAGCC (Gas6-Gla EGF deleted)
caaGGATCCCGGGCTGACTACAAAGACCATGACGGTGATTATAAAGATCATGACA
TCGACTACAAGGATGACGATGACAAGTGA (FLAG)

4. αFITC-Gas6 (FLAG tag, Gla EGF delete, GE-/-) SEQ ID NO: 146
ATGGCCCCTTCGCTCTCGCCCGGGCCCGCCGCCCTGCCGCGCGCCGCAGCTGC
TGCTGCTGCTGGCCGCGGAGTGCGCGCTTGCC (SS)
CAGGTTCAGCTGGTTGAGAGCGGAGGCAATCTGGTTCAGCCCGGTGGTAGTCTG
CGTCTGTCTTGTGCGGCGTCAGGGTTCACTTTCGGTAGTTTTTCAATGAGCTGGG
TCCGTCAGGCACCAGGCGGTGGGCTGGAATGGGTGGCAGGTCTGTCTGCACGTA
GCTCCCTGACCCACTATGCAGATAGTGTTAAAGGGCGGTTCACAATTTCACGCG
ACAACGCTAAGAATAGCGTCTACCTGCAAATGAACTCCCTGCGGGTCGAGGATA
CCGCAGTGTATTACTGCGCTCGCCGTTCTTATGACTCTAGTGGATACTGGGGCCA
TTTTTATAGCTACATGGATGTGTGGGGACAGGGCACTCTGGTGACCGTTTCCGGA
GGCGGTGGGTCTGGAGGCGGTGGGAGTGGAGGCGGTGGGTCAAGCGTTCTGACC
CAGCCGTCCTCTGTCAGCGCCGCGCCAGGCCAGAAAGTGACAATTTCCTGTTCTG
GAAGTACTTCAAACATCGGCAACAATTATGTTTCCTGGTATCAGCAGCACCCGG
GCAAAGCGCCCAAGCTGATGATTTATGATGTGTCTAAACGTCCAAGTGGTGTTCC
TGACCGGTTCAGCGGTTCCAAGTCTGGGAATAGTGCCTCACTGGACATCTCAGG
CCTGCAAAGCGAAGATGAGGCGGACTATTACTGCGCAGCTTGGGATGACAGCCT
GTCCGAATTTCTGTTCGGCACCGGGACAAAGCTGACCGTGCTGGGC (aFITC-scFv)
GGCGGGGGCGGCAGCGGCGGCGGTGGCAGC (Linker)
GACATCTTGCCGTGCGTGCCCTTCAGCGTGGCCAAGAGTGTGAAGTCCTTGTACC
TGGGCCGGATGTTCAGTGGGACCCCCGTGATCCGACTGCGCTTCAAGAGGCTGC
AGCCCACCAGGCTGGTAGCTGAGTTTGACTTCCGGACCTTTGACCCCGAGGGCA
TCCTCCTCTTTGCCGGAGGCCACCAGGACAGCACCTGGATCGTGCTGGCCCTGAG
AGCCGGCCGGCTGGAGCTGCAGCTGCGCTACAACGGTGTCGGCCGTGTCACCAG
CAGCGGCCCGGTCATCAACCATGGCATGTGGCAGACAATCTCTGTTGAGGAGCT
GGCGCGGAATCTGGTCATCAAGGTCAACAGGGATGCTGTCATGAAAATCGCGGT
GGCCGGGGACTTGTTCCAACCGGAGCGAGGACTGTATCATCTGAACCTCACCGT
GGGAGGTATTCCCTTCCATGAGAAGGACCTCGTGCAGCCTATAAACCCTCGTCTG
GATGGCTGTATGAGGAGCTGGAACTGGCTGAACGGAGAAGACACCACCATCCA
GGAAACGGTGAAAGTGAACACGAGGATGCAGTGCTTCTCGGTGACGGAGAGAG
GCTCTTTCTACCCCGGGAGCGGCTTCGCCTTCTACAGCCTGGACTACATGCGGAC
CCCTCTGGACGTCGGGACTGAATCAACCTGGGAAGTAGAAGTCGTGGCTCACAT
CCGCCCAGCCGCAGACACAGGCGTGCTGTTTGCGCTCTGGGCCCCCGACCTCCGT
GCCGTGCCTCTCTCTGTGGCACTGGTAGACTATCACTCCACGAAGAAACTCAAG
AAGCAGCTGGTGGTCCTGGCCGTGGAGCATACGGCCTTGGCCCTAATGGAGATC
AAGGTCTGCGACGGCCAAGAGCACGTGGTCACCGTCTCGCTGAGGGACGGTGAG
GCCACCCTGGAGGTGGACGGCACCAGGGGCCAGAGCGAGGTGAGCGCCGCGCA
GCTGCAGGAGAGGCTGGCCGTGCTCGAGAGGCACCTGCGGAGCCCCGTGCTCAC
CTTTGCCGGCGGCCTGCCAGATGTGCCGGTGACTTCAGCGCCAGTCACCGCGTTC
TACCGCGGCTGCATGACACTGGAGGTCAACCGGAGGCTGCTGGACCTGGACGAG
GCGGCGTACAAGCACAGCGACATCACGGCCCACTCCTGCCCCCCCGTGGAGCCC
GCCGCAGCC (Gas6-Gla EGF deleted)
caaGGATCCCGGGCTGACTACAAAGACCATGACGGTGATTATAAAGATCATGACA
TCGACTACAAGGATGACGATGACAAGtga (FLAG)

5. αAβ-Gas6 HA tag (Gla EGF delete, GE-/-) SEQ ID NO: 147
ATGGCCCCTTCGCTCTCGCCCGGGCCCGCCGCCCTGCCGCGCGCCGCAGCTGC
TGCTGCTGCTGGCCGCGGAGTGCGCGCTTGCC (SS)
GACATTCAGATGACTCAATCTCCTAGCTCTCTGAGCGCCTCCGTTGGAGATAGAG
TCACTATTACCTGCAGAGCCAGCCAATCCATCAGCTCTTTATCTAAATTGGTACCA
ACAGAAGCCCGGCAAAGCGCCAAAGCTGCTCATCTACGCTGCAAGCTCCTTACA
GAGCGGAGTACCCAGCAGATTCTCAGGCAGTGGCAGTGGGACTGACTTCACATT
GACGATTAGCTCTCTGCAGCCTGAAGACTTTGCCACATACTATTGTCAGCAGAGC
TATAGCACCCCGCTGACGTTTGGAGGCGGAACTAAGGTGGAAATCAAGAGAGG
AGGCGGGGGCTCCGGCGGGGGTGGCTCGGGGGAGGAGGCTCAGAGGTTCAGC
TTGTCGAGTCTGGGGGGGAGTCGTTCAGCCAGGTAGAAGCCTCAGACTGAGCT
GTGCCGCAAGTGGGTTTGCTTTTTCATCTTACGGTATGCACTGGGTGAGACAGGC
TCCTGGCAAAGGACTCGAGTGGGTCGCTGTAATATGGTTCGATGGTACAAAGAA
ATACTATACCGATAGTGTGAAAGGAAGATTCACCATTTCACGAGACAACAGTAA
AAATACCTTGTACCTTCAGATGAACACCCTGAGAGCAGAAGACACAGCCGTGTA
CTACTGCGCCAGAGATAGAGGTATCGGAGCAAGGCGTGGTCCCTATTATATGGA
TGTGTGGGGAAGGGAACAACAGTGACTGTGAGCTCT (Adu-scFv)
GGCGGGGGCGGCAGCGGCGGCGGTGGCAGC (Linker)
GACATCTTGCCGTGCGTGCCCTTCAGCGTGGCCAAGAGTGTGAAGTCCTTGTACC
TGGGCCGGATGTTCAGTGGGACCCCCGTGATCCGACTGCGCTTCAAGAGGCTGC
AGCCCACCAGGCTGGTAGCTGAGTTTGACTTCCGGACCTTTGACCCCGAGGGCA
TCCTCCTCTTTGCCGGAGGCCACCAGGACAGCACCTGGATCGTGCTGGCCCTGAG
AGCCGGCCGGCTGGAGCTGCAGCTGCGCTACAACGGTGTCGGCCGTGTCACCAG
CAGCGGCCCGGTCATCAACCATGGCATGTGGCAGACAATCTCTGTTGAGGAGCT
GGCGCGGAATCTGGTCATCAAGGTCAACAGGGATGCTGTCATGAAAATCGCGGT
GGCCGGGGACTTGTTCCAACCGGAGCGAGGACTGTATCATCTGAACCTGACCGT
GGGAGGTATTCCCTTCCATGAGAAGGACCTCGTGCAGCCTATAAACCCTCGTCTG
GATGGCTGCATGAGGAGCTGGAACTGGCTGAACGGAGAAGACACCACCATCCA
GGAAACGGTGAAAGTGAACACGAGGATGCAGTGCTTCTCGGTGACGGAGAGAG
GCTCTTTCTACCCCGGGAGCGGCTTCGCCTTCTACAGCCTGGACTACATGCGGAC
CCCTCTGGACGTCGGGACTGAATCAACCTGGGAAGTAGAAGTCGTGGCTCACAT
```

TABLE 4-continued

```
CCGCCCAGCCGCAGACACAGGCGTGCTGTTTGCGCTCTGGGCCCCCGACCTCCGT
GCCGTGCCTCTCTCTGTGGCACTGGTAGACTATCACTCCACGAAGAAACTCAAG
AAGCAGCTGGTGGTCCTGGCCGTGGAGCATACGGCCTTGGCCCTAATGGAGATC
AAGGTCTGCGACGGCCAAGAGCACGTGGTCACCGTCTCGCTGAGGGACGGTGAG
GCCACCCTGGAGGTGGACGGCACCAGGGGCCAGAGCGAGGTGAGCGCCGCGCA
GCTGCAGGAGAGGCTGGCCGTGCTCGAGAGGCACCTGCGGAGCCCCGTGCTCAC
CTTTGCTGGCGGCCTGCCAGATGTGCCGGTGACTTCAGCGCCAGTCACCGCGTTC
TACCGCGGCTGCATGACACTGGAGGTCAACCGGAGGCTGCTGGACCTGGACGAG
GCGGCGTACAAGCACAGCGACATCACGGCCCACTCCTGCCCCCCCGTGGAGCCC
GCCGCAGCC (Gas6-Gla EGF deleted)
GGCAGCGGCAGCGGCAGCGGCAGCGGCAGCGGCAGCTACCCATACGATGTTCC
AGATTACGCTTGA (HA)

6. Lentiviral Aducanumab IgG_IRES Zsgreen deleted SEQ ID NO: 148
GGATCCATGGGCTGGTCCTGCATCATCCTGTTCCTGGTGGCCACCGCCACCGGC
(SS)
GACATTCAGATGACTCAATCTCCTAGCTCTCTGAGCGCCTCCGTTGGAGATAGAG
TCACTATTACCTGCAGAGCCAGCCAATCCATCAGCTCTTATCTAAATTGGTACCA
ACAGAAGCCCGGCAAAGCGCCAAAGCTGCTCATCTACGCTGCAAGCTCCTTACA
GAGCGGAGTACCCAGCAGATTCTCAGGCAGTGGCAGTGGGACTGACTTCACATT
GACGATTAGCTCTCTGCAGCCTGAAGACTTTGCCACATACTATTGTCAGCAGAGC
TATAGCACCCCGCTGACGTTTGGAGGCGGAACTAAGGTGGAAATCAAGAGAAA
ACGAACTGTGGCTGCACCATCTGTCTTCATCTTCCCGCCATCTGATGAGCAGTTG
AAATCTGGAACTGCCTCTGTCGTGTGCCTGCTGAATAACTTCTATCCCAGAGAGG
CCAAAGTACAGTGGAAGGTGGATAACGCCCTCCAATGGGTAACTCCCAGGAGA
GTGTCACAGAGCAGGACAGCAAGGACAGCACCTACAGCCTCAGCAGCACCCTG
ACGCTGAGCAAAGCAGACTACGAGAAACACAAAGTCTACGCCTGCGAAGTCAC
CCATCAGGGCCTGTCCTCGCCCGTCACAAAGAGCTTCAACAGGGGAGAGTGT
(Adu-Light chain)
CGCAGAAAACGCGGAAGCGGAGAGGGCAGAGGAAGTCTTCTAACATGCGGTGA
CGTGGAGGAGAATCCCGGCCCT (T2A)
ATGGGCTGGTCCTGCATCATCCTGTTCCTGGTGGCCACCGCCACCGGC (SS)
GAGGTTCAGCTTGTCGAGTCTGGGGGGGGAGTCGTTCAGCCAGGTAGAAGCCTC
AGACTGAGCTGTGCCGCAAGTGGGTTTGCTTTTTCATCTTACGGTATGCACTGGG
TGAGACAGGCTCCTGGCAAAGGACTCGAGTGGGTCGCTGTAATATGGTTCGATG
GTACAAAGAAATACTATACCGATAGTGTGAAAGGAAGATTCACCATTTCACGAG
ACAACAGTAAAAATACCTTGTACCTTCAGATGAACACCCTGAGAGCAGAAGACA
CAGCCGTGTACTACTGCGCCAGAGATAGAGGTATCGGAGCAAGGCGTGGTCCT
ATTATATGGATGTGTGGGGGAAGGGAACAACAGTGACTGTGAGCTCTGCCTCCA
CCAAGGGCCCATCGGTCTTCCCCCTGGCACCCTCCTCCAAGAGCACCTCTGGGGG
CACAGCGGCCCTGGGCTGCCTGGTCAAGGACTACTTCCCCGAACCGGTGACGGT
GTCGTGGAACTCAGGCGCCCTGACCAGCGGCGTGCACACCTTCCCGGCTGTCCT
ACAGTCCTCAGGACTCTACTCCCTCAGCAGCGTGGTGACTGTGCCCTCTAGCAGC
TTGGGCACCCAGACCTACATCTGCAACGTGAATCACAAGCCCAGCAACACCAAG
GTGGACAAGAAAGTTGAGCCCAAATCTAGCGACAAAACTCACACAAGCCCACC
GTGCCCAGCACCTGAACTCCTGGGGGACCGTCAGTCTTCCTCTTCCCCCCAAAA
CCCAAGGACACCCTCATGATCTCCCGGACCCCTGAGGTCACATGCGTGGTGGTG
GACGTGAGCCACGAAGACCCTGAGGTCAAGTTCAACTGGTACGTGGACGGCGTG
GAGGTGCATAATGCCAAGACAAAGCCGCGGGAGGAGCAGTACAACAGCACGTA
CCGTGTGGTCAGCGTCCTCACCGTCCTGCACCAGGACTGGCTGAATGGCAAGGA
GTACAAGTGCAAGGTCTCCAACAAAGCCCTCCCAGCCCCCATCGAGAAAACCAT
CTCCAAAGCCAAAGGGCAGCCCCGAGAACCACAGGTGTACACCCTGCCCCCATC
CCGGGATGAGCTGACCAAGAACCAGGTCAGCCTGACCTGCCTGGTCAAAGGCTT
CTATCCCAGCGACATCGCCGTGGAGTGGGAGAGCAATGGGCAGCCGGAGAACA
ACTACAAGACCACGCCTCCCGTGCTGGACTCCGACGGCTCCTTCTTCCTCTACAG
CAAGCTCACCGTGGACAAGAGCAGGTGGCAGCAGGGGAACGTCTTCTCATGCTC
CGTGATGCATGAGGCTCTGCACAACCACTACACGCAGAAGAGCCTCTCCCTGTC
CCCGGGTAAAtga (Adu-Heavy chain)

7. Endogenous full sequence human Gas6 protein SEQ ID NO: 149
ATGGCCCCTTCGCTCTCGCCCGGGCCCGCCGCCCTGCGCCGCGCGCCGCAGCTGC
TGCTGCTGCTGCTGGCCGCGGAGTGCGCGCTTGCCGCGCTGTTGCCGGCGCGCG
AGGCCACGCAGTTCCTGCGGCCCAGGCAGCGCCGCGCCTTTCAGGTCTTCGAGG
AGGCCAAGCAGGGCCACCTGGAGAGGGAGTGCGTGGAGGAGCTGTGCAGCCGC
GAGGAGGCGCGGGAGGTGTTCGAGAACGACCCCGAGACGGATTATTTTTACCCA
AGATACTTAGACTGCATCAACAAGTATGGGTCTCCGTACACCAAAAACTCAGGC
TTCGCCACCTGCGTGCAAAACCTGCCTGACCAGTGCACGCCCAACCCTGCGAT
AGGAAGGGGACCCAAGCCTGCCAGGACCTCATGGGCAACTTCTTCTGCCTGTGT
AAAGCTGGCTGGGGGCCGGCTCTGCGACAAAGATGTCAACGAATGCAGCCA
GGAGAACGGGGCTGCCTCCAGATCTGCCACAACAAGCCGGGTAGCTTCCACTG
TTCCTGCCACAGCGGCTTCGAGCTCTCCTCTGATGGCAGGACCTGCCAAGACATA
GACGAGTGCGCAGACTCGGAGGCCTGCGGGGAGGCGCGCTGCAAGAACCTGCC
CGGCTCCTACTCCTGCCTCTGTGACGAGGGCTTTGCGTACAGCTCCCAGGAGAAG
GCTTGCCGAGATGTGGACGAGTGTCTGCAGGGCCGCTGTGAGCAGGTCTGCGTG
AACTCCCCAGGGAGCTACACCTGCCACTGTGACGGGCGTGGGGGCCTCAAGCTG
TCCCAGGACATGGACACCTGTGAGGACATCTTGCCGTGCGTGCCCTTCAGCGTG
GCCAAGAGTGTGAAGTCCTTGTACCTGGGCCGGATGTTCAGTGGGACCCCCGTG
ATCCGACTGCGCTTCAAGAGGCTGCAGCCCACCAGGCTGGTAGCTGAGTTTGAC
TTCCGGACCTTTGACCCCGAGGGCATCCTCCTCTTTGCCGGAGGCCACCAGGACA
GCACCTGGATCGTGCTGGCCCTGAGAGCCGGCCGGCTGGAGCTGCAGCTGCGCT
```

TABLE 4-continued

```
ACAACGGTGTCGGCCGTGTCACCAGCAGCGGCCCGGTCATCAACCATGGCATGT
GGCAGACAATCTCTGTTGAGGAGCTGGCGCGGAATCTGGTCATCAAGGTCAACA
GGGATGCTGTCATGAAAATCGCGGTGGCCGGGGACTTGTTCCAACCGGAGCGAG
GACTGTATCATCTGAACCTGACCGTGGGAGGTATTCCCTTCCATGAGAAGGACCT
CGTGCAGCCTATAAACCCTCGTCTGGATGGCTGCATGAGGAGCTGGAACTGGCT
GAACGGAGAAGACACCACCATCCAGGAAACGGTGAAAGTGAACACGAGGATGC
AGTGCTTCTCGGTGACGGAGAGAGGCTCTTTCTACCCCGGGAGCGGCTTCGCCTT
CTACAGCCTGGACTACATGCGGACCCCTCTGGACGTCGGGACTGAATCAACCTG
GGAAGTAGAAGTCGTGGCTCACATCCGCCCAGCCGCAGACACAGGCGTGCTGTT
TGCGCTCTGGGCCCCCGACCTCCGTGCCGTGCCTCTCTCTGTGGCACTGGTAGAC
TATCACTCCACGAAGAAACTCAAGAAGCAGCTGGTGGTCCTGGCCGTGGAGCAT
ACGGCCTTGGCCCTAATGGAGATCAAGGTCTGCGACGGCCAAGAGCACGTGGTC
ACCGTCTCGCTGAGGGACGGTGAGGCCACCCTGGAGGTGGACGGCACCAGGGG
CCAGAGCGAGGTGAGCGCCGCGCAGCTGCAGGAGAGGCTGGCCGTGCTCGAGA
GGCACCTGCGGAGCCCCGTGCTCACCTTTGCTGGCGGCCTGCCAGATGTGCCGGT
GACTTCAGCGCCAGTCACCGCGTTCTACCGCGGCTGCATGACACTGGAGGTCAA
CCGGAGGCTGCTGGACCTGGACGAGGCGGCGTACAAGCACAGCGACATCACGG
CCCACTCCTGCCCCCCCGTGGAGCCCGCCGCAGCC (full-length human Gas6)
caaGGATCCCGGGCTGACTACAAAGACCATGACGGTGATTATAAAGATCATGACA
TCGACTACAAGGATGACGATGACAAGTGA (FLAG)
```

Preparation Example 2. Gas6-Based Fusion Molecule Targeting Tau

To prepare a tau-specific chimeric phagocytosis inducer based on Gas6 protein, the Gla domain and the EGF repeat domain were first removed, and a single-chain variable fragment (scFv) of semorinemab, a tau-specific antibody fragment; scFv), was introduced at that position (αTau-Gas6). Table 5 below shows the amino acid sequence and nucleotide sequence of the chimeric phagocytosis inducer.

TABLE 5

```
1. αTau-Gas6 (Tau-VL-G4Sx3-VH-LG-HA-T2A-EGFP, amino acid
sequence) SEQ ID NO: 150
MAPSLSPGPAALRRAPQLLLLLLAAECALA (SS)
DDVLTQTPLSLPVTPGQPASISCRSSQSIVHSNGNTYLEWYLQKPGQSPQLLIYKVSN
RFSGVPDRFSGSGSGTDFTLKISRVEAEDVGVYYCFQGSLVPWTFGQGTKVEIKGGG
GSGGGGSGGGGSEVQLVESGGGLVQPGGSLRLSCAASGLIFRSYGMSWVRQAPGKG
LEWVATINSGGTYTYYPDSVKGRFTISRDNSKNTLYLQMNSLRAEDTAVYYCANSYS
GAMDYWGQGTLVTVSS (aTau-scFv)
GGGGSGGGGS (Linker)
DILPCVPFSVAKSVKSLYLGRMFSGTPVIRLRFKRLQPTRLVAEFDFRTFDPEGILLFAG
GHQDSTWIVLALRAGRLELQLRYNGVGRVTSSGPVINHGMWQTISVEELARNLVIK
VNRDAVMKIAVAGDLFQPERGLYHLNLTVGGIPFHEKDLVQPINPRLDGCMRSWNW
LNGEDTTIQETVKVNTRMQCFSVTERGSFYPGSGFAFYSLDYMRTPLDVGTESTWEV
EVVAHIRPAADTGVLFALWAPDLRAVPLSVALVDYHSTKKLKKQLVVLAVEHTALAL
MEIKVCDGQEHVVTVSLRDGEATLEVDGTRGQSEVSAAQLQERLAVLERHLRSPVL
TFAGGLPDVPVTSAPVTAFYRGCMTLEVNRRLLDLDEAAYKHSDITAHSCPPVEPAA
A (Gas6-Gla EGF deleted)
GSGSGSGSGSGSYPYDVPDYA (HA)
EGRGSLLTCGDVEENPGP (T2A)
VSKGEELFTGVVPILVELDGDVNGHKFSVSGEGEGDATYGKLTLKFICTTGKLPVPW
PTLVTTLTYGVQCFSRYPDHMKQHDFFKSAMPEGYVQERTIFFKDDGNYKTRAEVK
FEGDTLVNRIELKGIDFKEDGNILGHKLEYNYNSHNVYIMADKQKNGIKVNFKIRHN
IEDGSVQLADHYQQNTPIGDGPVLLPDNHYLSTQSALSKDPNEKRDHMVLLEFVTA
AGITLGMDELYK* (EGFP)

2. αTau-Gas6 (Tau-VL-G4Sx3-VH-LG-HA-T2A-EGFP, nucleotide
sequence) SEQ ID NO: 151
ATGGCCCCTTCGCTCTCGCCCGGGCCCGCCGCCCTGCGCCGCGCGCCGCAGCTGC
TGCTGCTGCTGGCCGCGGAGTGCGCGCTTGCC (SS)
GACGATGTATTAACACAAACTCCCCTATCATTGCCGGTGACCCCGGGCCAACCA
GCTTCGATCAGCTGCCGTAGCTCTCAGAGCATCGTGCACAGCAACGGTAATACC
TACCTGGAATGGTATTTGCAAAAACCGGGTCAATCCCCGCAGTTGCTGATTTATA
AAGTTTCGAATCGTTTCAGCGGTGTTCCGGATCGTTTCAGCGGCTCTGGCTCCGG
CACCGATTTTACGCTGAAGATCAGTCGCGTGGAAGCGGAGGACGTGGGTGTCTA
CTACTGCTTTCAGGGTAGTTTGGTGCCGTGGACCTTTGGTCAGGGTACTAAGGTG
GAAATTAAGGGTGGTGGGGGATCAGGTGGCGGCGGCAGCGGCGGTGGCGGGAG
CGAGGTACAACTAGTTGAATCAGGTGGAGGGTTGGTTCAGCCAGGTGGTTCGCT
GCGTCTGAGTTGTGCGGCAAGCGGTTTGATCTTTCGCAGCTATGGTATGAGCTGG
GTTCGTCAGGCGCCGGGCAAGGGTCTGGAGTGGGTGGCGACCATTAACTCTGGC
GGCACGTACACCTACTATCCCGACTCCGTGAAAGGCCGTTTCACCATCTCCCGCG
ACAATAGCAAAAACACCCTGTATTTGCAGATGAACTCGCTCCGCGCAGAGGACA
CCGCTGTGTACTACTGCGCCAATTCCTACAGCGGTGCTATGGATTATTGGGGTCA
GGGCACATTGGTGACTGTAAGCAGC (aTau-scFv)
GGCGGGGGCGGCAGCGGCGGCGGCGGTGGCAGC (Linker)
GACATCTTGCCGTGCGTGCCCTTCAGCGTGGCCAAGAGTGTGAAGTCCTTGTACC
TGGGCCGGATGTTCAGTGGGACCCCCGTGATCCGACTGCGCTTCAAGAGGCTGC
AGCCCACCAGGCTGGTAGCTGAGTTTGACTTCCGGACCTTTGACCCCGAGGGCA
TCCTCCTCTTTGCCGGAGGCCACCAGGACAGCACCTGGATCGTGCTGGCCCTGAG
```

TABLE 5-continued

```
AGCCGGCCGGCTGGAGCTGCAGCTGCGCTACAACGGTGTCGGCCGTGTCACCAG
CAGCGGCCCGGTCATCAACCATGGCATGTGGCAGACAATCTCTGTTGAGGAGCT
GGCGCGGAATCTGGTCATCAAGGTCAACAGGGATGCTGTCATGAAAATCGCGGT
GGCCGGGGACTTGTTCCAACCGGAGCGAGGACTGTATCATCTGAACCTGACCGT
GGGAGGTATTCCCTTCCATGAGAAGGACCTCGTGCAGCCTATAAACCCTCGTCTG
GATGGCTGCATGAGGAGCTGGAACTGGCTGAACGGAGAAGACACCACCATCCA
GGAAACGGTGAAAGTGAACACGAGGATGCAGTGCTTCTCGGTGACGGAGAGAG
GCTCTTTCTACCCCGGGAGCGGCTTCGCCTTCTACAGCCTGGACTACATGCGGAC
CCCTCTGGACGTCGGGACTGAATCAACCTGGGAAGTAGAAGTCGTGGCTCACAT
CCGCCCAGCCGCAGACACAGGCGTGCTGTTTGCGCTCTGGGCCCCCGACCTCCGT
GCCGTGCCTCTCTCTGTGGCACTGGTAGACTATCACTCCACGAAGAAACTCAAG
AAGCAGCTGGTGGTCCTGGCCGTGGAGCATACGGCCTTGGCCCTAATGGAGATC
AAGGTCTGCGACGGCCAAGAGCACGTGGTCACCGTCTCGCTGAGGGACGGTGAG
GCCACCCTGGAGGTGGACGGCACCAGGGGCCAGAGCGAGGTGAGCGCCGCGCA
GCTGCAGGAGAGGCTGGCCGTGCTCGAGAGGCACCTGCGGAGCCCCGTGCTCAC
CTTTGCTGGCGGCCTGCCAGATGTGCCGGTGACTTCAGCGCCAGTCACCGCGTTC
TACCGCGGCTGCATGACACTGGAGGTCAACCGGAGGCTGCTGGACCTGGACGAG
GCGGCGTACAAGCACAGCGACATCACGGCCCACTCCTGCCCCCCCGTGGAGCCC
GCCGCAGCC (Gas6-Gla EGF deleted)
GGCAGCGGCAGCGGCAGCGGCAGCGGCAGCGGCAGCtacccatacgatgttcca
gattacgct (HA)
GAGGGCAGAGGAAGTCTGCTAACATGCGGTGACGTCGAGGAGAATCCTGGCCC
A (T2A)
GTGAGCAAGGGCGAGGAGCTGTTCACCGGGGTGGTGCCCATCCTGGTCGAGCTG
GACGGCGACGTAAACGGCCACAAGTTCAGCGTGTCCGGCGAGGGCGAGGGCGA
TGCCACCTACGGCAAGCTGACCCTGAAGTTCATCTGCACCACCGGCAAGCTGCC
CGTGCCCTGGCCCACCCTCGTGACCACCCTGACCTACGGCGTGCAGTGCTTCAGC
CGCTACCCCGACCACATGAAGCAGCACGACTTCTTCAAGTCCGCCATGCCCGAA
GGCTACGTCCAGGAGCGCACCATCTTCTTCAAGGACGACGGCAACTACAAGACC
CGCGCCGAGGTGAAGTTCGAGGGCGACACCCTGGTGAACCGCATCGAGCTGAAG
GGCATCGACTTCAAGGAGGACGGCAACATCCTGGGGCACAAGCTGGAGTACAA
CTACAACAGCCACAACGTCTATATCATGGCCGACAAGCAGAAGAACGGCATCAA
GGTGAACTTCAAGATCCGCCACAACATCGAGGACGGCAGCGTGCAGCTCGCCGA
CCACTACCAGCAGAACACCCCCATCGGCGACGGCCCCGTGCTGCTGCCCGACAA
CCACTACCTGAGCACCCAGTCCGCCCTGAGCAAAGACCCCAACGAGAAGCGCGA
TCACATGGTCCTGCTGGAGTTCGTGACCGCCGCCGGGATCACTCTCGGCATGGAC
GAGCTGTACAAGtaa (EGFP)
```

Preparation Example 3. Gas6-Based Fusion Molecule Targeting Alpha-Synuclein

To prepare an alpha-synuclein-specific chimera phagocytosis inducer based on Gas6 protein, the Gla domain and the EGF repeat domain were first removed, and a single-chain variable region (scFv) of cinpanemab, an alpha-synuclein-specific antibody, was introduced at that position (ααSyn-Gas6). Table 6 below shows the amino acid sequence and nucleotide sequence of the chimeric phagocytosis inducer.

TABLE 6

| |
|---|
| 1. ααSyn-Gas6 (Cinpanemab (aSyn)_VL-G4Sx3-VH-LG-HA-T2A-EGFP, amino acid sequence) SEQ ID NO: 152 |
| MAPSLSPGPAALRRAPQLLLLLLAAECALA (SS) |
| SYELTQPPSVSVSPGQTARITCSGEALPMQFAHWYQQRPGKAPVIVVYKDSERPSGV |
| PERFSGSSSGTTATLTITGVQAEDEADYYCQSPDSTNTYEVFGGGTKLTVLGGGGSG |
| GGGSGGGGSEVQLVESGGGLVEPGGSLRLSCAVSGFDFEKAWMSWVRQAPGQGLQ |
| WVARIKSTADGGTTSYAAPVEGRFIISRDDSRNMLYLQMNSLKTEDTAVYYCTSAH |
| WGQGTLVTVSS (aaSyn-scFv) |
| GGGGSGGGGS (Linker) |
| DILPCVPFSVAKSVKSLYLGRMFSGTPVIRLRFKRLQPTRLVAEFDFRTFDPEGILLFA |
| GGHQDSTWIVLALRAGRLELQLRYNGVGRVTSSGPVINHGMWQTISVEELARNLVI |
| KVNRDAVMKIAVAGDLFQPERGLYHLNLTVGGIPFHEKDLVQPINPRLDGCMRSWN |
| WLNGEDTTIQETVKVNTRMQCFSVTERGSFYPGSGFAFYSLDYMRTPLDVGTESTW |
| EVEVVAHIRPAADTGVLFALWAPDLRAVPLSVALVDYHSTKKLKKQLVVLAVEHT |
| ALALMEIKVCDGQEHVVTVSLRDGEATLEVDGTRGQSEVSAAQLQERLAVLERHLR |
| SPVLTFAGGLPDVPVTSAPVTAFYRGCMTLEVNRRLLDLDEAAYKHSDITAHSCPPV |
| EPAAA (Gas6-Gla EGF deleted) |
| GSGSGSGSGSGSYPYDVPDYA (HA) |
| EGRGSLLTCGDVEENPGP (T2A) |
| VSKGEELFTGVVPILVELDGDVNGHKFSVSGEGEGDATYGKLTLKFICTTGKLPVPW |
| PTLVTTLTYGVQCFSRYPDHMKQHDFFKSAMPEGYVQERTIFFKDDGNYKTRAEVK |
| FEGDTLVNRIELKGIDFKEDGNILGHKLEYNYNSHNVYIMADKQKNGIKVNFKIRHN |
| IEDGSVQLADHYQQNTPIGDGPVLLPDNHYLSTQSALSKDPNEKRDHMVLLEFVTA |
| AGITLGMDELYK* |
| |
| 2. ααSyn-Gas6 (Cinpanemab (aSyn)_VL-G4Sx3-VH-LG-HA-T2A-EGFP, nucleotide sequence) SEQ ID NO: 153 |
| ATGGCCCCTTCGCTCTCGCCCGGGCCCGCCGCCCTGCGCCGCGCGCCGCAGCTGC |
| TGCTGCTGCTGCTGGCCGCGGAGTGCGCGCTTGCC (SS) |
| TCCTATGAGCTGACTCAGCCACCCTCGGTGTCAGTGTCCCCAGGACAGACGGCC |
| AGGATCACCTGCTCTGGAGAAGCATTGCCAATGCAATTTGCTCATTGGTACCAAC |

TABLE 6-continued

```
AGAGGCCAGGCAAGGCCCCAGTGATAGTGGTGTACAAAGACAGTGAGAGACCG
TCAGGTGTCCCTGAGCGATTCTCTGGCTCCAGCTCAGGGACAACAGCCACGTTG
ACCATCACTGGAGTCCAGGCAGAAGATGAGGCTGACTATTACTGCCAGTCGCCA
GACAGCACTAACACTTATGAAGTCTTCGGCGGAGGGACCAAGCTGACCGTCCTA
GGTGGTGGGGGATCAGGTGGCGGCGGCAGCGGCGGTGGCGGGAGCGAGGTGCA
GCTGGTGGAGTCTGGGGGAGGTCTGGTCGAGCCGGGGGGGTCCCTAAGACTCTC
CTGTGCAGTCTCCGGATTCGATTTCGAAAAAGCCTGGATGAGTTGGGTCCGCCA
GGCTCCAGGGCAGGGGCTACAGTGGGTTGCCCGTATCAAGAGCACAGCTGATGG
TGGGACAACAAGCTACGCCGCCCCCGTGGAAGGCAGGTTCATCATCTCAAGAGA
TGATTCGAGAAACATGCTTTATCTGCAAATGAACAGTCTGAAAACTGAAGCAC
AGCCGTCTATTATTGTACATCAGCCCACTGGGGCAGGGAACCCTGGTCACCGTC
TCCTCG (aaSyn-scFv)
GGCGGGGGCGGCAGCGGCGGCGGTGGCAGC (Linker)
GACATCTTGCCGTGCGTGCCCTTCAGCGTGGCCAAGAGTGTGAAGTCCTTGTACC
TGGGCCGGATGTTCAGTGGGACCCCCGTGATCCGACTGCGCTTCAAGAGGCTGC
AGCCCACCAGGCTGGTAGCTGAGTTTGACTTCCGGACCTTTGACCCCGAGGGCA
TCCTCCTCTTTGCCGGAGGCCACCAGGACAGCACCTGGATCGTGCTGGCCCTGAG
AGCCGGCCGGCTGGAGCTGCAGCTGCGCTACAACGGTGTCGGCCGTGTCACCAG
CAGCGGCCCGGTCATCAACCATGGCATGTGGCAGACAATCTCTGTTGAGGAGCT
GGCGCGGAATCTGGTCATCAAGGTCAACAGGGATGCTGTCATGAAAATCGCGGT
GGCCGGGGACTTGTTCCAACCGGAGCGAGGACTGTATCATCTGAACCTGACCGT
GGGAGGTATTCCCTTCCATGAGAAGGACCTCGTGCAGCCTATAAACCCTCGTCTG
GATGGCTGCATGAGGAGCTGGAACTGGCTGAACGGAGAAGACACCACCATCCA
GGAAACGGTGAAAGTGAACACGAGGATGCAGTGCTTCTCGGTGACGGAGAGAG
GCTCTTTCTACCCCGGGAGCGGCTTCGCCTTCTACAGCCTGGACTACATGCGGAC
CCCTCTGGACGTCGGGACTGAATCAACCTGGGAAGTAGAAGTCGTGGCTCACAT
CCGCCCAGCCGCAGACACAGGCGTGCTGTTTGCGCTCTGGGCCCCCGACCTCCGT
GCCGTGCCTCTCTCTGTGGCACTGGTAGACTATCACTCCACGAAGAAACTCAAG
AAGCAGCTGGTGGTCCTGGCCGTGGAGCATACGGCCTTGGCCCTAATGGAGATC
AAGGTCTGCGACGGCCAAGAGCACGTGGTCACCGTCTCGCTGAGGGACGGTGAG
GCCACCCTGGAGGTGGACGGCACCAGGGGCCAGAGCGAGGTGAGCGCCGCGCA
GCTGCAGGAGAGGCTGGCCGTGCTCGAGAGGCACCTGCGGAGCCCCGTGCTCAC
CTTTGCTGGCGGCCTGCCAGATGTGCCGGTGACTTCAGCGCCAGTCACCGCGTTC
TACCGCGGCTGCATGACACTGGAGGTCAACCGGAGGCTGCTGGACCTGGACGAG
GCGGCGTACAAGCACAGCGACATCACGGCCCACTCCTGCCCCCCGTGGAGCCC
GCCGCAGCC (Gas6-Gla EGF deleted)
GGCAGCGGCAGCGGCAGCGGCAGCGGCAGCGGCAGCTACCCATACGATGTTCC
AGATTACGCT (HA)
GAGGGCAGAGGAAGTCTGCTAACATGCGGTGACGTCGAGGAGAATCCTGGCCC
A (T2A)
GTGAGCAAGGGCGAGGAGCTGTTCACCGGGGTGGTGCCCATCCTGGTCGAGCTG
GACGGCGACGTAAACGGCCACAAGTTCAGCGTGTCCGGCGAGGGCGAGGGCGA
TGCCACCTACGGCAAGCTGACCCTGAAGTTCATCTGCACCACCGGCAAGCTGCC
CGTGCCCTGGCCCACCCTCGTGACCACCCTGACCTACGGCGTGCAGTGCTTCAGC
CGCTACCCCGACCACATGAAGCAGCACGACTTCTTCAAGTCCGCCATGCCCGAA
GGCTACGTCCAGGAGCGCACCATCTTCTTCAAGGACGACGGCAACTACAAGACC
CGCGCCGAGGTGAAGTTCGAGGGCGACACCCTGGTGAACCGCATCGAGCTGAAG
GGCATCGACTTCAAGGAGGACGGCAACATCCTGGGGCACAAGCTGGAGTACAA
CTACAACAGCCACAACGTCTATATCATGGCCGACAAGCAGAAGAACGGCATCAA
GGTGAACTTCAAGATCCGCCACAACATCGAGGACGGCAGCGTGCAGCTCGCCGA
CCACTACCAGCAGAACACCCCCATCGGCGACGGCCCCGTGCTGCTGCCCGACAA
CCACTACCTGAGCACCCAGTCCGCCCTGAGCAAAGACCCCAACGAGAAGCGCGA
TCACATGGTCCTGCTGGAGTTCGTGACCGCCGCCGGGATCACTCTCGGCATGGAC
GAGCTGTACAAGTAA (EGFP)
```

Preparation Example 4. ProS1-Based Fusion Molecule Targeting Beta-Amyloid

To prepare a beta-amyloid (Aβ)-specific chimeric phagocytosis inducer based on ProS1 protein, the Gla domain and the EGF repeat domain were first removed, and a single-chain variable fragment (scFv) of aducanumab, a beta-amyloid-specific antibody, was introduced at that position (αAβ-ProS1). Table 7 below shows the amino acid sequence and nucleotide sequence of the chimeric phagocytosis inducer.

TABLE 7

```
1. αAβ-ProS1 (αAβ-ProS1(GE-)-FLAG, amino acid sequence)
SEQ ID NO: 154
MRVLGGRCGALLACLLLVLPVSEA (SS)
DIQMTQSPSSLSASVGDRVTITCRASQSISSYLNWYQQKPGKAPKLLIYAASSLQSGV
PSRFSGSGSGTDFTLTISSLQPEDFATYYCQQSYSTPLTFGGGTKVEIKRGGGGSGGG
GSGGGGSEVQLVESGGGVVQPGRSLRLSCAASGFAFSSYGMHWVRQAPGKGLEWV
AVIWFDGTKKYYTDSVKGRFTISRDNSKNTLYLQMNTLRAEDTAVYYCARDRGIGA
RRGPYYMDVWGKGTTVTVSS (Adu-scFv)
GGGGSGGGS (Linker)
VVSVCLPLNLDTKYELLYLAEQFAGVVLYLKFRLPEISRFSAEFDFRTYDSEGVILYA
ESIDHSAWLLIALRGGKIEVQLKNEHTSKITTGGDVINNGLWNMVSVEELEHSISIKIA
KEAVMDINKPGPLFKPENGLLETKVYFAGFPRKVESELIKPINPRLDGCIRSWNLMK
```

TABLE 7-continued

```
QGASGIKEIIQEKQNKHCLVTVEKGSYYPGSGIAQFHIDYNNVSSAEGWHVNVTLNI
RPSTGTGVMLALVSGNNTVPFAVSLVDSTSEKSQDILLSVENTVIYRIQALSLCSDQQ
SHLEFRVNRNNLELSTPLKIETISHEDLQRQLAVLDKAMKAKVATYLGGLPDVPFSA
TPVNAFYNGCMEVNINGVQLDLDEAISKHNDIRAHSCPSVWKKTKNS (ProS1(GE-))
QGSRADYKDHDGDYKDHDIDYKDDDDK* (FLAG)

2. αAβ-ProS1 (αAβ-ProS1(GE-)-FLAG, nucleotide sequence)
SEQ ID NO: 155
ATGAGGGTCCTGGGTGGGCGCTGCGGGGCGCTGCTGGCGTGTCTCCTCCTAGTG
CTTCCCGTCTCAGAGGCA (SS)
GACATTCAGATGACTCAATCTCCTAGCTCTCTGAGCGCCTCCGTTGGAGATAGAG
TCACTATTACCTGCAGAGCCAGCCAATCCATCAGCTCTTATCTAAATTGGTACCA
ACAGAAGCCCGGCAAAGCGCCAAAGCTGCTCATCTACGCTGCAAGCTCCTTACA
GAGCGGAGTACCCAGCAGATTCTCAGGCAGTGGCAGTGGGACTGACTTCACATT
GACGATTAGCTCTCTGCAGCCTGAAGACTTTGCCACATACTATTGTCAGCAGAGC
TATAGCACCCCGCTGACGTTTGGAGGCGGAACTAAGGTGGAAATCAAGAGAGG
AGGCGGGGGCTCCGGCGGGGGTGGCTCGGGGGGAGGAGGCTCAGAGGTTCAGC
TTGTCGAGTCTGGGGGGGGAGTCGTTCAGCCAGGTAGAAGCCTCAGACTGAGCT
GTGCCGCAAGTGGGTTTGCTTTTTCATCTTACGGTATGCACTGGGTGAGACAGGC
TCCTGGCAAAGGACTCGAGTGGGTCGCTGTAATATGGTTCGATGGTACAAAGAA
ATACTATACCGATAGTGTGAAAGGAAGATTCACCATTTCACGAGACAACAGTAA
AAATACCTTGTACCTTCAGATGAACACCCTGAGAGCAGAAGACACAGCCGTGTA
CTACTGCGCCAGAGATAGAGGTATCGGAGCAAGGCGTGGTCCCTATTATATGGA
TGTGTGGGGGAAGGGAACAACAGTGACTGTGAGCTCT (Adu-scFv)
GGCGGGGGCGGCAGCGGCGGCGGTGGCAGC (Linker)
GTTGTTTCAGTGTGCCTTCCCTTGAACCTTGACACAAAGTATGAATTACTTTACTT
GGCGGAGCAGTTTGCAGGGGTTGTTTTATATTTAAAATTTCGTTTGCCAGAAATC
AGCAGATTTTCAGCAGAATTTGATTTCCGGACATATGATTCAGAAGGCGTGATA
CTGTACGCAGAATCTATCGATCACTCAGCGTGGCTCCTGATTGCACTTCGTGGTG
GAAAGATTGAAGTTCAGCTTAAGAATGAACATACATCCAAAATCACAACTGGAG
GTGATGTTATTAATAATGGTCTATGGAATATGGTGTCTGTGGAAGAATTAGAAC
ATAGTATTAGCATTAAAATAGCTAAAGAAGCTGTGATGGATATAAATAAACCTG
GACCCCTTTTAAGCCGGAAAATGGATTGCTGGAAACCAAAGTATACTTTGCAG
GATTCCCTCGGAAAGTGGAAAGTGAACTCATTAAACCGATTAACCCTCGTCTAG
ATGGATGTATACGAAGCTGGAATTTGATGAAGCAAGGAGCTTCTGGAATAAAGG
AAATTATTCAAGAAAAACAAAATAAGCATTGCCTGGTTACTGTGGAGAAGGGCT
CCTACTATCCTGGTTCTGGAATTGCTCAATTTCACATAGATTATAATAATGTATC
CAGTGCTGAGGGTTGGCATGTAAATGTGACCTTGAATATTCGTCCATCCACGGGC
ACTGGTGTTATGCTTGCCTTGGTTTCTGGTAACAACACAGTGCCCTTTGCTGTGTC
CTTGGTGGACTCCACCTCTGAAAAATCACAGGATATTCTGTTATCTGTTGAAAAT
ACTGTAATATATCGGATACAGGCCCTAAGTCTATGTTCCGATCAACAATCTCATC
TGGAATTTAGAGTCAACAGAAACAATCTGGAGTTGTCGACACCACTTAAAATAG
AAACCATCTCCCATGAAGACCTTCAAAGACAACTTGCCGTCTTGGACAAAGCAA
TGAAAGCAAAAGTGGCCACATACCTGGGTGGCCTTCCAGATGTTCCATTCAGTG
CCACACCAGTGAATGCCTTTTATAATGGCTGCATGGAAGTGAATATTAATGGTGT
ACAGTTGGATCTGGATGAAGCCATTTCTAAACATAATGATATTAGAGCTCACTCA
TGTCCATCAGTTTGGAAAAAGACAAAGAATTCT (ProS1(GE-))
CAAGGATCCCGGGCTGACTACAAAGACCATGACGGTGATTATAAAGATCATGAC
ATCGACTACAAGGATGACGATGACAAGtga (FLAG)
```

Preparation Example 5. Gas6-Based Fusion Molecules Targeting Beta-Amyloid (II): Beta-Amyloid-Binding Regions in the Form of Fab or Mab To prepare gas6 protein-based beta-amyloid (Aβ)-specific chimera phagocytosis inducer, the Gla domain, which rec-ognizes PS (phosphatidylserine) in apoptotic cells, was first removed, and an antigen-binding fragment (Fab) or mono-clonal antibody (Mab) of the beta-amyloid-specific antibody aducanumab was introduces at that position (αAβ[Fab]-Gas6, and αAβ[Mab]-Gas6). Tables 8-10 below show the amino acid sequences and nucleotide sequences of the two chimeric phagocytosis inducers.

TABLE 8

```
Second Region Light Chain (SEQ ID NO: 161) (the light
chain which is capable of specifically binding to beta-
amyloid can form a dimer with the peptide of sequence of
SEQ ID NO: 156 or SEQ ID NO: 158 to form Fab Adu-Gas6
or Mab Adu-Gas6, respectively):
MGWSCIILFLVATATG (SS)
DIQMTQSPSSLSASVGDRVTITCRASQSISSYLNWYQQKPGKAPKLLIYAASSLQSGV
PSRFSGSGSGTDFTLTISSLQPEDFATYYCQQSYSTPLTFGGGTKVEIKRKRTVAAPSV
FIFPPSDEQLKSGTASVVCLLNNFYPREAKVQWKVDNALQSGNSQESVTEQDSKDST
YSLSSTLTLSKADYEKHKVYACEVTHQGLSSPVTKSFNRGEC*(Adu Light Chain)

1. αAβ[Fab]-Gas6 (Aducanumab VH-CH1 (Fab)-Gas6-FLAG, amino
acid sequence) SEQ ID NO: 156
METDTLLLWVLLLWVPGSTGD (SS)
EVQLVESGGGVVQPGRSLRLSCAASGFAFSSYGMHWVRQAPGKGLEWVAVIWFDG
TKKYYTDSVKGRFTISRDNSKNTLYLQMNTLRAEDTAVYYCARDRGIGARRGPYY
```

TABLE 8-continued

```
MDVWGKGTTVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKKVE
PKSCDKTH (Adu-VH-CH1)
GGGGSGGGGS (Linker)
DILPCVPFSVAKSVKSLYLGRMFSGTPVIRLRFKRLQPTRLVAEFDFRTFDPEGILLFA
GGHQDSTWIVLALRAGRLELQLRYNGVGRVTSSGPVINHGMWQTISVEELARNLVI
KVNRDAVMKIAVAGDLFQPERGLYHLNLTVGGIPFHEKDLVQPINPRLDGCMRSWN
WLNGEDTTIQETVKVNTRMQCFSVTERGSFYPGSGFAFYSLDYMRTPLDVGTESTW
EVEVVAHIRPAADTGVLFALWAPDLRAVPLSVALVDYHSTKKLKKQLVVLAVEHT
ALALMEIKVCDGQEHVVTVSLRDGEATLEVDGTRGQSEVSAAQLQERLAVLERHLR
SPVLTFAGGLPDVPVTSAPVTAFYRGCMTLEVNRRLLDLDEAAYKHSDITAHSCPPV
EPAAA (Gas6-Gla EGF deleted)
DYKDHDGDYKDHDIDYKDDDDK* (FLAG)

2 αAβ[Fab]-Gas6 (Aducanumab(Fab)-Gas6-FLAG, nucleotide
sequence) SEQ ID NO: 157
ATGGAGACAGACACACTCCTGCTATGGGTACTGCTGCTCTGGGTTCCAGGTTCCA
CTGGTGAC (SS)
GAGGTTCAGCTTGTCGAGTCTGGGGGGGGAGTCGTTCAGCCAGGTAGAAGCCTC
AGACTGAGCTGTGCCGCAAGTGGGTTTGCTTTTTCATCTTACGGTATGCACTGGG
TGAGACAGGCTCCTGGCAAAGGACTCGAGTGGGTCGCTGTAATATGGTTCGATG
GTACAAAGAAATACTATACCGATAGTGTGAAAGGAAGATTCACCATTTCACGAG
ACAACAGTAAAAATACCTTGTACCTTCAGATGAACACCCTGAGAGCAGAAGACA
CAGCCGTGTACTACTGCGCCAGAGATAGAGGTATCGGAGCAAGGCGTGGTCCCT
ATTATATGGATGTGTGGGGGAAGGGAACAACAGTGACTGTGAGCTCTGCCTCCA
CCAAGGGCCCCATCGGTCTTCCCCCTGGCACCCTCCTCCAAGAGCACCTCTGGGGG
CACAGCGGCCCTGGGCTGCCTGGTCAAGGACTACTTCCCCGAACCGGTGACGGT
GTCGTGGAACTCAGGCGCCCTGACCAGCGGCGTGCACACCTTCCCGGCTGTCCT
ACAGTCCTCAGGACTCTACTCCCTCAGCAGCGTGGTGACTGTGCCCTCTAGCAGC
TTGGGCACCCAGACCTACATCTGCAACGTGAATCACAAGCCCAGCAACACCAAG
GTGGACAAGAAAGTTGAGCCCAAATCTTGTGACAAAACTCAC (Adu-VH-CH1)
GGCGGAGGTGGAAGCGGAGGCGGTGGAAGC (Linker)
GACATCTTGCCGTGCGTGCCCTTCAGCGTGGCCAAGAGTGTGAAGTCCTTGTACC
TGGGCCGGATGTTCAGTGGGACCCCCGTGATCCGACTGCGCTTCAAGAGGCTGC
AGCCCACCAGGCTGGTAGCTGAGTTTGACTTCCGGACCTTTGACCCCGAGGGCA
TCCTCCTCTTTGCCGGAGGCCACCAGGACAGCACCTGGATCGTGCTGGCCCTGAG
AGCCGGCCGGCTGGAGCTGCAGCTGCGCTACAACGGTGTCGGCCGTGTCACCAG
CAGCGGCCCGGTCATCAACCATGGCATGTGGCAGACAATCTCTGTTGAGGAGCT
GGCGCGGAATCTGGTCATCAAGGTCAACAGGGATGCTGTCATGAAAATCGCGGT
GGCCGGGGACTTGTTCCAACCGGAGCGAGGACTGTATCATCTGAACCTCACCGT
GGGAGGTATTCCCTTCCATGAGAAGGACCTCGTCAGCCTATAAACCCTCGTCTG
GATGGCTGTATGGAGCTGGAACTGGCTGAACGGAGAAGACACCACCATCCA
GGAAACGGTGAAAGTGAACACGAGGATGCAGTGCTTCTCGGTGACGGAGAGAG
GCTCTTTCTACCCCGGGAGCGGCTTCGCCTTCTACAGCCTGGACTACATGCGGAC
CCCTCTGGACGTCGGGACTGAATCAACCTGGGAAGTAGAAGTCGTGGCTCACAT
CCGCCCCAGCCGCAGACACAGGCGTGCTGTTTGCGCTCTGGGCCCCCGACCTCCGT
GCCGTGCCTCTCTGTGGCACTGGTAGACTATCACTCCACGAAGAAACTCAAG
AAGCAGCTGGTGGTCCTGGCCGTGGAGCATACGGCCTTGGCCCTAATGGAGATC
AAGGTCTGCGACGGCCAAGAGCACGTGGTCACCGTCTCGCTGAGGGACGGTGAG
GCCACCCTGGAGGTGGACGGCACCAGGGGCCAGAGCGAGGTGAGCGCCGCGCA
GCTGCAGGAGAGGCTGGCCGTGCTCGAGAGGCACCTGCGGAGCCCCGTGCTCAC
CTTTGCCGGCGGCCTGCCAGATGTGCCGGTGACTTCAGCGCCAGTCACCGCGTTC
TACCGCGGCTGCATGACACTGGAGGTCAACCGGAGGCTGCTGGACCTGGACGAG
GCGGCGTACAAGCACAGCGACATCACGGCCCACTCCTGCCCCCCGTGGAGCCC
GCCGCAGCC (Gas6-Gla EGF deleted)
GACTACAAAGACCATGACGGTGATTATAAAGATCATGACATCGACTACAAGGAT
GACGATGACAAGtga (FLAG)
```

TABLE 9

```
1. αAβ[Mab]-Gas6 (Aducanumab heavy chain (Mab)-Gas6-FLAG,
amino acid sequence) SEQ ID NO: 158
METDTLLLWVLLLWVPGSTGD (SS)
EVQLVESGGGVVQPGRSLRLSCAASGFAFSSYGMHWVRQAPGKGLEWVAVIWFDG
TKKYYTDSVKGRFTISRDNSKNTLYLQMNTLRAEDTAVYYCARDRGIGARRGPYY
MDVWGKGTTVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKKVE
PKSCDKTHTCPPCPAPELLGGPSVFLFPPKPKDTLMISRTPEVTCVVVDVSHEDPEVK
FNWYVDGVEVHNAKTKPREEQYNSTYRVVSVLTVLHQDWLNGKEYKCKVSNKAL
PAPIEKTISKAKGQPREPQVYTLPPSRDELTKNQVSLTCLVKGFYPSDIAVEWESNGQ
PENNYKTTPPVLDSDGSFFLYSKLTVDKSRWQQGNVFSCSVMHEALHNHYTQKSLS
LSPGK (Adu-Heavy chain)
GGGGSGGGGS (Linker)
DILPCVPFSVAKSVKSLYLGRMFSGTPVIRLRFKRLQPTRLVAEFDFRTFDPEGILLFA
GGHQDSTWIVLALRAGRLELQLRYNGVGRVTSSGPVINHGMWQTISVEELARNLVI
KVNRDAVMKIAVAGDLFQPERGLYHLNLTVGGIPFHEKDLVQPINPRLDGCMRSWN
WLNGEDTTIQETVKVNTRMQCFSVTERGSFYPGSGFAFYSLDYMRTPLDVGTESTW
```

TABLE 9-continued

EVEVVAHIRPAADTGVLFALWAPDLRAVPLSVALVDYHSTKKLKKQLVVLAVEHT
ALALMEIKVCDGQEHVVTVSLRDGEATLEVDGTRGQSEVSAAQLQERLAVLERHLR
SPVLTFAGGLPDVPVTSAPVTAFYRGCMTLEVNRRLLDLDEAAYKHSDITAHSCPPV
EPAAA (Gas6-Gla EGF deleted)
DYKDHDGDYKDHDIDYKDDDDK* (FLAG)

2. αAβ[Mab]-Gas6 (Aducanumab(Mab)-Gas6-FLAG, nucleotide
sequence) SEQ ID NO: 159
ATGGAGACAGACACACTCCTGCTATGGGTACTGCTGCTCTGGGTTCCAGGTTCCA
CTGGTGAC (SS)
GAGGTTCAGCTTGTCGAGTCTGGGGGGGGAGTCGTTCAGCCAGGTAGAAGCCTC
AGACTGAGCTGTGCCGCAAGTGGGTTTGCTTTTTCATCTTACGGTATGCACTGGG
TGAGACAGGCTCCTGGCAAAGGACTCGAGTGGGTCGCTGTAATATGGTTCGATG
GTACAAAGAAATACTATACCGATAGTGTGAAAGGAAGATTCACCATTTCACGAG
ACAACAGTAAAAATACCTTGTACCTTCAGATGAACACCCTGAGAGCAGAAGACA
CAGCCGTGTACTACTGCGCCAGAGATAGAGGTATCGGAGCAAGGCGTGGTCCCT
ATTATATGGATGTGTGGGGGAAGGGAACAACAGTGACTGTGAGCTCTGCCTCCA
CCAAGGGCCCATCGGTCTTCCCCCTGGCACCCTCCTCCAAGAGCACCTCTGGGGG
CACAGCGGCCCTGGGCTGCCTGGTCAAGGACTACTTCCCCGAACCGGTGACGGT
GTCGTGGAACTCAGGCGCCCTGACCAGCGGCGTGCACACCTTCCCGGCTGTCCT
ACAGTCCTCAGGACTCTACTCCCTCAGCAGCGTGGTGACTGTGCCCTCTAGCAGC
TTGGGCACCCAGACCTACATCTGCAACGTGAATCACAAGCCCAGCAACACCAAG
GTGGACAAGAAAGTTGAGCCCAAATCTTGTGACAAAACTCACACATGCCCACCG
TGCCCAGCACCTGAACTCCTGGGGGGACCGTCAGTCTTCCTCTTCCCCCCAAAAC
CCAAGGACACCCTCATGATCTCCCGGACCCCTGAGGTCACATGCGTGGTGGTGG
ACGTGAGCCACGAAGACCCTGAGGTCAAGTTCAACTGGTACGTGGACGGCGTGG
AGGTGCATAATGCCAAGACAAAGCCGCGGGAGGAGCAGTACAACAGCACGTAC
CGTGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACCATC
TCCAAAGCCAAAGGGCAGCCCCGAGAACCACAGGTGTACACCCTGCCCCCATCC
CGGGATGAGCTGACCAAGAACCAGGTCAGCCTGACCTGCCTGGTCAAAGGCTTC
TATCCCAGCGACATCGCCGTGGAGTGGGAGAGCAATGGGCAGCCGGAGAACAA
CTACAAGACCACGCCTCCCGTGCTGGACTCCGACGGCTCCTTCTTCCTCTACAGC
AAGCTCACCGTGGACAAGAGCAGGTGGCAGCAGGGGAACGTCTTCTCATGCTCC
GTGATGCATGAGGCTCTGCACAACCACTACACGCAGAAGAGCCTCTCCCTGTCC
CCGGGTAAA (Adu-Heavy chain)
GGCGGAGGTGGAAGCGGAGGCGGTGGAAGC (Linker)
GACATCTTGCCGTGCGTGCCCTTCAGCGTGGCCAAGAGTGTGAAGTCCTTGTACC
TGGGCCGGATGTTCAGTGGGACCCCCGTGATCCGACTGCGCTTCAAGAGGCTGC
AGCCCACCAGGCTGGTAGCTGAGTTTGACTTCCGGACCTTTGACCCCGAGGGCA
TCCTCCTCTTTGCCGGAGGCCACCAGGACAGCACCTGGATCGTGCTGGCCCTGAG
AGCCGGCCGGCTGGAGCTGCAGCTGCGCTACAACGGTGTCGGCCGTGTCACCAG
CAGCGGCCCGGTCATCAACCATGGCATGTGGCAGACAATCTCTGTTGAGGAGCT
GGCGCGGAATCTGGTCATCAAGGTCAACAGGGATGCTGTCATGAAAATCGCGGT
GGCCGGGGACTTGTTCCAACCGGAGCGAGGACTGTATCATCTGAACCTCACCGT
GGGAGGTATTCCCTTCCATGAGAAGGACCTCGTGCAGCCTATAAACCCTCGTCTG
GATGGCTGTATGAGGAGCTGGAACTGGCTGAACGGAGAAGACACCACCATCCA
GGAAACGGTGAAAGTGAACACGAGGATGCAGTGCTTCTCGGTGACGAGAGAG
GCTCTTTCTACCCCGGGAGCGGCTTCGCCTTCTACAGCCTGGACTACATGCGGAC
CCCTCTGGACGTCGGGACTGAATCAACCTGGGAAGTAGAAGTCGTGGCTCACAT
CCGCCCAGCCGCAGACACAGGCGTGCTGTTTGCGCTCTGGGCCCCCGACCTCCGT
GCCGTGCCTCTCTCTGTGGCACTGGTAGACTATCACTCCACGAAGAAACTCAAG
AAGCAGCTGGTGGTCCTGGCCGTGGAGCATACGGCCTTGGCCCTAATGGAGATC
AAGGTCTGCGACGGCCAAGAGCACGTGGTCACCGTCTCGCTGAGGGACGGTGAG
GCCACCCTGGAGGTGGACGGCACCAGGGGCCAGAGCGAGGTGAGCGCCGCGCA
GCTGCAGGAGAGGCTGGCCGTGCTCGAGAGGCACCTGCGGAGCCCCGTGCTCAC
CTTTGCCGGCGGCCTGCCAGATGTGCCGGTGACTTCAGCGCCAGTCACCGCGTTC
TACCGCGGCTGCATGACACTGGAGGTCAACCGGAGGCTGCTGGACCTGGACGAG
GCGGCGTACAAGCACAGCGACATCACGGCCCACTCCTGCCCCCCCGTGGAGCCC
GCCGCAGCC (Gas6-Gla EGF deleted)
GACTACAAAGACCATGACGGTGATTATAAAGATCATGACATCGACTACAAGGAT
GACGATGACAAG (FLAG)
TGA

Preparation Examples 6-8

As non-limiting exemplary embodiment of the binding molecule containing a scaffold protein between the first region and the second region, wherein the Gas6 and anti-amyloid antibody scFv (in this example, aducanumab scFv) are employed as the first region and the second region, respectively, a single chain Fc region with reduced or abolished Fc receptor binding affinity are manufactured. The sequences employed in the construction are shown in Table 10.

As another non-limiting exemplary embodiment of the binding molecule containing a scaffold protein between the first region and the second region, wherein the Gas6 and anti-amyloid antibody scFv (in this example, aducanumab scFv) are employed as the first region and the second region, respectively, a heterodimeric binding molecule is manufactured. The first polypeptide of the heterodimeric binding molecule comprises anti-amyloid antibody scFv, Fc region (DD), and Gas6, and the second polypeptide of the heterodimeric binding molecule comprises anti-amyloid antibody scFv region and Fc region (KK). Still another non-limiting exemplary embodiment of the binding molecule containing a scaffold protein between the first region and the second region, a homodimer comprising two polypeptides which each comprise anti-amyloid antibody scFv (as second region), Fc region (scaffold), and Gas6 is manufactured. The peptide sequences are shown in Table 10

TABLE 10

```
Preparation Example 6: Single polypeptide fusion molecule:
anti-amyloid antibody-MFc-Gas6-His (SEQ ID NO: 162)
METDTLLLWVLLLWVPGSTGD (SS)
DIQMTQSPSSLSASVGDRVTITCRASQSISSYLNWYQQKPGKAPKLLIYAASSLQSGV
PSRFSGSGSGTDFTLTISSLQPEDFATYYCQQSYSTPLTFGGGTKVEIKGGGGSGGGG
SGGGGSEVQLVESGGGVVQPGRSLRLSCAASGFAFSSYGMHWVRQAPGKGLEWVA
VIWFDGTKKYYTDSVKGRFTISRDNSKNTLYLQMNTLRAEDTAVYYCARDRGIGAR
RGPYYMDVWGKGTTVTVSS (anti-amyloid antibody-scFv)
GGGGSGGGGS (linker)
APEFLGGPSVFLFPPKPKDTLYITREPEVTCVVVDVSQEDPEVQFNWYVDGVEVHNA
KTKPREEQFNSTYRVVSVLTVLHQDWLNGKEYKCKVSNKGLPSSIEKTISKAKGQPR
EPQVYTFPPEQEEMTKNQVSLRCLVKGFYPSDIAVEWESNGQPENN
YKTTKPVLDSDGSFRLESRLTVDKSRWQEGNVESCSVMHEACSWHLCKSLSLSLGK
(Monomeric Fc with reduced or abolished Fc gamma receptor
binding affinity)
GGGGSGGGGSGGGGS (linker)
DILPCVPFSVAKSVKSLYLGRMESGTPVIRLRFKRLQPTRLVAEFDFRTFDPEGILLFA
GGHQDSTWIVLALRAGRLELQLRYNGVGRVTSSGPVINHGMWQTISVEELARNLVI
KVNRDAVMKIAVAGDLFQPERGLYHLNLTVGGIPFHEKDLVQPINPRLDGCMRSWN
WLNGEDTTIQETVKVNTRMQCFSVTERGSFYPGSGFAFYSLDYMRTPLDVGTESTW
EVEVVAHIRPAADTGVLFALWAPDLRAVPLSVALVDYHSTKKLKKQLVVLAVEHT
ALALMEIKVCDGQEHVVTVSLRDGEATLEVDGTRGQSEVSAAQLQERLAVLERHLR
SPVLTFAGGLPDVPVTSAPVTAFYRGCMTLEVNRRLLDLDEAAYKHSDITAHSCPPV
EPAAA (Gas6)
HHHHHH (His)

Preparation Example 7: Heterodimeric fusion molecule
comprising monovalent first region and monovalent second
region: First polypeptide comprising anti-amyloid
antibody-Fc(DD)-Gas6-His (SEQ ID NO: 163)
METDTLLLWVLLLWVPGSTGD (SS)
DIQMTQSPSSLSASVGDRVTITCRASQSISSYLNWYQQKPGKAPKLLIYAASSLQSGV
PSRFSGSGSGTDFTLTISSLQPEDFATYYCQQSYSTPLTFGGGTKVEIKGGGGSGGGG
SGGGGSEVQLVESGGGVVQPGRSLRLSCAASGFAFSSYGMHWVRQAPGKGLEWVA
VIWFDGTKKYYTDSVKGRFTISRDNSKNTLYLQMNTLRAEDTAVYYCARDRGIGAR
RGPYYMDVWGKGTTVTVSS (anti-amyloid antibody-scFv)
GGGGSGGGGS (linker)
DKTHTCPPCPAPELLGGPSVFLFPPKPKDTLYITREPEVTCVVVDVSHEDPEVKFNW
YVDGVEVHNAKTKPREEQYASTYRVVSVLTVLHQDWLNGKEYKCKVSNKALPAPI
EKTISKAKGQPREPQVYTLPPSREEMTKNQVSLTCLVKGFYPSDIAVEWESNGQPEN
NYDTTPPVLDSDGSFFLYSDLTVDKSRWQQGNVFSCSVMHEALHNHYTQKSLSLSP
GK (Fc(DD))
GGGGSGGGGSGGGGS (linker)
DILPCVPFSVAKSVKSLYLGRMFSGTPVIRLRFKRLQPTRLVAEFDFRTFDPEGILLFA
GGHQDSTWIVLALRAGRLELQLRYNGVGRVTSSGPVINHGMWQTISVEELARNLVI
KVNRDAVMKIAVAGDLFQPERGLYHLNLTVGGIPFHEKDLVQPINPRLDGCMRSWN
WLNGEDTTIQETVKVNTRMQCFSVTERGSFYPGSGFAFYSLDYMRTPLDVGTESTW
EVEVVAHIRPAADTGVLFALWAPDLRAVPLSVALVDYHSTKKLKKQLVVLAVEHT
ALALMEIKVCDGQEHVVTVSLRDGEATLEVDGTRGQSEVSAAQLQERLAVLERHLR
SPVLTFAGGLPDVPVTSAPVTAFYRGCMTLEVNRRLLDLDEAAYKHSDITAHSCPPV
EPAAA (Gas6)
HHHHHH (His)
Second polypeptide comprising anti-amyloid antibody-
Fc(KK)-Gas6-His (SEQ ID NO: 164)
METDTLLLWVLLLWVPGSTGD (SS)
DIQMTQSPSSLSASVGDRVTITCRASQSISSYLNWYQQKPGKAPKLLIYAASSLQSGV
PSRFSGSGSGTDFTLTISSLQPEDFATYYCQQSYSTPLTFGGGTKVEIKGGGGSGGGG
SGGGGSEVQLVESGGGVVQPGRSLRLSCAASGFAFSSYGMHWVRQAPGKGLEWVA
```

TABLE 10-continued

```
VIWFDGTKKYYTDSVKGRFTISRDNSKNTLYLQMNTLRAEDTAVYYCARDRGIAR
RGPYYMDVWGKGTTVTVSS (anti-amyloid antibody-scFv)
GGGGSGGGGS (linker)
DKTHTCPPCPAPELLGGPSVFLFPPKPKDTLYITREPEVTCVVVDVSHEDPEVKFNW
YVDGVEVHNAKTKPREEQYASTYRVVSVLTVLHQDWLNGKEYKCKVSNKALPAPI
EKTISKAKGQPREPQVYTLPPSRKEMTKNQVSLTCLVKGFYPSDIAVEWESNGQPEN
NYKTTPPVLKSDGSFFLYSKLTVDKSRWQQGNVFSCSVMHEALHNHYTQKSLSLSP
GK (Fc(KK))

Preparation Example 8: Single polypeptide fusion molecule
comprising monovalent first region, scaffold, and monovalent
second region: Anti-amyloid antibody-Fc-Gas6-His
(SEQ ID NO: 165)
METDTLLLWVLLLWVPGSTGD (SS)
DIQMTQSPSSLSASVGDRVTITCRASQSISSYLNWYQQKPGKAPKLLIYAASSLQSGV
PSRFSGSGSGTDFTLTISSLQPEDFATYYCQQSYSTPLTFGGGTKVEIKGGGGSGGGG
SGGGGSEVQLVESGGGVVQPGRSLRLSCAASGFAFSSYGMHWVRQAPGKGLEWVA
VIWFDGTKKYYTDSVKGRFTISRDNSKNTLYLQMNTLRAEDTAVYYCARDRGIAR
RGPYYMDVWGKGTTVTVSS (anti-amyloid antibody-scFv)
GGGGSGGGGS (linker)
DKTHTCPPCPAPELLGGPSVFLFPPKPKDTLYITREPEVTCVVVDVSHEDPEVKFNW
YVDGVEVHNAKTKPREEQYASTYRVVSVLTVLHQDWLNGKEYKCKVSNKALPAPI
EKTISKAKGQPREPQVYTLPPSREEMTKNQVSLTCLVKGFYPSDIAVEWESNGQPEN
NYKTTPPVLDSDGSFFLYSKLTVDKSRWQQGNVFSCSVMHEALHNHYTQKSLSLSP
GK (Fc region with reduced or abolished Fc gamma receptor
binding affinity)
GGGGSGGGGSGGGGS (linker)
DILPCVPFSVAKSVKSLYLGRMFSGTPVIRLRFKRLQPTRLVAEFDFRTFDPEGILLFA
GGHQDSTWIVLALRAGRLELQLRYNGVGRVTSSGPVINHGMWQTISVEELARNLVI
KVNRDAVMKIAVAGDLFQPERGLYHLNLTVGGIPPHEKDLVQPINPRLDGCMRSWN
WLNGEDTTIQETVKVNTRMQCFSVTERGSFYPGSGFAFYSLDYMRTPLDVGTESTW
EVEVVAHIRPAADTGVLFALWAPDLRAVPLSVALVDYHSTKKLKKQLVVLAVEHT
ALALMEIKVCDGQEHVVTVSLRDGEATLEVDGTRGQSEVSAAQLQERLAVLERHLR
SPVLTFAGGLPDVPVTSAPVTAFYRGCMTLEVNRRLLDLDEAAYKHSDITAHSCPPV
EPAAA (Gas6)
HHHHHH (His)
```

Preparation Example 9

As non-limiting exemplary embodiment of the binding molecule containing a scaffold protein between the first region and the second region, a bispecific antibody, wherein a scFv of anti-Axl antibody and anti-amyloid antibody are employed as the first region and the second region, respectively, is manufactured. See, FIG. 1J. A heavy chain of the bispecific antibody has the following sequence of Table 11 and the light chain of anti-amyloid antibody light chain has the sequence of SEQ ID NO: 161. The Fc region of the heavy chain contains NA mutation to reduced or abolish Fc gamma receptor binding affinity.

TABLE 11

```
Bispecific Antibody fusion molecule: Anti-amyloid
Ab-anti-Axl ScFv (first polypeptide)
(SEQ ID NO: 166)
METDTLLLWVLLLWVPGSTGD (SS)
EVQLVESGGGVVQPGRSLRLSCAASGFAFSSYGMHWVRQAPGKGLEWVA
VIWFDGTKKYYTDSVKGRFTISRDNSKNTLYLQMNTLRAEDTAVYYCAR
DRGIGARRGPYYMDVWGKGTTVTVSSASTKGPSVFPLAPSSKSTSGGTA
ALGCLVKDYFPEPVTVSWNSGALTSGVHTFPAVLQSSGLYSLSSVVTVP
SSSLGTQTYICNVNHKPSNTKVDKKVEPKSCDKTHTCPPCPAPELLGGP
SVFLFPPKPKDTLMISRTPEVTCVVVDVSHEDPEVKFNWYVDGVEVHNA
KTKPREEQYASTYRVVSVLTVLHQDWLNGKEYKCKVSNKALPAPIEKTI
SKAKGQPREPQVYTLPPSRDELTKNQVSLTCLVKGFYPSDIAVEWESNG
QPENNYKTTPPVLDSDGSFFLYSKLTVDKSRWQQGNVFSCSVMHEALHN
HYTQKSLS
LSPGK (anti-amyloid-antibody heavy chain)
GGGGSGGGGS (Linker)
EVKLVESGGDLVKPGGSLKLSCAASGFTFSSYGMSWVRQTPDKRLEWVA
TISSGGSYTYYPDSVKGRFTISRDNAKNTLYLQMSSLKSEDTAMYYCAR
HPIYYTYDDTMDYWGQGTSVTVSSGGGGSGGGGSGGGGSDIVLTQSPAI
```

TABLE 11-continued

```
MAASPGEKVTMTCSASSSVSSGNFHWYQQKPGTSPKLWIYRTSNLASGV
PARFSGSGSGTSYSLTISSMEAEDAATYYCQQWSGYPWTFGGGTKLEIK
(anti-Axl scFv)
```

Preparation Example 10

As non-limiting exemplary embodiment of the binding molecule containing a scaffold protein between the first region and the second region, a homodimeric bispecific antibody, wherein a scFv of anti-Axl antibody and a scFv region of an anti-amyloid antibody are employed as the first region and the second region, respectively, is manufactured. See FIG. 11. The bispecific antibody comprises a first polypeptide and a second polypeptide, which are identical to each other and each comprises the sequence of SEQ ID NO: 167. The structure of the first/second polypeptide is illustrated in Table 12, and the Fc region scaffold contains N—A mutation to reduced or abolish Fc gamma receptor binding affinity.

TABLE 12

```
Bispecific homodimeric comprising two polypeptides:
anti-amyloid Ab-anti-Axl ScFv (SEQ ID NO: 167)
METDTLLLWVLLLWVPGSTGD (SS)
EVQLVESGGGVVQPGRSLRLSCAASGFAFSSYGMHWVRQAPGKGLEWVAVI
WFDGTKKYYTDSVKGRFTISRDNSKNTLYLQMNTLRAEDTAVYYCARDRGI
GARRGPYYMDVWGKGTTVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYAST
YRVVSVLTVLHQDWLNGKEYKCKVSNKALPAPIEKTISKAKGQPREPQVYT
```

TABLE 12-continued

```
LPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGK
(anti-amyloid-antibody heavy chain)
GGGGSGGGGS (Linker)
EVKLVESGGDLVKPGGSLKLSCAASGFTFSSYGMSWVRQTPDKRLEWVATI
SSGGSYTYYPDSVKGRFTISRDNAKNTLYLQMSSLKSEDTAMYYCARHPIY
YTYDDTMDYWGQGTSVTVSSGGGGSGGGGSGGGGSDIVLTQSPAIMAASPG
EKVTMTCSASSSVSSGNFHWYQQKPGTSPKLWIYRTSNLASGVPARFSGSG
SGTSYSLTISSMEAEDAATYYCQQWSGYPWTFGGGTKLEIK (anti-Axl
scFv)
```

Preparation Example 11

As another non-limiting exemplary embodiment of the binding molecule containing a scaffold protein between the first region and the second region, a heterodimeric bispecific antibody, wherein a scFv of anti-Axl antibody and an anti-amyloid antibody are employed as the first region and the second region, respectively, is manufactured. The first polypeptide of a heavy chain of the bispecific antibody has the following sequence of SEQ ID NO: 168 of Table 13 below, the second polypeptide of a heavy chain of the bispecific antibody comprises the sequence of SEQ ID NO: 169 of Table 13 below, and the light chain of anti-amyloid antibody has the sequence of SEQ ID NO: 161. The Fc region contains NA mutation to reduce or abolish Fc gamma receptor binding affinity and the polypeptides of the Fc region form a hetero dimer (DD-KK).

TABLE 13

```
Bispecific heterodimeric comprising bivalent second
region and bivalent first region: first polypeptide
of heavy chain of anti-amyloid Ab-anti-Axl ScFv
(with Fc region DD) (SEQ ID NO: 168)
METDTLLLWVLLLWVPGSTGD (SS)
EVQLVESGGGVVQPGRSLRLSCAASGFAFSSYGMHWVRQAPGKGLEWVAVI
WFDGTKKYYTDSVKGRFTIRDNSKNTLYLQMNTLRAEDTAVYYCARDRGI
GARRGPYYMDVWGKGTTVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYAST
YRVVSVLTVLHQDWLNGKEYKCKVSNKALPAPIEKTISKAKGQPREPQVYT
LPPSRDELTKNQVSLTCLVKGFYPSDIAVEWESNGQPENNYDTTPPVLDSD
GSFFLYSDLTVDKSRWQQGNVFSCSVMHEALHNHYTQKSLSLSPGK
(anti-amyloid antibody heavy chain (DD))
GGGGSGGGGS (Linker)
EVKLVESGGDLVKPGGSLKLSCAASGFTFSSYGMSWVRQTPDKRLEWVATI
SSGGSYTYYPDSVKGRFTISRDNAKNTLYLQMSSLKSEDTAMYYCARHPIY
YTYDDTMDYWGQGTSVTVSSGGGGSGGGGSGGGGSDIVLTQSPAIMAASPG
EKVTMTCSASSSVSSGNFHWYQQKPGTSPKLWIYRTSNLASGVPARFSGSG
SGTSYSLTISSMEAEDAATYYCQQWSGYPWTFGGGTKLEIK (anti-Axl
scFv)
Second polypeptide of heavy chain of anti-amyloid
Ab (with Fc region KK) (SEQ ID NO: 169)
METDTLLLWVLLLWVPGSTGD (SS)
EVQLVESGGGVVQPGRSLRLSCAASGFAFSSYGMHWVRQAPGKGLEWVAVI
WFDGTKKYYTDSVKGRFTIRDNSKNTLYLQMNTLRAEDTAVYYCARDRGI
GARRGPYYMDVWGKGTTVTVSSASTKGPSVFPLAPSSKSTSGGTAALGCLV
KDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYAST
YRVVSVLTVLHQDWLNGKEYKCKVSNKALPAPIEKTISKAKGQPREPQVYT
LPPSRKELTKNQVSLTCLVKGFYPSDIAVEWESNGQPENNYKTTPPVLKSD
GSFFLYSKLTVDKSRWQQGNVFSCSVMHEALHNHYTQKSLSLSPGK
(anti-amyloid antibody heavy chain (KK))
```

Experimental Example 1. Gas6-Based Fusion Molecule Targeting Beta-Amyloid (I): Beta-Amyloid Binding Domain in scFv Form

1-1. Analysis of Expression of Fusion Molecule in Transfected Cells

Figure 2:
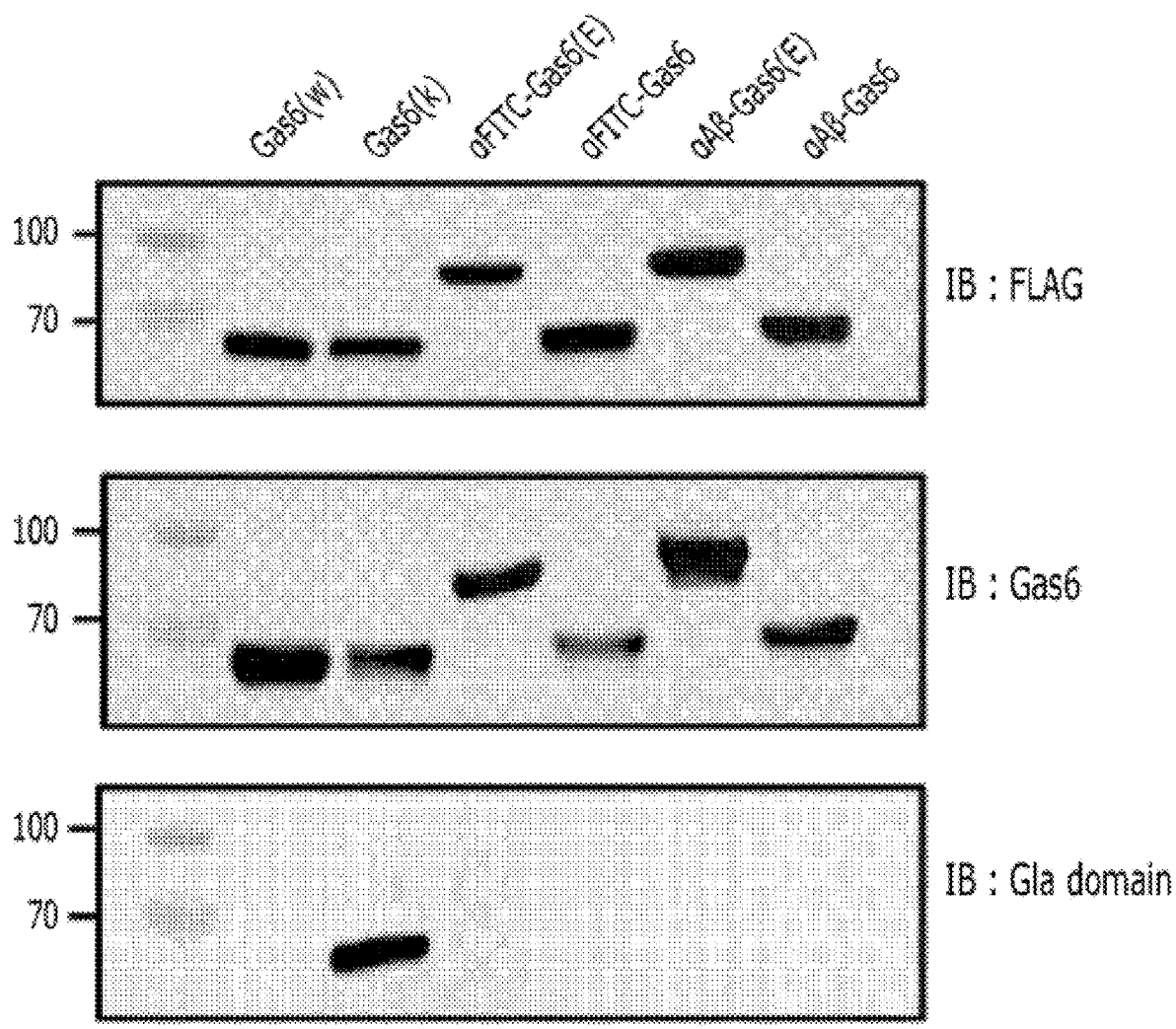
FIG. 2 shows the results of Western blot analysis of a non-limiting exemplary chimeric phagocytosis inducer comprising a FLAG Tag, produced according to Preparation Example 1.
Figure 3:
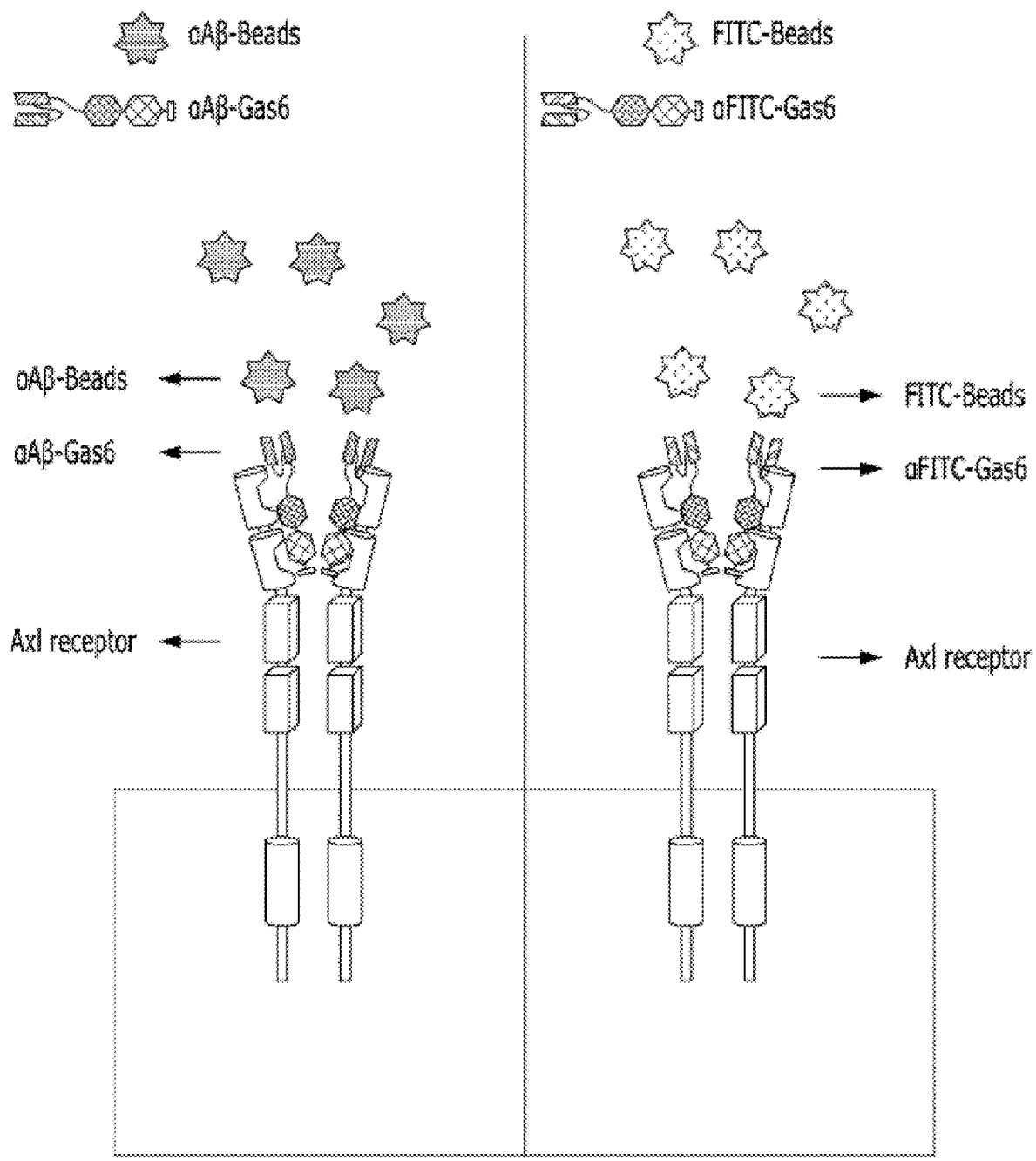
FIG. 3 schematically shows an action of a non-limiting exemplary chimeric phagocytosis inducer, produced according to Preparation Example 1, on TAM receptor.

After plasmid transfection into HEK293 cells, the expression of the fusion molecule containing the Flag tag according to Preparation Example 1 analyzed by Western blot analysis using the Flag tag, and the results are shown in FIG. 2.

Figure 4:
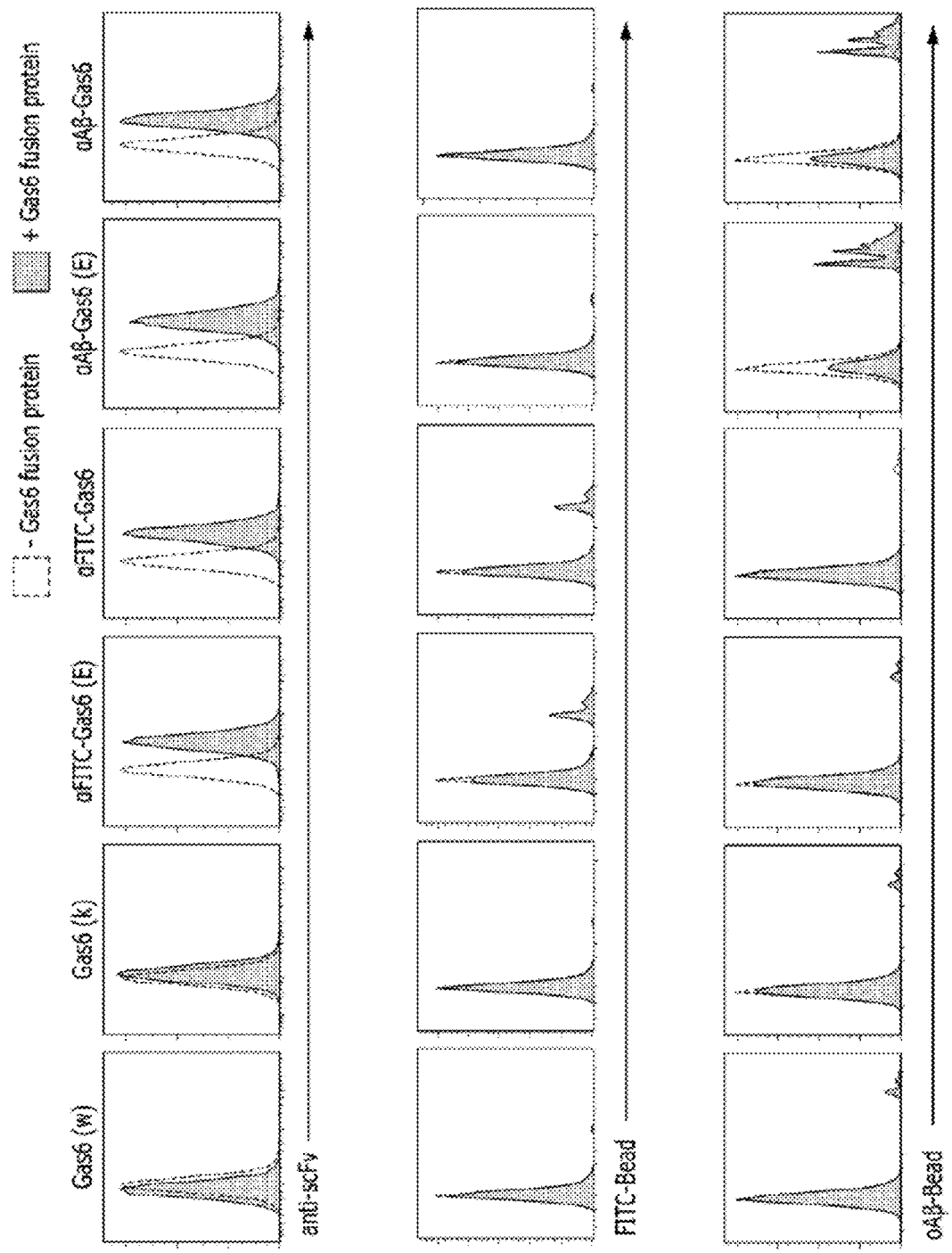
FIG. 4 shows the evaluation results for selective beta-amyloid clearing ability of αAβ-Gas6.

1-2. Analysis of Beta-Amyloid Specific Binding Affinity of Prepared Fusion Molecules To verify whether each of αAβ-Gas6(E), αAβ-Gas6, αFITC-Gas6(E), and αFITC-Gas6 can selectively recognize beta-amyloid and FITC, the culture broth secreted from the HEK293 transfected with each plasmid was collected and subjected to an experiment using beta-amyloid oligomer and FITC-conjugated beads. The results showed that αAβ-Gas6 (E) and αAβ-Gas6 recognized only beta-amyloid oligomer beads, and αFITC-Gas6 (E) and αFITC-Gas6 recognized only FITC beads, thereby inducing phagocytosis, as shown in FIG. 4.

Although αAβ-Gas6 (E) and αAβ-Gas6 were shown to exhibit similar activities, it was found that αAβ-Gas6 obtained by additionally removing the EGF domain of Gas6 could be obtained in high yield without aggregation in the protein purification process. Thus, αAβ-Gas6 was used in subsequent experiments.

1-3. Analysis of Mechanism of Action of Prepared Fusion Molecule (1) Analysis Using Cell Line An in vitro Aβ engulfment assay was developed, in which beta-amyloid oligomers are conjugated with a pH indicator and hence can emit red fluorescence in intracellular lysosomes when they are uptaken by phagocytosis.

Figure 5:
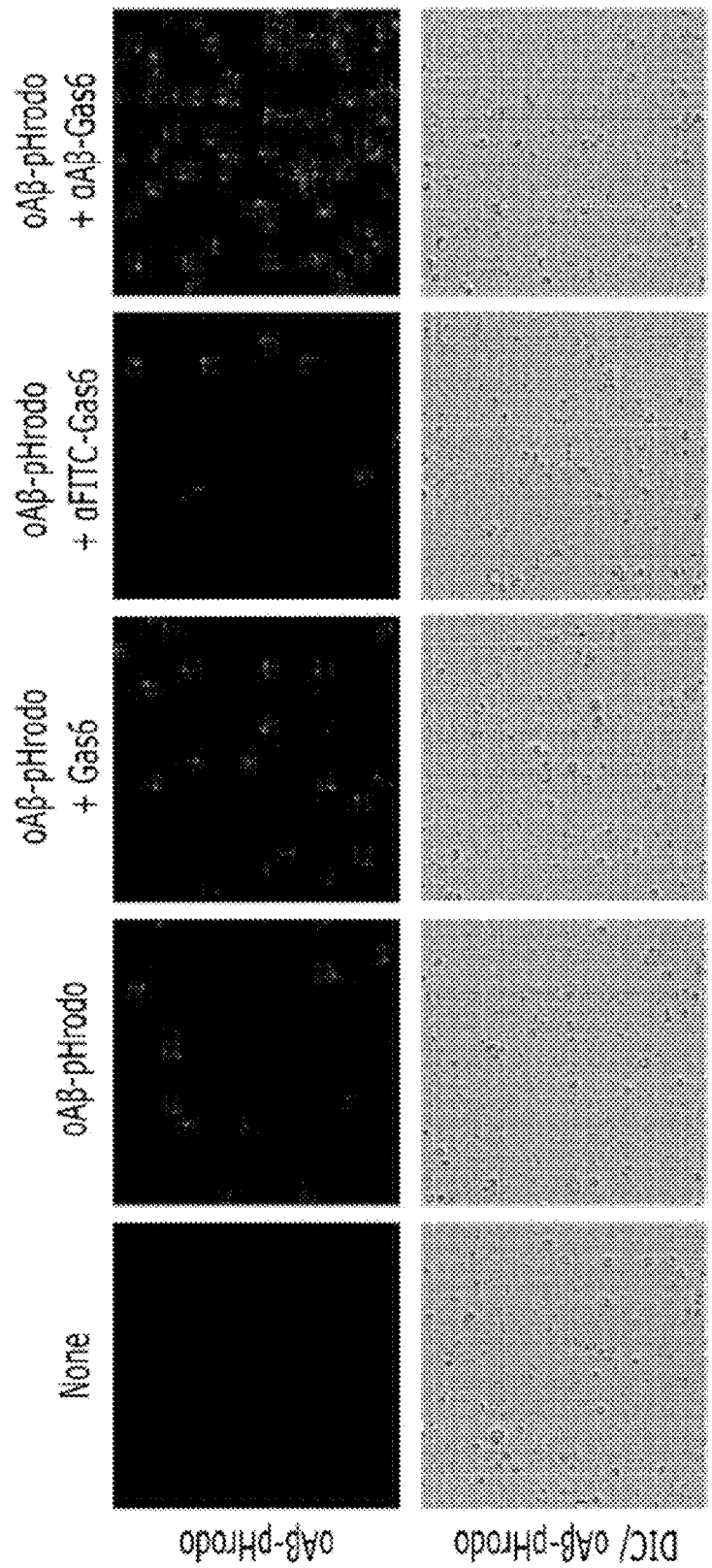
FIG. 5 shows the evaluation results for beta-amyloid clearing ability of αAβ-Gas6 in the HMC3 cell line by beta-amyloid engulfment assay in vitro.
Figure 6:
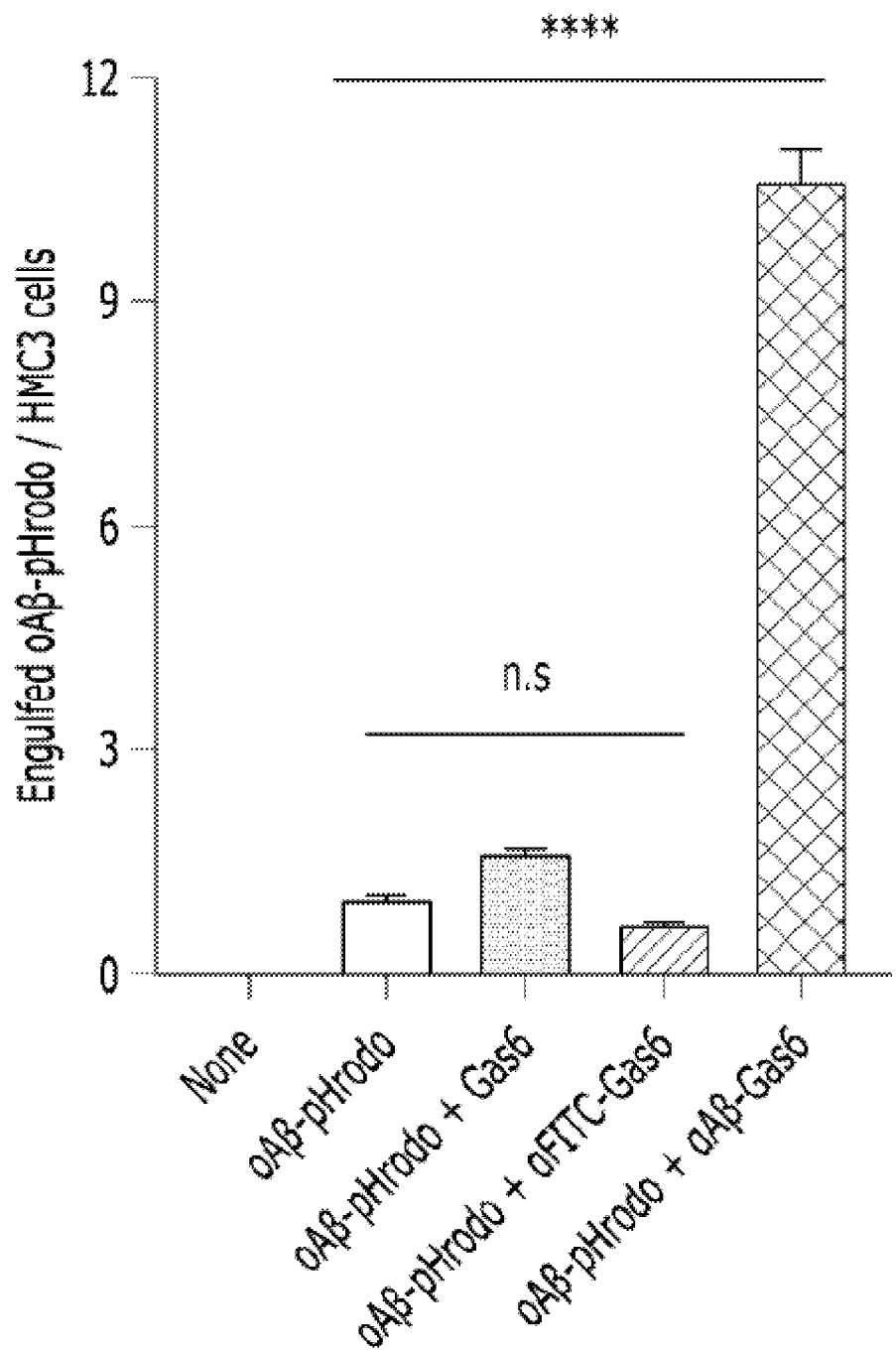
FIG. 6 shows the evaluation results for beta-amyloid clearing ability of αAβ-Gas6 in the HMC3 cell line by beta-amyloid engulfment assay in vitro.

As a result of performing the in vitro Aβ engulfment assay with HMC3 cells, a human microglial cell line expressing TAM receptors, it was shown that beta-amyloid oligomers were selectively cleared by αAβ-Gas6 (FIGS. 5 and 6).

Figure 7:
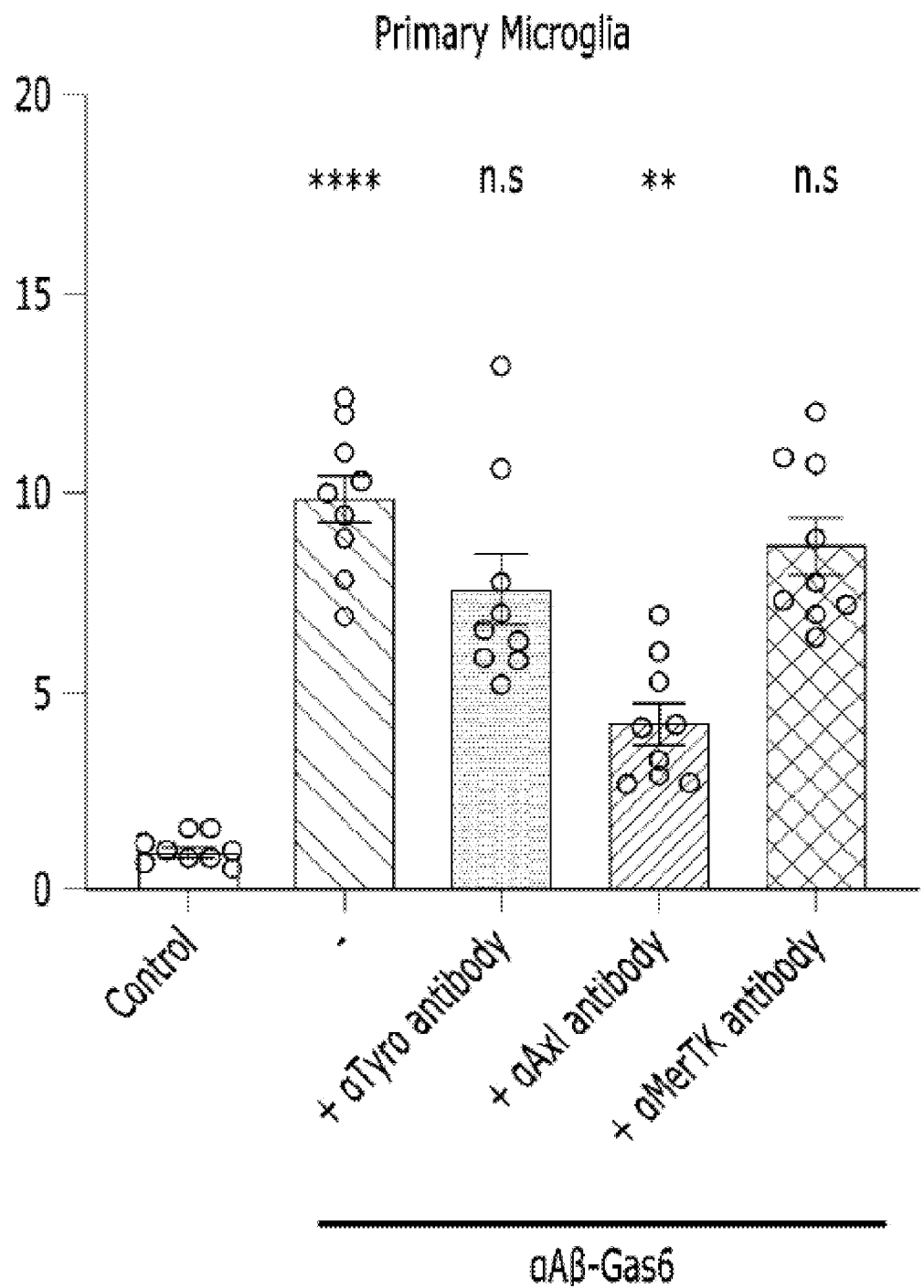
FIG. 7 shows results indicating that the beta-amyloid clearing ability of αAβ-Gas6 is associated with or dependent on Gas6 binding to Axl among TAM receptors.
Figure 8:
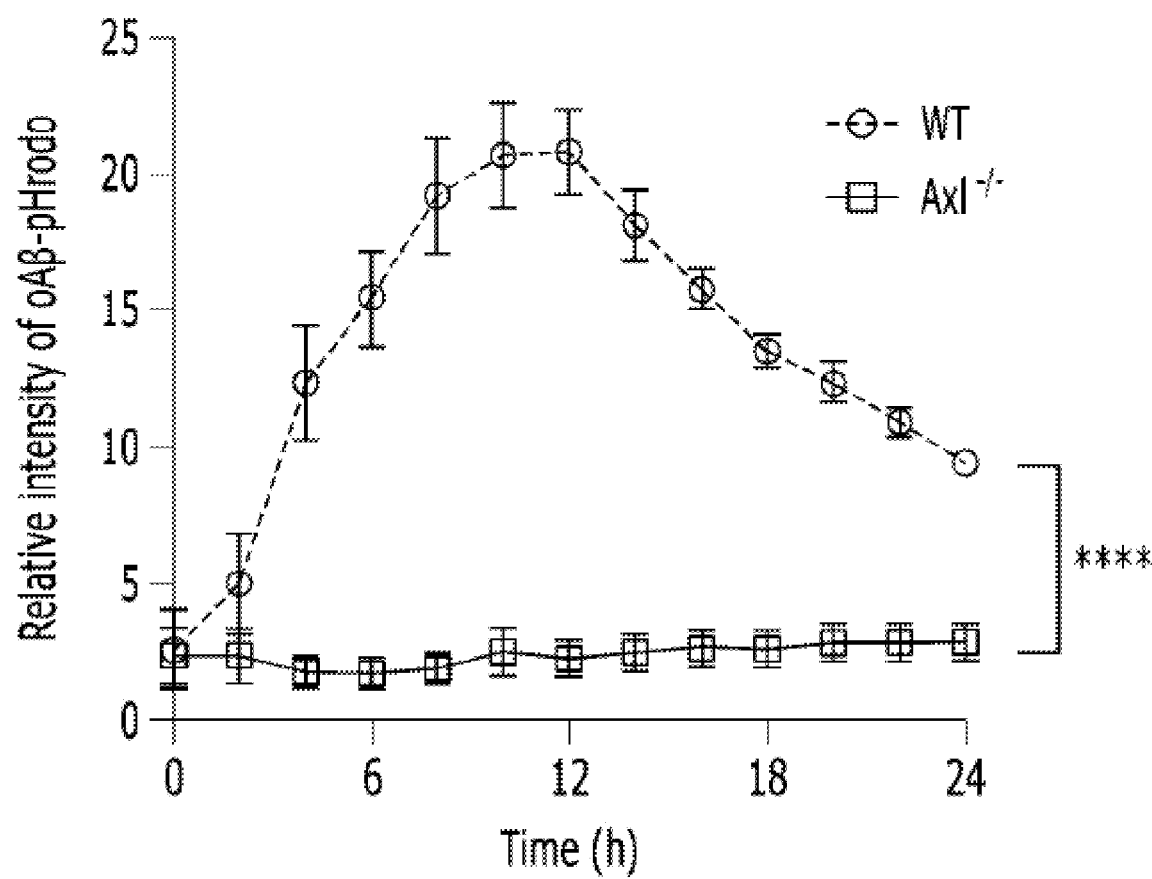
FIG. 8 shows results indicating that the beta-amyloid clearing ability of αAβ-Gas6 is associated with or dependent on Gas6 binding to Axl among TAM receptors.
Figure 9:
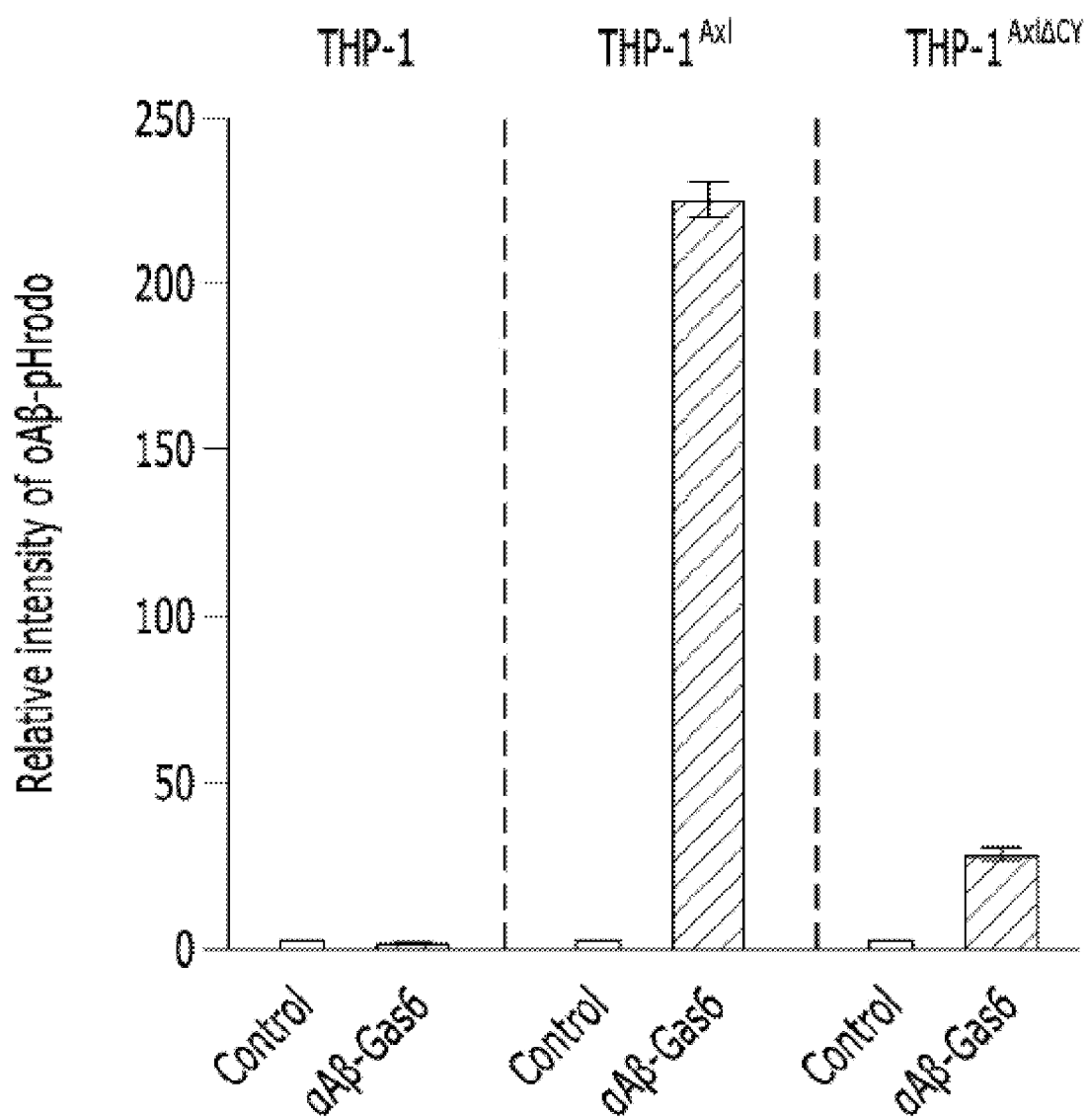
FIG. 9 shows results indicating that the beta-amyloid clearing ability of αAβ-Gas6 is associated with or dependent on Gas6 binding to Axl among TAM receptors.

In particular, in an experiment where cells were treated additionally with an antibody that interferes with the function of TAM receptors, it was confirmed that αAβ-Gas6 cleared beta-amyloid oligomers mainly through Axl among Tyro3, MerTK, and Axl (FIGS. 7 to 9). In fact, when Axl was removed from HMC3 cells, the activity of αAβ-Gas6 significantly decreased. In addition, THP-1, which is a human monocyte cell line that does not express TAM receptors, did not show an increase in beta-amyloid clearance by αAβ-Gas6, while THP-Axl cells overexpressing Axl exhibited a significantly increased ability to clear beta-amyloid fibrils in a manner dependent on αAβ-Gas6.

Figure 10:
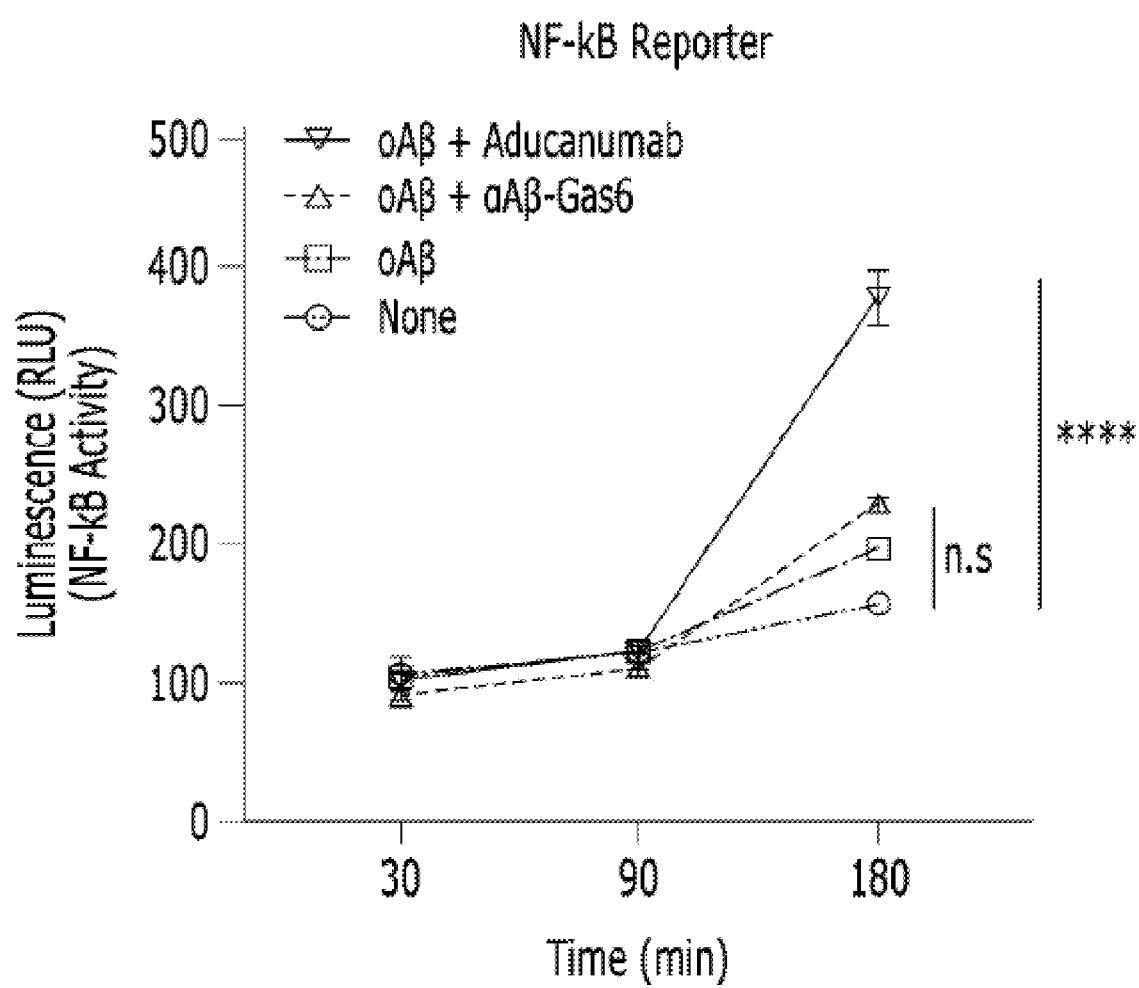
FIG. 10 shows the results of comparative analysis of the activation of inflammatory response signaling by αAβ-Gas6 and aducanumab using THP-Axl cells.
Figure 11:
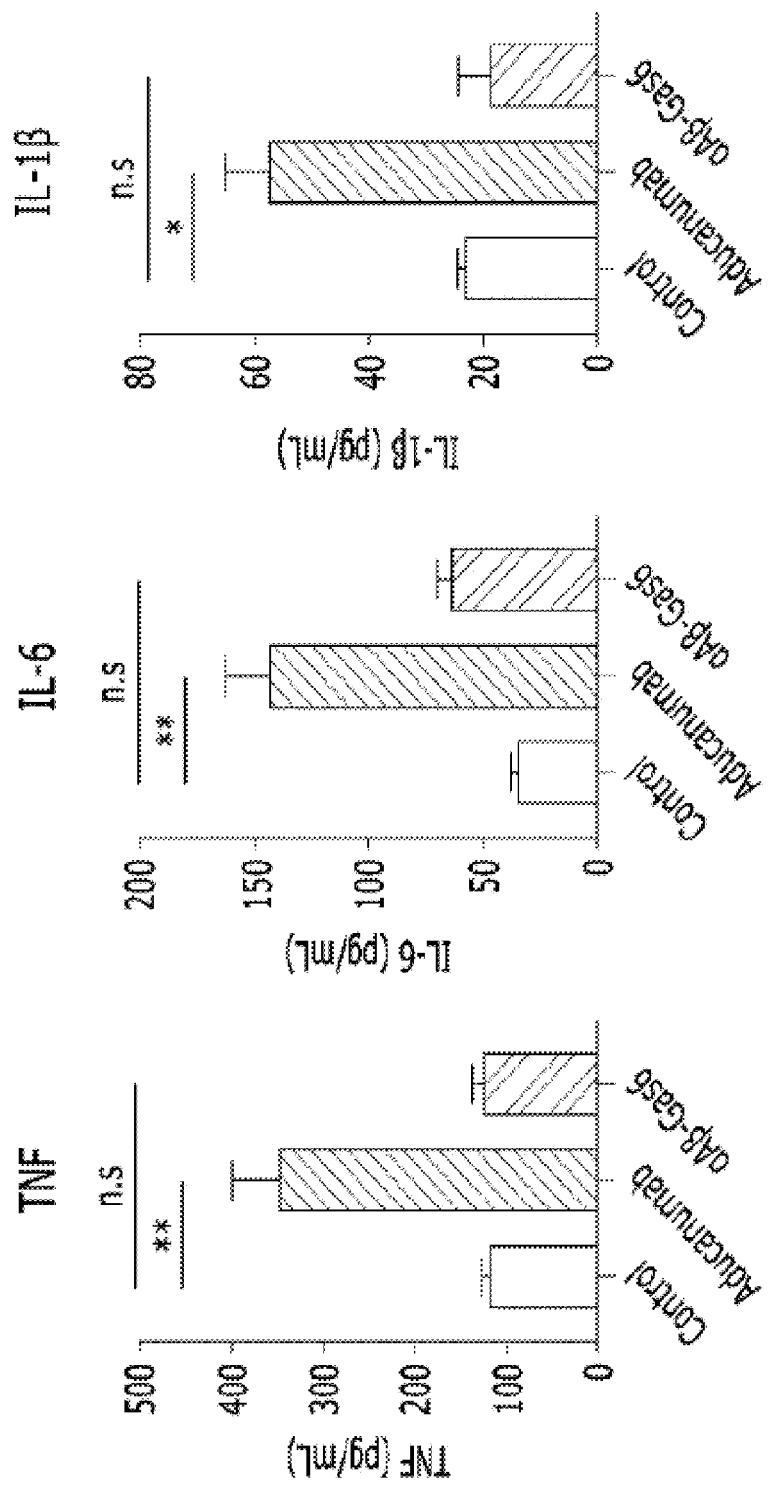
FIG. 11 shows the results of comparative analysis of the levels of pro-inflammatory cytokine secretion by αAβ-Gas6 and aducanumab using THP-Axl cells.

Next, since THP-Axl cells express both Axl and Fc receptors, the degree of inflammatory response induced upon beta-amyloid uptake by each of αAβ-Gas6 and aducanumab was analyzed in those cells. To this end, the NF-kB reporter was first expressed in THP-Axl cells, and each of a control, αAβ-Gas6 and aducanumab was added to the cells together with beta-amyloid oligomers. As a result, it was confirmed that, when aducanumab was added, the expression of the NF-kB reporter significantly increased, but when αAβ-Gas6 was added, the NF-kB reporter was expressed at or below the control level (FIG. 10). In addition, as a result of measuring the secreted protein levels of IL-1b, IL-6 and TNF, which are the three most representative inflammatory cytokines, it was shown that, when THP-Axl cells were treated with aducanumab, the protein levels of the inflammatory cytokines in the treated cells significantly increased compared to those in the control group (FIG. 11). In contrast, importantly, the levels of these inflammatory cytokines in the cells treated with αAβ-Gas6 did not increase compared to those in the control group. This is a key result that, as our hypothesis suggests, the αAβ-Gas6 fusion phagocytosis-inducing protein does not induce an inflammatory response when phagocytosing a target substance through a TAM receptor, which is similar to recognition and efferocytosis of naturally apoptotic cells.

Figure 12:
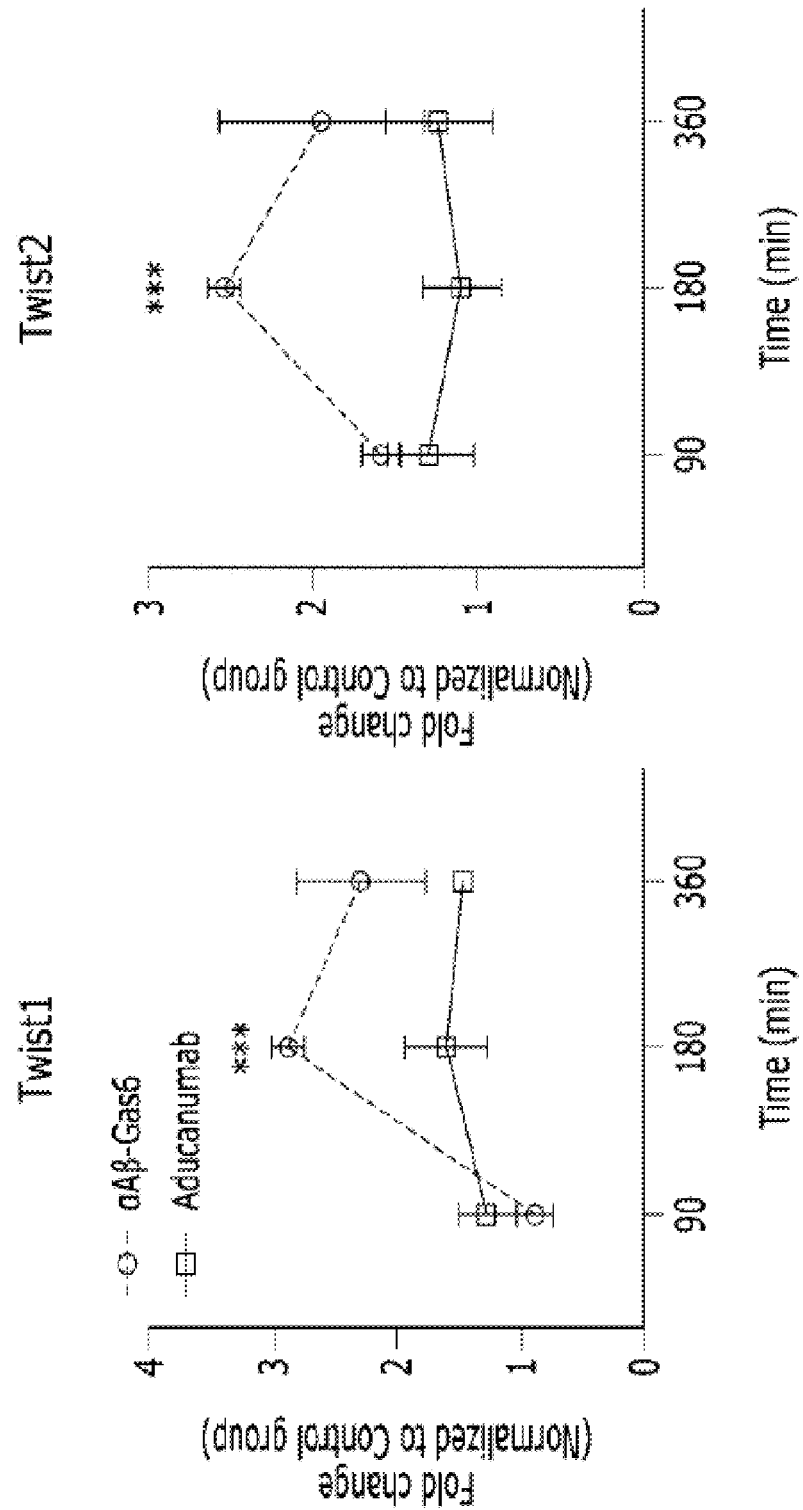
FIG. 12 shows the evaluation results for anti-inflammatory activity of αAβ-Gas6.

In addition, unlike aducanumab, αAβ-Gas6 increased the expression of Twist1/2 gene, which is known as a mechanism of suppressing inflammatory responses (FIG. 12).

(2) Analysis Using Astrocytes and Microglia

To examine whether astrocytes and microglia, which are cells expressing TAM receptors in the brain, can clear beta-amyloid through αAβ-Gas6, primary astrocytes and microglia obtained from mouse brains were separately purified and then cultured. Then, each of purified αAβ-Gas6 and aducanumab was added to the cells together with beta-amyloid fibrils, and the degree of clearance of beta-amyloid fibrils was measured in real time.

The results showed that αAβ-Gas6 increased the beta-amyloid clearing ability of microglia in a concentration-dependent manner, which is similar to the results obtained in HMC3 which is a cell line expressing Axl (FIG. 13). Importantly, it was shown that, when aducanumab was added, the beta-amyloid clearing ability of astrocytes did not change at all, but when αAβ-Gas6 was added, the beta-amyloid clearing ability of astrocytes significantly increased in a concentration-dependent manner (FIG. 14). This suggests that αAβ-Gas6 significantly enhances the beta-amyloid clearing ability of astrocytes, which was previously insignificant, because astrocytes do not express Fc receptors but express TAM receptors.

Figure 15:
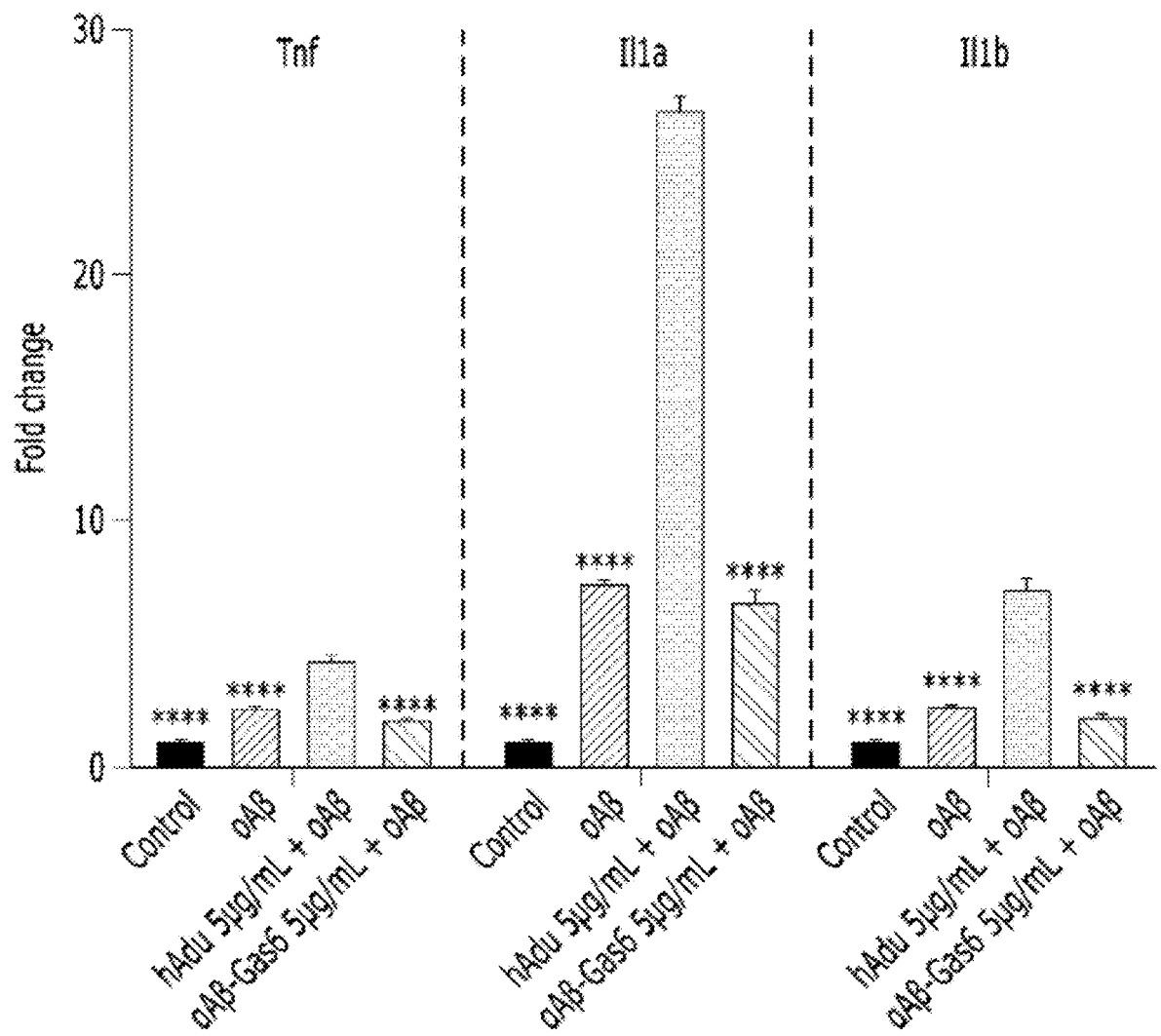
FIG. 15 shows results indicating that the transcriptional levels of pro-inflammatory cytokines in astrocytes were changed by αAβ-Gas6 and aducanumab.
Figure 16:
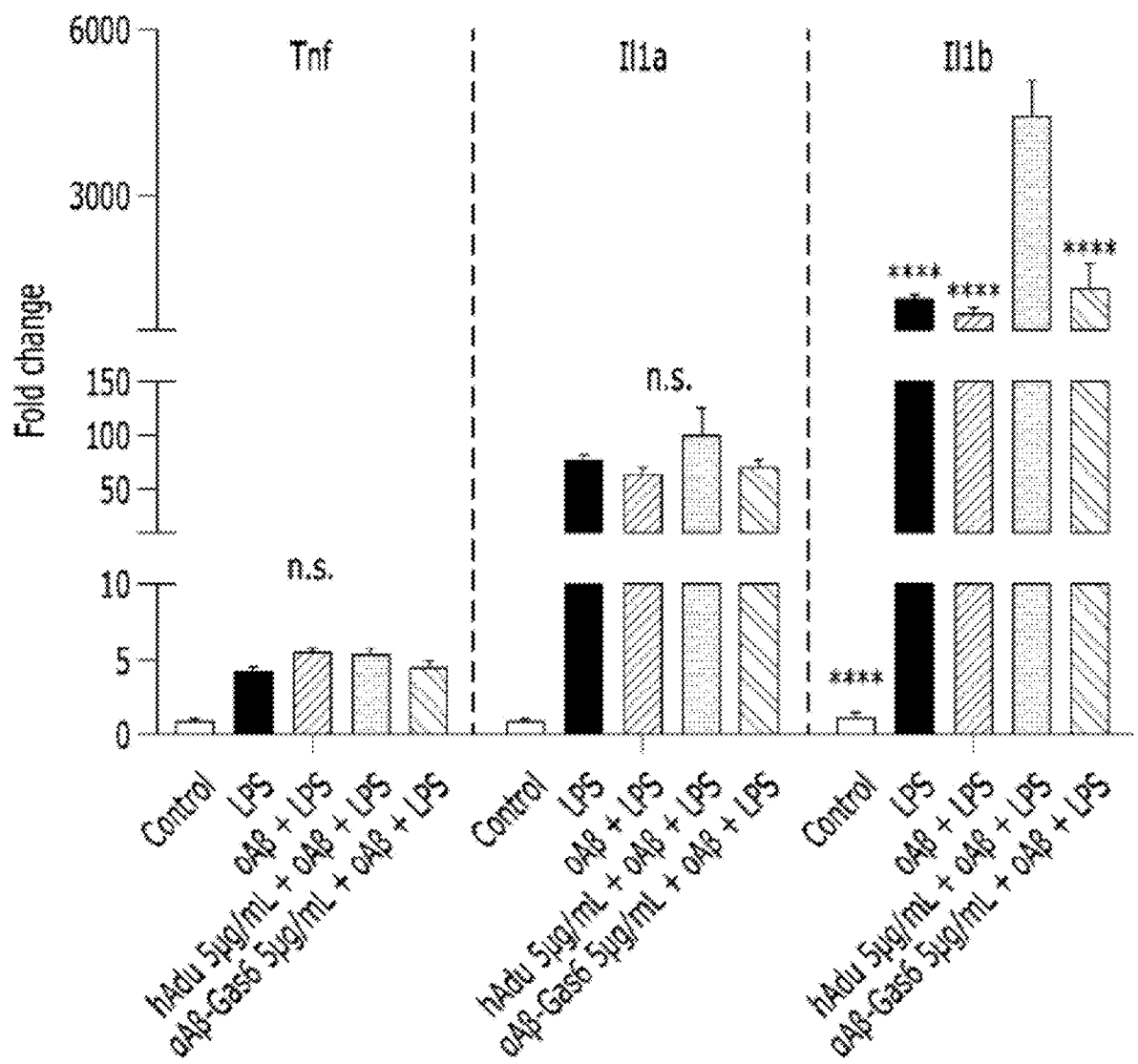
FIG. 16 shows results indicating that the transcriptional levels of pro-inflammatory cytokines in BV2 were changed by αAβ-Gas6 and aducanumab.
Figure 20:
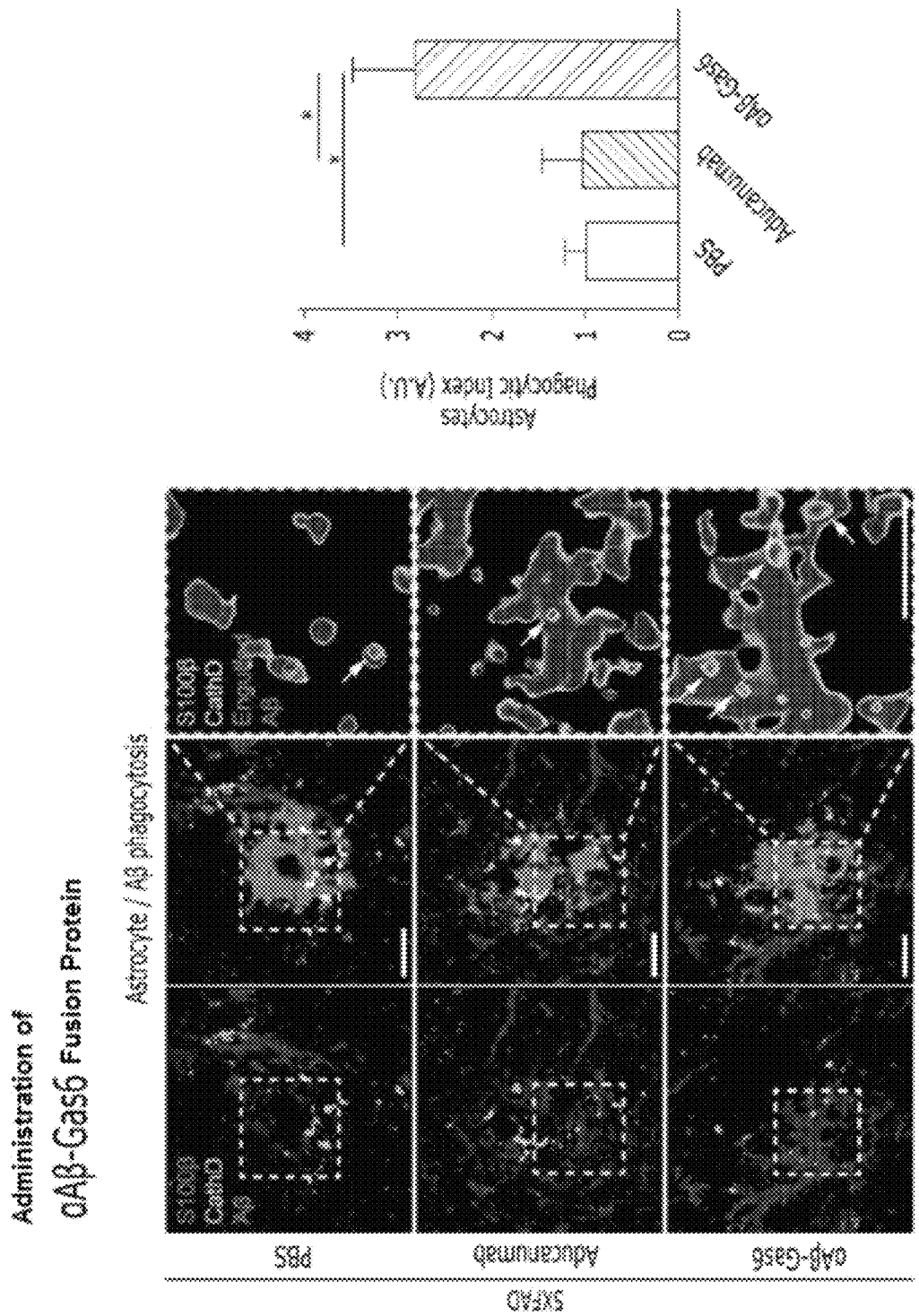
FIG. 20 shows results indicating that beta-amyloid contained in lysosomes were increased by astrocyte-mediated clearance in 5×FAD Alzheimer's disease model mice upon administration of αAβ-Gas6 protein.
Figure 21:
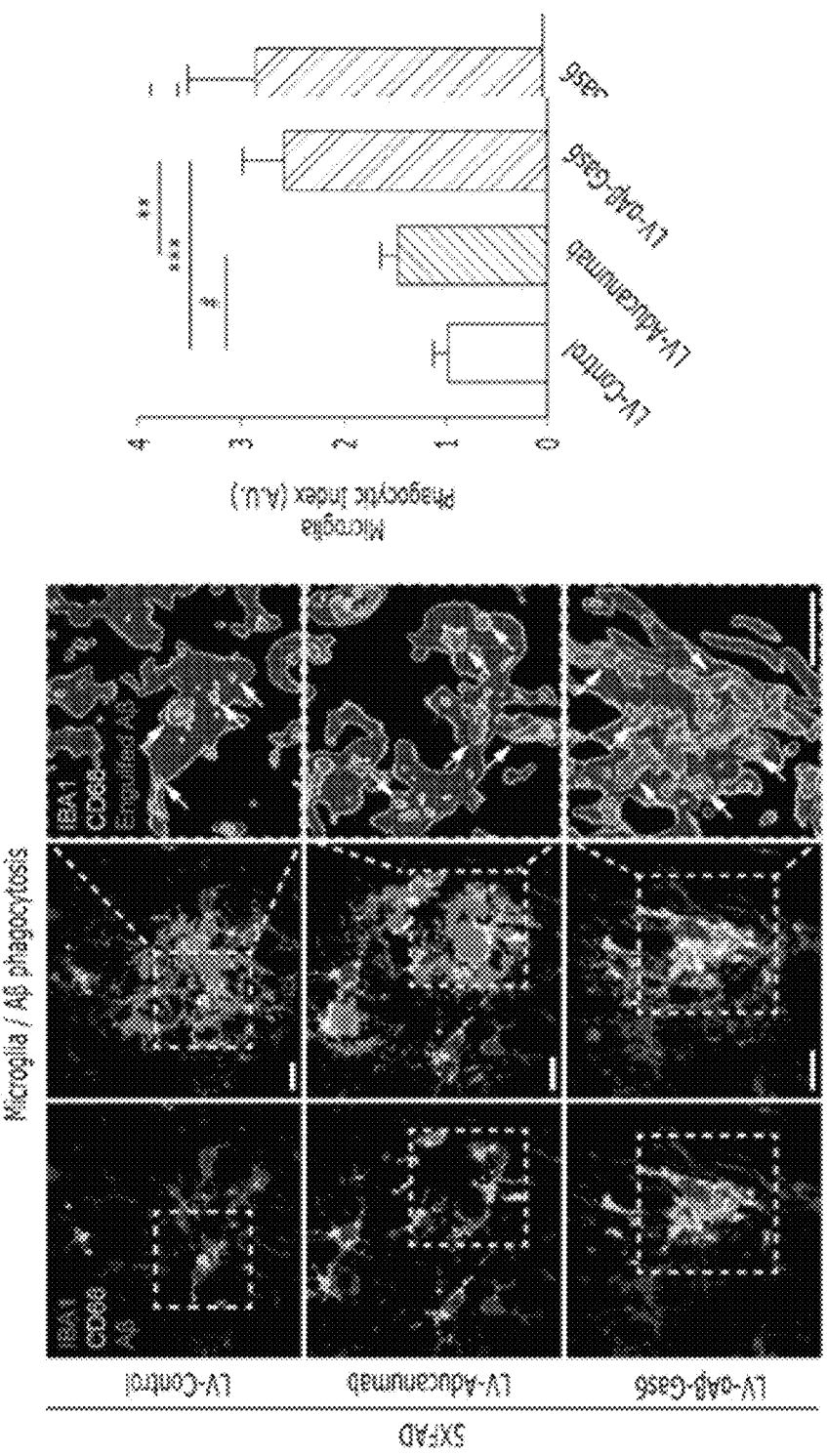
FIG. 21 shows results indicating that beta-amyloid contained in lysosomes were increased by microglia-mediated clearance in 5×FAD Alzheimer's disease model mice upon administration of αAβ-Gas6 virus.
Figure 22:
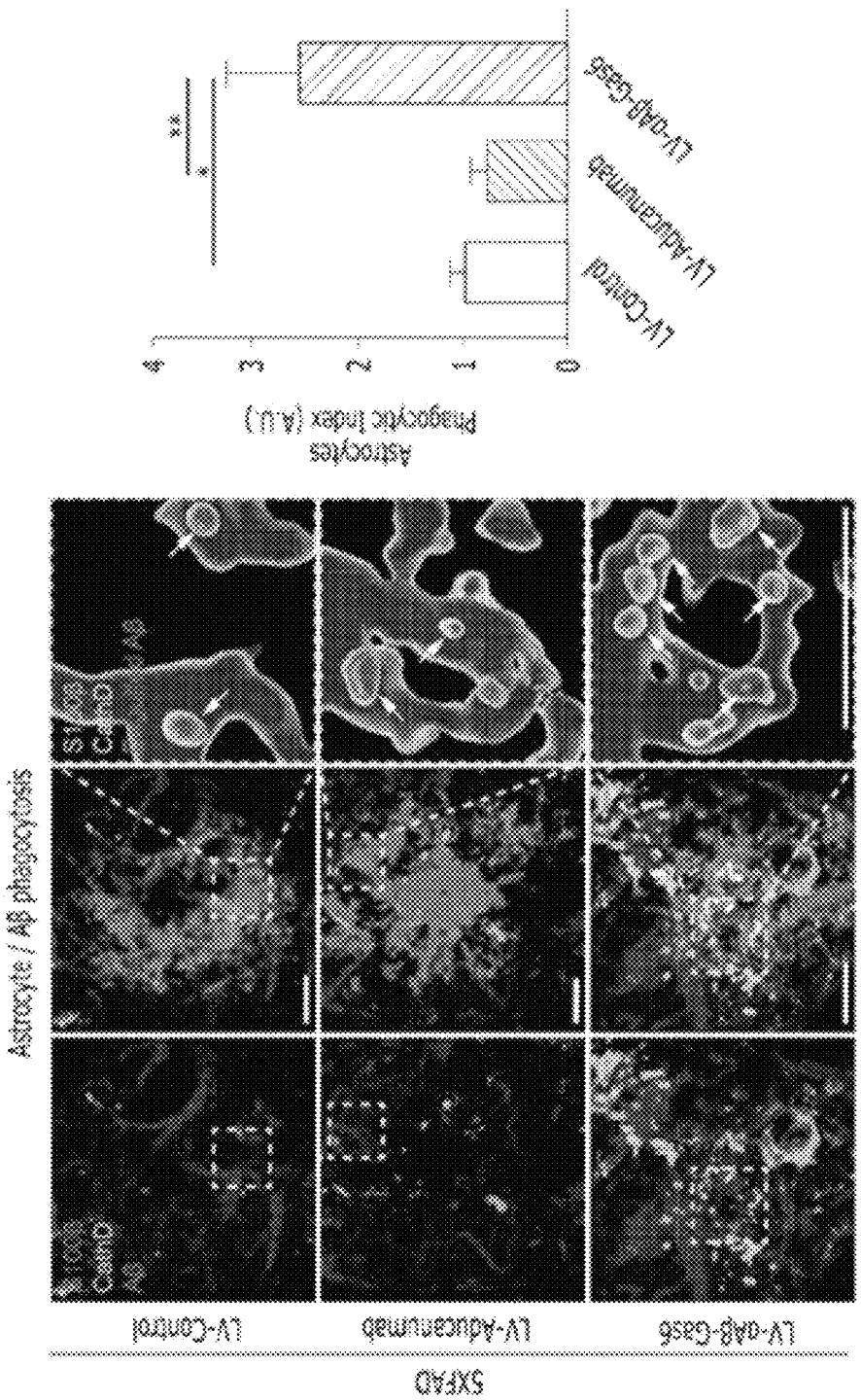
FIG. 22 shows results indicating that beta-amyloid contained in lysosomes were increased by astrocyte-mediated clearance in 5×FAD Alzheimer's disease model mice upon administration of αAβ-Gas6 virus.

Each of αAβ-Gas6 and aducanumab was added to astrocytes and the microglia cell line BV2 together with beta-amyloid fibrils to increase beta-amyloid uptake, and then the mRNA levels of TNF, IL-1a and IL-1b in each cell line were measured to determine the degree of inflammatory responses (FIGS. 15 and 16). As a result, similar to the results obtained in the cell lines, it was shown that, when the cells were treated with aducanumab, the levels of transcripts and proteins of the above inflammatory cytokines in the astrocytes and BV2 cells significantly increased compared to those in the control group, but when the cells were treated with αAβ-Gas6, the levels of these inflammatory cytokines in the cells did not increase compared to those in the control group.

As described above, it has been found that the use of the αAβ-Gas6 fusion phagocytosis inducer may be a groundbreaking method of effectively clearing beta-amyloid plaques accumulated in the patient's brain, through astrocytes and microglia without causing an inflammatory response, which is a serious side effect of existing monoclonal antibody therapeutics. This could be a very encouraging result that can significantly improve current treatment strategies.

1-4. Evaluation of In Vivo Efficacy (1) Efficacy According to Introduction of Fusion Molecule or Expression Vector Containing the Same 5×FAD mice were used as Alzheimer's disease model mice. Since 5×FAD mice simultaneously express 5 genes with mutations, the onset at which beta-amyloid plaques are generated in the mice is early, and pathological symptoms caused by beta-amyloid plaques can be studied from 3 to 4 months of age regardless of aging.

To verify the effect of αAβ-Gas6 in vivo through the 5×FAD model, αAβ-Gas6 was delivered to the brain in two different ways. Through previous studies, it is known that aducanumab is not delivered well to the brain by intravascular injection or intraperitoneal injection even in Alzheimer's disease model mice. Thus, to accurately compare and analyze the effects of αAβ-Gas6 with aducanumab, 1) direct cannulation was performed in the mouse brain, and each of purified αAβ-Gas6 and aducanumab was injected once a day into the ventricle of the brain for 3 weeks, and 2) each of αAβ-Gas6 and aducanumab was made in lentiviral form to be expressed in the hippocampus of the mouse through stereotaxic injection. Importantly, it was found that the number of beta-amyloid plaques significantly decreased both when the purified αAβ-Gas6 protein was added and when the gene was expressed in lentiviral form (FIGS. 17 and 18).

In addition, by quantifying the levels of beta-amyloid in lysosomes of microglia and astrocytes after αAβ-Gas6 was delivered to the brain in the form of protein or virus, it was shown that the ability to clear beta-amyloid significantly increased in both types of cells (FIGS. 19 to 22).

This suggests that, since TAM receptors are expressed in both microglia and astrocytes, microglia and astrocytes can recognize and clear beta-amyloid when αAβ-Gas6 is introduced therein, which is similar to the results of the in vitro studies.

Figure 24:
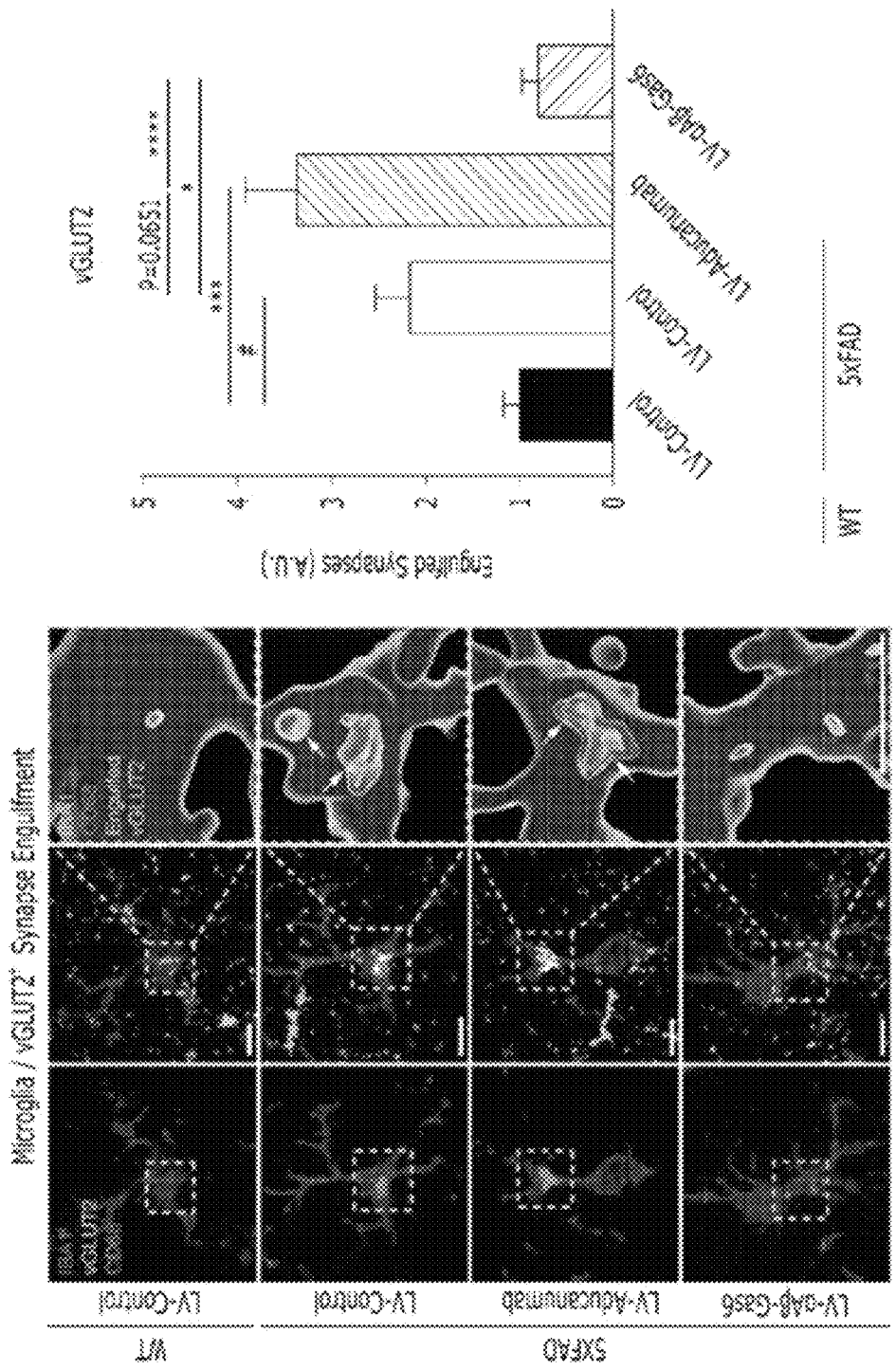
FIG. 24 shows results indicating that microglia-mediated synapse engulfment that abnormally increased in 5×FAD Alzheimer's disease model mice due to the side effect of aducanumab was significantly restored upon administration of αAβ-Gas6 virus.

(2) Comparison of Effects of Antibody Therapeutics and Fusion Molecule of the Present Invention It is known that, in Alzheimer's disease, synapses are indiscriminately removed by microglia, resulting in a decrease in the number of synapses. Surprisingly, this phenomenon was aggravated when aducanumab was delivered to Alzheimer's model mice, but when αAβ-Gas6 was expressed in a viral form, abnormal removal of synapses by microglia was restored to a normal level (FIGS. 23 and 24).

Figure 26:
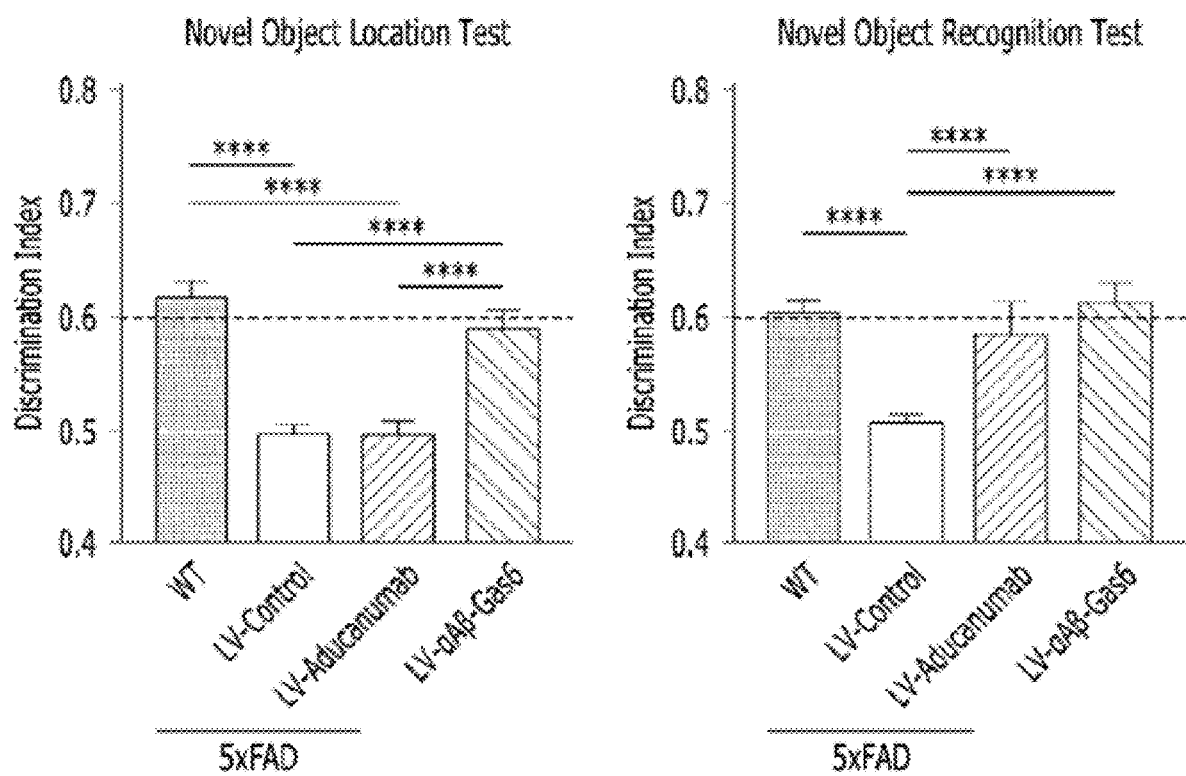
FIG. 26 shows results indicating that cognitive and memory abilities in 5×FAD Alzheimer's disease model mice were more restored upon administration of αAβ-Gas6 virus than administration of aducanumab.
Figure 28:
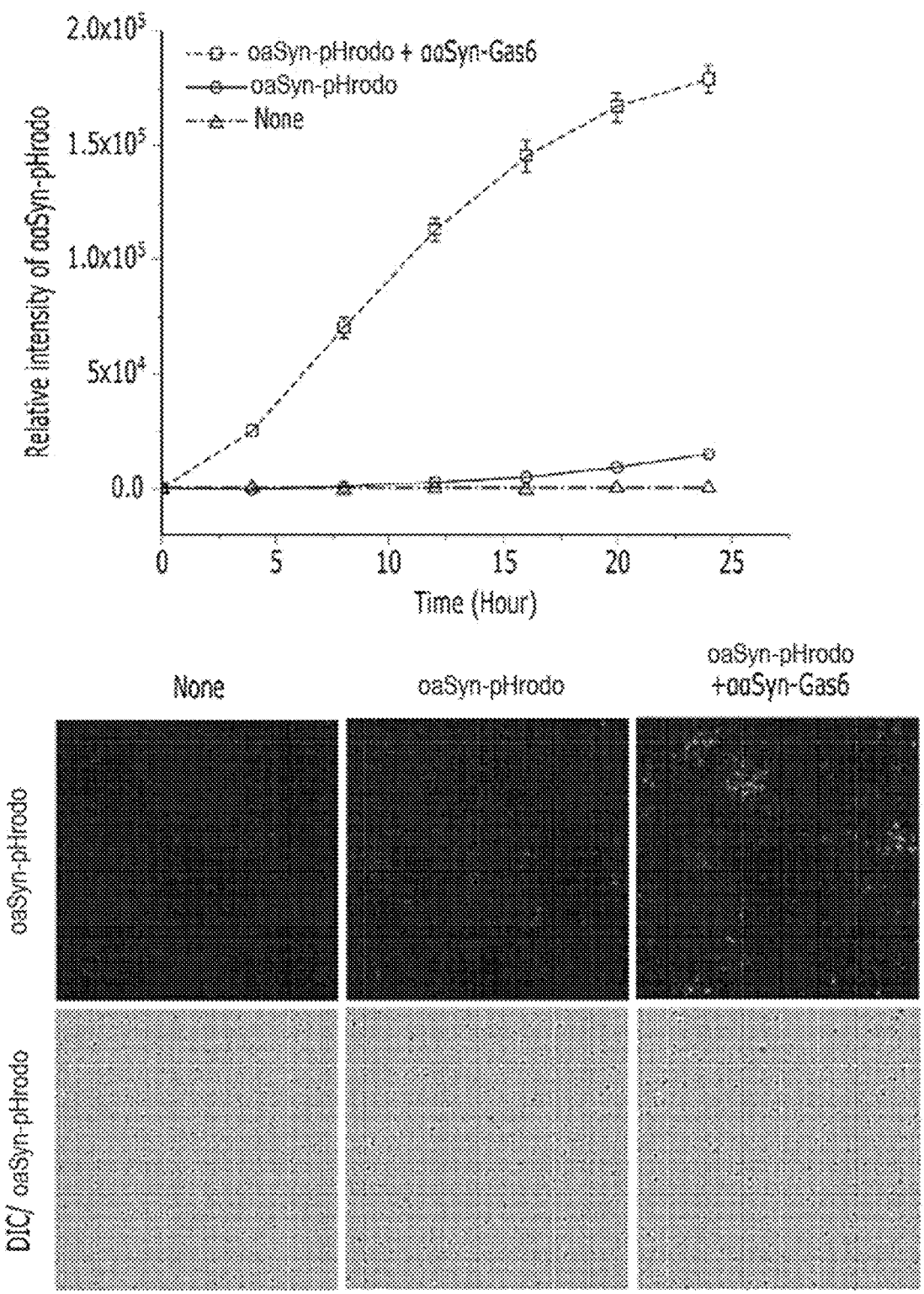
FIG. 28 shows the evaluation results for alpha-synuclein clearing ability of αTau-Gas6 in the HMC3 cell line by in vitro tau engulfment assay.

In addition, as in the results from a cognitive and memory test for remembering the shape or location of a new object in Alzheimer's model mice according to the protocol shown in FIG. 25, it was confirmed that the expression of αAβ-Gas6 exhibited significantly superior cognitive and memory recovery effects compared to aducanumab (FIG. 26).

In addition, to verify whether the chimeric phagocytic protein of the present disclosure is effective in clearing various target substances, phagocytosis-inducing proteins specific for tau and alpha-synuclein (αSyn) in addition to beta-amyloid were prepared as described in Preparation Examples 2 and 3, and the target substance clearing effects thereof were tested following protocols in Experimental Examples 2 and 3.

1-5. Assay of Fusion Molecules of Preparation Examples 6-11

By following the procedure of Example 1-1 through 1-4, the properties and in vivo efficacy of clearing amyloids are evaluated for the fusion molecules of Preparation Examples 6-11.

Experimental Example 2. Gas6-Based Fusion Molecule Targeting Tau

An in vitro tau engulfment assay was developed, in which tau oligomers are conjugated with a pH indicator and hence can emit red fluorescence in intracellular lysosomes when they are uptaken by phagocytosis. HMC3 cells, a human microglial cell line expressing TAM receptors, were treated with a culture medium expressing the phagocytosis-inducing protein [αTau-Gas6] according to Preparation Example 2, and in vitro tau engulfment assay was performed. As the result shown in FIG. 27, it was confirmed that tau oligomers were selectively cleared by αTau-Gas6.

Experimental Example 3. Gas6-Based Fusion Molecule Targeting Alpha-Synuclein An in vitro αSyn engulfment assay was developed, in which alpha-synuclein (αSyn) oligomers are conjugated with a pH indicator and hence can emit red fluorescence in intracellular lysosomes when they are uptaken by phagocytosis. HMC3 cells, a human microglial cell line expressing TAM receptors, were treated with a culture medium expressing the phagocytosis-inducing protein [ααSyn-Gas6] according to Preparation Example 3, and in vitro tau engulfment assay was performed. As the result shown in FIG. 27, it was confirmed that αSyn oligomers were selectively cleared by ααSyn-Gas6.

Experimental Example 4. ProS1-Based Fusion Molecule Targeting Beta-Amyloid

Figure 29:
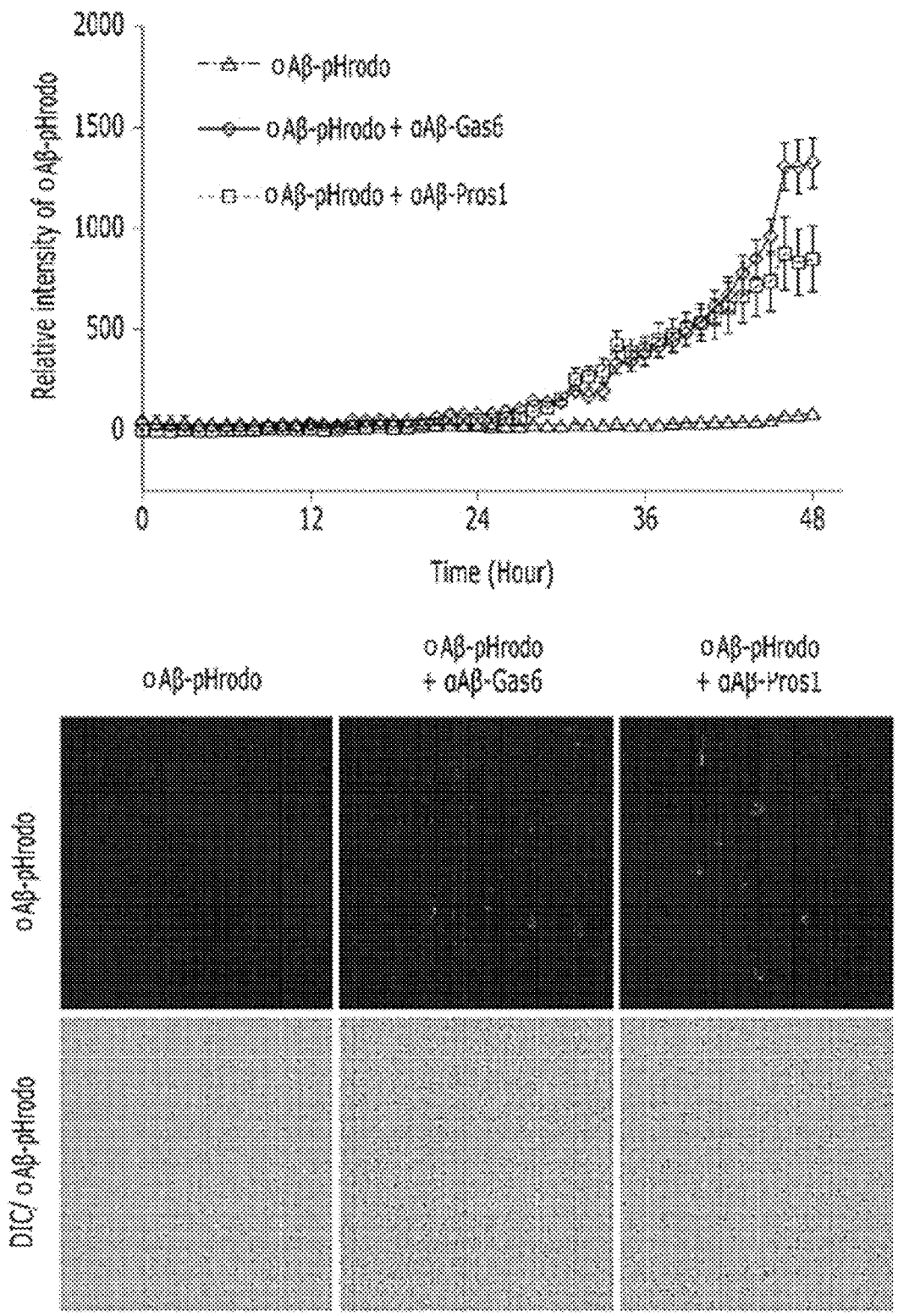
FIG. 29 shows the evaluation results for beta-amyloid clearing ability of αAβ-ProS1 in primary-cultured astrocytes by in vitro tau engulfment assay.

Next, to verify whether the chimeric phagocytosis-inducing protein prepared using a ligand for TAM receptor other than Gas6 is also effective, αAβ-ProS1 was prepared as described in Preparation Example 4 using the ProS1 ligand, and the efficacy thereof was evaluated. To this end, primary-cultured mouse astrocytes expressing TAM receptors were treated with a culture medium expressing αAβ-ProS1, and the in vitro Aβ engulfment assay used in Experimental Example 1-3 was performed. As the result shown in FIG. 29, it was confirmed that beta-amyloid oligomers were selectively cleared by αAβ-ProS1.

Figure 31:
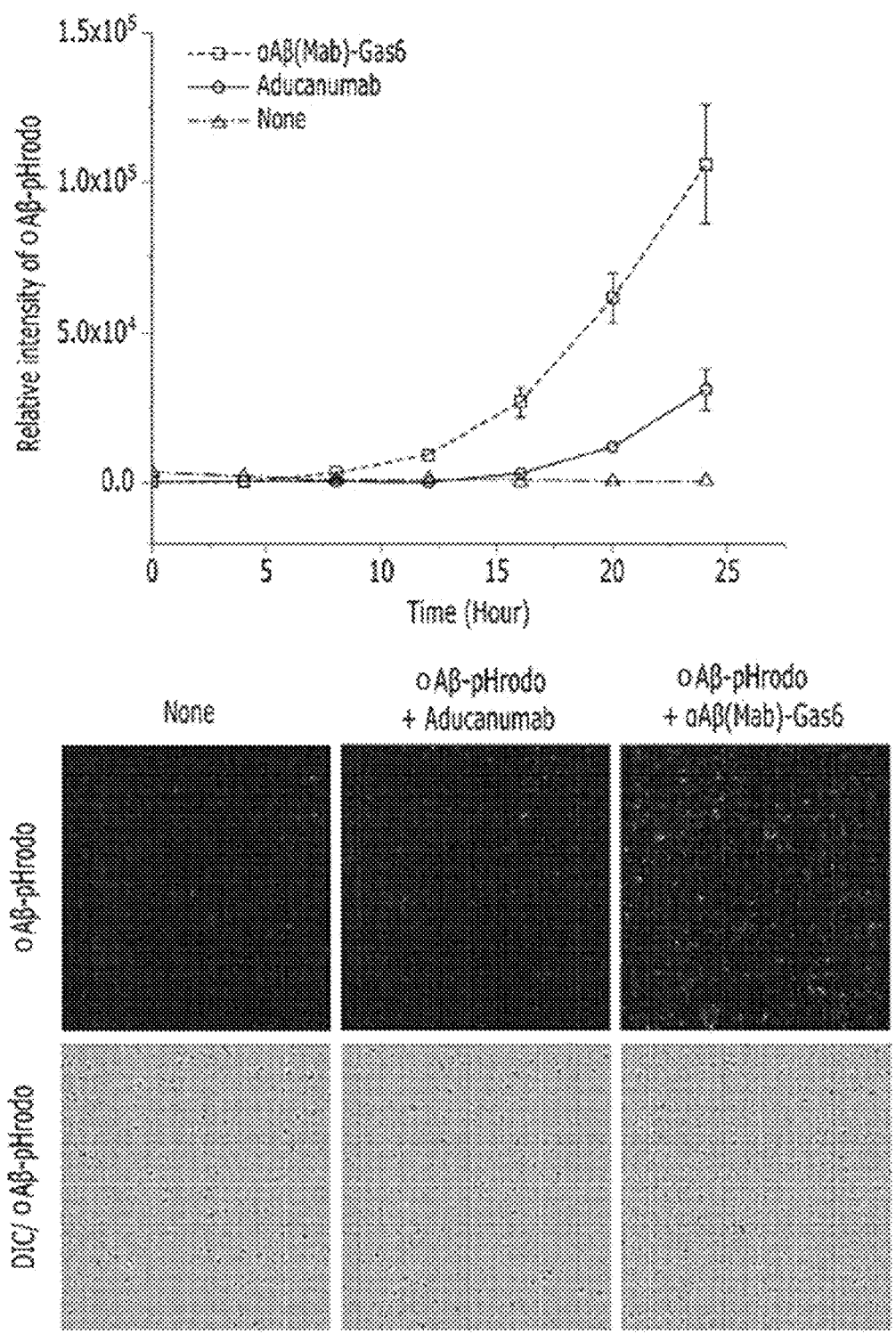
FIG. 31 shows the evaluation results for beta-amyloid clearing ability of αAβ(Fab)-Gas6 in the HMC3 cell line by in vitro tau engulfment assay.

Experimental Example 5. Gas6-Based Fusion Molecule Targeting Beta-Amyloid (II): Beta-Amyloid Binding Regions in the Forms of Fab and Mab Next, to verify whether various target-binding regions other than scFv may be used as target protein-binding domains in the preparation of chimeric phagocytosis-inducing proteins, phagocytosis-inducing proteins were prepared according to Preparation Example 5 using an antigen-binding fragment (Fab) or a complete-form monoclonal antibody (Mab) instead of an scFv and were subjected to an experiment (αAβ[Fab]-Gas6 and αAβ[Mab]-Gas6). To this end, HMC3 cells, a human microglial cell line expressing TAM receptors, were treated with a culture medium expressing each of αAβ[Fab]-Gas6 and αAβ[Mab]-Gas6, and the in vitro Aβ engulfment assay used in Experimental Example 1-3 was performed. As the results shown in FIGS. 30 and 31, it was confirmed that beta-amyloid oligomers were selectively cleaved by each of αAβ[Fab]-Gas6 and αAβ[Mab]-Gas6.

The scope of the present disclosure is defined by the appended claims, and all changes or modifications derived from the meaning and scope of the claims and equivalents thereto should be construed as being included in the scope of the present invention.

The fusion molecules having phagocytosis-inducing activity according to the embodiment of the present disclosure can solve the problem of tissue damage caused by activation of an inflammatory response, which occurs in the prior art. Accordingly, the fusion molecules could effectively clear abnormally accumulated substances such as beta-amyloid, tau, alpha-synuclein, huntingtin or prion protein, and thus may be used to prevent or treat diseases caused by these abnormally accumulated substances, for example, Alzheimer's disease, Parkinson's disease, Huntington's disease, or prion disease. Therefore, it may be used in the therapeutics industry for treatment of the above diseases.

All publications, patent applications, patents, and other references mentioned herein are expressly incorporated herein by reference in their entireties.

---

The invention claimed is:

1. A binding molecule comprising a first region capable of binding to a TAM (Tyro3, Axl, MerTK) receptor and a second region capable of specifically binding to a target substance, said target substance being a substance of which aberrant accumulation in a living tissue is characteristic of or associated with a disease, wherein the first region and the second region are coupled to each other directly or via a linker, wherein the first region comprises a Gas6 protein comprising (i) the sequence of SEQ ID NO: 5 or (ii) a sequence having sequence identity of at least 85% to the sequence of SEQ ID NO: 5 and comprising a sex hormone-binding globulin (SHBG)-like domain of Gas6 protein, wherein the first region does not comprise N-terminal gamma carboxyglutamic acid (GLA) domain and epidermal growth factor (EGF)-like domain, and wherein the binding molecule induces phagocytosis.

2. The binding molecule according to claim 1, wherein the Gas6 protein comprises the amino acid sequence of SEQ ID NO: 1 and the amino acid sequence of SEQ ID NO: 2.

3. The binding molecule according to claim 1, wherein the Gas6 protein comprises one or more sequences selected from the group consisting of SEQ ID NO: 5, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 71, SEQ ID NO: 72, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, and SEQ ID NO: 87.

4. The binding molecule according to claim 1, which is a monomer or multimer.

5. The binding molecule according to claim 1, wherein the target substance is β-amyloid.

6. The binding molecule according to claim 1, wherein the target substance is soluble amyloid, oligomeric amyloid, aggregated amyloid, or combinations thereof.

7. The binding molecule according to claim 1, wherein the second region that specifically binds to the target substance is selected from the group consisting of an antibody or an antigen-binding fragment thereof, an antibody-like protein, a peptide, an aptamer, and a soluble receptor, which each specifically bind to the target substance.

8. A pharmaceutical composition comprising the binding molecule of claim 1 and a pharmaceutically acceptable carrier.

9. The binding molecule according to claim 1, which further comprises an immunoglobulin Fc domain.

10. The binding molecule according to claim 9, wherein the immunoglobulin Fc domain has a reduced or abolished Fc receptor binding affinity, compared to wild-type immunoglobulin Fc domain.

11. The binding molecule according to claim 1, wherein the second region is an antibody or an antigen-binding fragment thereof that specifically binds to amyloid.

12. The binding molecule according to claim 1, wherein the first region comprises the sequence of SEQ ID NO: 5 or a sequence having at least 95% sequence identity thereto, and wherein the second region is an antibody or an antigen-binding fragment thereof that specifically binds to soluble amyloid, oligomeric amyloid, and/or aggregated amyloid.

13. The binding molecule according to claim 3, which further comprises an immunoglobulin Fc domain.

* * * * *